(12) United States Patent
Terakado et al.

(10) Patent No.: US 7,820,682 B2
(45) Date of Patent: Oct. 26, 2010

(54) LPA RECEPTOR ANTAGONIST

(75) Inventors: Masahiko Terakado, Mishima-gun (JP); Shinji Nakade, Mishima-gun (JP); Takuya Seko, Osaka (JP); Yoshikazu Takaoka, Mishima-gun (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 829 days.

(21) Appl. No.: 10/530,249

(22) PCT Filed: May 28, 2003

(86) PCT No.: PCT/JP03/06680

§ 371 (c)(1), (2), (4) Date: Apr. 4, 2005

(87) PCT Pub. No.: WO2004/031118

PCT Pub. Date: Apr. 15, 2004

(65) Prior Publication Data

US 2006/0148830 A1 Jul. 6, 2006
US 2010/0249157 A2 Sep. 30, 2010

(30) Foreign Application Priority Data

Oct. 3, 2002 (JP) .................. P.2002-291137

(51) Int. Cl.
- A01N 43/90 (2006.01)
- A01N 43/54 (2006.01)
- A61K 31/519 (2006.01)
- A61K 31/517 (2006.01)
- C07D 471/00 (2006.01)
- C07D 487/00 (2006.01)
- C07D 401/00 (2006.01)
- C07D 403/00 (2006.01)
- C07D 413/00 (2006.01)
- C07D 417/00 (2006.01)
- C07D 419/00 (2006.01)

(52) U.S. Cl. ............... 514/264.1; 514/266.2; 544/279; 544/284

(58) Field of Classification Search .................. None
See application file for complete search history.

(56) References Cited

U.S. PATENT DOCUMENTS

| | | | |
|---|---|---|---|
| 4,663,473 A * | 5/1987 | Geigel et al. ............... | 560/336 |
| 2007/0149595 A1* | 6/2007 | Tanaka et al. ............... | 514/408 |

FOREIGN PATENT DOCUMENTS

| DE | 2528846 A1 | 1/1976 |
|---|---|---|
| EP | 341081 A1 | 8/1989 |
| EP | 390215 A1 | 10/1990 |
| EP | 573271 A1 | 12/1993 |
| JP | 56/90067 A | 7/1981 |
| JP | 62-164661 A | 7/1987 |
| JP | 1-299283 A | 12/1989 |
| JP | 10/287634 A | 10/1998 |
| JP | 10-287651 A | 10/1998 |
| JP | 11/158144 A | 6/1999 |
| JP | 2001-226362 A | 8/2001 |
| JP | 2002-293764 A | 10/2002 |
| WO | WO 93/12095 A1 | 6/1993 |
| WO | WO 95/12572 A1 | 5/1995 |
| WO | WO 99/08501 A1 | 2/1999 |
| WO | WO 01/00206 A1 | 1/2001 |
| WO | WO 02/00646 A1 | 1/2002 |
| WO | WO 02/29001 A | 4/2002 |
| WO | WO 02/062389 A1 | 8/2002 |
| WO | WO 02/062798 A1 | 8/2002 |
| WO | 2004/002530 A1 | 1/2004 |
| WO | 2004/031118 A1 | 4/2004 |

OTHER PUBLICATIONS

Aldrich Chemical Company; Technical Bulletin AL-110, Oxalyl Chloride; Apr. 1996; p. 2.*
Roger Salmon; Oxalyl Chloride; Apr. 15, 2001; Encyclopedia of Reagents for Organic Synthesis; p. 6.*
Wouter I. Iwema Bakker et. al.; Lithium Diisopropylamide; Oct. 15, 2004; Encyclopedia of Reagents for Organic Synthesis; p. 2, 15-16.*
M.S. Kharasch, et. al.; Carboxylation II: The reaction of Oxalyl Chloride with Unsaturated Hydrocarbons; Journal of American Chemical Society; 64, 333 (1942).*
Luca Banfi et. al.; Sodium Borohydride; Apr. 15, 2001; Encyclopedia of Reagents for Organic Synthesis; p. 1, 2, and 7.*
Chawla et. al.; Current Research & Information on Pharmaceutical Science, 2004, 5(1), p. 9, col. 2, para.1.*

(Continued)

Primary Examiner—James O Wilson
Assistant Examiner—Jeffrey H Murray
(74) Attorney, Agent, or Firm—Sughrue Mion, PLLC

(57) ABSTRACT

A compound of the general formula (I) or a non-toxic salt thereof. This compound engages in LPA receptor bonding and antagonism and is useful in the prevention and/or treatment of urinary system disease (symptom with prostatic hypertrophy or neurogenic bladder dysfunction disease, symptom to be caused by spinal cord neoplasm, nucleous hernia, spinal canal stenosis or diabetes, occlusion disease of lower urinary tract, inflammatory disease of lower urinary tract, polyuria), carcinoma-associated disease (solid tumor, solid tumor metastasis, angiofibroma, myeloma, multiple myeloma, Kaposi's sarcoma, leucemia and carcinomatous infiltration transition), proliferative disease (disorder with aberrant angiogenesis, artery obstruction and pulmonary fibrosis), inflammation/immune system disease (psoriasis, nephropathy, hepatitis and pneumonitis symptom), disease caused by secretory dysfunction (Sjogren syndrome), brain-related disease (brain infarction, cerebral apoplexy and brain or peripheral neuropathy) or chronic disease (chronic asthma, glomerulonephritis, obesity, prostate hyperplasia, diseases caused by arteriosclerosis process, rheumatism or atopic dermatitis).

2 Claims, No Drawings

OTHER PUBLICATIONS

Schiaffino et. al., J.Behav.Med., 1995, 18(6), p. 531-548.*
http://www.msakc.org/Articles/MSPain.htm.*
Newman et. al.; Drug Discovery Today, 2003, 8(19), p. 899, col. 2, Box 1.*
Dorwald F. A. Side Reactions in Organic Synthesis, 2005, Wiley: VCH, Weinheim p. IX of Preface.*
International Search Report for PCT/JP04/019456 Apr. 12, 2005.
Contos et al., Lysophasphatidic Acid Receptors, Mol Pharmacol, vol. 58: 1188-1196, 2000.
U.S. Office Action dated Oct. 1, 2009 (U.S. Appl. No. 12/112,563).
Banker, et al., "Modern Pharmaceuticals," 3rd Ed., pp. 596 (1996).
Wolff, et al., "Burger's Medicinal Chemistry and Drug Discovery," 5th Ed. Pat 1, pp. 975-977 (1995).
Kubinyi, H.; 3D Qsar in Drug Design: Ligand-Protein Interactions and Molecular Similarity, vol. 2-3, Springer, 1998, pp. 800.
International Search Report for PCT/JP03/06680 dated Aug. 19, 2003.

* cited by examiner

LPA RECEPTOR ANTAGONIST

TECHNICAL FIELD

The present invention relates to a carboxylic acid derivative having antagonisitic activity against lysophosphatidic acid receptor (especially EDG-2 receptor) which is useful as medicament, a process for producing the same and the use thereof.

BACKGROUND ART

It is known that various lipid mediators such as eicosanoid and platelet activating factor (PAF) are produced by the activity of phospholipase from cell membranes.

Lysophosphatidic acid (hereinafter abbreviated as LPA) of formula (A)

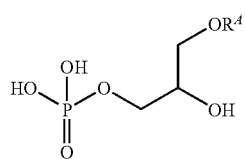

(wherein $R^A$ is acyl, alkenyl or alkyl)

is a lipid which is produced from cell membranes or phospholipid which is present in the blood, acts as a mediator for signal transduction and delivers various signals into cells. LPA that exists naturally is L-α-LPA.

Recently, the existence of three subtypes of LPA receptor has been disclosed and it is gradually proved that their physiological activities are via LPA receptor. Three subtypes of LPA receptor are called EDG (Endothelial differentiation gene)-2, 4 and 7, respectively, and form part of EDG receptor family as well as EDG-1, 3, 5, 6 and 8 that are sphingosine-1-phosphate receptor. EDG-2 is also called LPA1 or VZG (Ventricular zone gene)-1 (*Mol. Pharmacol.*, 2000 December; 58(6): 1188-96). LPA receptor to which LPA binds delivers signals into cells via G-protein coupled to the receptor. Gs, Gi, Gq, etc. are known as G-proteins that can bind to LPA receptor, and the receptors are said to relate to the response to the action of increase or, adversely, decrease of cell growth. Furthermore, since MAP-kinase systems operate in the downstreams of G-proteins, it has been known that LPA receptors deliver various signals.

Since localization of LPA receptors is different between their subtypes although they exist widely in living body, it is considered that the role of each receptor is different by the organ.

The increase of blood pressure in rats, and the contraction of colon in rats and ileum in guinea pigs have been known as the pharmacological activity induced by LPA (*J. Pharm. Pharmacol.* 1991, 43, 774, *J. Pharm. Pharmacol.* 1982, 34, 514). In addition, the effect of LPA on urethral contraction is set forth in WO02/062389 specification and the suppressive effect of LPA on secretion of pancreatic juice is set forth in WO03/007991 specification. Furthermore, the effect of LPA on chronic disease is set forth in the specification of Japan Patent Application (Tokugan 2002-185542).

In addition, concerning to the relationship between LPA and carcinoma, until now it is known that LPA enhances the proliferation of the epithelial cancer cells originated from prostate gland (*J Cellular Physiol.* 1998 174, 261) and ovarian cancer cells (*J. Urol.* 2000, 163, 1027).

In addition, it is known that LPA is related to the function of growth of various cells such as airway smooth muscle cells (*Am. J. Physiol. Lung Cell Mol. Physiol.*, 2002, 282(1): L91), fibroblast (*Mol. Cell Biol.*, 1998, 18(12): 7119), mesangial cells (*Clin. Science* 1999, 96, 431), hepatocyte, liver stellate cells (*Biochem. Biophys. Res. Commun.*, 1998, 248, 436), vasucular smooth muscle cells (*Am. J. Physiol.*, 1994, 267 (Cell Physiol. 36): C204), vascular endothelial cells (*Am. J. Physiol. Cell Physiol.*, 2000, 278(3): C612), glia cells/Schwann cells (*Proc. Natl. Acad. Sci. USA*, 1999, 96, 5233), adipocytes (*J. Clin. Invest.*, 1998, 101, 1431) as well as cancer cells. In addition, it is known that LPA is related to the function of chemotaxis of inflammatory cells as well as cancer cells besides cell growth (*Biochem Biophys Res Commun.*, 1993, 15; 193(2), 497). Moreover proliferation and cytokine-secreting activity in response to LPA of immune cells (*J. Immunol.* 1999, 162, 2049), platelet aggregation activity to LPA (*Biochem. Biophys. Res. Commun.*, 1981, 99, 391) are known. Besides, from analysis of knockout mouse of EDG-2 which is one of the LPA receptor, EDG-2 is concerned to be related to the brain function (*Proc. Natl. Acad. Sci. USA*, 2000, 97, 13384).

From these evidences, it is thought that a drug antagonizing to LPA receptor is useful for prevention and/or treatment of diseases such as various kinds of disease namely urinary system disease, carcinoma-associated disease, proliferative disease, inflammation/immune system disease, disease by secretory dysfunction, brain-related disease or chronic disease.

For example, for urinary system disease, prostatic hypertrophy or neurogenic bladder dysfunction disease, and dysuria (micturation initiation delay, extension between on urination, urinary stream very small, intermission micturation, two steps of micturation, etc.), pollakiuria, night urination, urodynia, etc. are known as symptoms with a urinary system disease. Similar urologic symptoms are symptoms caused by cerebrovascular disorder, Parkinson disease, cerebral oncosis, a multiple sclerosis, Shy-Drager symptom, spinal cord neoplasm, nucleous hernia, spinal canal stenosis, diabetes, etc. (such as dysuria (micturation initiation delay, extension between on urination, urinary stream very small, intermission micturation, two steps of miction), pollakiuria, night urination, urodynia). For other example, for urinary system disease, lower urinary tract symptom (for example, occlusion disease of lower urinary tract), inflammatory disease of lower urinary tract (such as infection), and polyuria are thought about. And these diseases are considered to be controlled by LPA receptor antagonists.

For example, for carcinoma-associated disease, solid tumor, solid tumor metastasis, angiofibroma, myeloma, multiple myeloma, Kaposi's sarcoma, leucemia are given. In solid tumor, mammary cancer, lung cancer, gastric cancer, carcinoma oesophagi, colon rectal cancer, liver cancer, ovarian cancer, theca cell tumor, androblastoma, cervix cancer, endometrial carcinoma, prostate cancer, kidney cancer, carcinoma cutaneum, osteosarcoma, pancreas cancer, urinary tract carcinoma, thyroid cancer, or cerebral oncosis, etc. are given. In addition, it is thought that carcinomatous infiltration transition is suppressed by LPA receptor antagonist.

For example, for proliferative disease, the disease with aberrant angiogenesis are given (for example, re-arctation, diabetic retinopathy, angiogenesis-related glaucoma, crystalline lens fiber multiplication symptom, thyroid gland hyperplasia (including Basedow's disease), lung inflammation, nephrotic syndrome or osteoporosis), and also artery obstruction, or pulmonary fibrosis, etc. are given.

For example, for inflammation/immune system disease, psoriasis, nephropathy (for example, IgA nephropathy, etc.), nephritis by other inflammation/immunopathy, hepatitis, or pneumonitis symptom, etc. are given.

For example, for secretory dysfunction, secretory dysfunction by autonomic nervous system dysfunction is given, for example, for secretory dysfunction by autonomic nervous system dysfunction, Sjogren syndrome, etc. is given.

For example, for brain-related disease, brain infarction, cerebral apoplexy, brain or peripheral neuropathy, etc. are given.

For example, for chronic disease, chronic asthma, glomerulonephritis, obesity, prostate hyperplasia, diseases caused by arteriosclerosis process, rheumatism or atopic dermatitis, etc. are given.

The compound of formula (B)

[wherein $R^{1B}$ represents optionally substituted alkyl, aryl, heterocyclic radical, alkyloxy, aryloxy, alkylthio, arylthio or halogen atom, $R^{2B}$ represents optionally substituted alkyl, aryl, heterocyclic radical, alkyloxy, aryloxy or halogen atom, $R^{3B}$ represents hydrogen atom, lower alkyl or alkyl substituted with halogen atom, $R^{4B}$ represents a radical selected from (a) optionally substituted phenyl, aryl or heterocyclic radical, (b) substituted or non-substituted alkyl or (c) substituted or non-substituted alkenyl, $X^B$ represents oxygen atom or sulfur atom. With the proviso that $R^{3B}$ and $R^{4B}$ may form a five- to ten-membered cyclic structure together with a carbon atom to which they bind, and when $R^{3B}$ is a hydrogen atom, $R^{4B}$ represents a group other than methyl.]

or a salt thereof is known as a compound having the LPA receptor antagonistic activity (WO01/60819).

The compound of formula (C)

or a salt thereof is known as a compound having the angiotensin II antagonistic activity (EP443983).

DISCLOSURE OF THE INVENTION

An agent of prevention and/or treatment of urinary system disease, carcinoma-associated disease, proliferative disease, inflammation/immune system disease, disease caused by secretory dysfunction, brain-related disease and chronic disease, etc. is useful for drug. It is eagerly desired to development of an LPA receptor (EDG-2, especially) antagonist which is excel at oral absorption, and safety.

The inventors of the present invention have carried out intensive studies for finding compounds which specifically binds to LPA receptors (EDG-2 receptor, especially) and exerts antagonistic activity, and as a result, they have found that a carboxylic acid derivative of formula (I) achieves the problem to accomplish the present invention.

The present invention can provide the novel compound which becomes various kinds of treatment of disease medicine by showing antagonistic activity to LPA receptor. For example, it may be an agent of prevention and/or treatment such as the urinary system disease that does not influence blood pressure is provided.

The carboxylic acid derivative of formula (I) of the present invention is the novel compound which is not known till now.

The present invention relates to the followings and the like:

(1) A compound of formula (I)

wherein R represents an aliphatic hydrocarbon group which may be substituted, or a cyclic group which may have a substituent(s);

G represents a bond or a spacer having from 1 to 8 atoms in its principle chain;

T represents —$CH_2$—, or a spacer having one atom in its principle chain, the principle chain containing a hydrogen bond acceptable group which may have a substituent(s);

J represents a nitrogen atom or a carbon atom;

B represents an aliphatic hydrocarbon group which may be substituted, or a cyclic group which may have a substituent(s);

K represents (1) a bond, or (2) a spacer having from 1 to 8 atoms in its principle chain which may form a ring together with a substituent of the cyclic group in R, the ring D or a substituent on the ring D;

Q represents (1) a bond, or (2) a spacer having from 1 to 8 atoms in its principle chain which may form a ring together with the cyclic group in R, a substituent of the cyclic group in R or K;

ring D represents a cyclic group which may have an additional substituent(s);

L represents a bond, or a spacer having from 1 to 3 atoms in its principle chain;

ring E represents a cyclic group which may have an additional substituent(s);

M represents a bond, or a spacer having from 1 to 8 atoms in its principle chain;

Z represents an acidic group; and t represents 0 or 1, or a salt thereof (2) A prodrug of the compound according to (1).

(3) The compound according to (1), wherein R is an aliphatic hydrocarbon group which may be substituted.

(4) The compound according to (1), wherein R is a cyclic group which may have a substituent(s).

(5) The compound according to (4), wherein the cyclic group is a C3-15 mono-, bi- or tricyclic carbocyclic group, a bicyclic carbocyclic group having a spiro bond or a bicyclic bridged carbocyclic group.

(6) The compound according to (5), wherein the cyclic group is a C3-15 mono-, bi- or tricyclic aromatic carbocyclic group.

(7) The compound according to (5), wherein the cyclic group is a cyclopentane, cyclopentene, cyclohexane, benzene or naphthalene ring.

(8) The compound according to (6), wherein the cyclic group is a benzene ring.

(9) The compound according to (4), wherein the cyclic group is a three- to fifteen-membered monocyclic, bicyclic or tricyclic heterocyclic group, a bicyclic heterocyclic group having a spiro bond or a bicyclic bridged heterocyclic group containing from 1 to 5 hetero atoms selected from an oxygen atom(s), a nitrogen atom(s) and a sulfur atom(s).

(10) The compound according to (9), wherein the cyclic group is a three- to fifteen-membered monocyclic, bicyclic or tricyclic aromatic heterocyclic group containing from 1 to 5 hetero atoms selected from an oxygen atom(s), a nitrogen atom(s) and a sulfur atom(s).

(11) The compound according to (9), wherein the cyclic group is a furan, isoxazole, thiophene, 1,2,3-thiadiazole, pyrrole, pyrazole, benzothiophene, indole, 1,3-dioxaindan, pyridine or cinnoline ring.

(12) The compound according to (10), wherein the cyclic group is a pyridine ring.

(13) The compound according to (1), wherein G is a bond.

(14) The compound according to (1), wherein T is —CHOH—, or —CO—.

(15) The compound according to (1), wherein J is a nitrogen atom.

(16) The compound according to (1), wherein J is a carbon atom.

(17) The compound according to (1), wherein K is a spacer having from 1 to 4 atoms in its principle chain.

(18) The compound according to (17), wherein K is C1-4 alkylene which may be substituted.

(19) The compound according to (18), wherein K is trimethylene, or trimethylene substituted with two halogen atoms.

(20) The compound according to (1), wherein B is a C3-15 mono-, bi- or tricyclic carbocyclic group, a bicyclic carbocyclic group having a spiro bond or a bicyclic bridged carbocyclic group.

(21) The compound according to (20), wherein B is a C3-15 mono-, bi- or tricyclic aromatic carbocyclic group.

(22) The compound according to (20), wherein B is a cyclohexane, benzene, indan, tetrahydronaphthalene or naphthalene ring.

(23) The compound according to (21), wherein B is a benzene ring.

(24) The compound according to (1), wherein B is a three- to fifteen-membered monocyclic, bicyclic or tricyclic heterocyclic group, a bicyclic heterocyclic group having a spiro bond or a bicyclic bridged heterocyclic group containing from 1 to 5 hetero atoms selected from an oxygen atom(s), a nitrogen atom(s) and a sulfur atom(s).

(25) The compound according to (24), wherein B is a three- to fifteen-membered monocyclic, bicyclic or tricyclic aromatic heterocyclic group containing from 1 to 5 hetero atoms selected from an oxygen atom(s), a nitrogen atom(s) and a sulfur atom(s).

(26) The compound according to (24), wherein B is a pyrrolidine, piperidine, piperazine, morpholine, pyridine, thiazole, imidazole, pyrrole, pyrazole, indol or thiophene ring.

(27) The compound according to (25), wherein B is a thiophene ring.

(28) The compound according to (1), wherein Q is a spacer having from 1 to 4 atoms in its principle chain.

(29) The compound according to (28), wherein Q is C1-4 alkylene which may be substituted.

(30) The compound according to (29), wherein Q is methylene.

(31) The compound according to (1), wherein ring D is a C3-15 mono-, bi- or tricyclic carbocyclic group, bicyclic carbocyclic group having a spiro bond or a bicyclic bridged carbocyclic group.

(32) The compound according to (31), wherein ring D is a C3-15 mono-, bi- or tricyclic aromatic carbocyclic group.

(33) The compound according to (31), wherein ring D is a cyclohexane or benzene ring.

(34) The compound according to (32), wherein ring D is a benzene ring.

(35) The compound according to (1), wherein ring D is a three- to fifteen-membered monocyclic, bicyclic or tricyclic heterocyclic group, a bicyclic heterocyclic group having spiro bond or a bicyclic bridged heterocyclic group containing from 1 to 5 hetero atoms selected from an oxygen atom(s), a nitrogen atom(s) and a sulfur atom(s).

(36) The compound according to (35), wherein ring D is a three- to fifteen-membered monocyclic, bicyclic or tricyclic aromatic heterocyclic group containing from 1 to 5 hetero atoms selected from an oxygen atom(s), a nitrogen atom(s) and a sulfur atom(s).

(37) The compound according to (35), wherein ring D is a piperidine, pyrrole, pyrazole, pyridine, 1,3,4-oxadiazole, thiazole, dihydrobenzoxazine or indol ring.

(38) The compound according to (36), wherein ring D is a pyrrole or indol ring.

(39). The compound according to (1s), wherein L is a bond.

(40) The compound according to (1), wherein L is a spacer having from 1 to 3 atoms in its principle chain.

(41) The compound according to (40), wherein L is —CH$_2$—, —O—, —S—, —SO—, —SO$_2$—, or —NH—.

(42) The compound according to (40), wherein L is —O— or —S—.

(43) The compound according to (1), wherein ring E is a C3-15 mono-, bi- or tricyclic carbocyclic group, bicyclic carbocyclic group having a spiro bond or a bicyclic bridged carbocyclic group.

(44) The compound according to (43), wherein ring E is a C3-15 mono-, bi- or tricyclic aromatic carbocyclic group.

(45) The compound according to (44), wherein ring E is a benzene ring.

(46) The compound according to (1), wherein ring E is a three- to fifteen-membered monocyclic, bicyclic or tricyclic heterocyclic group, a bicyclic heterocyclic group having spiro bond or a bicyclic bridged heterocyclic group containing from 1 to 5 hetero atoms selected from an oxygen atom(s), a nitrogen atom(s) and a sulfur atom(s).

(47) The compound according to (46), wherein ring E is a three- to fifteen-membered monocyclic, bicyclic or tricyclic aromatic heterocyclic group containing from 1 to 5 hetero atoms selected from an oxygen atom(s), a nitrogen atom(s) and a sulfur atom(s).

(48) The compound according to (46), wherein ring E is a piperidine, isoxazole, pyrazole, pyridine, thiazole, imidazole, thiophene, pyrrole or pyrrolidine ring.

(49) The compound according to (1), wherein M is a bond.

(50) The compound according to (1), wherein M is a spacer having from 1 to 4 atoms in its principle chain.

(51) The compound according to (50), wherein M is C1-4 alkylene which may be substituted.

(52) The compound according to (51), wherein M is methylene.

(53) The compound according to (1), wherein Z is $-COOR^5$, in which $R^5$ represents a hydrogen atom, an aliphatic hydrocarbon group which may be substituted, or a cyclic group which may have a substituent(s).

(54) The compound according to (53), wherein $R^5$ is a hydrogen atom, or C1-4 alkyl.

(55) The compound according to (1), wherein Z is tetrazole.

(56) The compound according to (1), which is a compound of formula (I-J) in which K forms a ring together with a substituent of the cyclic group in R:

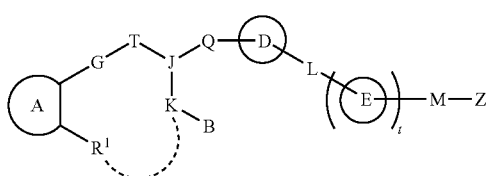

(I-J)

wherein ring A represents a cyclic group which may have a substituent(s) in R;
$R^1$ represents a substituent of the cyclic group R; and
other symbols have the same meanings as described in (1).

(57) The compound according to (56), which is represented by formula (I-J-1):

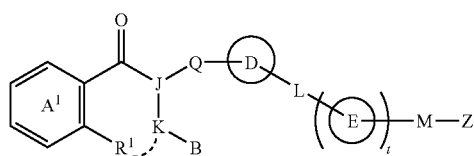

(I-J-1)

wherein ring $A^1$ has the same meaning as the ring A described in (56), with the proviso that it represents a benzene ring which may have a substituent(s); and
other symbols have the same meanings as described in (1).

(58) The compound according to (57), which is represented by formula (I-J-1-1):

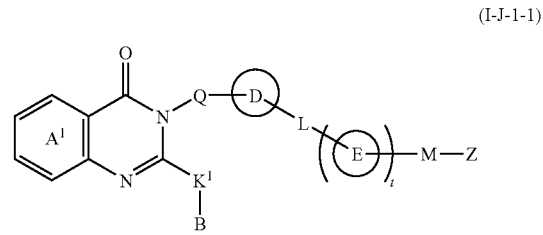

(I-J-1-1)

$K^1$ has the same meaning as K described in (1), with the proviso that it represents a spacer having from 1 to 7 atoms in its principle chain; and
other symbols have the same meaning as described in (1) or (57).

(59) The compound according to (1), which is a compound of either formula (I-K) or formula (I-N) in which K forms a ring together with the ring D or a substituent on the ring D:

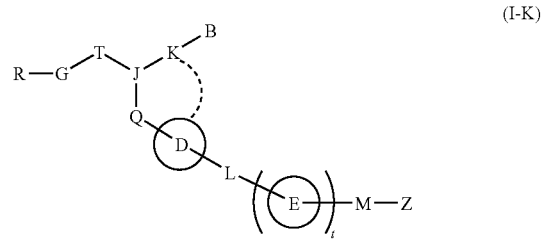

(I-K)

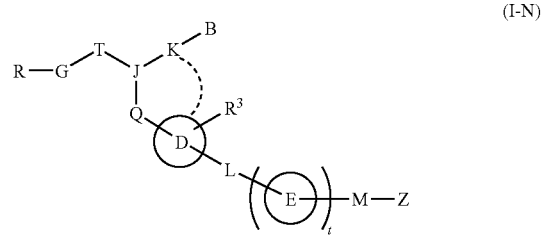

(I-N)

wherein all symbols have the same meanings as described in (1).

(60) The compound according to (59), which is a compound of either following formula (I-K-1) or formula (I-N-1):

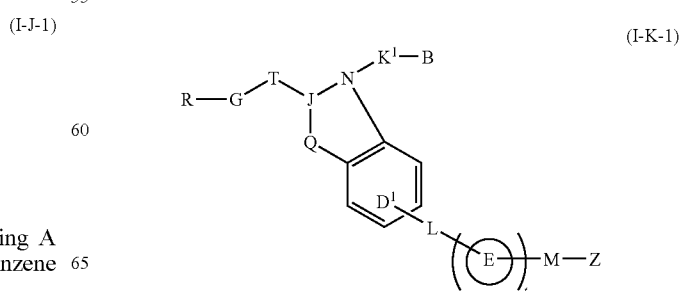

(I-K-1)

-continued (I-N-1)

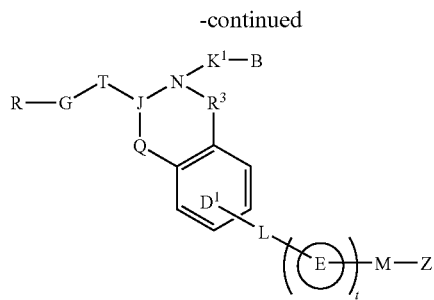

wherein ring $D^1$ has the same meaning as the ring D described in (1), with the proviso that it represents a benzene ring which may have a substituent(s);

$R^3$ represents a substituent on the ring D; and other symbols have the same meanings as described in (1) or (58).

(61) The compound according to (60), which is a compound of either following formula (I-K-1-1), formula (I-K-1-2) or formula (I-N-1-1):

(I-K-1-1)

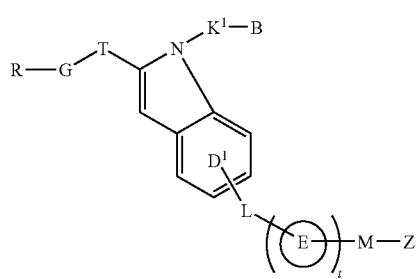

(I-K-1-2)

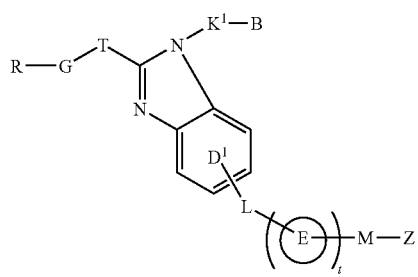

(I-N-1-1)

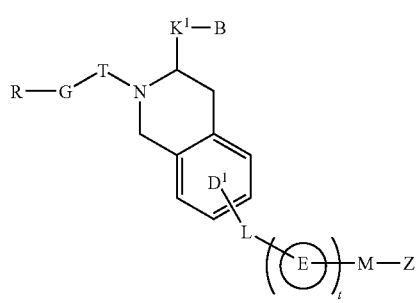

wherein all symbols have the same meanings as described in (1), (58) or (60).

(62) The compound according to (1), which is a compound of either formula (I-L) or formula (I-O) in which Q forms a ring together with a cyclic group of R or a substituent of the cyclic group in R:

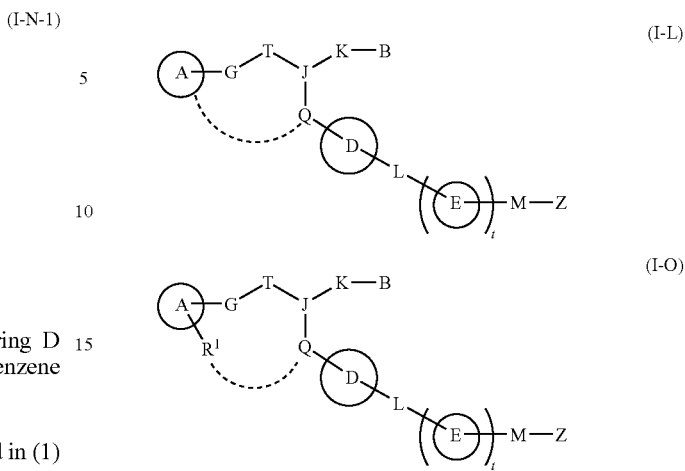

wherein all symbols have the same meanings as described in (1) or (56).

(63) The compound according to (62), which is a compound of either following formula (I-L-1) or formula (I-O-1):

(I-L-1)

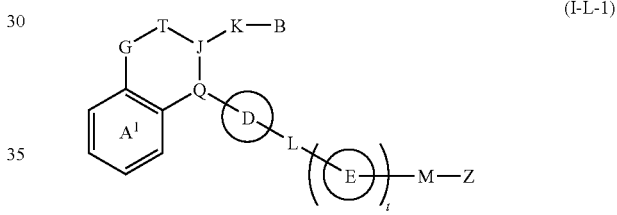

(I-O-1)

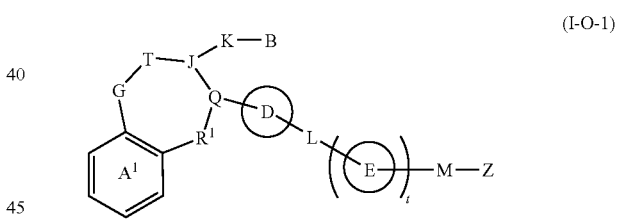

wherein all symbols have the same meanings as described in (1), (56) or (57).

(64) The compound according to (63), which is a compound of either following formula (I-L-1-1), formula (I-O-1-1), formula (I-O-1-2), formula (I-O-1-3), formula (I-O-1-4) or formula (I-O-1-5):

(I-L-1-1)

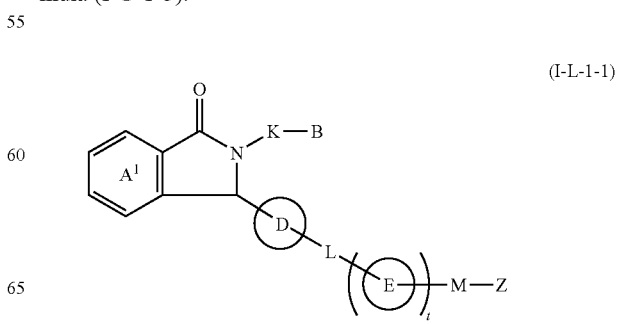

-continued (I-O-1-1)
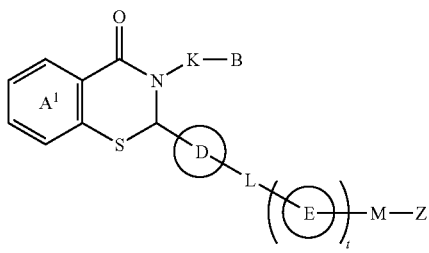

(I-O-1-2)
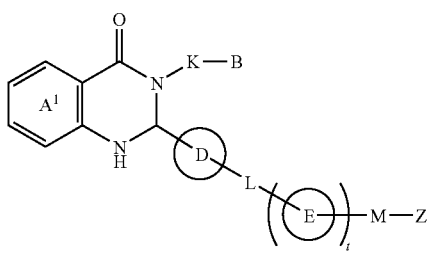

(I-O-1-3)
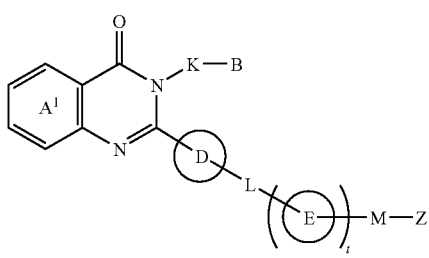

(I-O-1-4)
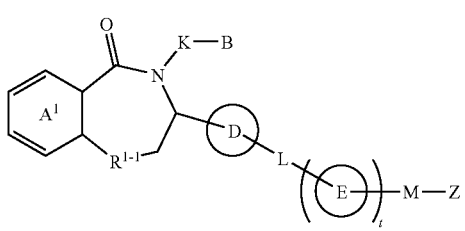

(I-O-1-5)
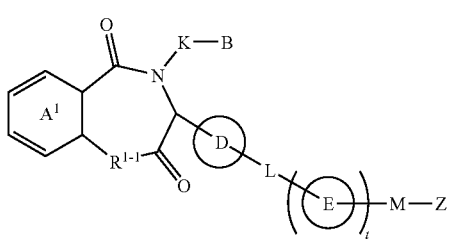

wherein $R^{1-1}$ represents —$CH_2$—, —O—, —S— or —NH—; and other symbols have the same meanings as described in (1) or (57).

(65) The compound according to (1), which is a compound of formula (I-M) in which Q forms a ring together with K:

(I-M)

wherein all symbols have the same meanings as described in (1).

(66) The compound according to (65), which is represented by formula (I-M-1):

(I-M-1)
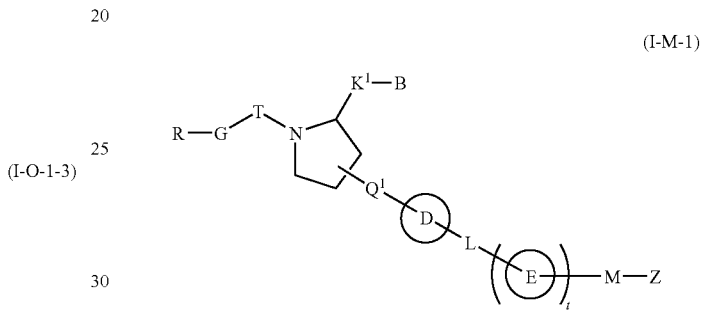

wherein $Q^1$ has the same meaning as Q described in (1), with the proviso that it represents a spacer having from 1 to 7 atoms in its principle chain; and other symbols have the same meanings as described in (1) or (58).

(67) The compound according to (66), which is a compound of either following formula (I-M-1-1), formula (I-M-1-2) or formula (I-M-1-3):

(I-M-1-1)
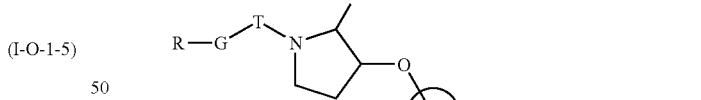

(I-M-1-2)

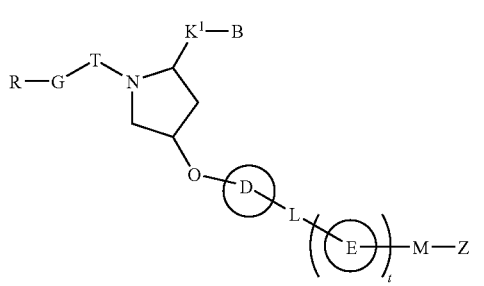

-continued (I-M-1-3)

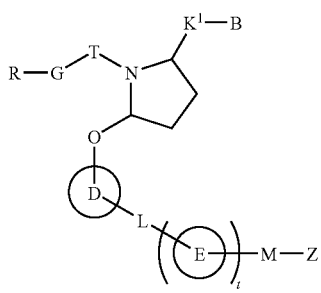

wherein all symbols have the same meanings as described in (1) or (58).

(68) The compound according to (1), which is a compound of either following formula (I-A), formula (I-B), formula (I-C), formula (I-D) or formula (I-E):

(I-A)

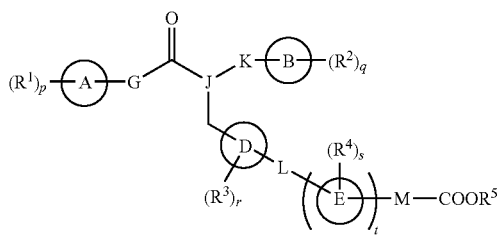

(I-B)

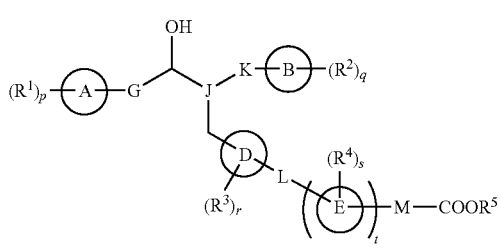

(I-C)

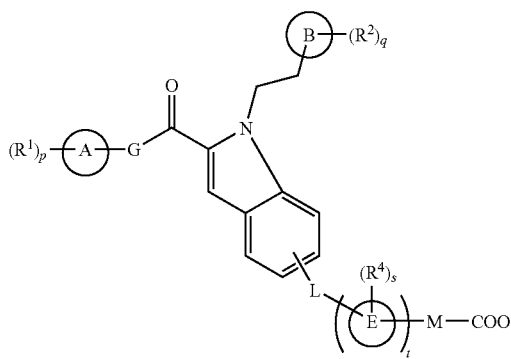

(I-D)

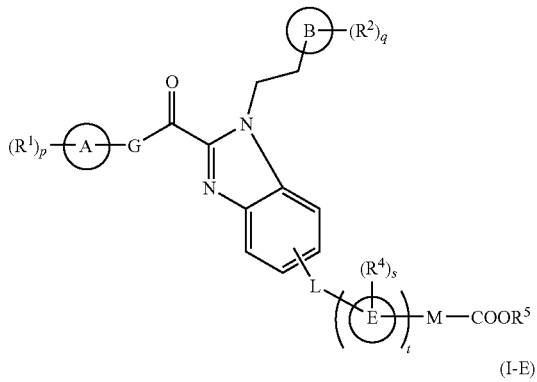

(I-E)

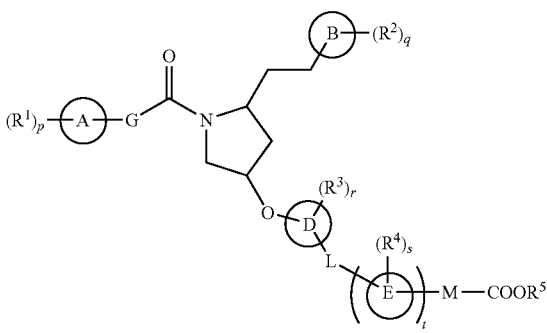

wherein $R^1$, $R^2$, $R^3$ and $R^4$ each independently represents (1) C1-8 alkyl, (2) C2-8 alkenyl, (3) C2-8 alkynyl, (4) a halogen atom, (5) trihalomethyl, (6) nitro, (7) cyano, (8) Cycl, (9) —$OR^6$, (10) —$SR^7$, (11) —$NR^8R^9$, (12) —$CONR^{10}R^{11}$, (13) —$NR^{12}COR^{13}$, (14) —$SO_2NR^{14}R^{15}$, (15) —$NR^{16}SO_2R^{17}$, (16) —$SO_2R^{18}$, (17) —$COR^{19}$, (18) —$COOR^{20}$, or (19) C1-8 alkyl substituted with —$OR^6$, —$SR^7$, —$NR^8R^9$ or Cycl;

$R^6$ represents (1) a hydrogen atom, (2) C1-8 alkyl, (3) C2-8 alkenyl, (4) C2-8 alkynyl, (5) Cycl, (6) methyl substituted with 1 to 3 halogen, or (7) C1-8 alkyl substituted with Cycl;

$R^7$ to $R^{16}$ and $R^{20}$ each independently represents (1) a hydrogen atom, (2) C1-8 alkyl, (3) C2-8 alkenyl, (4) C2-8 alkynyl, or (5) Cycl;

$R^{17}$, $R^{18}$ and $R^{19}$ each independently represents (1) C1-8 alkyl, (2) C2-8 alkenyl, (3) C2-8 alkynyl, or (4) Cycl;

Cycl represents a C3-10 monocyclic or bicyclic carbocyclic group or a three- to ten-membered monocyclic or bicyclic heterocyclic group which contains 1 to 5 hetero atoms selected from an oxygen atom(s), a nitrogen atom(s) and a sulfur atom(s);

G, K and M each independently represents (1) a bond, (2) C1-8 alkylene, (3) C2-8 alkenylene, or (4) C2-8 alkynylene;

J represents a nitrogen atom or a carbon atom;

L represents a bond, an oxygen atom or a sulfur atom;

Ring A, ring B and ring D each independently represents a C3-10 monocyclic or bicyclic carbocyclic group or a three- to ten-membered monocyclic or bicyclic heterocyclic group which contains 1 to 5 hetero atoms selected from an oxygen atom(s), a nitrogen atom(s) and a sulfur atom(s);

Ring E represents a C3-7 monocyclic carbocyclic group or a three- to seven-membered monocyclic heterocyclic group which contains 1 to 5 hetero atoms selected from an oxygen atom(s), a nitrogen atom(s) and a sulfur atom(s);

p, q, r and s each independently represents 0 or an integer of from 1 to 5, in which $R^1$s are the same or different when p represents 2 or more; $R^2$s are the same or different when q represents 2 or more; $R^3$s are the same or different when r represents 2 or more; and $R^4$s are the same or different when s represents 2 or more, respectively;

t represents 0 or 1; and $R^5$ represents (1) a hydrogen atom, (2) C1-8 alkyl, (3) C2-8 alkenyl, or (4) C2-8 alkynyl, or a salt thereof

(69) A pharmaceutical composition comprising the compound according to (1) or the prodrug according to (2).

(70) The pharmaceutical composition according to (69), which is an LPA receptor antagonist.

(71) The pharmaceutical composition according to (70), wherein the LPA receptor is EDG-2 receptor.

(72) The pharmaceutical composition according to (71), which is an agent for prevention and/or treatment for urinary system disease.

(73) The pharmaceutical composition according to (71), which is an agent for prevention and/or treatment for carcinoma-associated disease, proliferative disease, inflammation/immune system disease, disease caused by secretory dysfunction or brain-related disease.

(74) A method for prevention and/or treatment of diseases referred from EDG-2, which comprises administering an effective amount of the compound according to (1) or a salt thereof to a mammal.

(75) The method for prevention and/or treatment according to (74), wherein the disease referred from EDG-2 is urinary system disease.

(76) The method for prevention and/or treatment according to (74), wherein the disease referred from EDG-2 is carcinoma-associated disease, proliferative disease, inflammation/immune system disease, disease caused by secretory dysfunction or brain-related disease.

(77) Use of the compound according to (1) or a salt thereof for manufacture of a pharmaceutical for prevention and/or treatment of diseases referred from EDG-2.

(78) The use according to (77), wherein the disease referred from EDG-2 is urinary system disease.

(79) The use according to (77), wherein the disease referred from EDG-2 is carcinoma-associated disease, proliferative disease, inflammation/immune system disease, disease caused by secretory dysfunction or brain-related disease.

(80) A pharmaceutical composition for prevention and/or treatment of urinary system disease comprising a combination of an LPA receptor antagonist containing the compound according to (1) or a prodrug thereof as an active ingredient and one or two more agent(s) selected from other LPA receptor antagonist, α1 blocking agent, anticholinergic agent, 5α-reductase inhibitor and/or anti-androgenic agent.

Examples of the "aliphatic hydrocarbon group" in the "aliphatic hydrocarbon group which may be substituted" represented by R in formula (I) include "straight chain or branched aliphatic hydrocarbon group". Examples of the "straight chain or branched aliphatic hydrocarbon group" include "straight chain or branched alkyl, alkenyl or alkynyl group".

Examples of the "straight chain or branched alkyl" include straight chain or branched C1-10 alkyl and the like, such as methyl, ethyl, propyl, isopropyl, butyl, isobutyl, sec-butyl, tert-butyl, pentyl, isopentyl, neopentyl, hexyl, heptyl, octyl, nonyl and decyl.

Examples of the "straight chain or branched alkenyl" include straight chain or branched C2-10 alkenyl and the like, such as ethenyl, propenyl, butenyl, butadienyl, pentenyl, pentadienyl, hexenyl, hexadienyl, heptenyl, heptadienyl, octenyl, octadienyl, nonenyl, nonadienyl, decenyl and decadienyl.

Examples of the "straight chain or branched alkynyl" include straight chain or branched C2-10 alkynyl and the like, such as ethynyl, propynyl, butynyl, butadiynyl, pentynyl, pentadiynyl, hexynyl, hexadiynyl, heptynyl, heptadiynyl, octynyl, octadyenyl, nonynyl, nonadiynyl, decynyl and decadiynyl.

Examples of the "cyclic group" in the "cyclic group which may have a substituent(s)" represented by R include carbocyclic group or heterocyclic group.

Carbocyclic group includes, for example, C3-15 mono-, bi- or tricyclic carbocyclic group, bicyclic carbocyclic group having spiro bond or bicyclic bridged carbocyclic group. C3-15 mono-, bi- or tricyclic carbocyclic group include C3-15 mono-, bi- or tricyclic unsaturated carbocyclic group, and partially saturated or fully saturated carbocyclic group, for example, cyclopropane, cyclobutane, cyclopentane, cyclohexane, cycloheptane, cyclooctane, cyclononane, cyclodecane, cycloundecane, cyclododecane, cyclotridodecane, cyclotetradecane, cyclopentadecane, cyclopentene, cyclobexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indan, naphthalene, dihydronaphthalene, teterahydronaphthalene, perhydronaphthalene, heptalene, perhydroheptalene, biphenylene, as-indacene, s-indacene, acenaphthylene, acenaphthene, fluorene, phenalene, phenanthrene, anthracene, spiro[4.4]nonane, spiro[4.5]decane, spiro[5.5]undecane, bicyclo[2.2.1]heptane, bicyclo[2.2.1]hept-2-ene, bicyclo[3.1.1]heptane, bicyclo[3.1.1]hept-2-ene, bicyclo[3.2.1]octane, bicyclo[2.2.2]octane, bicyclo[2.2.2]oct-2-ene, adamantane and noradamantane. Among these, C3-15 mono-, bi- or tricyclic aromatic carbocyclic group includes, for example, benzene, azulene, naphthalene, phenanthrene, anthracene ring.

Heterocyclic group includes, for example, three- to fifteen-membered monocyclic, bicyclic or tricyclic heterocyclic groups, bicyclic heterocyclic group having spiro bond or bicyclic bridged heterocyclic group containing from 1 to 5 hetero atoms selected from an oxygen atom(s), a nitrogen atom(s) and a sulfur atom(s). Three- to fifteen-membered monocyclic, bicyclic or tricyclic heterocyclic groups containing from 1 to 5 hetero atoms selected from an oxygen atom(s), a nitrogen atom(s) and a sulfur atom(s) include the three- to fifteen-membered mono-, bi- or tricyclic unsaturated heterocyclic group, and partially saturated or fully saturated heterocyclic groups containing from 1 to 5 hetero atoms selected from an oxygen atom(s), a nitrogen atom(s) and a sulfur atom(s), for example, pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzoxepine, benzoxazepine, benzoxadiazepine, benzothiepine, benzothiazepine, benzothiadiazepine, benzazepine, benzodiazepine, benzofurazan, benzothiadiazole, benzotriazole, carbazole, β-carboline, acridine, phenazine, dibenzofuran, xanthene, dibenzothiophene, phenothiazine, phenoxazine, phenoxathiin, thianthrene, phenanthridine, phenanthroline, perimidine, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, dihydrocarbazole, tetrahydrocarbazole, perhydrocarbazole, dihydroacridine, tetrahydroacridine, perhydroacridine, dihydrodibenzofuran, dihydrodibenzothiophene, tetrahydrodibenzofuran, tetrahydrodibenzothiophene, perhydrodibenzofuran, perhydrodibenzothiophene, dioxolane, dioxane, dithiolane, dithiane, dioxaindan, benzodioxane, chroman, benzodithiolane and benzodithiane ring.

Bicyclic heterocyclic group having spiro bond include, for example, azaspiro[4.4]nonane, azaspiro[4.5]decane, azaspiro[5.5]undecane ring, etc. Bicyclic bridged heterocyclic group include, for example, azabicyclo[2.2.1]heptane, azabicyclo[3.1.1]heptane, azabicyclo[3.2.1]octane, azabicyclo[2.2.2]octane ring, etc. Among these, three- to fifteen-membered monocyclic, bicyclic or tricyclic aromatic heterocyclic groups containing from 1 to 5 hetero atoms selected from an oxygen atom(s), a nitrogen atom(s) and a sulfur atom(s) include, for example, pyrrole, imidazole, triazole, tetrazole, pyrazole, pyridine, pyrazine, pyrimidine, pyridazine, furan, thiophene, oxazole, isoxazole, thiazole, isothiazole, furazan, oxadiazole, thiadiazole, indole, isoindole, benzofuran, isobenzofuran, benzothiophene, isobenzothiophene, indazole, quinoline, isoquinoline, purine, phthalazine, pteridine, naphthyridine, quinoxaline, quinazoline, cinnoline, benzoxazole, benzothiazole, benzimidazole, benzofurazan, benzothiadiazole, benzotriazole, carbazole, β-carboline, acridine, phenazine, dibenzofuran, dibenzothiophene, phenanthridine, phenanthroline, perimidine ring.

Examples of the "substituent" in the "aliphatic hydrocarbon group which may be substituted" or "cyclic group which may have a substituent(s)" represented by R include (a) alkyl which may be substituted, (b) alkenyl which may be substituted, (c) alkynyl which may be substituted, (d) a carbocyclic group which may have a substituent(s), (e) a heterocyclic group which may have a substituent(s), (f) hydroxyl which may be substituted, (g) thiol which may be substituted, (h) amino which may be substituted, (i) carbamoyl which may be substituted, (j) sulfamoyl which may be substituted, (k) carboxyl, (l) alkoxycarbonyl (e.g., C1-6 alkoxycarbonyl, such as methoxycarbonyl, ethoxycarbonyl or t-butoxycarbonyl, etc.), (m) sulfo (—SO$_3$H), (n) sulfino, (o) phosphono, (p) nitro, (q) oxo, (r) thioxo, (s) cyano, (t) amidino, (u) imino, (v) —B(OH)$_2$, (w) a halogen atom (e.g., fluorine, chlorine, bromine or iodine), (x) alkylsulfinyl (e.g., C1-6 alkylsulfinyl, such as methylsulfinyl or ethylsulfinyl, etc.), (y) arylsulfinyl (e.g., C6-10 arylsulfinyl, such as phenylsulfinyl, etc.), (z) alkylsulfonyl (e.g., C1-6 alkylsulfonyl, such as methylsulfonyl or ethylsulfonyl, etc.), (aa) arylsulfonyl (e.g., C6-10 arylsulfonyl, such as phenylsulfonyl, etc.), (bb) acyl (e.g., C1-6 alkanoyl, such as formyl, acetyl, propanoyl or pivaloyl, e.g., C6-10 arylcarbonyl, such as benzoyl, etc.) and the like, and 1 to 5 of these optional substituents may be substituted at replaceable positions.

Examples of the "alkyl" in the "alkyl which may be substituted" as the substituent include straight chain or branched C1-10 alkyl and the like, such as methyl, ethyl, propyl, isopropyl, butyl, isobutyl, sec-butyl, tert-butyl, pentyl, isopentyl, neopentyl, hexyl, heptyl, octyl, nonyl and decyl. In this case, examples of the substituent of alkyl include hydroxyl, amino, carboxyl, nitro, mono- or di-C1-6 alkylamino (e.g., methylamino, ethylamino, propylamine, dimethylamino, diethylamino, etc.), C1-6 alkoxy (e.g., methoxy, ethoxy, propoxy, hexyloxy, etc.), C1-6 alkylcarbonyloxy (e.g., acetoxy, ethylcarbonyloxy, etc.), phenyl, halogen atom (e.g., fluorine, chlorine, bromine or iodine) and the like, and 1 to 4 of these optional substituents may be substituted at replaceable positions.

Examples of the "alkenyl" in the "alkenyl which may be substituted" as the substituent include straight chain or branched C2-10 alkenyl and the like, such as ethenyl, propenyl, butenyl, butadienyl, pentenyl, pentadienyl, hexenyl, hexadienyl, heptenyl, heptadienyl, octenyl, octadienyl, nonenyl, nonadienyl, decenyl and decadienyl. In this case, the substituent of alkenyl has the same meaning as the substituent in the above-described "alkyl which may be substituted".

Examples of the "alkynyl" in the "alkynyl which may be substituted" as the substituent include straight chain or branched C2-10 alkynyl and the like, such as ethynyl, propynyl, butynyl, butadiynyl, pentynyl, pentadiynyl, hexynyl, hexadiynyl, heptynyl, heptadiynyl, octynyl, octadiynyl, nonynyl, nonadiynyl, decynyl and decadiynyl. In this case, the substituent of alkynyl has the same meaning as the substituent in the above-described "alkyl which may be substituted".

The carbocyclic group in the "carbocyclic group which may have a substituent(s)" as the substituent has the same meaning as the carbocyclic group in the "cyclic group" of the above-described "cyclic group which may have a substituent(s)". In this case, examples of the substituent of the carbocyclic group include straight chain or branched C1-10 alkyl (the same meaning as the alkyl in the above-described "alkyl which may be substituted"), straight chain or branched C2-10 alkenyl (the same meaning as the alkenyl in the above-described "alkenyl which may be substituted"), straight chain or branched C2-10 alkynyl (the same meaning as the alkynyl in the above-described "alkynyl which may be substituted"), hydroxyl, C1-6 alkoxy (e.g., methoxy, ethoxy, propoxy, isopropoxy, butoxy, isobutyloxy, tert-butoxy, pentyloxy, hexyloxy, etc.), thiol, C1-6 alkylthio (e.g., methylthio, ethylthio, propylthio, isopropylthio, butylthio, isobutylthio, tert-butylthio, pentylthio, hexylthio, etc.), amino, mono- or di-C1-6 alkylamino (e.g., methylamino, ethylamino, propylamino, isopropylamino, butylamino, isobutylamino, tert-butylamino, pentylamino, hexylamino, dimethylamino, diethylamino, dipropylamine, N-methyl-N-ethylamino, etc.), halogen atom (the same meaning as described above), cyano, nitro, trifluoromethyl, trifluoromethoxy and the like, and 1 to 5 of these optional substituents may be substituted at replaceable positions.

The heterocyclic group in the "heterocyclic group which may have a substituent(s)" as the substituent has the same meaning as the heterocyclic group in the "cyclic group" of the above-described "cyclic group which may have a substituent(s)". In this case, the substituent of the heterocyclic group has the same meaning as the substituent of the above-described "carbocyclic group which may have a substituent(s)".

Examples of the "substituent" of the "hydroxyl which may be substituted", "thiol which may be substituted" and "amino which may be substituted" as the substituent include (i) alkyl which may be substituted (the same meaning as described above), (ii) alkenyl which may be substituted (the same meaning as described above), (iii) alkynyl which may be substituted (the same meaning as described above), (iv) a carbocyclic group which may have a substituent(s) (the same meaning as described above), (v) a heterocyclic group which may have a substituent(s) (the same meaning as described above), (vi) acyl (e.g., C1-6 alkanoyl, such as formyl, acetyl, propanoyl, pivaloyl, butanoyl, pentanoyl or hexanoyl, an isomer group thereof, etc., e.g., C6-10 aromatic carbocyclic carbonyl, such as benzoyl, etc.), (vii) carbamoyl which may be substituted (the same meaning as described below), (viii) alkylsulfonyl (e.g., C1-6 alkylsulfonyl, such as methylsulfonyl or ethylsulfonyl, etc.), (ix) arylsulfonyl (e.g., C6-10 arylsulfonyl, such as phenylsulfonyl, etc.) and the like.

Examples of the "carbamoyl which may be substituted" as the substituent include unsubstituted carbamoyl, N-mono-C1-6 alkylcarbamoyl (e.g., N-methylcarbamoyl, N-ethylcarbamoyl, N-propylcarbamoyl, N-isopropylcarbamoyl, N-butylcarbamoyl, N-isobutylcarbamoyl, N-(tert-butyl)carbamoyl, N-pentylcarbamoyl, N-hexylcarbamoyl, etc.), N-mono-C6-10 arylcarbamoyl such as N-phenylcarbamoyl, N,N-di-C1-6 alkylcarbamoyl (e.g., N,N-dimethylcarbamoyl, N,N-diethylcarbamoyl, N,N-dipropylcarbamoyl, N,N-dibutylcarbamoyl, N,N-dipentylcarbamoyl, N,N-dihexylcarbamoyl, N-methyl-N-ethylcarbamoyl, etc.), N-di-C6-10 arylcarbamoyl such as N,N-diphenylcarbamoyl, N—C6-10 aryl-N—C1-6 alkylcarbamoyl (e.g., N-phenyl-N-methylcarbamoyl, N-phenyl-N-ethylcarbamoyl, N-phenyl-N-propylcarbamoyl, N-phenyl-N-butylcarbamoyl, N-phenyl-N-pentylcarbamoyl, N-phenyl-N-hexylcarbamoyl, etc.) and the like.

Examples of the "sulfamoyl which may be substituted" as the substituent include unsubstituted sulfamoyl, N-mono-C1-6 alkylsulfamoyl (e.g., N-methylsulfamoyl, N-ethylsulfamoyl, N-propylsulfamoyl, N-isopropylsulfamoyl, N-butylsulfamoyl, N-isobutylsulfamoyl, N-(tert-butyl)sulfamoyl, N-pentylsulfamoyl, N-hexylsulfamoyl, etc.), N-mono-C6-10 arylsulfamoyl such as N-phenylsulfamoyl, N,N-di-C1-6 alkylsulfamoyl (e.g., N,N-dimethylsulfamoyl, N,N-diethylsulfamoyl, N,N-dipropylsulfamoyl, N,N-dibutylsulfamoyl, N,N-dipentylsulfamoyl, N,N-dihexylsulfamoyl, N-methyl-N-ethylsulfamoyl, etc.), N-di-C6-10 arylsulfamoyl such as N,N-diphenylsulfamoyl, N—C6-10 aryl-N—C1-6 alkylsulfamoyl (e.g., N-phenyl-N-methylsulfamoyl, N-phenyl-N-ethylsulfamoyl, N-phenyl-N-propylsulfamoyl, N-phenyl-N-butylsulfamoyl, N-phenyl-N-pentylsulfamoyl, N-phenyl-N-hexylsulfamoyl, etc.) and the like.

The "spacer having from 1 to 8 atoms in its principle chain" represented by G means a space formed by 1 to 8 continued atoms. In this case, the "number of atoms of the principal atoms" should be counted such that atoms of the principal chain becomes minimum. Examples of the "spacer having from 1 to 8 atoms in its principle chain" include C1-8 alkylene which may have a substituent(s) (e.g., methylene, ethylene, trimethylene, tetramethylene, pentamethylene, hexamethylene, heptamethylene, octamethylene, etc.), C2-8 alkenylene which may have a substituent(s) (e.g., ethenylene, propenylene, butenylene, butadienylene, pentenylene, pentadienylene, hexenylene, hexadienylene, heptenylene, heptadienylene, octenylene, octadienylene, etc.), C2-8 alkynylene which may have a substituent(s) (e.g., ethynylene, propynylene, butynylene, butadiynylene, pentynylene, pentadiynylene, hexynylene, hexadiynylene, heptynylene, heptadiynylene, octynylene, octadiynylene, etc.) and the like. In this case, the carbon atom of the C1-8 alkylene, C2-8 alkenylene and C2-8 alkynylene may be replaced with an oxygen atom, a sulfur atom which may be oxidized (e.g., S, SO, $SO_2$, etc.) or a nitrogen atom which may be substituted [examples of the substituent include (i) alkyl which may be substituted (the same meaning as described above), (ii) a carbocyclic group which may have a substituent(s) (the same meaning as described above), (iii) a heterocyclic group which may have a substituent(s) (the same meaning as described above), (iv) acyl (the same meaning as described above) and the like]. In this case, examples of the "substituent" as the "C1-8 alkylene which may have a substituent(s)", "C2-8 alkenylene which may have a substituent(s)" and "C2-8 alkynylene which may have a substituent(s)" include alkyl which may be substituted (the same meaning as described above), halogen atom (e.g., fluorine, chlorine, bromine or iodine), hydroxyl which may be substituted (the same meaning as described above), amino which may be substituted (the same meaning as described above), oxo, imino which may be substituted (e.g., C1-6 alkylimino, hydroxyimino, C1-6 alkoxyimino, cyanoimino, etc.) and the like, and 1 to 3 of these optional substituents may be substituted at replaceable positions.

The "hydrogen bond acceptable group" of the "a spacer having one atom in its principle chain, the principle chain containing a hydrogen bond acceptable group which may have a substituent(s)" represented by T may be any group which contains an atom having an unshared electron pair. This means that the atom has one space. In this case, the "number of atoms of the principal atoms" should be counted such that atoms of the principal chain becomes minimum.

Examples of the "spacer having one atom in its principle chain, the principle chain containing a hydrogen bond acceptable group which may have a substituent(s)" include carbonyl (e.g., —CO—, etc.), thiocarbonyl (e.g., —CS—, etc.), imino which may be substituted (the same meaning as described above), sulfonyl (e.g., —SO$_2$—, etc.), sulfinyl (e.g., —SO—, etc.), methylene substituted with hydroxyl (e.g., —CHOH—, etc.) and the like.

The "aliphatic hydrocarbon group which may be substituted" represented by B has the same meaning as the above-described "aliphatic hydrocarbon group which may be substituted". The "cyclic group which may have a substituent(s)" represented by B has the same meaning as the above-described "cyclic group which may have a substituent(s)".

The "spacer having from 1 to 8 atoms in its principle chain" in the "spacer having from 1 to 8 atoms in its principle chain which may form a ring together with a substituent of the cyclic group in R, the ring D or a substituent on the ring D" represented by K has the same meaning as the above-described "spacer having from 1 to 8 atoms in its principle chain". The ring which is formed together with a substituent of the cyclic group in R, the ring D or a substituent on the ring D in the "spacer having from 1 to 8 atoms in its principle chain which may form a ring together with a substituent of the cyclic group in R, the ring D or a substituent on the ring D" represented by K has the same meaning as the above-described "cyclic group".

The "spacer having from 1 to 8 atoms in its principle chain" in the "spacer having from 1 to 8 atoms in its principle chain which may form a ring together with the cyclic group in R, a substituent of the cyclic group in R or K" represented by Q has the same meaning as the above-described "spacer having from 1 to 8 atoms in its principle chain". The ring which is formed together with the cyclic group in R, a substituent of the cyclic group in R or K in the "spacer having from 1 to 8 atoms in its principle chain which may form a ring together with the cyclic group in R, a substituent of the cyclic group in R or K" represented by Q has the same meaning as the above-described "cyclic group".

The "cyclic group which may have a substituent(s)" represented by the ring D has the same meaning as the above-described "cyclic group which may have a substituent(s)".

The "spacer having from 1 to 3 atoms in its principle chain" represented by L means a space formed by 1 to 3 continued atoms. In this case, the "number of atoms of the principal atoms" should be counted such that atoms of the principal chain becomes minimum. Examples of the "spacer having from 1 to 3 atoms in its principle chain" represented by L include C1-3 alkylene which may have a substituent(s) (e.g., —CH$_2$—, —(CH$_2$)$_2$—, —(CH$_2$)$_3$—, etc.), —O—, —S—, —SO—, —SO$_2$—, —NR$^6$—, —CONR$^6$—, —NR$^6$CO—, —SO$_2$NR$^6$—, —NR$^6$SO$_2$—, —NR$^6$CONR7- [wherein R$^6$ and R$^7$ each independently represents a hydrogen atom, an aliphatic hydrocarbon group which may be substituted (the same meaning as described above) or a cyclic group which may have a substituent(s) (the same meaning as described above)] and the like. In this case, examples of the substituent of C1-3 alkylene include halogen atom (e.g., fluorine, chlorine, bromine or iodine), hydroxyl, amino, oxo and the like, and 1 to 3 of these optional substituents may be substituted at replaceable positions.

The "cyclic group which may have a substituent(s)" represented by the ring E has the same meaning as the above-described "cyclic group which may have a substituent(s)".

The "spacer having from 1 to 8 atoms in its principle chain" represented by M has the same meaning as the above-described "spacer having from 1 to 8 atoms in its principle chain".

Examples of the "acidic group" represented by Z include —COOR$^5$ (R$^5$ represents a hydrogen atom, an aliphatic hydrocarbon group which may be substituted, or a cyclic group which may have a substituent(s)), sulfo (—SO$_3$H), —SO$_2$NHR$^5$ (R$^5$ has the same meaning as described above), —NHSO$_2$R$^5$ (R$^5$ has the same meaning as described above), phosphono (—PO(OH)$_2$), phenol (—C$_6$H$_4$OH) or various types of Brønsted acid such as a nitrogen-containing ring residue having hydrogen from which can be removed as proton. The "Brønsted acid" means a substance which gives hydrogen ion to other substance. Examples of the "nitrogen-containing ring residue having hydrogen from which can be removed as proton" include:

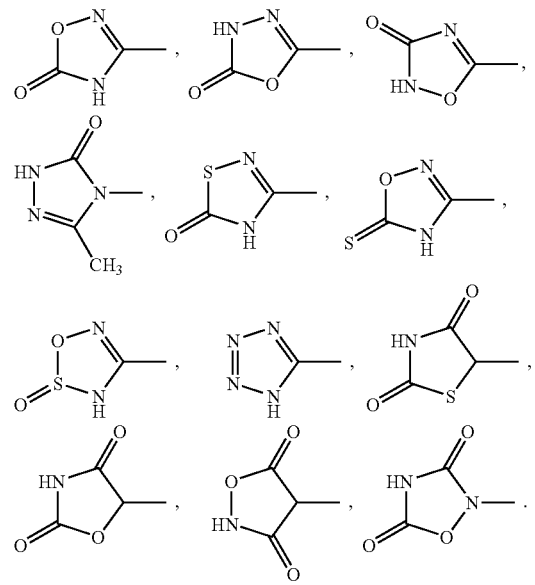

The "aliphatic hydrocarbon group which may be substituted" represented by R$^5$ has the same meaning as the above-described "aliphatic hydrocarbon group which may be substituted".

The "cyclic group which may have a substituent(s)" represented by R$^5$ has the same meaning as the above-described "cyclic group which may have a substituent(s)".

In formula (I), preferred as R is, for example, a cyclic group which may have a substituent(s) and the like; more preferred is, for example, a C3-15 monocyclic, bicyclic or tricyclic carbocyclic group which may have a substituent(s), or a three- to fifteen-membered monocyclic, bicyclic or tricyclic heterocyclic group which contains 1 to 5 hetero atoms selected from an oxygen atom(s), a nitrogen atom(s) and a sulfur atom(s); and particularly preferred is, for example, a cyclopentane ring which may have a substituent(s), a cyclopentane ring which may have a substituent(s), a benzene ring which may have a substituent(s), a naphthalene ring which may have a substituent(s), furan which may have a substituent(s), an isoxazole ring which may have a substituent(s), a 1,2,3-thiadiazole ring which may have a substituent(s), a pyrrole ring which may have a substituent(s), a pyrazole ring which may have a substituent(s), a benzothiophene ring which may have a substituent(s), an indole ring which may have a substituent(s), a 1,3-dioxaindan ring which may have a substituent(s), a pyridine ring which may have a substituent(s), a cinnoline ring which may have a substituent(s) or the like. In addition, preferred as the cyclic group which may have a substituent(s) is, for example, a C3-15 monocyclic, bicyclic or tricyclic carbocyclic group which may have a substituent(s), a three- to fifteen-membered monocyclic, bicyclic or tricyclic heterocyclic group which contains 1 to 5 hetero atoms selected from an oxygen atom(s), a nitrogen atom(s) and a sulfur atom(s) and which may have a substituent(s), or the like; most preferred is, for example, a C5-6 monocyclic aromatic carbocyclic group which may have a substituent(s), a 5 or 6-membered monocyclic aromatic heterocyclic group which contains 1 to 5 hetero atoms selected from an oxygen atom(s), a nitrogen atom(s) and a sulfur atom(s) and which may have a substituent(s), or the like; and particularly preferred is, for example, a benzene ring which may have a substituent(s), a pyridine ring which may have a substituent(s), or the like. Preferred as the substituents, in this case, is alkyl which may be substituted, a carbocyclic group which may have a substituent(s), a heterocyclic group which may have a substituent(s), hydroxyl which may be substituted, thiol which may be substituted, amino which may be substituted, sulfamoyl which may be substituted, carboxyl, nitro, halogen, alkylsulfonyl, acyl or the like; more preferred are, for example, alkyl which may be substituted, hydroxyl which may be substituted, halogen atom or the like; and most preferred are methyl, fluorine atom, chlorine atom, methoxy, ethoxy, difluoromethoxy, hydroxyl or the like. One to 5 of these optional substituents may be substituted at replaceable positions, and preferred is a substitution of 0 or from 1 to 3 groups.

Preferred as G is, for example, a bond, C1-8 alkylene which may have a substituent(s), C2-8 alkenylene which may have a substituent(s); more preferred is, for example, a bond, a spacer having from 1 to 4 atoms in its principle chain (e.g., C1-4 alkylene which may have a substituent(s), C2-4 alkenylene which may have a substituent(s), etc.) or the like; and particularly preferred is a bond, methylene which may have a substituent(s), ethylene which may have a substituent(s), ethenylene which may have a substituent(s), or the like, wherein the carbon atom may be replaced with an oxygen atom, a sulfur atom which may be oxidized (e.g., S, SO, $SO_2$, etc.) or a nitrogen atom which may be substituted, preferably, it may be replaced with a nitrogen atom which may be substituted or the like; and more preferred is —NH— or the like. Preferred as the substituents in G is, for example, alkyl which may be substituted, halogen atom, hydroxyl which may be substituted, oxo or the like; more preferred is, for example, methyl, ethyl, fluorine atom, methoxy or oxo. One to 3 of these optional substituents may be substituted at replaceable positions, and preferred is a substitution of 1 or 2 groups. Particularly preferred as G is, for example, a bond or the like.

Preferred as T is, for example, —CO—, —CS—, imino which may be substituted, —$SO_2$—, —SO—, —CHOH— or the like; and more preferred is, for example, —CHOH—, —CO— or the like.

Preferred as J is, for example, a nitrogen atom, a carbon atom or the like.

Preferred as K is, for example, a bond, C1-8 alkylene which may have a substituent(s), C2-8 alkenylene which may have a substituent(s), or the like; more preferred is, for example, a bond, a spacer having from 1 to 4 atoms in its principle chain (e.g., C1-4 alkylene which may have a substituent(s), C2-4 alkenylene which may have a substituent(s), etc.) or the like; and particularly preferred is, for example, a bond, methylene, ethylene, trimethylene, tetramethylene, ethenylene, propenylene or the like, wherein the carbon atom may be replaced with an oxygen atom, a sulfur atom which may be oxidized (e.g., S, SO, $SO_2$ or the like) or a nitrogen atom which may be substituted, preferably an oxygen atom, a sulfur atom which may be oxidized (e.g., S, SO, $SO_2$, etc.) or the like; and more preferably an oxygen atom, a sulfur atom or the like. Preferred as the substituents in K is, for example, alkyl which may be substituted, halogen atom, hydroxyl which may be substituted, oxo or the like; more preferred is, for example, methyl, fluorine atom, hydroxyl or oxo. One to 3 of these optional substituents may be substituted at replaceable positions; and preferred is a substitution of 1 or 2 groups. Particularly preferred as K is, for example, trimethylene, 1,1-difluorotrimethylene or the like.

Preferred as B is, for example, C1-6 alkyl which may be substituted, a C3-15 monocyclic, bicyclic or tricyclic carbocyclic group which may have a substituent(s), a three- to fifteen-membered monocyclic, bicyclic or tricyclic heterocyclic group which contains 1 to 5 hetero atoms selected from an oxygen atom(s), a nitrogen atom(s) and a sulfur atom(s) and which may have a substituent(s), or the like; and more preferred is, for example, propyl which may be substituted, cyclohexane ring which may have a substituent(s), a benzene ring which may have a substituent(s), an indan ring which may have a substituent(s), a tetrahydronaphthalene ring which may have a substituent(s), a naphthalene ring which may have a substituent(s), a pyrrolidine ring which may have a substituent(s), a piperidine ring which may have a substituent(s), a piperazine ring which may have a substituent(s), a morpholine ring which may have a substituent(s), a pyridine ring which may have a substituent(s), a thiazole ring which may have a substituent(s), an imidazole ring which may have a substituent(s), a pyrrole ring which may have a substituent(s), a pyrazole ring which may have a substituent(s), an indole ring which may have a substituent(s), a thiophene ring which may have a substituent(s) or the like. In addition, preferred as B is, for example, a C3-15 monocyclic, bicyclic or tricyclic aromatic carbocyclic group which may have a substituent(s), or a three- to fifteen-membered monocyclic, bicyclic or tricyclic aromatic heterocyclic group which contains 1 to 5 hetero atoms selected from an oxygen atom(s), a nitrogen atom(s) and a sulfur atom(s) and which may have a substituent(s); particularly preferred is, for example, a C5 or C6 monocyclic aromatic carbocyclic group which may have a substituent(s), a 5- or 6-membered monocyclic aromatic heterocyclic group which contains 1 to 5 hetero atoms selected from an oxygen atom(s), a nitrogen atom(s) and a sulfur atom(s) and which may have a substituent(s), or the like; and most preferred is, for example, a benzene ring which may have a substituent(s), a thiophene ring which may have a substituent(s), or the like. Preferred as the substituents, in this case, is alkyl which may be substituted, a carbocyclic group which may have a substituent(s), hydroxyl which may be substituted, nitro, halogen, oxo or the like; more preferred is, for example, alkyl which may be substituted, halogen atom or the like; and most preferred is methyl, fluorine atom, chlorine atom or the like. One to 5 of these optional substituents may be substituted at replaceable positions, and preferred is a substitution of 0 or 1 to 2 groups.

Preferred as Q is, for example, a bond, C1-8 alkylene which may have a substituent(s), C2-8 alkenylene which may have a substituent(s), or the like; more preferred is, for example, a bond, a spacer having from 1 to 4 atoms in its principle chain (e.g., C1-4 alkylene which may have a substituent(s), C2-4 alkenylene which may have a substituent(s), etc.) or the like; and particularly preferred is, for example, a bond, methylene, ethylene, trimethylene, tetramethylene or the like, wherein the carbon atom may be replaced with an oxygen atom, a sulfur atom which may be oxidized (e.g., S, SO, SO$_2$, etc.) or a nitrogen atom which may be substituted, preferably, for example, an oxygen atom, a sulfur atom which may be oxidized (e.g., S, SO, SO$_2$, etc.) or the like, and more preferably an oxygen atom, a sulfur atom or the like. Preferred as the substituents in Q is, for example, alkyl which may be substituted, more preferably, for example, methyl. One to 3 of these optional substituents may be substituted at replaceable positions, preferably one substitution. Particularly preferred as Q is, for example, methylene or the like.

Preferred as the ring D is, for example, a C3-15 monocyclic, bicyclic or tricyclic carbocyclic group which may have a substituent(s), a three- to fifteen-membered monocyclic, bicyclic or tricyclic heterocyclic group which contains 1 to 5 hetero atoms selected from an oxygen atom(s), a nitrogen atom(s) and a sulfur atom(s) and which may have a substituent(s), or the like; and more preferred is, for example, a benzene ring which may have a substituent(s), a cyclohexane ring which may have a substituent(s), a piperidine ring which may have a substituent(s), a pyrrole ring which may have a substituent(s), a pyrazole ring which may have a substituent(s), a pyridine ring which may have a substituent(s), a 1,3,4-oxadiazole ring which may have a substituent(s), a thiazole ring which may have a substituent(s), a dihydrobenzoxazine ring which may have a substituent(s), an indole ring which may have a substituent(s), or the like. Further preferred as the ring D is, for example, a C3-15 monocyclic, bicyclic or tricyclic aromatic carbocyclic group which may have a substituent(s), a three- to fifteen-membered monocyclic, bicyclic or tricyclic aromatic heterocyclic group which contains 1 to 5 hetero atoms selected from an oxygen atom(s), a nitrogen atom(s) and a sulfur atom(s) and which may have a substituent(s), or the like; and particularly preferred is, for example, a benzene ring which may have a substituent(s), a pyrrole ring which may have a substituent(s), an indole ring which may have a substituent(s), or the like. Preferred as the substituent, in this case, is alkyl which may be substituted, hydroxyl which may be substituted, carboxyl, halogen atom or the like; more preferred is, for example, alkyl which may be substituted, halogen atom or the like; and most preferred is methyl, fluorine atom, chlorine atom or the like. One to 5 of these optional substituents may be substituted at replaceable positions, and preferred is 0 or 1 substitution.

Preferred as L is, for example, a bond, —CH$_2$—, —O—, —S—, —SO—, —SO$_2$—, —NH— or the like; and more preferred is a bond, —O— or —S—.

Preferred as the ring E is, for example, a C3-15 monocyclic, bicyclic or tricyclic carbocyclic group which may have a substituent(s), a three- to fifteen-membered monocyclic, bicyclic or tricyclic heterocyclic group which contains 1 to 5 hetero atoms selected from an oxygen atom(s), a nitrogen atom(s) and a sulfur atom(s) and which may have a substituent(s), or the like; and more preferred is, for example, a benzene ring which may have a substituent(s), a piperidine ring which may have a substituent(s), a isoxazole ring which may have a substituent(s), a pyrazole ring which may have a substituent(s), a pyridine ring which may have a substituent(s), a thiazole ring which may have a substituent(s), an imidazole ring which may have a substituent(s), thiophene which may have a substituent(s), a pyrrole ring which may have a substituent(s), a pyrrolidine ring which may have a substituent(s), or the like. Further preferred as the ring E is, for example, a C3-15 monocyclic, bicyclic or tricyclic aromatic carbocyclic group which may have a substituent(s), a three- to fifteen-membered monocyclic, bicyclic or tricyclic aromatic heterocyclic group which contains 1 to 5 hetero atoms selected from an oxygen atom(s), a nitrogen atom(s) and a sulfur atom(s) and which may have a substituent(s), or the like; particularly preferred is, for example, a C5 or C6 monocyclic aromatic carbocyclic group which may have a substituent(s), a 5- or 6-membered monocyclic aromatic heterocyclic group which contains 1 to 5 hetero atoms selected from an oxygen atom(s), a nitrogen atom(s) and a sulfur atom(s) and which may have a substituent(s), or the like; and most preferred is, for example, a benzene ring which may have a substituent(s), or the like. Preferred as the substituents, in this case, is alkyl which may be substituted, a carbocyclic group which may have a substituent(s), hydroxyl which may be substituted, halogen atom or the like; and more preferred is, for example, methyl, chlorine atom, fluorine atom, methoxy, ethoxy or the like. One to 5 of these optional substituents may be substituted at replaceable positions, and preferred is a substitution of 0 or 1 group.

Preferred as t is 0 or 1.

Preferred as M is, for example, a bond, C1-8 alkylene which may have a substituent(s), C2-8 alkenylene which may have a substituent(s), or the like; more preferred is, for example, a bond, a spacer having from 1 to 4 atoms in its principle chain (e.g., C1-4 alkylene which may have a substituent(s), C2-4 alkenylene which may have a substituent(s), etc.) or the like; and particularly preferred is, for example, a bond, methylene, ethylene, trimethylene or the like, wherein preferred as the substituents in M are, for example, alkyl which may be substituted, more preferably, for example, methyl. From 1 to 3 of these optional substituents may be substituted at replaceable positions, preferably 1 or 2 substitution. Particularly preferred as M is, for example, a bond, methylene or the like.

Preferred as Z is, for example, —COOR$^5$ or tetrazole or the like.

Preferred as R$^5$ is, for example, a hydrogen atom, C1-8 alkyl or the like; more preferred is, for example, a hydrogen atom, C1-4 alkyl or the like; and particularly preferred is, for example, a hydrogen atom, methyl, ethyl or the like.

The ring which is formed together with a substituent of the cyclic group in R represented by K is a cyclic group, preferably a compound represented, for example, by formula (I-J):

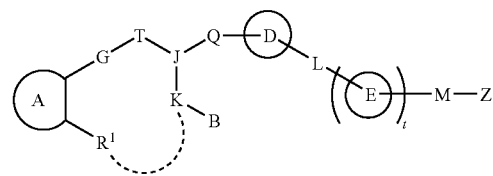

(I-J)

(wherein ring A represents a cyclic group which may have a substituent(s) in R; R$^1$ represents a substituent of the cyclic group in R; and other symbols have the same meanings as described above) or the like, more preferably a compound represented, for example, by formula (I-J-1):

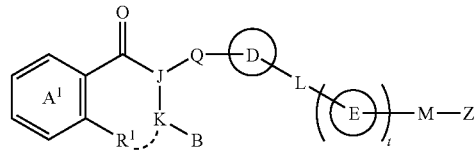

(I-J-1)

(wherein ring A¹ has the same meaning as the ring A, with the proviso that it represents a benzene ring which may have a substituent(s); and other symbols have the same meanings as described above) or the like, particularly preferably a compound represented, for example, by formula (I-J-1-1):

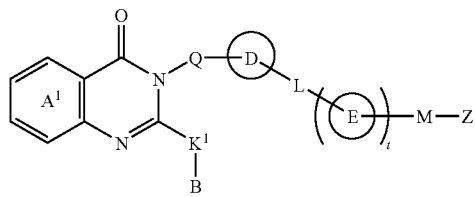

(I-J-1-1)

(K¹ has the same meaning as K, with the proviso that it represents a spacer having from 1 to 7 atoms in its principle chain; and other symbols have the same meanings as described above) or the like.

The ring which is formed together with a ring D represented by K or a substituent on the ring D is a cyclic group, preferably a compound selected, for example, from formula (I-K) or (I-N):

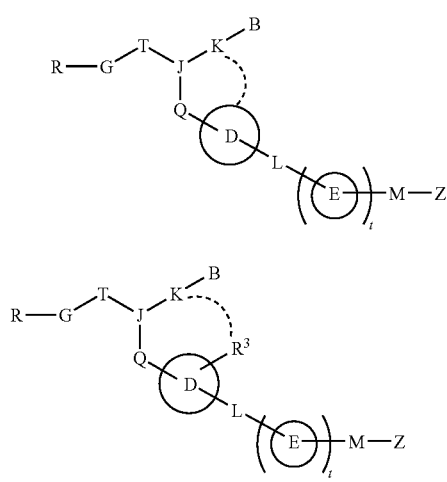

(I-K)

(I-N)

(wherein all symbols have the same meanings as described above) or the like, more preferably a compound selected, for example, from formula (I-K-1) or formula (I-N-1):

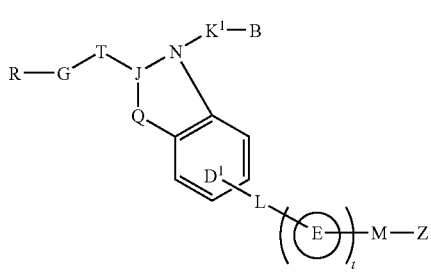

(I-K-1)

-continued

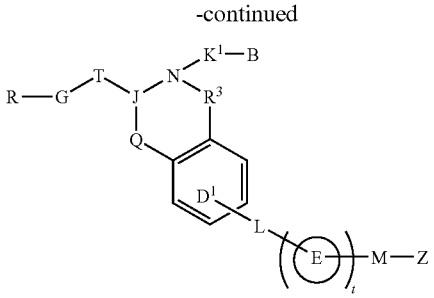

(I-N-1)

(wherein ring D¹ has the same meaning as the ring D, with the proviso that it represents benzene ring which may have a substituent(s); R³ represents a substituent on the ring D; and other symbols have the same meanings as described above) or the like, particularly preferably a compound selected, for example, from the following formula (I-K-1-1), formula (I-K-1-2) or formula (I-N-1-1):

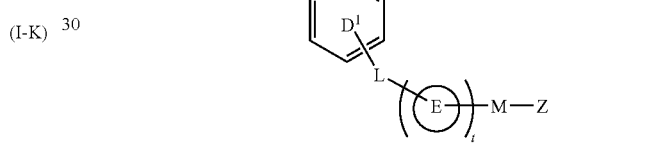

(I-K-1-1)

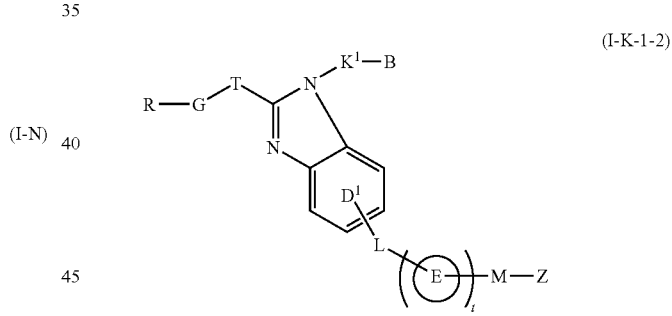

(I-K-1-2)

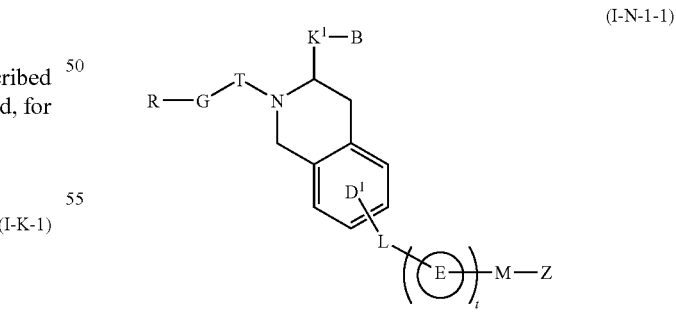

(I-N-1-1)

(wherein all symbols have the same meanings as described above) or the like.

The ring which is formed together with a cyclic group of R represented by Q or a substituent of the cyclic group in R is a cyclic group, preferably a compound selected, for example, from formula (I-L) or formula (I-O):

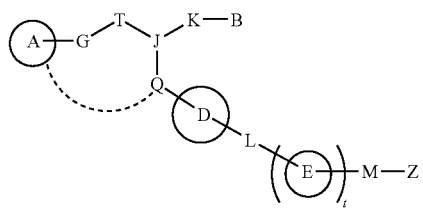
(I-L)

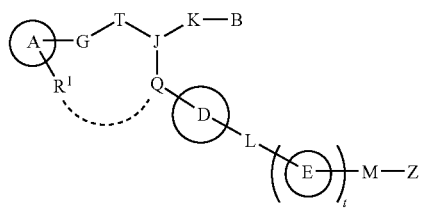
(I-O)

(wherein all symbols have the same meanings as described above) or the like, more preferably a compound selected, for example, from formula (I-L-1) or formula (I-O-1):

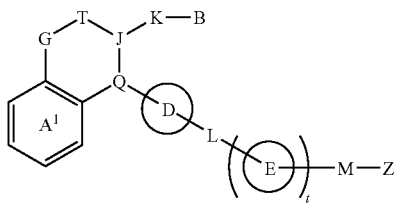
(I-L-1)

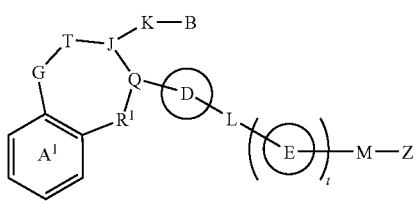
(I-O-1)

(wherein all symbols have the same meanings as described above) or the like, particularly preferably a compound selected, for example, from the following formula (I-L-1-1), formula (I-O-1-1), formula (I-O-1-2), formula (I-O-1-3), formula (I-O-1-4) or formula (I-O-1-5):

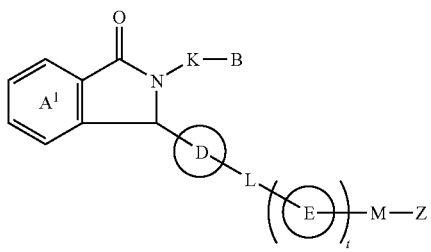
(I-L-1-1)

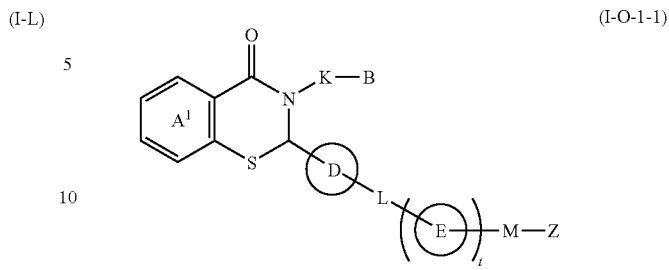
(I-O-1-1)

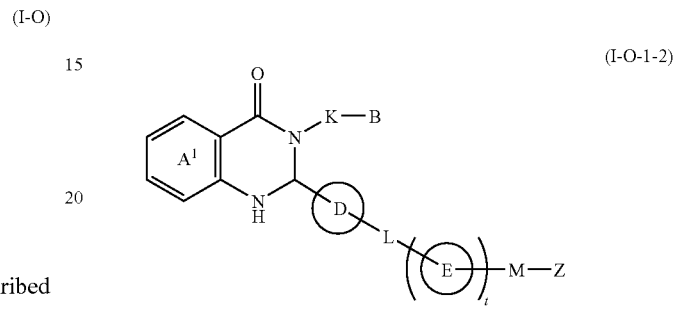
(I-O-1-2)

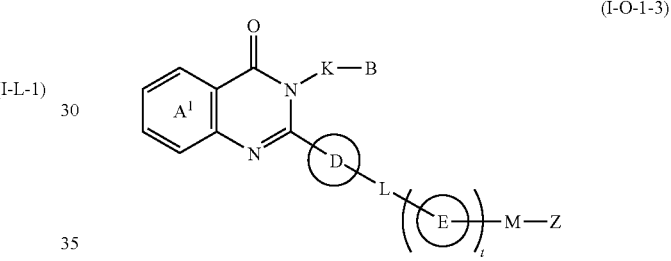
(I-O-1-3)

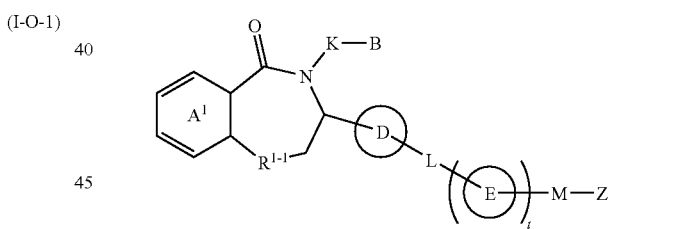
(I-O-1-4)

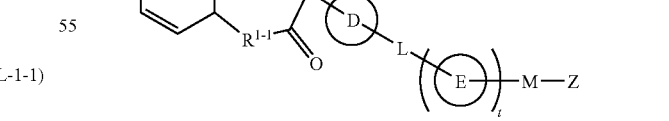
(I-O-1-5)

(wherein $R^{1-1}$ represents —$CH_2$—, —O—, —S— or —NH—; and other symbols have the same meanings as described above) or the like.

The ring which is formed together with K represented by Q is a cyclic group, preferably a compound represented, for example, by formula (I-M):

(I-M)

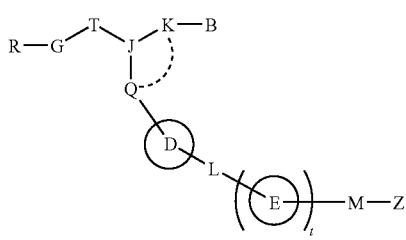

(wherein all symbols have the same meanings as described above) or the like, more preferably a compound represented, for example, by formula (I-M-1):

(I-M-1)

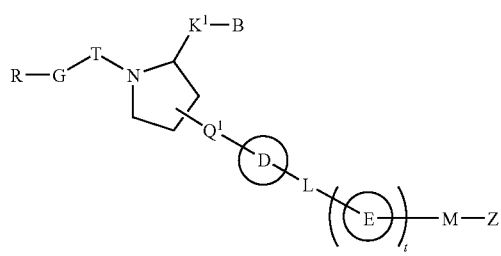

(wherein $Q^1$ has the same meaning as Q, with the proviso that it represents a spacer having from 1 to 7 atoms in its principle chain; and other symbols have the same meanings as described above) or the like, particularly preferably a compound selected, for example, from formula (I-M-1-1), formula (I-M-1-2) or formula (I-M-1-3):

(I-M-1-1)

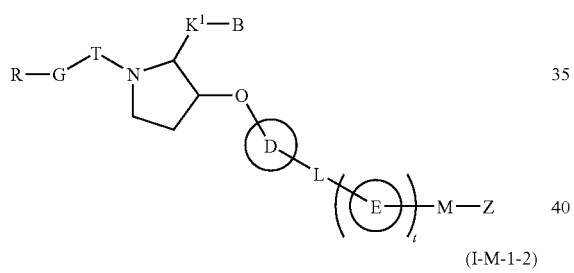

(I-M-1-2)

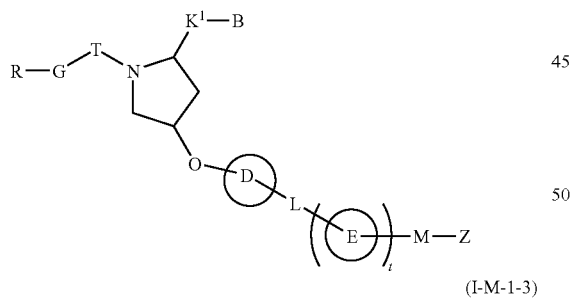

(I-M-1-3)

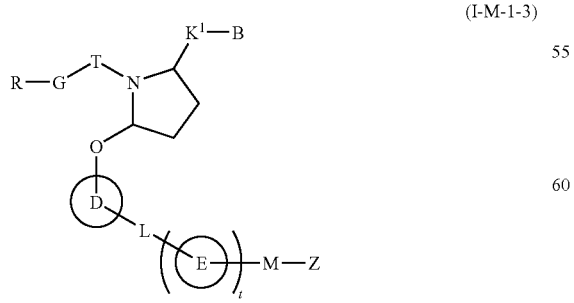

(wherein all symbols have the same meanings as described above) or the like.

Among formula (I), preferably, formula (I-A), (I-B), (I-C), (I-D) or (I-E) shown below is also preferable.

That is, a compound selected from the following or a salt thereof is preferable:

(I-A)

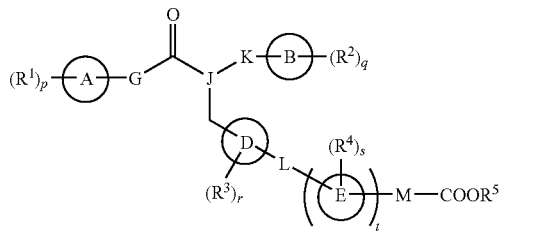

(I-B)

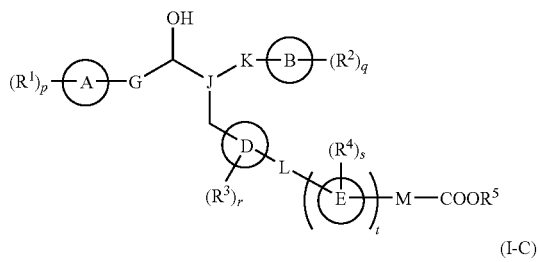

(I-C)

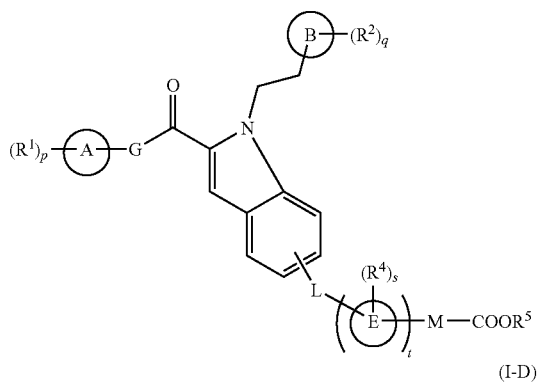

(I-D)

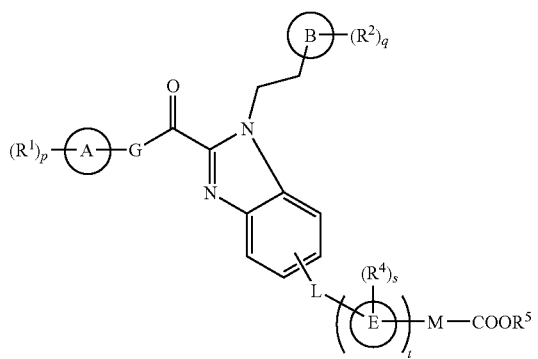

(I-E)

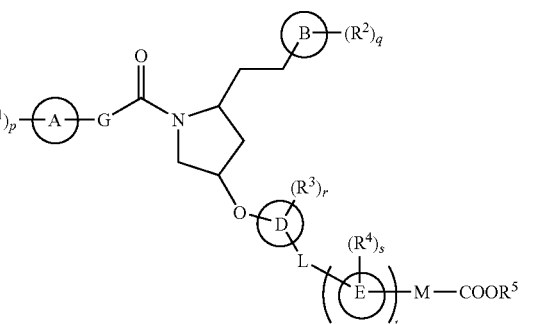

[wherein $R^1$, $R^2$, $R^3$ and $R^4$ each independently represents (1) C1-8 alkyl, (2) C2-8 alkenyl, (3) C2-8 alkynyl, (4) a halogen atom, (5) trihalomethyl, (6) nitro, (7) cyano, (8) Cycl, (9) —$OR^6$, (10) —$SR^7$, (11) —$NR^8R^9$, (12) —$CONR^{10}R^{11}$, (13) —$NR^{12}COR^{13}$, (14) —$SO_2NR^{14}R^{15}$, (15) —$NR^{16}SO_2R^{17}$, (16) —$SO_2R^{18}$, (17) —$COR^{19}$, (18) —$COOR^{20}$, or (19) C1-8 alkyl substituted with —$OR^6$, —$SR^7$, —$NR^8R^9$ or Cycl;

$R^6$ represents (1) a hydrogen atom, (2) C1-8 alkyl, (3) C2-8 alkenyl, (4) C2-8 alkynyl, (5) Cycl, (6) methyl substituted with 1 to 3 halogen atom(s), or (7) C1-8 alkyl substituted with Cycl;

$R^7$ to $R^{16}$ and $R^{20}$ each independently represents (1) a hydrogen atom, (2) C1-8 alkyl, (3) C2-8 alkenyl, (4) C2-8 alkynyl, or (5) Cycl;

$R^{17}$, $R^{18}$ and $R^{19}$ each independently represents (1) C1-8 alkyl, (2) C2-8 alkenyl, (3) C2-8 alkynyl, or (4) Cycl;

Cycl represents a C3-10 monocyclic or bicyclic carbocyclic group or a three- to ten-membered monocyclic or bicyclic heterocyclic group which contains 1 to 5 hetero atoms selected from an oxygen atom(s), a nitrogen atom(s) and a sulfur atom(s);

G, K and M each independently represents (1) a bond, (2) C1-8 alkylene, (3) C2-8 alkenylene, or (4) C2-8 alkynylene;

J represents a nitrogen atom or a carbon atom;

L represents a bond, an oxygen atom or a sulfur atom;

Ring A, ring B and ring D each independently represents a C3-10 monocyclic or bicyclic carbocyclic group or a three- to ten-membered monocyclic or bicyclic heterocyclic group which contains 1 to 5 hetero atoms selected from an oxygen atom(s), a nitrogen atom(s) and a sulfur atom(s);

Ring E represents a C3-7 monocyclic carbocyclic group or a three- to seven-membered monocyclic heterocyclic group which contains 1 to 5 hetero atoms selected from an oxygen atom(s), a nitrogen atom(s) and a sulfur atom(s);

p, q, r and s each independently represents 0 or an integer of from 1 to 5, and wherein $R^1$s are the same or different when p represents 2 or more, $R^2$s are the same or different when q represents 2 or more, $R^3$s are the same or different when r represents 2 or more, and $R^4$s are the same or different when s represents 2 or more, respectively;

t represents 0 or 1; and $R^5$ represents (1) a hydrogen atom, (2) C1-8 alkyl, (3) C2-8 alkenyl, or (4) C2-8 alkynyl].

In formula (I-A), (I-B), (I-C), (I-D) or (I-E), the C1-8 alkyl means methyl, ethyl, propyl, butyl, pentyl, hexyl, heptyl, octyl and isomers thereof In formula (I-A), (I-B), (I-C), (I-D) or (I-E), the C2-8 alkenyl means C2-8 alkylene which may have 1 to 4 (preferably 1 or 2) double bonds. Examples include vinyl, propenyl, butenyl, pentenyl, hexenyl, heptenyl, octenyl, butadienyl, pentadienyl, hexadienyl, heptadienyl, octadienyl, hexatrienyl, heptatrienyl, octatrienyl and isomer groups thereof and the like.

In formula (I-A), (I-B), (I-C), (I-D) or (I-E), the C2-8 alkynyl means C2-8 alkylene which may have 1 to 4 (preferably 1 or 2) triple bonds. Examples include ethynyl, propynyl, butynyl, pentynyl, hexynyl, heptynyl, octynyl, butadiynyl, pentadiynyl, hexadiynyl, heptadiynyl, octadiynyl, hexatriynyl, heptatriynyl, octatriynyl and isomer groups thereof and the like.

In formula (I-A), (I-B), (I-C), (I-D) or (I-E), the halogen atom means fluorine, chlorine, bromine and iodine atom.

In formula (I-A), (I-B), (I-C), (I-D) or (I-E), the trihalomethyl means methyl substituted with 3 halogen atoms, and examples include trifluoromethyl, trichloromethyl, tribromomethyl and triiodomethyl.

In formula (I-A), (I-B), (I-C), (I-D) or (I-E), examples of the methyl substituted with 1 to 3 halogen atoms include fluoromethyl, chloromethyl, bromomethyl, iodomethyl, difluoromethyl, dichloromethyl, dibromomethyl, diiodomethyl, trifluoromethyl, trichloromethyl, tribromomethyl and triiodomethyl.

In formula (I-A), (I-B), (I-C), (I-D) or (I-E), the C1-8 alkylene means methylene, ethylene, trimethylene, tetramethylene, pentamethylene, hexamethylene, heptamethylene, octamethylene and isomers thereof.

In formula (I-A), (I-B), (I-C), (I-D) or (I-E), the C2-8 alkenylene means C2-8 alkenylene which may have 1 to 4 (preferably 1 or 2) double bonds, and examples include ethenylene, propenylene, butenylene, butadienylene, pentenylene, pentadienylene, hexenylene, hexadienylene, heptenylene, heptadienyl, octenylene, octadienylene, hexatrienylene, heptatrienylene, octatrienylene and isomers thereof In formula (I-A), (I-B), (I-C), (I-D) or (I-E), the C2-8 alkynylene means C2-8 alkynylene which may have 1 to 4 (preferably 1 or 2) triple bonds, and examples include ethynylene, propynylene, butynylene, butadiynylene, pentynylene, pentadiynylene, hexynylene hexadiynylene, heptynylene, heptadiynylene, octynylene, octadiynylene, hexatriynylene, heptatriynylene, octatriynylene and isomers thereof The monocyclic or bicyclic unsaturated carbocyclic groups of C3-10 and carbocyclic groups of the same in which they are partially or fully saturated are included in the C3-10 monocyclic or bicyclic carbocyclic groups to be used in formula (I-A), (I-B), (I-C), (I-D) or (I-E). Examples include cyclopropane, cyclobutane, cyclopentane, cyclohexane, cycloheptane, cyclooctane, cyclononane, cyclodecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indan, naphthalene, dihydronaphthalene, tetrahydronaphthalene, perhydronaphthalene and the like.

Three- to ten-membered monocyclic or bicyclic unsaturated heterocyclic groups containing from 1 to 5 hetero atoms selected from an oxygen atom(s), a nitrogen atom(s) and a sulfur atom(s) and heterocyclic groups of the same in which they are partially or fully saturated are included in the three- to ten-membered monocyclic or bicyclic heterocyclic groups containing from 1 to 5 hetero atoms selected from an oxygen atom(s), a nitrogen atom(s) and a sulfur atom(s) to be used in formula (I-A), (I-B), (I-C), (I-D) or (I-E). Examples of the three- to ten-membered monocyclic or bicyclic unsaturated heterocyclic group containing from 1 to 5 hetero atoms selected from an oxygen atom(s), a nitrogen atom(s) and a sulfur atom(s) include pyrrole, imidazole, triazole, tetrazole, pyrazole, pyridine, pyrazine, pyrimidine, pyridazine, azepin, diazepin, furan, pyran, oxepin, thiophene, thiopyran, thiepin, oxazole, isoxazole, thiazole, isothiazole, furazane, oxadiazole, oxazine, oxadiazine, oxazepin, oxadiazepin, thiadiazole, thiazine, thiadiazine, thiazepin, thiadiazepin, indole, iso indole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzoimidazole, chromene, benzofuran, benzothiadiazole and benzotriazole rings and the like. Examples of the three- to ten-membered monocyclic or bicyclic heterocyclic group which may be partially or fully saturated and which contains from 1 to 5 hetero atoms selected from an oxygen atom(s), a nitrogen atom(s) and a sulfur atom(s) include aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepin, tetrahydroazepin, perhydroazepin, dihydrodiazepin, tetrahydrodiazepin, perhydrodiazepin, oxirane, oxetane, dihydrofuran, tetrahydrofuran, dihydropyran, tetrahydropyran, dihydrooxepin, tetrahydrooxepin, perhydrooxepin, thiirane, thiethane, dihydrothiophene, tetrahydrothiophene, dihydrothiopyran, tetrahydrothiopyran, dihydrothiepin, tetrahydrothiepin, perhydrothiepin, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazane, tetrahydrofurazane, dihydrooxadiazole, tetrahydrooxadiazole (oxadiazolidine), dihydrooxazine, tetrahydrooxazine, dihydrooxadiazine, tetrahydrooxadiazine, dihydrooxazepin, tetrahydrooxazepin, perhydrooxazepin, dihydrooxadiazepin, tetrahydrooxadiazepin, perhydrooxadiazepin, dihydrothiadiazole, tetrahydrothiadiazole (thiadiazolidine), dihydrothiazine, tetrahydrothiazine, dihydrothidiazine, tetrahydrothiadiazine, dihydrothiazepin, tetrahydrothiazepin, perhydrothiazepin, dihydrothiadiazepin, tetrahydrothiadiazepin, perhydrothiadiazepin, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine , tetrahydrophthalazine, perhydrophthalazine, dihydronaphthilidine, tetrahydronaphthilidine, perhydronaphthilidine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathian, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzoimidazole, perhydrobenzoimidazole, dioxolan, dioxane, dithiolan, dithian, dioxaindan, benzodioxane, chroman, benzothiolan and benzodithian rings and the like.

C3-7 monocyclic unsaturated carbocyclic groups and the same carbocyclic groups which are partially or fully saturated are included in the C3-7 monocyclic carbocyclic groups to be used in formula (I-A), (I-B), (I-C), (I-D) or (I-E). Examples include cyclopropane, cyclobutane, cyclopentane, cyclohexane, cycloheptane, cyclopentene, cyclohexene, cycloheptene, cyclopentadiene, cyclohexadiene, cycloheptadiene, benzene and the like.

Three- to seven-membered monocyclic unsaturated heterocyclic groups containing from 1 to 5 hetero atoms selected from an oxygen atom(s), a nitrogen atom(s) and a sulfur atom(s) and heterocyclic groups of the same in which they are partially or fully saturated are included in the three- to seven-membered monocyclic heterocyclic groups containing from 1 to 5 hetero atoms selected from an oxygen atom(s), a nitrogen atom(s) and a sulfur atom(s) to be used in formula (I-A), (I-B), (I-C), (I-D) or (I-E).

Examples of the three- to seven-membered monocyclic unsaturated heterocyclic group containing from 1 to 5 hetero atoms selected from an oxygen atom(s), a nitrogen atom(s) and a sulfur atom(s) include pyrrole, imidazole, triazole, tetrazole, pyrazole, pyridine, pyrazine, pyrimidine, pyridazine, azepin, diazepin, furan, pyran, oxepin, thiophene, thiopyran, thiepin, oxazole, isoxazole, thiazole, isothiazole, furazane, oxadiazole, oxazine, oxadiazine, oxazepin, oxadiazepin, thiadiazole, thiazine, thiadiazine, thiazepin and thiadiazepin rings and the like. Examples of the three- to seven-membered monocyclic group which may be partially or fully saturated and which contains from 1 to 5 hetero atoms selected from an oxygen atom(s), a nitrogen atom(s) and a sulfur atom(s) include aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepin, tetrahydroazepin, perhydroazepin, dihydrodiazepin, tetrahydrodiazepin, perhydrodiazepin, oxirane, oxetane, dihydrofuran, tetrahydrofuran, dihydropyran, tetrahydropyran, dihydrooxepin, tetrahydrooxepin, perhydrooxepin, thiirane, thiethane, dihydrothiophene, tetrahydrothiophene, dihydrothiopyran, tetrahydrothiopyran, dihydrothiepin, tetrahydrothiepin, perhydrothiepin, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazane, tetrahydrofurazane, dihydrooxadiazole, tetrahydrooxadiazole (oxadiazolidine), dihydrooxazine, tetrahydrooxazine, dihydrooxadiazine, tetrahydrooxadiazine, dihydrooxazepin, tetrahydrooxazepin, perhydrooxazepin, dihydrooxadiazepin, tetrahydrooxadiazepin, perhydrooxadiazepin, dihydrothiadiazole, tetrahydrothiadiazole (thiadiazolidine), dihydrothiazine, tetrahydrothiazine, dihydrothidiazine, tetrahydrothiadiazine, dihydrothiazepin, tetrahydrothiazepin, perhydrothiazepin, dihydrothiadiazepin, tetrahydrothiadiazepin, perhydrothiadiazepin, morpholine, thiomorpholine, oxathiane, dioxolan, dioxane, dithiolan and dithian rings and the like.

In formula (I-A), (I-B), (I-C), (I-D) or (I-E), preferred as $R^1$ are, for example, C1-8 alkyl, halogen atom, trihalomethyl, nitro, —$OR^6$, —$SR^7$, —$NR^8R^9$ and the like; more preferred are, for example, methyl, fluorine atom, chlorine atom, trifluoromethyl, nitro, methoxy, ethoxy, difluoromethoxy, hydroxyl, methylthio, dimethylamino and the like; and particularly preferred are, for example, methyl, fluorine atom, chlorine atom, methoxy, ethoxy, difluoromethoxy, hydroxyl and the like.

In formula (I-A), (I-B), (I-C), (I-D) or (I-E), preferred as ring A are, for example, a C3-7 monocyclic carbocyclic group or three- to seven-membered monocyclic heterocyclic group containing from 1 to 5 hetero atoms selected from an oxygen atom(s), a nitrogen atom(s) and a sulfur atom(s), and the like; more preferred are, for example, a C5 or C6 monocyclic carbocyclic group or 5- or 6-membered monocyclic heterocyclic group containing from 1 to 5 hetero atoms selected from an oxygen atom(s), a nitrogen atom(s) and a sulfur atom(s), and the like; and particularly preferred are, for example, cyclopentane, cyclohexane, benzene, pyrrole, imidazole, pyridine, piperidine, piperazine and morpholine rings and the like. As the ring A, a C5 or C6 monocyclic aromatic carbocyclic group or 5- or 6-membered monocyclic aromatic heterocyclic group containing from 1 to 5 hetero atoms selected from an oxygen atom(s), a nitrogen atom(s) and a sulfur atom(s) is also preferable. Most preferable is, for example, a benzene, pyrrole, imidazole or pyridine ring or the like.

In formula (I-A), (I-B), (I-C), (I-D) or (I-E), preferred as G is, for example, a bond, C1-8 alkylene or the like; more preferred is, for example, a bond, C1-4 alkylene or the like; particularly preferred is, for example, a bond, methylene, ethylene or the like.

In formula (I-A), preferred as J is, for example, a nitrogen atom or a carbon atom, and more preferred is, for example, a nitrogen atom or the like.

In formula (I-A) or (I-B), preferred as K is, for example, a bond, C1-8 alkylene, C2-8 alkenylene or the like; more preferred is, for example, C1-6 alkylene, C2-6 alkenylene or the like; particularly preferred is, for example, trimethylene, tetramethylene, pentamethylene, propenylene, butenylene, butadienylene, pentenylene or the like.

In formula (I-A), (I-B), (I-C), (I-D) or (I-E), preferred as ring B is, for example, a C3-7 monocyclic carbocyclic group or three- to seven-membered monocyclic heterocyclic group containing from 1 to 5 hetero atoms selected from an oxygen atom(s), a nitrogen atom(s) and a sulfur atom(s), or the like; more preferred is, for example, a C5 or C6 monocyclic carbocyclic group or 5- or 6-membered monocyclic heterocyclic group containing from 1 to 5 hetero atoms selected from an oxygen atom(s), a nitrogen atom(s) and a sulfur atom(s), or the like; and particularly preferred is, for example, a cyclopentane, cyclohexane, benzene, pyrrole, imidazole, pyridine, piperidine, piperazine or morpholine ring or the like. As the ring B, a C5 or C6 monocyclic aromatic carbocyclic group or a 5- or 6-membered monocyclic aromatic heterocyclic group containing from 1 to 5 hetero atoms selected from an oxygen atom(s), a nitrogen atom(s) and a sulfur atom(s) is also preferable. Most preferable is, for example, a benzene, pyrrole, imidazole, pyridine or thiophene ring or the like.

In formula (I-A), (I-B), (I-C), (I-D) or (I-E), preferred as $R^2$ is, for example, C1-8 alkyl, halogen atom, trihalomethyl, nitro, —$OR^6$, —$SR^7$, —$NR^8R^9$ or the like; more preferred is, for example, methyl, fluorine atom, chlorine atom, trifluoromethyl, nitro, methoxy, ethoxy, hydroxyl, methylthio, dimethylamino or the like; and particularly preferred is, for example, methyl, fluorine atom, chlorine atom, trifluoromethyl, methoxy, ethoxy, hydroxyl or the like.

In formula (I-A), (I-B) or (I-E), preferred as ring D is, for example, a C3-10 monocyclic or bicyclic carbocyclic group or a three- to ten-membered monocyclic or bicyclic heterocyclic group containing from 1 to 5 hetero atoms selected from an oxygen atom(s), a nitrogen atom(s) and a sulfur atom(s), or the like; more preferred is, for example, a C3-10 monocyclic or bicyclic aromatic carbocyclic group or a three- to ten-membered monocyclic or bicyclic aromatic heterocyclic group containing from 1 to 5 hetero atoms selected from an oxygen atom(s), a nitrogen atom(s) and a sulfur atom(s), or the like; and particularly preferred is, for example, a benzene, pyrrole, imidazole, pyridine or indole ring or the like.

In formula (I-A), (I-B) or (I-E), preferred as $R^3$ is, for example, C1-8 alkyl, halogen atom, trihalomethyl, nitro, —$OR^6$, —$SR^7$, —$NR^8R^9$ or the like; more preferred is, for example, methyl, fluorine atom, chlorine atom, trifluoromethyl, nitro, methoxy, ethoxy, hydroxyl, methylthio, dimethylamino or the like; and particularly preferred is, for example, methyl, fluorine atom, chlorine atom, trifluoromethyl methoxy or the like.

In formula (I-A), (I-B), (I-C), (I-D) or (I-E), preferred as L is, for example, a bond, an oxygen atom, a sulfur atom or the like; and more preferred is, for example, a bond, an oxygen or the like.

In formula (I-A), (I-B), (I-C), (I-D) or (I-E), preferred as ring E is, for example, a C3-7 monocyclic carbocyclic group or three- to seven-membered monocyclic heterocyclic group containing from 1 to 5 hetero atoms selected from an oxygen atom(s), a nitrogen atom(s) and a sulfur atom(s), or the like; more preferred is, for example, a C5 or C6 monocyclic aromatic carbocyclic group or a 5- or 6-membered monocyclic aromatic heterocyclic group containing from 1 to 5 hetero atoms selected from an oxygen atom(s), a nitrogen atom(s) and a sulfur atom(s), or the like; and particularly preferred is, for example, a benzene, pyrrole, imidazole or pyridine ring or the like.

In formula (I-A), (I-B), (I-C), (I-D) or (I-E), preferred as $R^4$ is, for example, C1-8 alkyl, halogen atom, trihalomethyl, nitro, —$OR^6$, —$SR^7$, —$NR^8R^9$ or the like; more preferred is, for example, methyl, fluorine atom, chlorine atom, trifluoromethyl, nitro, methoxy, ethoxy, hydroxyl, methylthio, dimethylamino or the like; and particularly preferred is, for example, methyl, fluorine atom, chlorine atom, trifluoromethyl methoxy, ethoxy, hydroxyl or the like.

In formula (I-A), (I-B), (I-C), (I-D) or (I-E), preferred as M is, for example, a bond, C1-8 alkylene or the like; more preferred is, for example, a bond, C1-4 alkylene or the like; and particularly preferred is, for example, a bond, methylene, ethylene, propylene or the like.

In formula (I-A), (I-B), (I-C), (I-D) or (I-E), preferred as $R^5$ is, for example, hydrogen atom, C1-8 alkyl or the like; more preferred is, for example, hydrogen atom, C1-4 alkyl or the like; and particularly preferred is, for example, hydrogen atom, methyl, ethyl or the like.

In formula (I-A), (I-B), (I-C), (I-D) or (I-E), preferred as p is, for example, 0 or an integer of from 1 to 5 or the like; and more preferred is, for example, 0 or an integer of from 1 to 3 or the like.

In formula (I-A), (I-B), (I-C), (I-D) or (I-E), preferred as q is, for example, 0 or an integer of from 1 to 3 or the like; and more preferred is, for example, 0 or an integer of 1 or the like.

In formula (I-A) or (I-B), preferred as r is, for example, 0 or an integer of from 1 to 3 or the like; and more preferred is, for example, 0 or an integer of 1 or the like.

In formula (I-A), (I-B), (I-C), (I-D) or (I-E), preferred as s is, for example, 0 or an integer of from 1 to 5 or the like; and more preferred is, for example, 0 or an integer of from 1 to 3 or the like.

In formula (I-A), (I-B), (I-C), (I-D) or (I-E), preferred as t is, for example, 0 or an integer of 1 or the like.

Among compounds of formula (I-A), a more preferred is, for example, a compound of formula (I-A-1)

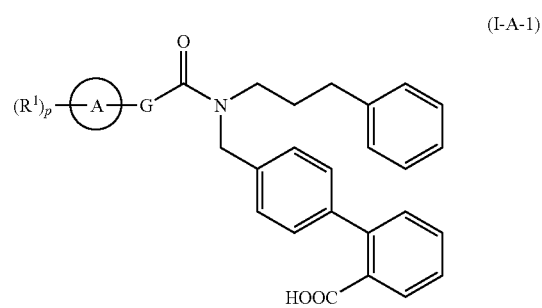

(I-A-1)

(wherein all symbols have the same meanings as described above), formula (I-A-2)

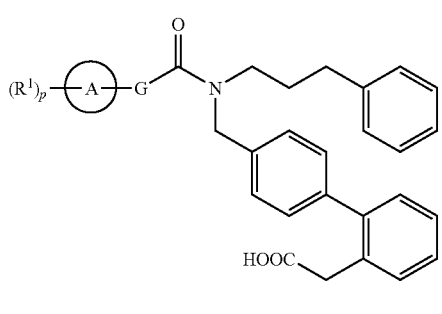

(I-A-2)

(wherein all symbols have the same meanings as described above), formula (I-A-3)

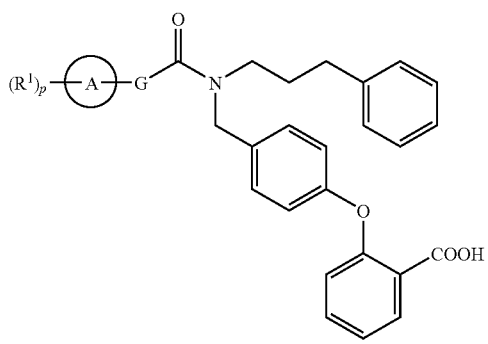

(I-A-3)

(wherein all symbols have the same meanings as described above), formula (I-A-4)

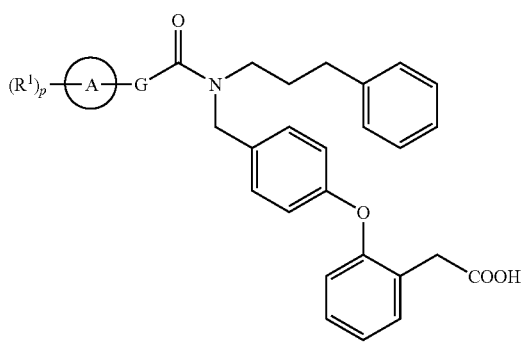

(I-A-4)

(wherein all symbols have the same meanings as described above), formula (I-A-5)

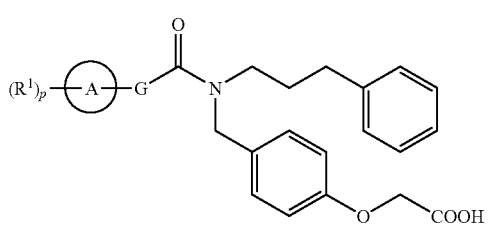

(I-A-5)

(wherein all symbols have the same meanings as described above), formula (I-A-6)

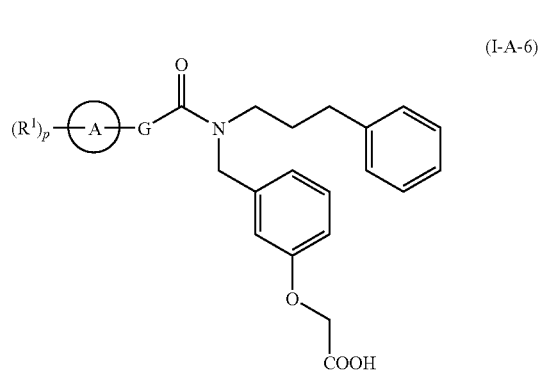

(I-A-6)

(wherein all symbols have the same meanings as described above), formula (I-A-7)

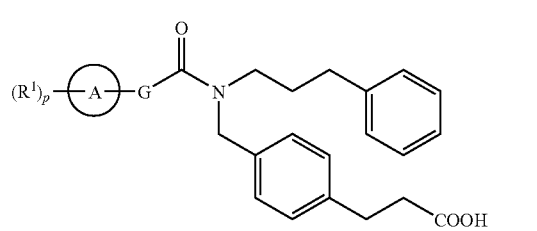

(I-A-7)

(wherein all symbols have the same meanings as described above), formula (I-A-8)

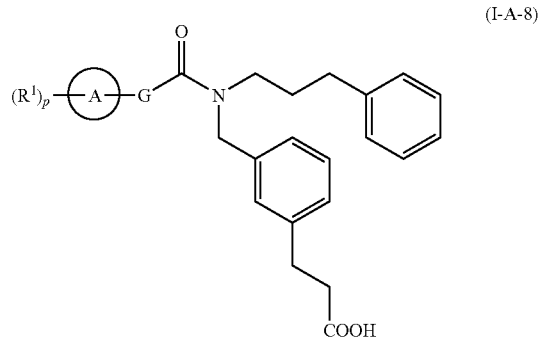

(I-A-8)

(wherein all symbols have the same meanings as described above), formula (I-A-9)

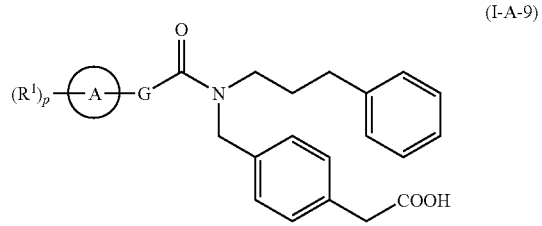

(I-A-9)

(wherein all symbols have the same meanings as described above), formula (I-A-10)

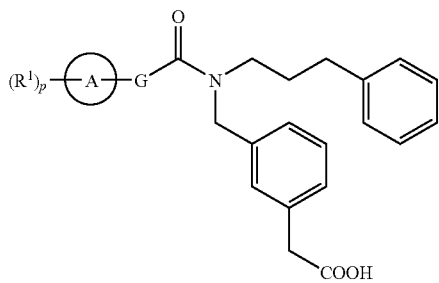

(wherein all symbols have the same meanings as described above), formula (I-A-11)

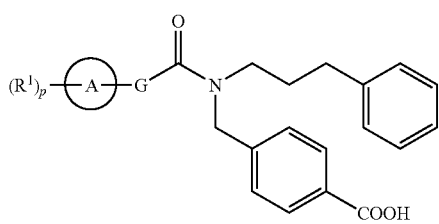

(wherein all symbols have the same meanings as described above), formula (I-A-12)

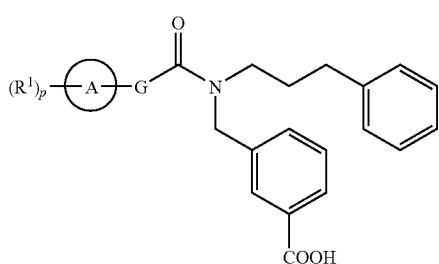

(wherein all symbols have the same meanings as described above), formula (I-A-13)

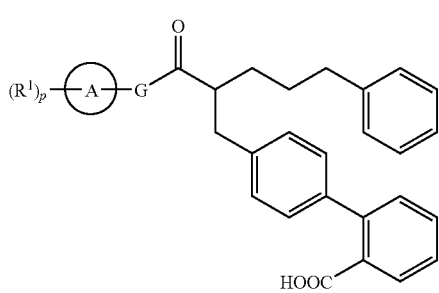

(wherein all symbols have the same meanings as described above), formula (I-A-14)

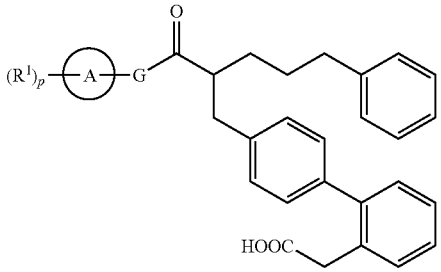

(wherein all symbols have the same meanings as described above), formula (I-A-15)

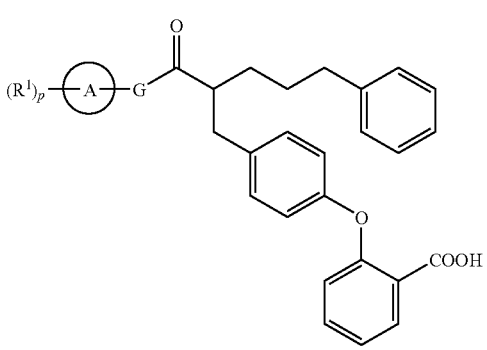

(wherein all symbols have the same meanings as described above), formula (I-A-16)

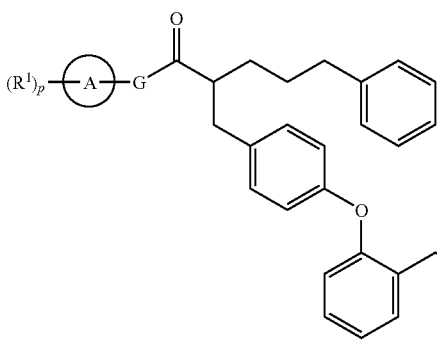

(wherein all symbols have the same meanings as described above), formula (I-A-17)

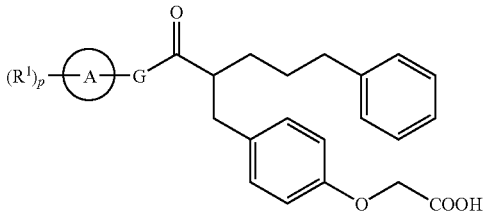

(wherein all symbols have the same meanings as described above), formula (I-A-18)

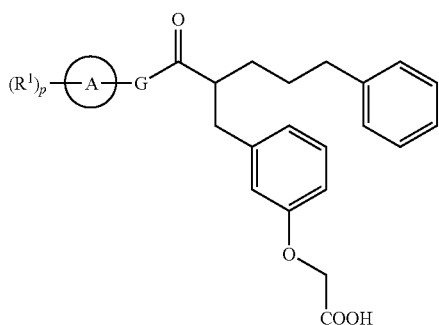

(wherein all symbols have the same meanings as described above), formula (I-A-19)

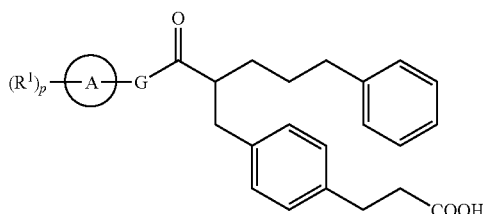

(wherein all symbols have the same meanings as described above), formula (I-A-20)

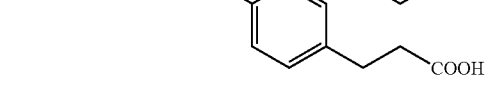

(wherein all symbols have the same meanings as described above), formula (I-A-21)

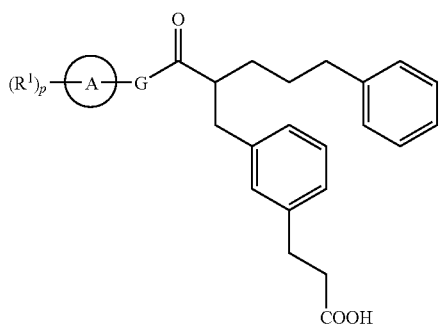

(wherein all symbols have the same meanings as described above), formula (I-A-22)

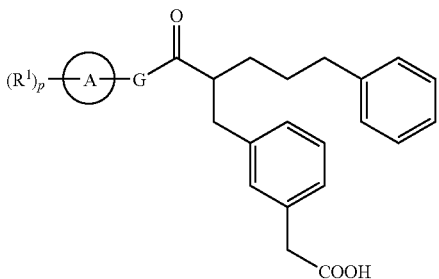

(wherein all symbols have the same meanings as described above), formula (I-A-23)

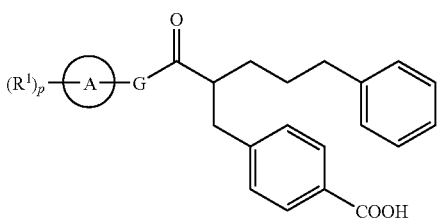

(wherein all symbols have the same meanings as described above), formula (I-A-24)

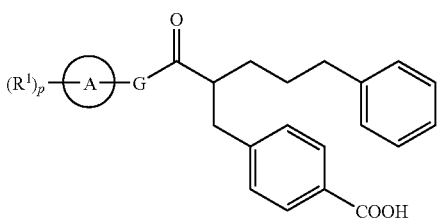

(wherein all symbols have the same meanings as described above), and a salt thereof, etc.

A specific example of a preferred compound of the present invention is, for example, a compound described in Example or a salt thereof, etc.

In the present invention, a compound, which includes any combinations of meanings enumerated above as a preferred group and a preferred ring of formula (I) is also preferable.

Unless otherwise specifically mentioned, all isomers are included in the present specification. For example, alkyl, alkenyl, alkynyl, alkoxy, alkylthio, alkylene, alkenylene and alkynylene include straight chain and branched ones. Moreover, all of isomers due to double bond, ring and fused ring (E-, Z-, cis- and trans-forms), isomers due to presence of asymmetric carbon(s), etc. R-, S-, α- and β-configuration, enantiomer and diastereomer), optically active substances having optical rotation (D-, L-, d- and l-forms), polar compound by chromatographic separation (high-polar compound and low-polar compound), equilibrium compounds, rotational isomers, a mixture thereof in any proportion and a racemic mixture are included in the present invention.

The salt of the compound of formula (I) includes all of the salt which are pharmaceutically acceptable. With regard to the pharmaceutically acceptable salts, those which are non-toxic and soluble in water are preferred. Examples of appropriate salts are salt with alkaline metal (such as potassium, sodium and lithium), salt with alkaline earth metal (such as calcium and magnesium), ammonium salt (such as tetramethylammonium salt and tetrabutylammonium salt), salt with organic amine (such as triethylamine, methylamine, dimethylamine, cyclopentylamine, benzylamine, phenethylamine, piperidine, monoethanolamine, diethanolamine, tris(hydroxymethyl) methylamine, lysine, arginine and N-methyl-D-glucamine) and acid addition salt [such as inorganic acid salt (e.g., hydrochloride, hydrobromide, hydroiodide, sulfate, phosphate and nitrate) and organic acid salt (e.g., acetate, trifluoroacetate, lactate, tartrate, oxalate, fumarate, maleate, benzoate, citrate, methanesulfonate, ethanesulfonate, benzenesulfonate, toluenesulfonate, isothionate, glucuronate and gluconate), etc.]. The salt of the compound of the present invention also includes solvates and also solvates with the above-mentioned alkaline (earth) metal salt, ammonium salt, organic amine salt and acid addition salt. The solvate is preferably non-toxic and water-soluble. Examples of an appropriate solvate are solvates with water and with alcoholic solvent (such as ethanol). The compounds of the present invention are converted to pharmaceutically acceptable salts by known methods.

Additionally, the salt includes a quaternary ammonium salt thereof A quaternary ammonium salt means a salt of a compound of formula (I) which nitrogen is quaternarized by $R^o$.

$R^o$ represents C1-8 alkyl, C1-8 alkyl substituted with phenyl.

The compounds of the present invention can be converted to N-oxide by arbitrary methods. N-oxide means a compound of formula (I) which nitrogen is oxidized.

A prodrug of the compound of formula (I) means a compound which is converted to the compound of formula (I) by reaction with an enzyme, gastric acid or the like in the living body. For example, with regard to a prodrug of the compound of formula (I), when the compound of formula (I) has an amino group, compounds in which the amino group is, for example, acylated, alkylated or phosphorylated (e.g., compounds in which the amino group of the compound of formula (I) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, acetoxymethylated, tert-butylated, etc.); when the compound of formula (I) has a hydroxyl group, compounds where the hydroxyl group is, for example, acylated, alkylated, phosphorylated or borated (e.g., compounds in which the hydroxyl group of the compound of formula (I) is acetylated, palmitoylated, propanoylated, pivaloylated, succinylated, fumarylated, alanylated or dimethylaminomethylcarbonylated); and that the carboxyl group of the compound of formula (I) is, for example, esterified or amidated (e.g., compounds in which the carboxyl group of the compound of formula (I) is made into ethyl ester, phenyl ester, phenylethyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester; cyclohexyloxycarbonylethyl ester or methylamide). Those compounds may be produced by a known method per se. The prodrug of the compound of formula (I) may be either a hydrate or a non-hydrate. A prodrug of the compound of formula (I) may also be a compound which is converted to the compound of formula (I) under physiologic condition as described in "*Iyakuhin no kaihatsu*, Vol. 7. (Bunshi-sekkei), pp. 163-198 (Hirokawa-Shoten), 1990". And the compound of formula (I) may also be labeled by a radio isotope (such as $^3H$, $^{14}C$, $^{35}S$, $^{125}I$, etc,).

Processes for the Preparation of the Compound of the Present Invention

The compound of the present invention of formula (I) can be prepared by a conventionally known method, such as a method described below, a method according to that, or a method described in Examples. In each method described below, a starting material can be used as a salt thereof An example of the salt includes a salt of compound of formula (I) described above.

Among the compounds of formula (I), a compound in which T represents carbonyl and J represents nitrogen, namely, a compound of formula (I-1):

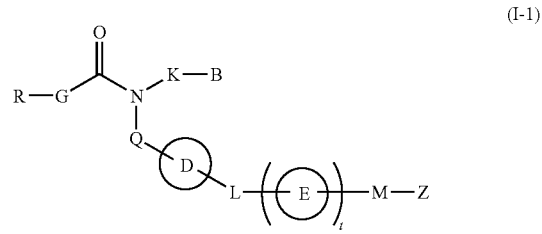

[wherein all symbols have the same meanings as described above]

can be prepared by a method described below.

A compound of formula (I-1) can be produced by amidation of a compound of formula (2)

[wherein all symbols have the same meanings as described above]

with a compound of formula (3)

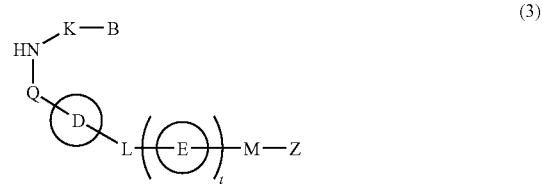

[wherein all symbols have the same meanings as described above].

Amidation reaction has been known and its examples are (1) a process using an acyl halide, (2) a process using a mixed acid anhydride and (3) a process using a condensing agent.

Such processes will be specifically illustrated as follows.

(1) A process using an acyl halide is carried out, for example, in such a manner that carboxylic acid reacts with an agent for producing an acyl halide (such as oxalyl chloride, thionyl chloride, phosphorous oxychloride, phosphorous trichloride or phosphorous pentachloride, etc.) in an organic solvent (such as chloroform, dichloromethane, diethyl ether and tetrahydrofuran alone, or a mixed solvent containing two or more solvents thereof at an optional ratio) or without solvent at −20° C. to refluxing temperature and the resulting acyl halide reacts with an amine in the presence or no-presence of a base (such as pyridine, triethylamine, N,N-dimethylaniline, N,N-dimethylaminopyridine and diisopropylethylamine) in an organic solvent (such as chloroform, dichloromethane, diethyl ether and tetrahydrofuran alone, or a mixed solvent containing two or more solvents thereof at an optional ratio) at the temperature of −20 to 40° C. It is also possible to conduct the reaction with an acyl halide at −20 to 40° C. in an organic solvent (such as 1,4-dioxane and tetrahydrofuran alone, or a mixed solvent containing two or more solvents thereof at an optional ratio) using an aqueous solution of alkali (such as aqueous solution of sodium hydrogen carbonate or an aqueous solution of sodium hydroxide).

(2) A process using a mixed acid anhydride is carried out, for example, in such a manner that carboxylic acid is made to react with an acyl halide (such as pivaloyl chloride, tosyl chloride or mesyl chloride) or with an acid derivative (such as ethyl chloroformate and isobutyl chloroformate) at −20 to 40° C. in an organic solvent (such as chloroform, dichloromethane, diethyl ether and tetrahydrofuran etc. alone, or a mixed solvent containing two or more solvents thereof at an optional ratio) or without a solvent in the presence of a base (such as pyridine, triethylamine, N,N-dimethylaniline, N,N-dimethylaminopyridine and diisopropylethylamine) and the resulting mixed acid anhydride is made to react with an amine at −20 to 40° C. in an organic solvent (such as chloroform, dichloromethane, diethyl ether and tetrahydrofuran etc. alone, or a mixed solvent containing two or more solvents thereof at an optional ratio).

(3) A process using a condensing agent is carried out, for example, in such a manner that carboxylic acid and an amine are subjected to a reaction at 0 to 40° C. with or without 1-hydroxybenztriazole (HOBt) using a condensing agent (such as 1,3-dicyclohexylcarbodiimide (DCC), 1-ethyl-3-[3-(dimethylamino)propyl]carbodiimide (EDC), 1,1'-carbonyldiimidazole (CDI), 2-chloro-1-methylpyridinium iodide and 1-propanephosphonic acid cyclic anhydride (PPA), PS-carbodiimide etc.) in the presence or absence of a base (such as pyridine, triethylamine, N,N-dimethylanilin and N,N-dimethylaminopyridine) in an organic solvent (such as chloroform, dichloromethane, N,N-dimethylformamide, diethyl ether and tetrahydrofuran etc. alone, or a mixed solvent containing two or more solvents thereof at an optional ratio) or without a solvent.

It is preferred that all of the reactions (1), (2) and (3) are carried out in an atmosphere of inert gas (such as argon and nitrogen) under an anhydrous condition.

Amidation can also be carried out by means described in "*Comprehensive Organic Transformations: A Guide to Functional Group Preparations,* 2nd Edition (Richard C. Larock, John, Wiley & Sons Inc, 1999)" other than above-mentioned method.

The compound of formula (I-1), at least one group of which represents a group having carboxyl, hydroxy, amino or thiol, can be prepared by a deprotection of a compound protected by protecting group(s).

The protective group for carboxyl includes such as methyl, ethyl, allyl, t-butyl, trichloroethyl, benzyl (Bn), or phenacyl.

The protective group for hydroxyl includes such as methyl, trityl, methoxymethyl (MOM), 1-ethoxyethyl (EE), methoxyethoxymethyl (MEM), 2-tetrahydropyranyl (THP), trimethylsilyl (TMS), triethylsilyl (TES), t-butyldimethylsilyl (TBDMS), t-butyldiphenylsilyl (TBDPS), acetyl (Ac), pivaloyl, benzoyl, benzyl (Bn), p-methoxybenzyl, allyloxycarbonyl (Alloc) and 2,2,2-trichloroethoxycarbonyl (Troc) and the like.

The protective group of amino includes such as benzyloxycarbonyl, tert-butoxycarbonyl, allyloxycarbonyl (Alloc), 1-methyl-1-(4-biphenyl)ethoxycarbonyl (Bpoc), trifluoroacetyl, 9-fluorenylmethoxycarbonyl, benzyl (Bn), p-methoxybenzyl, benzyloxymethyl (BOM) and 2-(trimethylsilyl)ethoxymethyl (SEM) and the like.

The protective group of thiol includes such as benzyl, methoxybenzyl, methoxymethyl (MOM), 2-tetrahydropyranyl (THP), diphenylmethyl and acetyl (Ac) and the like.

With regard to the protective group for carboxyl, hydroxyl, for amino and for thiol, there is no particular limitation to the above ones so far as it is a group which is able to be easily and selectively detached. For example, a deprotection reaction may be carried out by a method mentioned in "T. W Greene, *Protective Groups in Organic Synthesis*, John Wiley & Sons Inc, 1999".

Deprotection reaction of a protective group for carboxyl, hydroxyl, amino or thiol is known and its examples are as follows.

(1) a hydrolyzing reaction with an alkali;

(2) a deprotection reaction under an acidic condition;

(3) a deprotection reaction by hydrogenolysis;

(4) a deprotection reaction of silyl;

(5) a deprotection reaction using metal; and (6) a deprotection reaction using an organic metal.

Those methods will be specifically illustrated as follows.

(1) A deprotection reaction using an alkali is carried out, for example, at the temperature of 0 to 40° C. using a hydroxide of alkaline metal (such as sodium hydroxide, potassium hydroxide and lithium hydroxide), a hydroxide of alkaline earth metal (such as barium hydroxide and calcium hydroxide), a carbonate (such as sodium carbonate and potassium carbonate), an aqueous solution thereof or a mixture thereof in an organic solvent (such as methanol, tetrahydrofuran and 1,4-dioxane etc. alone, or a mixed solvent containing two or more solvents thereof at an optional ratio).

(2) A deprotection reaction under an acidic condition is carried out, for example, at the temperature of 0 to 100° C. in an organic acid (such as acetic acid, trifluoroacetic acid, methanesulfonic acid and p-toluenesulfonic acid), an inorganic acid (hydrochloric acid and sulfuric acid) or a mixture thereof (such as hydrogen bromide/acetic acid) in an organic solvent (such as dichloromethane, chloroform, 1,4-dioxane, ethyl acetate and anisole etc. alone, or a mixed solvent containing two or more solvents thereof at an optional ratio).

(3) A deprotection reaction by hydrogenolysis is carried out, for example, at the temperature of 0 to 200° C. in a hydrogen atmosphere of ordinary pressure or high pressure or in the presence of ammonium formate in the presence of a catalyst (such as palladium-carbon, palladium black, palladium hydroxide, platinum oxide and Raney nickel) in a solvent [such as an ether type (such as tetrahydrofuran, 1,4-dioxane, dimethoxyethane and diethyl ether), an alcohol type (such as methanol and ethanol), a benzene type (such as benzene and toluene), a ketone type (such as acetone and methyl ethyl ketone), a nitrile type (such as acetonitrile), an amide type (such as N,N-dimethylformamide), water, ethyl acetate, acetic acid or a mixed solvent comprising two or more thereof].

(4) A deprotection reaction of silyl is carried out, for example, at the temperature of 0 to 40° C. using tetrabutylammonium fluoride in an organic solvent miscible with water (such as tetrahydrofuran and acetonitrile etc. alone, or a mixed solvent containing two or more solvents thereof at an optional ratio).

(5) A deprotection reaction using metal is carried out, for example, at the temperature of 0 to 40° C. with or without ultrasonic wave in the presence of powdery zinc in an acidic solvent (such as acetic acid, a buffer of pH 4.2 to 7.2 and a mixed solution of a solution thereof with an organic solvent such as tetrahydrofuran).

(6) A deprotection reaction using a metal complex is carried out, for example, at the temperature of 0 to 40° C. using a metal complex [such as tetrakistriphenylphosphine palladium (0), bis(triphenylphosphine) palladium (II) dichloride, palladium (II) acetate and tris(triphenylphosphine) rhodium (I) chloride] in the presence or absence of a phosphine agent (such as triphenyl phosphine) in the presence of a trap reagent (such as tributyltin hydride, triethylsilane, dimedone, morpholine, diethylamine and pyrrolidine), an organic acid (such as acetic acid, formic acid and 2-ethylhexanoic acid) and/or an organic acid salt (such as sodium 2-ethylhexanoate and potassium 2-ethylhexanoate) in an organic solvent (such as dichloromethane, N,N-dimethylformamide, tetrahydrofuran, ethyl acetate, acetonitrile, 1,4-dioxane and ethanol), water or a mixed solvent thereof.

Besides the above-mentioned method, for example, a deprotection reaction may be carried out by a method mentioned in "T. W. Greene, *Protective Groups in Organic Synthesis*, John Wiley & Sons Inc, 1999".

As persons skilled in the art can easily understand that the aimed compound of the present invention is able to be easily produced by using appropriate ones among those deprotection reactions.

The reaction can be followed by conversion to a desired non-toxic salt therof by a known method, if necessary.

Among the compounds of formula (I-1), a compound in which Z represents —COOR$^5$ and R$^5$ represents hydrogen, namely, a compound of formula (I-1-2):

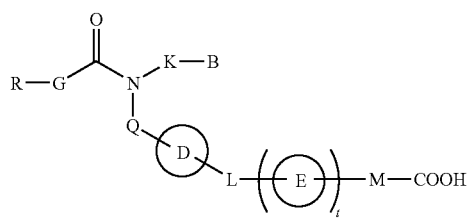

(I-1-2)

[wherein all symbols have the same meanings as described above]

can be produced by deprotection of the protecting group of a compound in which Z represents —COOR$^5$ and R$^5$ does not represents hydrogen, namely, a compound of formula (I-1-1)

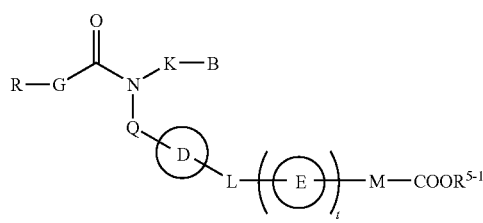

(I-1-1)

[wherein R$^{5-1}$ have the same meanings as R$^5$, provided R$^{5-1}$ does not represent hydrogen, and other symbols have the same meanings as described above]

and then to deprotection of the other protecting group, if necessary.

The protective group for carboxyl includes such as methyl, ethyl, allyl, t-butyl, trichloroethyl, benzyl (Bn), phenacyl, p-methoxybenzyl, trityl, 2-chlorotrityl or solid-phase carrier bound by these units, etc.

Deprotection reaction of carboxyl has been well known and its examples are as follows.

(1) Hydrolysis with an alkali,
(2) a deprotection reaction under an acidic condition,
(3) a deprotection reaction by hydrogenolysis,
(4) a deprotection reaction using metal and
(5) a deprotection reaction using organic metal.

These reaction are carried out by the above-described method.

The deprotection of protecting group can be carried out by the above-described method.

Among the compounds of formula (I), a compound in which T represents carbonyl, J represents nitrogen, a part of Q and K together form 5-membered ring, namely, a compound of formula (I-2):

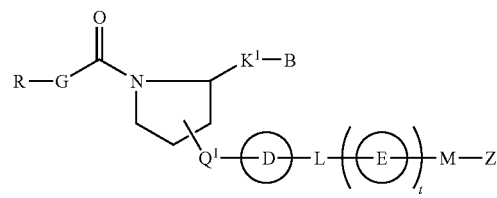

(I-2)

[wherein K$^1$ has the same meaning as K, with the proviso that it represents a spacer having from 1 to 7 atoms of the principal chain; and Q$^1$ has the same meaning as Q, with the proviso that it represents a spacer having from 1 to 7 atoms of the principal chain; and other symbols have the same meanings as described above]

can be produced by subjecting the above-described compound of formula (2) and a compound of formula (4)

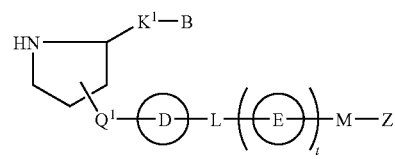

(4)

[wherein all symbols have the same meanings as described above]

to amidation and then to deprotection of the protecting group, if necessary.

The amidation and the deprotection of protecting group can be carried out by the above-described method.

Among the compounds of formula (I), a compound in which T represents carbonyl, J represents nitrogen, Q represents methylene, and a part of K and ring D together form tetrahydroisoquinoline ring, namely, a compound of formula (I-3):

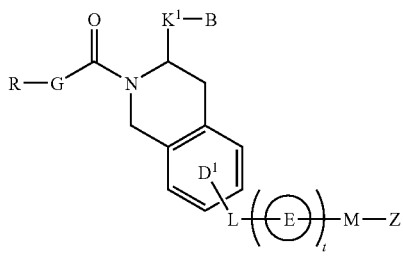
(I-3)

[wherein ring $D^1$ has the same meaning as ring D, with the proviso that it represents a benzene ring which may have a substituent(s); and other symbols have the same meanings as described above]

can be produced by reacting the above-described compound of formula (2) and a compound of formula (5)

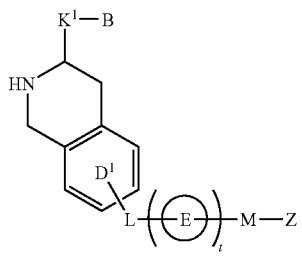
(5)

[wherein all symbols have the same meanings as described above]

to amidation and then to deprotection of the protecting group, if necessary.

The amidation and deprotection of protecting group can be carried out by the above-described method.

Among the compounds of formula (I), a compound in which T represents sulfonyl and J represents nitrogen, namely, a compound of formula (I-4):

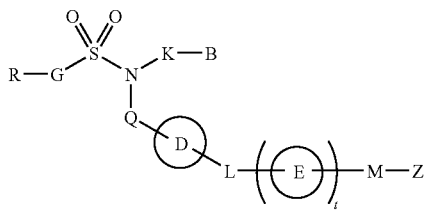
(I-4)

[wherein all symbols have the same meanings as described above]

can be produced by subjecting a compound of formula (6)

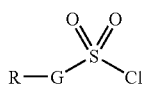
(6)

[wherein all symbols have the same meanings as described above]

and the above-described compound of formula (3) to sulfonamidation and then to deprotection of the protecting group, if necessary.

The sulfonamidation is conventionally known and carried out, for example, by reacting sulfonyl chloride with an amine at a temperature of from 0 to 40° C. in an organic solvent (chloroform, dichloromethane, diethyl ether, tetrahydrofuran, etc. alone, or a mixed solvent containing two or more solvents thereof at an optional ratio), in the presence or absence of a base (pyridine, triethylamine, N,N-dimethylaniline, N,N-dimethylaminopyridine, diisopropylethylamine, etc.). This reaction can also be carried out by reacting sulfonyl chloride with an amine at a temperature of from 0 to 40° C. in an organic solvent (1,4-dioxane, tetrahydrofuran, etc. alone, or a mixed solvent containing two or more solvents thereof at an optional ratio), using an alkali aqueous solution (sodium bicarbonate aqueous solution, sodium hydroxide aqueous solution, etc.). In addition, it can be produced by further subjecting to deprotection of the protecting group, if necessary. In addition to the above, sulfonamidation can also be carried out by using the method described in *Comprehensive Organic Transformations: A Guide to Functional Group Preparations,* 2nd Edition (Richard C. Larock, John Wiley & Sons, Inc, 1999).

The deprotection of protecting group can be carried out by the above-described method.

Among the compounds of formula (I), a compound in which D represents nitrogen, T represents carbonyl and J represents nitrogen, namely, a compound of formula (I-5):

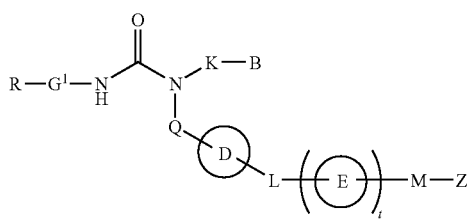
(I-5)

[wherein $G^1$ has the same meaning as G, with the proviso that it represents a bond or a spacer having from 1 to 7 atoms of the principal chain; and other symbols have the same meanings as described above]

can be produced by subjecting a compound of formula (7)

R-$G^1$-NCO (7)

[wherein all symbols have the same meanings as described above]

and the above-described compound of formula (3) to urea formation and then to deprotection of the protecting group, if necessary.

The urea formation is conventionally known and carried out, for example, by reacting an isocyanate derivative with an amine at a temperature of from 0 to 130° C. in an organic solvent (chloroform, dichloromethane, toluene, diethyl ether, tetrahydrofuran, etc. alone, or a mixed solvent containing two or more solvents thereof at an optional ratio), in the presence or absence of a base (pyridine, triethylamine, N,N-dimethylaniline, N,N-dimethylaminopyridine, diisopropylethylamine, etc.). This can be produced by further subjecting to deprotection of the protecting group, if necessary.

The deprotection of protecting group can be carried out by the above-described method.

Among the compounds of formula (I), a compound in which T represents methylene, J represents nitrogen and Q represents a group containing carbonyl (the carbonyl being bound to J), namely, a compound of formula (I-6):

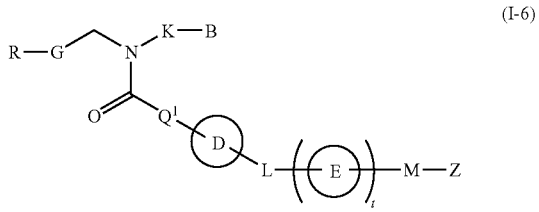

(I-6)

[wherein all symbols have the same meanings as described above]

can be produced by subjecting a compound of formula (8):

(8)

[wherein all symbols have the same meanings as described above]

and a compound of formula (9)

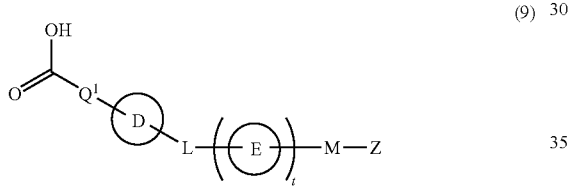

(9)

[wherein all symbols have the same meanings as described above]

to amidation and then to deprotection of the protecting group, if necessary.

The amidation and deprotection of protecting group can be carried out by the above-described method.

Among the compounds of formula (I), a compound in which T represents methylene and J represents nitrogen, namely, a compound of formula (I-7):

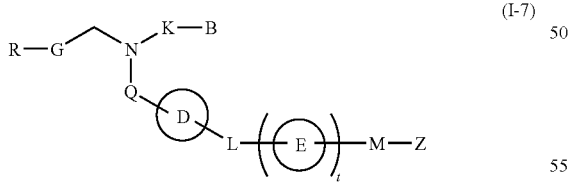

(I-7)

[wherein all symbols have the same meanings as described above]

can be produced by subjecting a compound of formula (10)

(10)

[wherein all symbols have the same meanings as described above]

and the above-described compound of formula (3) to reductive amination and then to deprotection of the protecting group, if necessary.

The reductive amination is conventionally known and carried out, for example, by reaction at a temperature of from 0 to 100° C. in an organic solvent (N,N-dimethylformamide, dichloromethane, etc. alone, or a mixed solvent containing two or more solvents thereof at an optional ratio) using a reducing agent (sodium triacetoxy-borohydride, sodium cyano-borohydride, tetrabutylammonium borohydride, etc.), in the presence or absence of an organic acid (acetic acid, etc.) or in the presence or absence of a base (triethylamine, sodium hydrogencarbonate, etc.). This can be produced by further subjecting to deprotection of the protecting group, if necessary.

The deprotection of protecting group can be carried out by the above-described method.

Among the compounds of formula (I), a compound in which T represents carbonyl and J represents carbon, namely, a compound of formula (I-8):

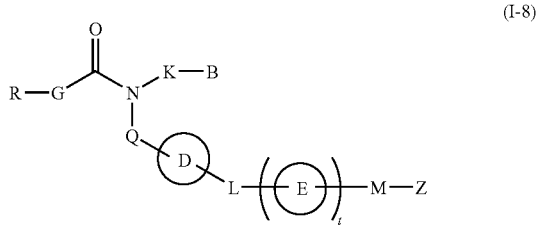

(I-8)

[wherein all symbols have the same meanings as described above]

can be produced by reacting a compound of formula (11)

(11)

[wherein all symbols have the same meanings as described above]

with a compound of formula (12)

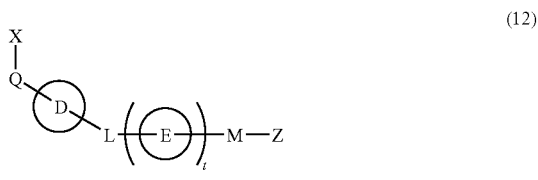

(12)

[wherein X represents a leaving group (the leaving group means halogen atom, methanesulfonyloxy (OMs), p-toluenesulfonyloxy (OTs), trifluoromethanesulfonyloxy (OTf), etc.); and other symbols have the same meanings as described above], followed by deprotection of the protecting group, if necessary.

This reaction is conventionally known and carried out, for example, by reaction at a temperature of from −78 to 40° C. in an organic solvent (tetrahydrofuran, diethyl ether, acetonitrile, dimethyl sulfoxide, etc. alone, or a mixed solvent containing two or more solvents thereof at an optional ratio), in the presence of a base (lithium diisopropylamine (carried out in the presence of an amine (N,N,N',N'',N''-pentamethyldiethylenetriamine, N,N,N',N'-tetramethylethylenediamine, etc.)), potassium carbonate, cesium carbonate, etc.).

The deprotection of protecting group can be carried out by the above-described method.

Among the compounds of formula (I), a compound in which T represents —CHOH— and J represents carbon atom, namely, a compound of formula (I-8-3):

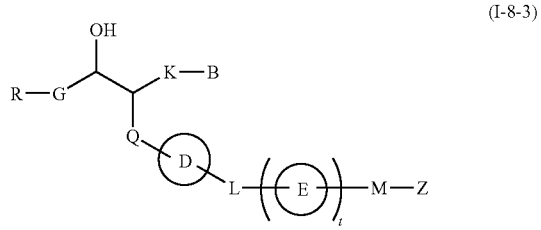

[wherein all symbols have the same meanings as described above]

can be produced by subjecting carbonyl of the above-described compound of formula (I-8) to reduction and then to deprotection of the protecting group, if necessary.

The reduction of carbonyl is conventionally known and carried out, for example, by reaction at a temperature of from 0 to 100° C. in an organic solvent (methanol, tetrahydrofuran, a mixed solvent thereof, etc.) using a reducing agent (sodium borohydride, sodium triacetoxy-borohydride, sodium cyanoborohydride, tetrabutylammonium borohydride, etc.).

The deprotection of protecting group can be carried out by the above-described method.

Among the compounds of formula (I), a compound in which T represents carbonyl, J represents carbon, Q represents carbon, and ring D and K together form indole ring, namely, a compound of formula (I-9):

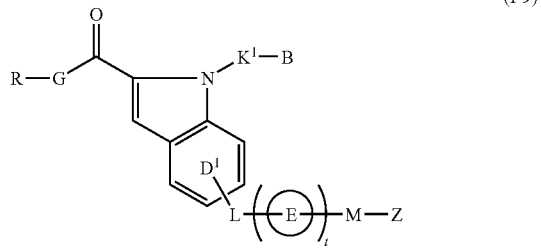

[wherein all symbols have the same meanings as described above]

can be produced by reacting a compound of formula (13):

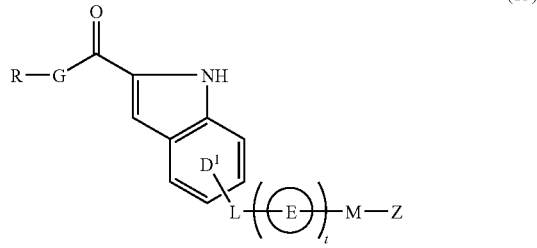

[wherein all symbols have the same meanings as described above]

with a compound of formula (14):

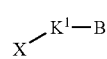

[wherein X represents a leaving group (the leaving group means halogen atom, methanesulfonyloxy (OMs), p-toluenesulfonyloxy (OTs), trifluoromethanesulfonyloxy (OTf) or the like); and other symbols have the same meanings as described above], followed by deprotection of the protecting group, if necessary.

This reaction is conventionally known and carried out, for example, by reaction at a temperature of from −78 to 40° C. in an organic solvent (tetrahydrofuran, diethyl ether, N,N-dimethylformamide, etc. alone, or a mixed solvent containing two or more solvents thereof at an optional ratio), in the presence of a base (lithium diisopropylamine (carried out in the presence of an amine (N,N,N',N'',N''-pentamethyldiethylenetriamine, N,N,N',N'-tetramethylethylenediamine, etc.)), sodium hydride, potassium carbonate, cesium carbonate, etc.).

The deprotection of protecting group can be carried out by the above-described method.

Among the compounds of formula (I), a compound in which T represents carbonyl, J represents carbon atom, Q represents nitrogen atom, and ring D and K together form benzimidazole ring, namely, a compound of formula (I-10):

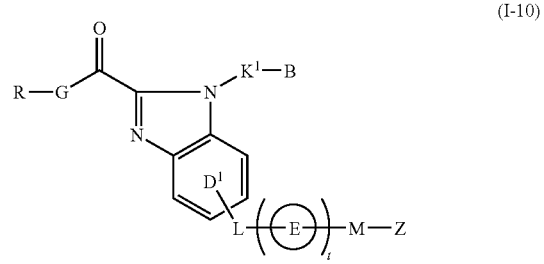

[wherein all symbols have the same meanings as described above]

can be produced by reacting a compound of formula (15):

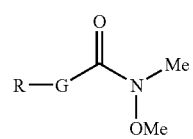

[wherein all symbols have the same meanings as described above]

with a compound of formula (16):

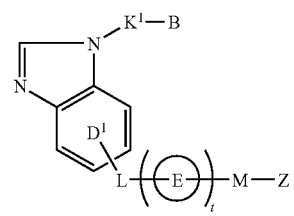

followed by deprotection of the protecting group, if necessary.

This reaction is conventionally known and carried out, for example, by reaction at a temperature of from −78 to 40° C. in an organic solvent (tetrahydrofuran, diethyl ether, etc. alone, or a mixed solvent containing two or more solvents thereof at an optional ratio), in the presence of a base (lithium diisopropylamine (carried out in the presence of an amine (N,N,N',N'',N''-pentamethyldiethylenetriamine, N,N,N',N'-tetramethylethylenediamine, etc.)), n-butyl lithium, etc.).

The deprotection of protecting group can be carried out by the above-described method.

Among the compounds of formula (I), a compound in which Z represents tetrazole, namely, a compound of formula (I-11):

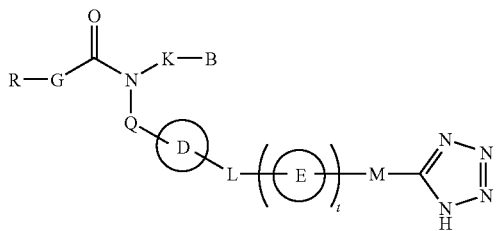

(I-11)

[wherein all symbols have the same meanings as described above]

can be produced by reacting a compound of formula (17):

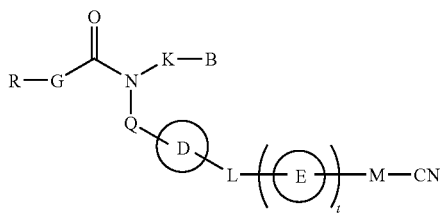

(17)

[wherein all symbols have the same meanings as described above]

with an azide compound, followed by deprotection of the protecting group, if necessary.

This reaction is conventionally known and carried out, for example, by reacting the material compound with an azide compound (e.g., sodium azide, lithium azide, trimethylsilyl azide, trimethyltin azide, tributyltin azide, etc.) at a temperature of from 20 to 150° C. in water or an organic solvent (benzene, toluene, xylene, N,N-dimethylformamide, tetrahydrofuran, 1,4-dioxane, isopropanol, etc.) alone or a mixed solvent containing two or more solvents thereof at an optional ratio, in the presence or absence of an additive agent (e.g., zinc bromide, lithium chloride, ammonium chloride, acetic acid, trifluoroacetic acid, triethylamine, pyridine, etc.).

The compounds of formulae (2) to (17) to be used as the starting materials or reagents are conventionally known by themselves or can be easily produced by using conventionally known methods, for example the methods described in *Comprehensive Organic Transformations: A Guide to Functional Group Preparations,* 2nd Edition (Richard C. Larock, John Willey & Sons Inc, 1999).

Among the compounds of the invention of formula (I), compounds other than the above-described ones can be produced by using a combination of Examples described in this description, or the conventionally known methods, for example the methods described in *Comprehensive Organic Transformations: A Guide to Functional Group Preparations,* 2nd Edition (Richard C. Larock, John Willey & Sons Inc, 1999).

In each reaction in this description, the reaction product can be purified by general purification techniques, such as distillation under ordinary pressure or a reduced pressure, high performance liquid chromatography using silica gel or magnesium silicate, thin layer chromatography, column chromatography, washing, recrystallization and the like. Purification may be carried out for each reaction or after completion of several reactions.

Toxicity

Toxicity of the compound of the present invention of formula (I) is sufficiently low and it was confirmed to be sufficiently safe to be used as pharmaceuticals.

Industrial Applicability

Application to Pharmaceuticals

Since the compound of the present invention of formula (I) is antagonistic to LPA receptors, they are believed to be useful for prevention and/or treatment of diseases such as various kinds of disease namely urinary system disease, carcinoma-associated disease, proliferative disease, inflammation/immune system disease, disease caused by secretory dysfunction, brain-related disease or chronic disease.

For example, for urinary system disease, prostatic hypertrophy or neurogenic bladder dysfunction disease, and dysuria (micturation initiation delay, extension between on urination, urinary stream very small, intermission micturation, two steps of micturation, etc.), pollakiuria, night urination, urodynia, etc. are known as symptoms with a urinary system disease. Similar urologic symptoms are symptoms caused by cerebrovascular disorder, Parkinson disease, cerebral oncosis, a multiple sclerosis, Shy-Drager symptom, spinal cord neoplasm, nucleous hernia, spinal canal stenosis, diabetes, etc. (such as dysuria (micturation initiation delay, extension between on urination, urinary stream very small, intermission micturation, two steps of miction), pollakiuria, night urination, urodynia). Other example of urinary system disease include lower urinary tract symptom (for example, occlusion disease of lower urinary tract), inflammatory disease of lower urinary tract (such as infection), polyuria. And these diseases and symptoms are considered to be cured by LPA receptor antagonists.

For example, for carcinoma-associated disease, solid tumor, solid tumor metastasis, angiofibroma, myeloma, multiple myeloma, Kaposi's sarcoma, leucemia are given. In solid tumor, mammary cancer, lung cancer, gastric cancer, carcinoma oesophagi, colon rectal cancer, liver cancer, ovarian cancer, theca cell tumor, androblastoma, cervix cancer, endometrial carcinoma, prostate cancer, kidney cancer, carcinoma cutaneum, osteosarcoma, pancreas cancer, urinary tract carcinoma, thyroid cancer, cerebral oncosis are given. In addition, it is thought that carcinomatous infiltration transition is suppressed by LPA receptor antagonist.

For example, for proliferative disease, disorder with aberrant angiogenesis (for example, re-arctation, diabetic retinopathy, angiogenesis-related glaucoma, crystalline lens fiber multiplication symptom, thyroid gland hyperplasia (including Basedow's disease), lung inflammation, nephrotic syndrome and osteoporosis), artery obstruction, pulmonary fibrosis are given.

For example, for inflammation/immune system disease, psoriasis, nephropathy (for example, IgA nephropathy), nephritis by other inflammation/immunopathy, hepatitis, pneumonitis symptom are given.

For example, for disease caused by secretory dysfunction, secretion fault by autonomic nervous system anomaly is given, for example, for disease caused by secretory dysfunction by autonomic nervous system anomaly, Sjogren syndrome is given.

For example, for brain-related disease, brain infarction, cerebral apoplexy, brain or peripheral neuropathy are given.

For example, for chronic disease, chronic asthma, glomerulonephritis, obesity, prostate hyperplasia, diseases caused by arteriosclerosis process, rheumatism or atopic dermatitis are given.

The compound of the present invention of formula (I), prodrug thereof or non-toxic salt thereof may be administered as a combined preparation by combining with other pharmaceuticals for the purpose of 1) supplementing and/or enhancing of prevention and/or treatment effect of the compound, 2) improvement in pharmacokinetics and absorption and reduction of dose of the compound, and/or 3) reduction of side effect of the compound.

The combined preparation of the compound of the present invention of formula (I) with other pharmaceuticals may be administered in a form of a compounded agent in which both components are compounded in a preparation or may be in a form in which they are administered by means of separate preparations. The case of administration by means of separate preparations includes a simultaneous administration and administrations with time difference. In the case of administrations with time difference, the compound of the present invention of formula (I) may be firstly administered followed by administering the other pharmaceutical or the other pharmaceutical may be administered firstly followed by administering the compound of the present invention of formula (I). Methods for each of the administration are the same or different.

There is no particular limitation for the diseases showing prevention and/or treatment effect by the above-mentioned combined preparation, so far as it is a disease in which the prevention and/or treatment effect of the compound of present invention of formula (I) are supplemented and/or enhanced.

The other pharmaceutical for supplementing and/or enhancing the prevention and/or treatment effect of the compound of the present invention of formula (I) for urinary system disease includes other urologic disease therapeutic agent such as other LPA receptor antagonist, α1 blocking agent, anticholinergic agent, 5α-reductase inhibitor and/or anti-androgenic agent. But anticholinergic agent is used only by case without prostatic hypertrophy. It is mainly used by remedy of pollakiuria or anischuria of case without prostatic hypertrophy.

The other pharmaceutical for supplementing and/or enhancing the prevention and/or treatment effect of the compound of the present invention of formula (I) for carcinoma disease region includes such as other carcinoma treatment of disease agent.

Examples of the other pharmaceutical preparations for compensating for and/or enhancing the preventive and/or treatment effect of the compound of the present invention of formula (I) on chronic asthma include steroids, $\beta_2$ adrenoreceptor stimulant, leukotriene receptor antagonist, thromboxane synthetase inhibitor, thromboxane $A_2$ receptor antagonist, mediator releasing inhibitor, antihistamines, xanthine derivatives, anticholinergic agent, cytokine inhibitor, prostaglandins, forskolin, phosphodiesterase inhibitor, elastase inhibitor, metalloproteinase inhibitor, expectorant, and antibiotic.

Examples of the other pharmaceutical preparations for compensating for and/or enhancing the preventive and/or treatment effect of the compound of the present invention of formula (I) on prostatic hypertrophy include anti-androgenic agent, α1 receptor blocking agent, and 5α-reductase inhibitor, etc.

Examples of the other pharmaceutical preparations for compensating for and/or enhancing the preventive and/or treatment effect of the compound of the present invention of formula (I) on disease caused by progress of arterial sclerosis include HMG-CoA reductase inhibitor, fibrate preparations, probucol preparations, anion-exchange resin, EPA preparations, nicotinic acid preparations, MTP (Microsomal Triglyceride Transfer Protein) inhibitor, PPAR agonist preparations, and other antihypercholesterolemic agent, etc.

Examples of the other pharmaceutical preparations for compensating for and/or enhancing the preventive and/or treatment effect of the compound of the present invention of formula (I) on rheumatism include nonsteroid-based antiphlogistic, disease modifying anti-rheumatic drug (slow-acting anti-rheumatic drug), steroids, immunosuppressant agent, antiinflammatory enzyme preparations, chondroprotective agents, T-cell inhibitors, TNFα inhibitor (include protein preparation such as anti-TNFα antibody), prostaglandin synthase inhibitor, IL-6 inhibitor (include protein preparation such as anti-IL-6 receptor antibody), interferon gamma agonists, IL-1 inhibitor, prostaglandins, phosphodiesterase inhibitor, metalloproteinase inhibitor, etc.

Examples of the other pharmaceutical preparations for compensating for and/or enhancing the preventive and/or treatment effect of the compound of the present invention of formula (I) on atopic dermatitis include steroids, nonsteroid-based antiphlogistic, immunosuppressant agent, prostaglandins, antiallergic agent, mediator releasing depressant, antihistamine drug, forskolin preparations, phosphodiesterase inhibitor, Decoy preparations such as NF-kB, cannabinoid-2 receptor stimulator, etc.

The other LPA receptor antagonist includes such as methyl 3-({4-[4-({[1-(2-chlorophenyl)ethoxy]carbonyl}amino)-3-methyl-5-isoxazolyl]benzyl}sulfanyl)propanoate, etc.

The α1 blocking agent includes such as terazosin hydrochloride, Bunazosin Hydrochloride, urapidil, tamsulosin hydrochloride, doxazosin mesilate, prazosin hydrochloride, indolamine, naftopidil, alfuzosin hydrochloride and AIO-8507L, etc.

The anticholinergic agent includes such as oxybutinin hydrochloride, bethanechol chloride, propiverine hydrochloride, propantheline bromide, methylbenactyzium bromide, scopolamine butylbromide, tolterodine tartrate, trospium chloride, Z-338, UK-112166-04, KRP-197, darifenacin and YM-905, etc.

The 5α-reductase inhibitor includes such as finasteride and GI-998745, etc.

The anti-androgenic agent includes such as oxendolone, osaterone acetate and bicalutamide, etc.

The other carcinoma treatment of disease agent includes alkylating agent (such as nitrogen mustard N-oxide hydrochloride, cyclophosphamide, ifosfamide, melphalan, thiotepa, carboquone, busulfan), nitrosourea derivative (such as nimustine hydrochloride, ranimustine), an antimetabolite (such as methotrexate, mercaptopurine, 6-mercapropurinboside, fluorouracil, tegafur, UFT, carmofur, doxifluridine, cytarabine, enocitabine), anticancer antibiotics (such as actionmycin D, mitomycin C, daunorubicin hydrochloride, doxorubicin hydrochloride, aclarubicin hydrochloride, neocarzinostatin, pirarubicin, epirubicin, idarubicin, chromomycin A3, bleomycin, peplomycin sulfate), plant alkaloid (such as vinblastine sulfate, vincristine sulfate, vindesine sulfate), hormone (such as estramustine phosphate sodium, mepitiostane, epitiostanol, tamoxifen citrate, diethylstilbestrol phosphate, medroxyprogesterone acetate), immunopotentiation agent (such as lentinan, picibanil, krestin, shizophyllan, ubenimex, interferon), others (such as L-asparaginase, procarbazine hydrochloride, mitoxantrone hydrochloride, cisplatin, carboplatin), etc.

Examples of the steroids for external application include clobetasol propionate, diflorasone acetate, fluocinonide, monometasone furancarboxylate, betamesone dipropionate, betamesone butyropropionate, betamesone valerate, difluprednate, budesonide, diflucortolone valerate, amcinonide, halcinonide, dexamethasone, dexamethasone propionate, dexamethasone valerate, dexamethasone acetate, hydrocortisone acetate, hydrocortisone butyrate, hydrocortisone acetopropionate, deprodone propionate, prednisolone valeroacetate, fluocinolone acetonide, beclometasone dipropionate, triamcinonide acetonide, flumethasone pivalate, prednisolone, beclometasone propionate, and fludroxycortide, etc.

Examples of the steroids for internal use or injection include cortisone acetate, hydrocortisone, hydrocortisone sodium phosphate, hydrocortisone sodium succinate, fludrocortisone acetate, prednisolone, prednisolone acetate, prednisolone sodium succinate, prednisolone butylacetate, prednisolone sodium phosphate, halopredon acetate, methyl prednisolone, methyl prednisolone acetate, methyl prednisolone sodium succinate, triamicinolon, triamicinolon acetate, triamicinonolon acetonide, dexamethasone, dexamethasone acetate, dexamethasone sodium phosphate, dexamethasone palmitate, paramethasone acetate, and betamethasone, etc.

Examples of the steroids as an inhalant include beclomethasonepropionate, fluticasone propionate, budesonide, flunisolide, triamicinolon, ST-126P, ciclesonide, dexamethasone palomitionate, monometasone furancarboxylate, prasterone sulfonate, deflazacort, methylprednisolone suleptanate, and methylprednisolone sodium succinate, etc.

Examples of the $\beta_2$ adrenoreceptor stimulant include fenoterol hydrobromide, salbutamol sulfate, terbutaline sulfate, formoterol fumarate, salmeterol xinafoate, isoprotenol sulfate, orciprenalin sulfate, chloroprenalin sulfate, epinephrine, trimetoquinol hydrochloride, hexoprenalinmesyl sulfate, procaterol hydrochloride, tulobuterol hydrochloride, tulobuterol, pirbuterol hydrochloride, clenbuterol hydrochloride, mabuterol hydrochloride, ritodrine hydrochloride, bambuterol, dopexamine hydrochloride, meradrin tartrate, AR-C68397, levosalbutamol, R,R-formoterol, KUR-1246, KUL-7211, AR-C89855, and S-1319, etc.

Examples of the leukotriene receptor antagonist include pranlukast hydrate, montelukast, zafirlukast, seratrodast, MCC-847, KCA-757, CD-615, YM-158, L-740515, CP-195494, LM-1484, RS-635, A-93178, S-36496, BIIL-284, and ONO-4057, etc.

Examples of the thromboxane synthetase inhibitor include ozagrel hydrochloride, and imitrodast sodium, etc.

Examples of the thromboxane $A_2$ receptor antagonist include seratrodast, ramatroban, domitroban calcium dihydrate, and KT-2-962, etc.

Examples of the mediator releasing inhibitor include tranilast, sodium cromoglicate, anlexanox, repirinast, ibudilast, tazanolast, and pemilolast sodium, etc.

Examples of the antihistamines include ketotifen fumarate, mequitazine, azelastine hydrochloride, oxatomide, terfenadine, emedastine fumarate, epinastine hydrochloride, astemizole, ebastin, cetirizine hydrochloride, bepotastine, fexofenadine, lolatadine, deslolatadine, olopatadine hydrochloride, TAK-427, ZCR-2060, NIP-530, mometasone furoate, mizolastine, BP-294, andolast, auranofin, and acribastin, etc.

Examples of the xanthine derivatives include aminophylline, thoeophyline, doxophylline, cipamfylline, and diprophilline, etc.

Examples of the anticholinergic agent include ipratropium bromide, oxitropium bromide, flutropium bromide, temiverine, tiotropium bromide, and revatropate (UK-112166), etc.

Examples of the cytokine inhibitor include suplatast tosilate (trade name: IPD), etc.

Examples of the prostaglandins (hereinafter abbreviated as "PG") include PG receptor agonist, and PG receptor antagonist, etc.

Examples of PG receptor include PGE receptors ($EP_1$, $EP_2$, $EP_3$, $EP_4$), PGD receptors (DP, CRTH2), PGF receptors (FP), PGI receptors (IP) and TX receptors (TP), etc.

Examples of the phosphodiesterase inhibitor include, for example, rolipram, cilomilast (trade name: Ariflo), Bay 19-8004, NIK-616, roflumilast (BY-217), cipamfylline (BGL-61063), atizolam (CP-80633), SCH-351591, YM-976, V-11294A, PD-168787, D-4386, and IC-485 as PDE-4 inhibitor, etc.

Examples of the elastase inhibitors include ONO-5046, ONO-6818, MR-889, PBI-1101, EPI-HNE-4, R-665, ZD-0892, ZD-8321, GW-311616, and AE-3763 etc.

Examples of the expectorant include foeniculated ammonia spirit, sodium hydrogencarbonate, bromhexine hydrochloride, carbocisteine, ambroxol hydrochloride, sustained release ambroxol hydrochloride, methylcysteine hydrochloride, acetyl cysteine, L-ethylcysteine hydrochloride, and tyloxapol, etc.

Examples of the HMG-CoA reductase inhibitor include, for example, simvastatin, lovastatin, pravastatin, fluvastatin, atorvastatin, pitavastatin, and rosuvastatin.

Examples of the fibrate preparations include, for example, fenofibrate, clinofibrate, clofibrate, aluminium clofibrate, simfibrate, and bezafibrate.

Examples of the probucol preparations include, for example, probucol.

Examples of the nicotinic acid preparations include, for example, tocopherol nicotinate, nicomol, and niceritrol.

Examples of the other antihypercholesterolemic agent include, for example, cholestyramine, soysterol, and colestimide.

Examples of the nonsteroid-based antiphlogistic include sasapyrine, sodium salicylate, aspirin, aspirin dialuminate formulation, diflunisal, indomethacin, suprofen, ufenamate, dimethylisopropyl azulen, bufexamac, felbinac, diclofenac, tolmetin sodium, Clinoril, fenbufen, napmetone, proglumetacin, indomethacin farnesil, acemetacin, proglumetacin maleate, amfenac sodium, mofezolac, etodolac, ibuprofen, ibuprofen piconol, naproxen, flurbiprofen, flurbiprofen axethyl, ketoprofen, fenoprofen calcium, tiaprofenen, oxaprozin, pranoprofen, loxoprofen sodium, aluminoprofen, zaltoprofen, mefenamic acid, aluminum mefenamate, tolfenamic acid, floctafenine, ketophenylbutazone, oxyfenbutazone, piroxicam, tenoxicam, anpiroxicam, napageln cream, epirizole, tiaramide hydrochloride, tinoridine hydrochloride, emorfazone, sulpyrine, Migrenin, Saridon, Sedes G, Amipylo N, Sorbon, pyrine system antipyretics, acetaminophen, phenacetin, dimethothiazine mesylate, simetride formulation, and antipyrine system antipyretics, etc.

Examples of the disease modifying anti-rheumatic drug (slow-acting anti-rheumatic drug) include, for example, gold thioglucose, aurothiomalate sodium, auranofin, actarit, D-penicillamine preparations, lobenzarit disodium, bucillamine, hydroxychloroquine, and salazosulfapyridine, etc.

Examples of the chondroprotective agents include, for example, hyaluronate sodium, glucosamine, chondroitin sulfate, and glucosaminoglycan polysulfate, etc.

Examples of the prostaglandin synthase inhibitor include, for example, salazosulfapyridine, mesalazine, olsalazine, 4-aminosalicylic acid, JTE-522, auranofin, carprofen, diphenpyramid, flunoxaprofen, flurbiprofen, indomethacin, ketoprofen, lornoxicam, loxoprofen, Meloxicam, oxaprozin, parsalmide, piproxen, piroxicam, piroxicam betadex, piroxicam cinnamate, tropine indomethacinate, zaltoprofen, and pranoprofen, etc.

There is no particular limitation for the ratio by weight of the compound of formula (I) to other pharmaceuticals.

With regard to other pharmaceuticals, any two or more may be compounded and administered.

With regard to other pharmaceuticals which supplement and/or enhance the prevention and/or treatment effect of the compound of formula (I), not only that which has been found up to now but also that which will be found in future on the basis of the above-mentioned mechanism are included.

When the compound of formula (I) which are used in the present invention, or concomitant drug combined the compound of formula (I) with other drugs are used for the above-described purpose, it is usually administered systemically or topically via an oral or parenteral route.

The dose of these compounds depends on the age, weight and symptom of the patient, the remedial value, the administration method, the treatment time, etc. In practice, however, these compounds are administered orally once or several times per day each in an amount of from 0.01 mg to 1000 mg, preferably 0.1 mg to 500 mg or more preferably 0.1 mg to 300 mg per adult, parenterally once or several times per day each in an amount of from 0.01 mg to 500 mg, preferably 0.1 mg to 100 mg or more preferably 0.1 mg to 50 mg per adult or continuously administered into vein for 1 hour to 24 hours per day.

It goes without saying that the dose of these compounds may be less than the aforementioned value or may need to exceed the aforementioned range because the dose varies under various conditions as mentioned above.

When the compound of formula (I) which are used in the present invention, or concomitant drug combined the compound of formula (I) with other drugs is administered, they are used in the form of solid or liquid agent for oral administration, injection, agent for external application, suppository, eye drops or inhalant for parenteral administration or the like.

Examples of the solid agent for oral administration include tablet, pill, capsule, powder, and pellet. Examples of the capsule include hard capsule, and soft capsule.

In such a solid agent for internal application, one or more active materials are used in the form of preparation produced by an ordinary method singly or in admixture with a vehicle (e.g., lactose, mannitol, glucose, microcrystalline cellulose, starch), binder (e.g., hydroxypropyl cellulose, polyvinyl pyrrolidone, magnesium metasilicoaluminate), disintegrant (e.g., calcium fibrinoglycolate), glidant (e.g., magnesium stearate), stabilizer, dissolution aid (e.g., glutamic acid, aspartic acid) or the like. The solid agent may be coated with a coating agent (e.g., white sugar, gelatin, hydroxypropyl cellulose, hydroxypropyl methyl cellulose phthalate) or two or more layers. Alternatively, the solid agent may be capsulized by an absorbable material such as gelatin.

Examples of the liquid agent for oral administration include pharmaceutically acceptable aqueous solution, suspension, emulsion, syrup, and elixir. In such a liquid agent, one or more active agents are dissolved, suspended or emulsified in a commonly used diluent (e.g., purified water, ethanol, mixture thereof). Furthermore, such a liquid agent may comprise a wetting agent, a suspending agent, an emulsifier, a sweetening agent, a flavor, a preservative, a buffer, etc.

The agent for parenteral administration may be in the form of, e.g., ointment, gel, cream, wet compress, paste, liniment, nebula, inhalant, spray, aerosol, eye drops, collunarium or the like. These agents each contain one or more active materials and are prepared by any known method or commonly used formulation.

The ointment is prepared by any known or commonly used formulation. For example, one or more active materials are triturated or dissolved in a base to prepare such an ointment. The ointment base is selected from known or commonly used materials. In some detail, higher aliphatic acid or higher aliphatic acid ester (e.g., adipic acid, myristic acid, palmitic acid, stearic acid, oleic acid, adipic acid ester, myristic acid ester, palmitc acid ester, stearic acid ester, oleic acid ester), wax (e.g., beeswax, whale wax, ceresin), surface active agent (e.g., polyoxyethylenealkylether phosphoric acid ester), higher alcohol (e.g., cetanol, stearyl alcohol, setostearyl alcohol), silicon oil (e.g., dimethyl polysiloxane), hydrocarbon (e.g., hydrophilic petrolatum, white petrolatum, purified lanolin, liquid paraffin), glycol (e.g., ethylene glycol, diethylene glycol, propylene glycol, polyethylene glycol, macrogol), vegetable oil (e.g., castor oil, olive oil, sesame oil, turpentine oil), animal oil (mink oil, vitelline oil, squalane, squalene), water, absorption accelerator and rash preventive may be used singly or in admixture of two or more thereof The base may further comprise a humectant, a preservative, a stabilizer, an antioxidant, a perfume, etc.

The gel is prepared by any known or commonly used formulation. For example, one or more active materials are dissolved in a base to prepare such a gel. The gel base is selected from known or commonly used materials. For example, lower alcohol (e.g., ethanol, isopropyl alcohol), gelling agent (e.g., carboxymethyl cellulose, hydroxyethyl cellulose, hydroxypropyl cellulose, ethyl cellulose), neutralizing agent (e.g., triethanolamine, diisopropanolamine), surface active agent (e.g., polyethylene glycol monostearate), gum, water, absorption accelerator, and rash preventive are used singly or in admixture of two or more thereof The gel base may further comprise a humectant, an antioxidant, a perfume, etc.

The cream is prepared by any known or commonly used formulation. For example, one or more active materials are dissolved in a base to prepare such a cream. The cream base is selected from known or commonly used materials. For example, higher aliphatic acid ester, lower alcohol, hydrocarbon, polyvalent alcohol (e.g., propylene glycol, 1,3-butylene glycol), higher alcohol (e.g., 2-hexyl decanol, cetanol), emulsifier (e.g., polyoxyethylene alkyl ether, aliphatic acid ester), water, absorption accelerator, and rash preventive are used singly or in admixture of two or more thereof The cream base may further comprise a humectant, an antioxidant, a perfume, etc.

The wet compress is prepared by any known or commonly used formulation. For example, one or more active materials are dissolved in a base to prepare a kneaded mixture which is then spread over a support to prepare such a wet compress. The wet compress base is selected from known or commonly used materials. For example, thickening agent (e.g., polyacrylic acid, polyvinyl pyrrolidone, gum arabic, starch, gelatin, methyl cellulose), wetting agent (e.g., urea, glycerin, propylene glycol), filler (e.g., kaolin, zinc oxide, talc, calcium, magnesium), water, dissolution aid, tackifier, and rash preventive may be used singly or in admixture of two or more thereof The wet compress base may further comprise a humectant, an antioxidant, a perfume, etc.

The pasting agent is prepared by any known or commonly used formulation. For example, one or more active materials are dissolved in a base to prepare a kneaded mixture which is then spread over a support to prepare such a pasting agent. The pasting agent base is selected from known or commonly used materials. For example, polymer base, fat and oil, higher aliphatic acid, tackifier and rash preventive may be used singly or in admixture of two or more thereof The pasting agent base may further comprise a humectant, an antioxidant, a perfume, etc.

The liniment is prepared by any known or commonly used formulation. For example, one or more active materials are dissolved, suspended or emulsified in water, alcohol (e.g., ethanol, polyethylene glycol), higher aliphatic acid, glycerin, soap, emulsifier, suspending agent, etc., singly or in combination of two or more thereof, to prepare such a liniment. The liniment may further comprise a humectant, an antioxidant, a perfume, etc.

The nebula, inhalant and spray each may comprise a stabilizer such as sodium hydrogensulfite and a buffer capable of providing isotonicity such as isotonic agent (e.g., sodium chloride, sodium citrate, citric acid). For the process for the preparation of spray, reference can be made to U.S. Pat. Nos. 2,868,691 and 3,095,355.

The injection for parenteral administration may be in the form of solution, suspension, emulsion or solid injection to be dissolved or suspended in a solvent in use. The injection is prepared by dissolving, suspending or emulsifying one or more active materials in a solvent. As such a solvent there may be used distilled water for injection, physiological saline, vegetable oil, alcohol such as propylene glycol, polyethylene glycol and ethanol, etc., singly or in combination. The injection may further comprise a stabilizer, a dissolution aid (e.g., glutamic acid, aspartic acid, Polysolvate 80 (trade name)), a suspending agent, an emulsifier, a soothing agent, a buffer, a preservative, etc. The injection is sterilized at the final step or prepared by an aseptic process. Alternatively, an aseptic solid agent such as freeze-dried product which has previously been prepared may be rendered aseptic or dissolved in an aseptic distilled water for injection or other solvent before use.

The eye drops for parenteral administration may be in the form of liquid, suspension, emulsion, formulation to be dissolved before use, or ointment or may be dissolved in a solvent in use.

These eye drops are prepared by any known method. For example, one or more active materials are dissolved, suspended or emulsified in a solvent. As such a solvent for eye drops there may be used sterilized purified water, physiological saline and other aqueous or nonaqueous solvents (e.g., vegetable oil), singly or in combination. The eye drops may comprise an isotonic agent (e.g., sodium chloride, concentrated glycerin), a buffering agent (e.g., sodium phosphate, sodium acetate), a surface active agent (e.g., Polysolvate 80 (trade name), polyoxyl stearate 40, polyoxyethylene-hardened castor oil), a stabilizer (sodium citrate, sodium edetate), a preservative (e.g., benzalconium chloride, Paraben), etc. properly selectively as necessary. The eye drops are sterilized at the final step or prepared by an aseptic process. Alternatively, an aseptic solid agent such as freeze-dried product which has previously been prepared may be rendered aseptic or dissolved in an aseptic distilled water for injection or other solvent before use.

The inhalant for parenteral administration may be in the form of aerosol, powder for inhalation or liquid for inhalation.

The liquid for inhalation may be dissolved or suspended in water or other proper medium in use.

These inhalants are prepared by an known method.

For these inhalants, the liquid for inhalation is prepared from materials properly selected from preservatives (e.g., benzalconium chloride, Paraben), colorants, buffering agents (e.g., sodium phosphate, sodium acetate), isotonic agents (e.g., sodium chloride, concentrated glycerin), thickening agents (e.g., carboxyvinyl polymer), absorption accelerators, etc. as necessary.

The powder for inhalation is prepared from materials properly selected from glidants (e.g., stearic acid and salt thereof), binders (e.g., starch, dextrin), vehicles (e.g., lactose, cellulose), colorants, preservatives (e.g., benzalconium chloride, Paraben), absorption accelerators, etc., if necessary.

In order to administer the liquid for inhalation, a sprayer (e.g., atomizer, nebulizer) is normally used. In order to administer the powder for inhalation, a powder inhaler is normally used.

Other examples of the composition for oral administration include sublingual medication for sublingual administration, suppository for rectal administration and pessary for vaginal administration prepared by an ordinary formulation comprising one or more active materials.

Referring to the local administration of the compound of formula (I) of the present invention, medicament may be locally administered to site of disease. The form of medicament is not limited to its administration method. The medicament may be in the form of injection which is administered to intramuscular, subcutaneous, organic or articular site, solid agent (such as embedding agent, pellet and powder) or ointment.

The sustained release formulation of the compound of formula (I) of the present invention is not limited to its form so far as medicament can be continuously administered to site of disease. The sustained release formulation may be in the form of, e.g., sustained release injection (e.g., microcapsuled formulation, microspheric formulation, nanospheric formulation), embedding formulation (e.g., film-like formulation) or the like.

The microcapsuled formulation, microspheric formulation and nanospheric formulation of the invention each are particulate pharmaceutical composition with an biodegradable polymer comprising the compound of formula (I) of the present invention, or concomitant drug combined the compound of formula (I) of the present invention with other drugs as active components.

Examples of the biodegradable polymer of the invention include aliphatic acid ester polymers and copolymers thereof, polyacrylic acid esters, polyhydroxybutyric acids, polyalkylene oxalates, polyorthoesters, polycarbonates, and polyaminoacids. These compounds may be used singly or in admixture of two or more thereof Examples of the aliphatic acid ester polymers and copolymers thereof include polylactic acid, polyglycolic acid, polycitric acid, polymalic acid, and lactic acid-glycolic acid copolymer. These compounds may be used singly or in admixture of two or more thereof Besides these compounds, poly-α-cyanoacrylic acid esters, poly-β-hydroxybutyric acids, polytrimethyleneoxalates, polyorthoesters, polyorthocarbonates, polyethylene carbonates, poly-γ-benzyl-L-glutamic acids and poly-L-alanines may be used singly or in admixture of two or more thereof Preferred among these compounds are polylactic acids, polyglycolic acids and lactic acid-glycolic acid copolymers, more preferably lactic acid-glycolic acid copolymers.

The average molecular weight of these biodegradable polymers to be used in the invention is preferably from about 2,000 to 800,000, more preferably from about 5,000 to 200,000. For example, the polylactic acid preferably has a weight-average molecular weight of from about 5,000 to 100,000, more preferably from about 6,000 to 50,000. The polylactic acid can be synthesized according to any known preparation method per se. In the lactic acid-glycolic acid copolymer, the composition ratio of the lactic acid to the glycolic acid is preferably from about 100/0 to 50/50 (w/w), particularly from about 90/10 to 50/50. The weight-average molecular weight of the lactic acid-glycolic acid copolymer is preferably from about 5,000 to 100,000, more preferably from about 10,000 to 80,000. The lactic acid-glycolic acid copolymer can be synthesized according to any known preparation method per se.

The term "weight-average molecular weight" as used herein is meant to indicate molecular weight in polystyrene equivalence determined by gel permeation chromatography (GPC).

The aforementioned biodegradable polymer may be changed depending on the intensity of pharmacological activity of the compound of formula (I) which are used in the present invention, or concomitant drug combined the compound of formula (I) with other drugs and the desired medicines to be released so far as the aforementioned aims of the invention are accomplished. For example, the biodegradable polymer may be used in an amount of from about 0.2 to 10,000 times (by weight), preferably from about 1 to 1,000 times (by weight), more preferably from about 1 to 100 times (by weight) that of the physiologically active material.

The nomenclature of the compound of the present invention is described below.

The nomenclature in the present specification was done by means of a method according as a rule of IUPAC, or ACD/Name™ (Version 6.00, Advanced Chemistry Development Inc.), which is a computerized system to denominate a compound generally according to rule of IUPAC.

BEST MODE FOR CARRYING OUT THE INVENTION

The following reference examples and examples illustrate the present invention, but they do not limit the present invention.

The solvents in the parentheses show the developing solvents or eluting solvents and the ratios of the solvents used are by volume in chromatographic separations or TLC. The solvents in the parentheses in NMR show the solvents for measurement.

Electrospray ionization (ESI, condition: Pos., 20 V) was used as a method of Mass measurement.

HPLC conditions are outlined below.

Column: Xterra® MS $C_{18}$, 4.6×50 mm I.D., 5 µm, 100 Å

Flow rate: 3 ml/min

Solvent

Liquid A: 0.1% trifluoroacetic acid aqueous solution

Liquid B: 0.1% trifluoroacetic acid—acetonitrile solution

Mix propotion of liquid A and B during 0.5 minutes from a beginning of measurement was held 95/5. Then the propotion was gradually changed to 0/100 for 2.5 minutes and held 0/100 for 0.5 minutes. Finally the propotion was gradually changed to 95/5 for 0.01 minutes.

Reference Example 1

2-(4-formylphenyl)benzoic acid methyl ester

Under atmosphere of argon, to a solution of 4-formylphenylboric acid (6.7 g) in N,N-dimethylformamide (100 ml), 2-bromobenzoic acid methyl ester(6.5 g), tetrakis(triphenylphosphine)palladium [Pd(PPh$_3$)$_4$] (1.0 g) and tripotassium phosphate (23 g) were added and the mixture was stirred for 5 hours at 75° C.

The reaction mixture was filtered and the filtrate was concentrated. 1 N Hydrochloric acid was added to the residue and the mixture was extracted by ethyl acetate. The extract was washed with saturated aqueous solution of sodium hydrogen carbonate and brine sequentially, dried over anhydrous sodium sulfate, concentrated under reduced pressure. The residue was purified by column chromatography on silica gel (Hexane:Ethyl acetate=9:1) to give the title compound (4.1 g) having the following physical data.

TLC: Rf 0.50 (Hexane:Ethyl acetate=2:1);

NMR (CDCl$_3$): δ 10.07 (s, 1H), 7.96-7.89 (m, 3H), 7.63-7.34 (m, 5H), 3.66 (s, 3H).

Reference Example 2

2-(4-(3-phenylpropylaminomethyl)phenyl)benzoic acid methyl ester

To a solution of the compound prepared in Reference example 1 (1.2 g) in a mixed solvent of acetic acid (4 ml) and N,N-dimethylformamide (36 ml), 3-phenylpropylamine (1 g) and sodium triacetoxyborohydride (1.6 g) were added sequentially and the mixture was stirred for 2.5 hours at room temperature.

Saturated aqueous solution of sodium hydrogen carbonate was added to the reaction mixture and the mixture was extracted with ethyl acetate. The extract was washed with saturated aqueous solution of sodium hydrogen carbonate and brine sequentially, dried over anhydrous sodium sulfate, concentrated under reduced pressure to give the title compound (1.8 g) having the following physical data.

TLC: Rf 0.59 (Dichloromethane:Methanol=9:1).

Example 1

2-(4-(N-(3,4,5-trimethoxyphenylcarbonyl)-N-(3-phenylpropyl)aminomethyl)phenyl)benzoic acid methyl ester To a solution of 3,4,5-trimethoxybenzoic acid (368 mg) in N,N-dimethylformamide (10 ml), the compound prepared in Reference example 2 (416 mg), 1-ethyl-3-[3-(dimethylamino)propyl]carbodiimide hydrochloride (461 mg) and 1-hydroxybenztriazole hydrate (260 mg) were added sequentially and the mixture was stirred for 4 hours at room temperature.

1 N Hydrochloric acid was added to the reaction mixture and the mixture was extracted with ethyl acetate. The extract was washed with saturated aqueous solution of sodium hydrogen carbonate and brine sequentially, dried over anhydrous sodium sulfate, concentrated under reduced pressure. The residue was purified by column chromatography on silica gel (Hexane:Ethyl acetate=2:1) to give the compound of the present invention (273 mg) having the following physical data.

TLC: Rf 0.33 (Hexane:Ethyl acetate=1:1);
NMR (CDCl$_3$): δ 8.20-7.00 (m, 13H), 6.64 (s, 2H), 4.80-4.50 (m, 2H), 4.00-3.20 (m, 14H), 2.80-2.40 (m, 2H), 2.20-1.80 (m, 2H).

Examples 1(1)-1(4)

The following compounds of the present invention were obtained by the same procedures as described in Reference example 2 and Example 1 using corresponding aldehyde instead of the compound prepared in Reference example 1 and corresponding amine instead of 3-phenylpropylamine.

Example 1(1)

(2-(4-(N-(3,4,5-trimethoxyphenylcarbonyl)-N-(3-phenylpropyl)aminomethyl)phenyl)phenyl)acetic acid methyl ester TLC: Rf 0.39 (Hexane:Ethyl acetate=1:1);
NMR (CDCl$_3$): δ 7.43-6.91 (m, 13H), 6.42 (s, 2H), 4.83-4.51 (m, 2H), 3.95-3.50 (m, 15H), 3.41-3.16 (n, 1H), 2.79-2.38 (m, 2H), 2.11-1.79 (m, 2H).

Example 1(2)

2-(4-(N-(3,5-dimethoxyphenylcarbonyl)-N-(3-phenylpropyl)aminomethyl)phenyloxy)-4-chlorobenzoic acid methyl ester TLC: Rf 0.24 (Hexane:Ethyl acetate=2:1);
NMR (CDCl$_3$): δ 7.87 (d, J=8.7 Hz, 1H), 7.40-7.00 (m, 9H), 6.93 (d, J=8.4 Hz, 2H), 6.60-6.40 (m, 3H), 4.80-4.40 (m, 2H), 3.90-3.70 (m, 9H), 3.60-3.10 (m, 2H), 2.70-2.40 (m, 2H), 2.10-1.80 (m, 2H).

Example 1(3)

2-(4-(N-(3,5-dimethoxy-4-methylphenylcarbonyl)-N-(3-phenylpropyl)aminomethyl)phenyloxy)-4-methylbenzoic acid methyl ester TLC: Rf 0.33 (Hexane:Ethyl acetate=2:1);
NMR (CDCl$_3$): δ 7.84 (d, J=8.1 Hz, 1H), 7.34-6.87 (m, 10H), 6.78 (m, 1H), 6.54 (s, 2H), 4.78-4.59 (m, 2H), 3.89-3.63 (m, 9H), 3.52 (m, 1H), 3.21 (m, 1H), 2.77-2.35 (m, 2H), 2.34 (s, 3H), 2.12-1.77 (m, 5H).

Example 1(4)

(4-(N-(3,5-dimethoxy-4-methylphenylcarbonyl)-N-(3-phenylpropyl)aminomethyl)phenyl)acetic acid methyl ester TLC: Rf 0.44 (Hexane:Ethyl acetate=2:1);
NMR (CDCl$_3$): δ 7.34-6.90 (m, 9H), 6.53 (s, 2H), 4.77-4.42 (m, 2H), 3.86-3.10 (m, 13H), 2.76-2.32 (m, 2H), 2.12-1.75 (m, 5H).

Example 2

2-(4-(N-(3,4,5-trimethoxyphenylcarbonyl)-N-(3-phenylpropyl)aminomethyl)phenyl)benzoic acid To a solution of the compound prepared in Example 1 (270 mg) in a mixed solvent of methanol (2 ml) and tetrahydrofuran (4 ml), 1 N aqueous solution of sodium hydroxide (2 ml) was added sequentially and the mixture was refluxed for 4 hours.

1 N Hydrochloric acid was added to the reaction mixture and the mixture was extracted with ethyl acetate. The extract was washed with saturated aqueous solution of sodium hydrogen carbonate and brine sequentially, dried over anhydrous sodium sulfate, concentrated under reduced pressure to give the compound of the present invention (246 mg) having the following physical data.

TLC: Rf 0.56 (Dichloromethane:Methanol=9:1);
NMR (DMSO-d$_6$): δ 7.75-7.00 (m, 13H), 6.65 (s, 2H), 4.80-4.50 (m, 2H), 3.90-3.50 (m, 9H), 3.50-3.10 (m, 2H), 2.70-2.30 (m, 2H), 2.00-1.80 (m, 2H).

Examples 2(1)-2(4)

The following compounds of the present invention were obtained by the same procedures as described in Example 2 using the compounds prepared in Examples 1(1)-1(4) instead of the compound prepared in Example 1.

Example 2(1)

(2-(4-(N-(3,4,5-trimethoxyphenylcarbonyl)-N-(3-phenylpropyl)aminomethyl)phenyl)phenyl)acetic acid TLC: Rf 0.80 (Dichloromethane:Methanol=9:2);
NMR (DMSO-d$_6$): δ 7.40-6.90 (m, 15H), 6.66 (s, 2H), 4.80-4.50 (m, 2H), 3.90-3.10 (m, 11H), 2.70-2.30 (m, 2H), 2.00-1.80 (m, 2H).

Example 2(2)

2-(4-(N-(3,5-dimethoxyphenylcarbonyl)-N-(3-phenylpropyl)aminomethyl)phenyloxy)-4-chlorobenzoic acid TLC: Rf 0.34 (Dichloromethane:Methanol=12:1);
NMR (CDCl$_3$): δ 8.13 (d, J=8.7 Hz, 1H), 7.40-6:90 (m, 11H), 6.50-6.40 (m, 3H), 4.80-4.40. (m, 2H), 3.90-3.70 (m, 6H), 3.60-3.10 (m, 2H), 2.80-2.40 (m, 2H), 2.00-1.80 (m, 2H).

Example 2(3)

2-(4-(N-(3,5-dimethoxy-4-methylphenylcarbonyl)-N-(3-phenylpropyl)aminomethyl)phenyloxy)-4-methylbenzoic acid TLC: Rf 0.54 (Dichloromethane:Methanol=9:1);
NMR (CDCl$_3$): δ 8.10 (d, J=8.1 Hz, 1H), 7.40-6.90 (m, 10H), 6.66-6.59 (m, 1H), 6.54 (s, 2H), 4.81-4.45 (m, 2H), 3.90-3.65 (m, 6H), 3.61-3.15 (m, 2H), 2.78-2.36 (m, 2H), 2.32 (s, 3H), 2.18-1.79 (m, 5H).

Example 2(4)

(4-(N-(3,5-dimethoxy-4-methylphenylcarbonyl)-N-(3-phenylpropyl)aminomethyl)phenyl)acetic acid TLC: Rf 0.61 (Dichloromethane:Methanol=9:1);
NMR (CDCl$_3$): δ 7.34-6.90 (m, 9H), 6.52 (s, 2H), 4.70, 4.50 (s, 2H), 3.78 (s, 2H), 3.64 (s, 6H), 3.63, 3.19 (s, 2H), 2.65, 2.41 (s, 2H), 2.13-1.78 (m, 5H).

Examples 3(1)-3(58)

The following compounds of the present invention were obtained by the same procedures as described in Reference example 2, Example 1 and Example 2 using the compounds prepared in Reference example 1 or corresponding aldehyde and 3-phenylpropylamine or corresponding amine.

Example 3(1)

2-(4-(N-phenylcarbonyl-N-(2-phenylethyl)aminomethyl)phenyl)benzoic acid

TLC: Rf 0.63 (Chloroform:Methanol=14:1);
NMR (DMSO-$d_6$): δ 7.72 (dd, J=7.5, 1.5 Hz, 1H), 7.55-7.51 (m, 1H), 7.45-7.38 (m, 4H), 7.36-7.22 (m, 9H), 7.20-7.16 (m, 1H), 7.09-7.05 (m, 2H), 4.63 (s, 2H), 3.54 (t, J=7.5 Hz, 2H), 2.85 (t, J=7.5 Hz, 2H).

Example 3(2)

2-(4-(N-cyclopentylcarbonyl-N-(2-phenylethyl)aminomethyl)phenyl)benzoic acid

TLC: Rf 0.63 (Chloroform:Methanol=14:1);
NMR (DMSO-$d_6$): δ 7.71 (dd, J=7.5, 1.5 Hz, 1H), 7.54-7.50 (m, 1H), 7.44-7.40 (m, 1H), 7.36-7.17 (m, 10H), 4.59 (s, 2H), 3.56 (t, J=7.5 Hz, 2H), 3.00-2.90 (m, 1H), 2.83 (t, J=7.5 Hz, 2H), 1.80-1.50 (m, 8H).

Example 3(3)

2-(4-(N-phenylcarbonyl-N-(2-(2-methoxyphenyl)ethyl)aminomethyl)phenyl)benzoic acid TLC: Rf 0.57 (Chloroform:Methanol=9:1);
NMR (DMSO-$d_6$): δ 7.72 (dd, J=7.5, 1.5 Hz, 1H), 7.53 (dt, J=1.5, 7.5 Hz, 1H), 7.45-7.27 (m, 11H), 7.20-7.16 (m, 1H), 7.02-6.99 (m, 1H), 6.89 (d, J=8.0 Hz, 1H), 6.84 (t, J=8.0 Hz, 1H), 4.64 (brs, 2H), 3.66 (s, 3H), 3.49 (t, J=7.5 Hz, 2H), 2.84 (t, J=7.5 Hz, 2H).

Example 3(4)

2-(4-(N-phenylcarbonyl-N-(2-(3-methoxyphenyl)ethyl)aminomethyl)phenyl)benzoic acid TLC: Rf 0.57 (Chloroform:Methanol=9:1);
NMR (DMSO-$d_6$): δ 7.72 (d, J=6.5 Hz, 1H), 7.55-7.52 (m, 1H), 7.45-7.28 (m, 11H), 7.15 (t, J=7.7 Hz, 1H), 6.76 (dd, J=8.5, 1.5 Hz, 1H), 6.67-6.62 (m, 2H), 4.63 (brs, 2H), 3.72 (s, 3H), 3.53 (t, J=7.2 Hz, 2H), 2.82 (t, J=7.2 Hz, 2H).

Example 3(5)

2-(4-(N-phenylcarbonyl-N-(2-(4-methoxyphenyl)ethyl)aminomethyl)phenyl)benzoic acid TLC: Rf 0.57 (Chloroform:Methanol=9:1);
NMR (DMSO-$d_6$): δ 7.72 (dd, J=7.5, 1.5 Hz, 1H), 7.54 (dt, J=1.5, 7.5 Hz, 1H), 7.45-7.28 (m, 11H), 7.00-6.96 (m, 2H), 6.84-6.80 (m, 2H), 4.62 (brs, 2H), 3.73 (s, 3H), 3.49 (t, J=7.2 Hz, 2H), 2.78 (t, J=7.2 Hz, 2H).

Example 3(6)

2-(4-(N-phenylcarbonyl-N-(2-(2-chlorophenyl)ethyl)aminomethyl)phenyl)benzoic acid TLC: Rf 0.62 (Chloroform:Methanol=9:1);
NMR (DMSO-$d_6$): δ 7.72 (dd, J=7.5, 1.5 Hz, 1H), 7.54 (dt, J=1.5, 7.5 Hz, 1H), 7.45-7.17 (m, 15H), 4.65 (brs, 2H), 3.57 (t, J=7.3 Hz, 2H), 2.99 (t, J=7.3 Hz, 2H).

Example 3(7)

2-(4-(N-phenylcarbonyl-N-(2-(4-chlorophenyl)ethyl)aminomethyl)phenyl)benzoic acid TLC: Rf 0.62 (Chloroform:Methanol=9:1);
NMR (DMSO-$d_6$): δ 7.73-7.71 (m, 1H), 7.56-7.52 (m, 1H), 7.45-7.26 (m, 13H), 7.12-7.07 (m, 2H), 4.62 (brs, 2H), 3.54 (t, J=7.3 Hz, 2H), 2.84 (t, J=7.3 Hz, 2H).

Example 3(8)

2-(4-(N-phenylcarbonyl-N-(2-(3,4-dichlorophenyl)ethyl)aminomethyl)phenyl)benzoic acid TLC: Rf 0.62 (Chloroform:Methanol=9:1);
NMR (DMSO-$d_6$): δ 7.73-7.71 (m, 1H), 7.56-7.52 (m, 1H), 7.49-7.27 (m, 13H), 7.08-7.04 (m, 1H), 4.63 (brs, 2H), 3.57 (t, J=7.3 Hz, 2H), 2.86 (t, J=7.3 Hz, 2H).

Example 3(9)

2-(4-(N-phenylcarbonyl-N-(2-(4-methylphenyl)ethyl)aminomethyl)phenyl)benzoic acid TLC: Rf 0.67 (Chloroform:Methanol=9:1);
NMR (DMSO-$d_6$): δ 7.72 (d, J=7.5 Hz, 1H), 7.55-7.52 (m, 1H), 7.44-7.28 (m, 11H), 7.07-7.04 (m, 2H), 6.96-6.93 (m, 2H), 4.62 (s, 2H), 3.50 (t, J=7.5 Hz, 2H), 2.80 (t, J=7.5 Hz, 2H), 2.25 (s, 3H).

Example 3(10)

2-(4-(N-(4-methylphenylcarbonyl)-N-(2-phenylethyl)aminomethyl)phenyl)benzoic acid TLC: Rf 0.50 (Chloroform:Methanol=9:1);
NMR (DMSO-$d_6$): δ 7.73-7.71 (m, 1H), 7.53 (dt, J=1.5, 7.5 Hz, 1H), 7.43 (dt, J=1.5, 7.5 Hz, 1H), 7.36-7.16 (m, 12H), 7.10-7.06 (m, 2H), 4.62 (brs, 2H), 3.54 (t, J=7.3 Hz, 2H), 2.85 (t, J=7.3 Hz, 2H), 2.34 (s, 3H).

Example 3(11)

2-(4-(N-(4-chlorophenylcarbonyl)-N-(2-phenylethyl)aminomethyl)phenyl)benzoic acid TLC: Rf 0.50 (Chloroform:Methanol=9:1);
NMR (DMSO-$d_6$): δ 7.72 (dd, J=7.5, 1.5 Hz, 1H), 7.53 (dt, J=1.5, 7.5 Hz, 1H), 7.45-7.41 (m, 3H), 7.36-7.24 (m, 9H), 7.21-7.17 (m, 1H), 7.11-7.06 (m, 2H), 4.62 (brs, 2H), 3.55 (t, J=7.3 Hz, 2H), 2.86 (t, J=7.3 Hz, 2H).

Example 3(12)

2-(4-(N-(4-nitrophenylcarbonyl)-N-(2-phenylethyl)aminomethyl)phenyl)benzoic acid TLC: Rf 0.50 (Chloroform:Methanol=9:1);
NMR (DMSO-$d_6$): δ 8.20 (d, J=8.5 Hz, 2H), 7.73 (d, J=7.5 Hz, 1H), 7.56-7.51 (m, 3H), 7.43 (t, J=7.5 Hz, 1H), 7.36-7.24 (m, 7H), 7.22-7.18 (m, 1H), 7.14-7.05 (m, 2H), 4.64 (brs, 2H), 3.60-3.52 (m, 2H), 2.88 (t, J=7.5 Hz, 2H).

Example 3(13)

2-(4-(N-(4-methoxyphenylcarbonyl)-N-(3-phenylpropyl)aminomethyl)phenyl)benzoic acid TLC: Rf 0.48 (Chloroform:Methanol=9:1);
NMR (DMSO-$d_6$): δ 12.70 (s, 1H), 7.72 (dd, J=1.5, 7.8 Hz, 1H), 7.57 (dt, J=1.5, 7.8 Hz, 1H), 7.45 (dt, J=1.5, 7.8 Hz, 1H), 7.40-7.00 (m, 12H), 6.94 (d, J=8.4 Hz, 2H), 4.65 (m, 2H), 3.79 (s, 3H), 3.30 (m, 2H), 2.60-2.40 (m, 2H), 1.95-1.80 (m, 2H).

Example 3(14)

2-(4-(N-(4-butoxyphenylcarbonyl)-N-(3-phenylpropyl)aminomethyl)phenyl)benzoic acid TLC: Rf 0.60 (Chloroform:Methanol=9:1);
NMR (DMSO-$d_6$): δ 7.91 (dd, J=1.2, 7.5 Hz, 1H), 7.55 (dt, J=1.5, 7.5 Hz, 1H), 7.40 (dt, J=1.5, 7.5 Hz, 1H), 7.35-7.10 (m, 12H), 6.84 (d, J=9.0 Hz, 2H), 4.80-4.60 (m, 2H), 3.95 (t, J=6.6 Hz, 2H), 3, 60-3.40 (m, 2H), 2.70-2.40 (m, 2H), 2.00 (m, 4H), 1.60-1.40 (m, 2H), 0.97 (t, J=7.5 Hz, 3H).

Example 3(15)

2-(4-(N-phenylcarbonyl-N-(3-phenylpropyl)aminomethyl)phenyl)benzoic acid

TLC: Rf 0.24 (Hexane:Ethyl acetate=2:1);
NMR (DMSO-$d_6$): δ 12.70 (s, 1H), 7.72 (dd, J=1.2, 7.2 Hz, 1H), 7.56 (dt, J=1.2, 7.5 Hz, 1H), 7.50-6.95 (m, 16H), 4.80-4.40 (m, 2H), 3.50-3.10 (m, 2H), 2.70-2.30 (m, 2H), 2.00-1.80 (m, 2H).

Example 3(16)

2-(4-(N-(1-phenyl-5-propylpyrazol-4-ylcarbonyl)-N-(3-phenylpropyl)aminomethyl)phenyl)benzoic acid TLC: Rf 0.26 (Dichloromethane:Ethyl acetate=2:1);
NMR (DMSO-$d_6$): δ 12.60 (s, 1H), 7.80-7.10 (m, 19H), 4.74 (s, 2H), 3.42 (t, J=7.2 Hz, 2H), 2.75 (t, J=7.8 Hz, 2H), 2.60-2.50 (m, 2H), 2.00-1.80 (m, 2H), 1.40-1.30 (m, 2H), 0.70 (t, J=7.5 Hz, 3H).

Example 3(17)

2-(4-(N-(naphthalen-1-ylcarbonyl)-N-(3-phenylpropyl)aminomethyl)phenyl)benzoic acid TLC: Rf 0.50 (Chloroform:Methanol=9:1);
NMR (DMSO-$d_6$): δ 12.85-12.60 (br, 1H), 8.00-7.95 (m, 2H), 7.80-7.02 (m, 17H), 6.76-6.73 (m, 1H), 4.86 and 4.36-4.27 (m, 2H), 3.85-3.66 and 3.40-3.20 and 3.10-2.85 (br, 2H), 2.69-2.64 and 2.21-2.16 (m, 2H), 2.06-1.96 and 1.77-1.61 (m, 2H).

Example 3(18)

2-(4-(N-(2-chloro-4,5-dimethoxyphenylcarbonyl)-N-(3-phenylpropyl)aminomethyl)phenyl)benzoic acid TLC: Rf 0.50 (Dichloromethane:Methanol=15:1);
NMR (DMSO-$d_6$): δ 12.70 (brs, 1H), 7.75-6.85 (m, 15H), 5.05-4.30 (m, 2H), 3.82-3.60 (m, 6H), 3.20-2.95 (m, 2H), 2.70-2.60 (m, 1H), 2.40-2.30 (m, 1H), 2.00-1.60 (m, 2H).

Example 3(19)

2-(4-(N-(4-difluoromethoxyphenylcarbonyl)-N-(3-phenylpropyl)aminomethyl)phenyl)benzoic acid TLC: Rf 0.44 (Dichloromethane:Ethyl acetate=19:1);
NMR (DMSO-$d_6$): δ 7.72-7.00 (m, 18H), 4.80-4.40 (m, 2H), 3.50-3.00 (m, 2H), 2.70-2.30 (m, 2H), 2.00-1.80 (m, 2H).

Example 3(20)

2-(4-(N-(2,5-dichlorophenylcarbonyl)-N-(3-phenylpropyl)aminomethyl)phenyl)benzoic acid TLC: Rf 0.46 (Dichloromethane:Methanol=19:1);
NMR (DMSO-$d_6$): δ 8.00-6.90 (m, 16H), 5.00-4.30 (m, 2H), 3.80-2.90 (m, 2H), 2.70-2.30 (m, 2H), 2.00-1.70 (m, 2H).

Example 3(21)

2-(4-(N-(2,5-dimethoxyphenylcarbonyl)-N-(3-phenylpropyl)aminomethyl)phenyl)benzoic acid TLC: Rf 0.81 (Dichloromethane:Methanol=5:1);
NMR (DMSO-$d_6$): δ 7.80-6.80 (m, 16H), 5.00-4.40 (m, 1H), 4.36-3.75 (m, 1H), 3.74-3.60 (m, 6H), 3.30-2.95 (m, 2H), 2.70-2.30 (m, 2H), 1.90-1.60 (m, 2H).

Example 3(22)

2-(4-(N-(4-methoxyphenylmethylcarbonyl)-N-(3-phenylpropyl)aminomethyl)phenyl)benzoic acid TLC: Rf 0.64 (Dichloromethane:Methanol=5:1);
NMR (DMSO-d6): δ 7.80-6.80 (m, 17H), 4.65-4.50 (m, 2H), 3.73-3.60 (m, 5H), 3.40-3.20 (m, 2H), 2.60-2.40 (m, 2H), 1.80-1.70 (m, 2H).

Example 3(23)

2-(4-(N-(2,5-dichlorophenylcarbonyl)-N-(3-(4-methoxyphenyl)propyl)aminomethyl)phenyl)benzoic acid TLC: Rf 0.50 (Dichloromethane:Methanol=15:1);
NMR (DMSO-$d_6$): δ 7.80-7.10 (m, 12H), 6.85-6.65 (m, 3H), 5.00-4.30 (m, 2H), 3.80-3.60 (m, 3H), 3.20-2.80 (m, 2H), 2.60-2.20 (m, 2H), 2.00-1.60 (m, 2H).

Example 3(24)

2-(4-(N-(3,5-dimethoxyphenylmethyl)-N-(2-phenylethylcarbonyl)aminomethyl)phenyl)benzoic acid TLC: Rf 0.42 (Dichloromethane:Methanol=9:1);
NMR (CDCl$_3$): δ 7.93 (dd, J=6.6, 6.6 Hz, 1H), 7.55 (m, 1H), 7.42 (m, 1H), 7.35 (d, J=7.5 Hz, 1H), 7.38-7.02 (m, 9H), 6.36 (s, 2H), 6.21 (d, J=2.1 Hz, 1H), 4.64 (s, 1H), 4.55 (s, 1H), 4.43 (s, 1H), 4.35 (s, 1H), 3.75 (s, 3H), 3.74 (s, 3H), 3.02 (m, 2H), 2.72 (m, 2H).

Example 3(25)

2-(4-(N-(3,5-dichlorophenylmethyl)-N-(2-phenylethylcarbonyl)aminomethyl)phenyl)benzoic acid TLC: Rf 0.44 (Dichloromethane:Methanol=9:1);
NMR (CDCl$_3$): δ 7.94 (m, 1H), 7.54 (m, 1H), 7.45-6.90 (m, 14H), 4.62-4.25 (m, 4H), 3.10-2.98 (m, 2H), 2.80-2.56 (m, 2H).

Example 3(26)

2-(4-(N-(2-(4-trifluoromethylphenyl)ethylcarbonyl)-N-(4-fluorophenylmethyl)aminomethyl)phenyl)benzoic acid TLC: Rf 0.40 (Dichloromethane:Methanol=9:1);
NMR (CDCl$_3$): δ 7.94 (dd, J=8.4, 8.4 Hz, 1H), 7.62-6.92 (m, 15H), 4.57 (m, 2H), 4.40 (m, 2H), 3.09 (t, J=7.5 Hz, 2H), 2.74 (m, 2H).

Example 3(27)

2-(4-(N-(2-(2,6-dichlorophenyl)ethylcarbonyl)-N-(4-fluorophenylmethyl)aminomethyl)phenyl)benzoic acid TLC: Rf 0.42 (Dichloromethane:Methanol=9:1);
NMR (CDCl$_3$): δ 7.95 (dd, J=6.9, 6.9 Hz, 1H), 7.60-6.95 (m, 14H), 4.61 (m, 2H), 4.46 (m, 2H), 3.36 (m, 2H), 2.70 (m, 2H).

Example 3(28)

2-(4-(N-(2-(4-trifluoromethylphenyl)ethylcarbonyl)-N-(3-fluorophenylmethyl)aminomethyl)phenyl)benzoic acid TLC: Rf 0.36 (Dichloromethane:Methanol=9:1);
NMR (CDCl$_3$): δ 7.95 (dd, J=7.5, 7.5 Hz, 1H), 7.62-7.15 (m, 12H), 7.10-6.70 (m, 3H), 4.61 (m, 2H), 4.42 (m, 2H), 3.10 (t, J=7.5 Hz, 2H), 2.80-2.65 (m, 2H).

Example 3(29)

2-(4-(N-(2-(2,6-dichlorophenyl)ethylcarbonyl)-N-(3-fluorophenylmethyl)aminomethyl)phenyl)benzoic acid TLC: Rf 0.33 (Dichloromethane:Methanol=9:1);
NMR (CDCl$_3$): δ 7.95 (dd, J=7.5, 7.5 Hz, 1H), 7.58 (m, 1H), 7.44 (m, 1H), 7.40-7.15 (m, 9H), 7.10-6.92 (m, 3H), 4.65 (m, 2H), 4.49 (m, 2H), 3.41-3.32 (m, 2H), 2.78-2.60 (m, 2H).

Example 3(30)

2-(4-(N-(2-(2,6-dichlorophenyl)ethylcarbonyl)-N-(3,5-dichlorophenylmethyl)aminomethyl)phenyloxy)benzoic acid TLC: Rf 0.40 (Dichloromethane:Methanol=9:1);
NMR (DMSO-d$_6$): δ 7.82 (d, J=7.2 Hz, 1H), 7.59-6.83 (m, 13H), 4.63-4.55 (m, 4H), 3.15-3.05 (m, 2H), 2.70-2.50 (m, 2H).

Example 3(31)

2-(4-(N-(2-(3-trifluoromethoxyphenyl)ethylcarbonyl)-N-(3,5-dichlorophenylmethyl)aminomethyl)phenyloxy)benzoic acid TLC: Rf 0.39 (Dichloromethane:Methanol=9:1);
NMR (DMSO-d$_6$): δ 7.82 (d, J=7.5 Hz, 1H), 7.55 (m, 1H), 7.47 (m, 1H), 7.35 (m, 1H), 7.29-7.06 (m, 8H), 6.92 (m, 1H), 6.87-6.80 (m, 2H), 4.60-4.45 (m, 4H), 2.95-2.65 (m, 4H).

Example 3(32)

2-(4-(N-(4-difluoromethoxyphenylcarbonyl)-N-(3-phenylpropyl)aminomethyl)phenyloxy)benzoic acid TLC: Rf 0.68 (Dichloromethane:Methanol=9:1);
NMR (DMSO-d$_6$): δ 8.00-6.80 (m, 18H), 4.80-4.40 (m, 2H), 3.50-3.00 (m, 2H), 2.70-2.20 (m, 2H), 2.00-1.70 (m, 2H).

Example 3(33)

2-(4-(N-(3,5-dimethoxyphenylcarbonyl)-N-(3-phenylpropyl)aminomethyl)phenyloxy)benzoic acid TLC: Rf 0.50 (Dichloromethane:Methanol=9:1);
NMR (DMSO-d$_6$): δ 7.85-6.40 (m, 16H), 4.70-4.30 (m, 2H), 3.80-3.60 (m, 6H), 3.40-3.30 (m, 2H), 2.60-2.30 (m, 2H), 1.90-1.70 (m, 2H).

Example 3(34)

2-(4-(N-(4-difluoromethoxyphenylcarbonyl)-N-(3-phenylpropyl)aminomethyl)phenyloxy)-4-methoxybenzoic acid TLC: Rf 0.65 (Dichloromethane:Methanol=9:1);
NMR (DMSO-d$_6$): δ 7.90-6.45 (m, 17H), 4.70-4.40 (m, 2H), 3.76 (s, 3H), 3.40-3.00 (m, 2H), 2.70-2.30 (m, 2H), 1.80-1.70 (m, 2H).

Example 3(35)

2-(4-(N-(3,5-dimethoxyphenylcarbonyl)-N-(3-phenylpropyl)aminomethyl)phenyloxy)-4-methoxybenzoic acid TLC: Rf 0.73 (Dichloromethane:Methanol=9:1);
NMR (DMSO-d$_6$): δ 7.90-6.45 (m, 15H), 4.70-4.30 (m, 2H), 3.80-3.60 (m, 9H), 3.40-3.00 (m, 2H), 2.60-2.30 (m, 2H), 1.90-1.70 (m, 2H).

Example 3(36)

2-(4-(N-(3,4,5-trimethoxyphenylcarbonyl)-N-(3-phenylpropyl)aminomethyl)phenyloxy)benzoic acid TLC: Rf 0.63 (Dichloromethane:Methanol=9:1);
NMR (DMSO-$d_6$): δ 7.83 (dd, J=1.5, 7.8 Hz, 1H), 7.60-7.50 (m, 1H), 7.40-6.90 (m, 9H), 6.89 (d, J=8.7 Hz, 2H), 6.63 (s, 2H), 4.70-4.40 (m, 2H), 3.80-3.60 (m, 9H), 3.40-3.00 (m, 2H), 2.80-2.30 (m, 2H), 2.00-1.80 (m, 2H).

Example 3(37)

2-(4-(N-(2,5-dichlorophenylcarbonyl)-N-(3-phenylpropyl)aminomethyl)phenyloxy)benzoic acid TLC: Rf 0.64 (Dichloromethane:Methanol=9:1);
NMR (DMSO-$d_6$): δ 7.90-6.80 (m, 16H), 4.90-4.20 (m, 2H), 3.80-2.80 (m, 2H), 2.70-2.30 (m, 2H), 1.95-1.60 (m, 2H).

Example 3(38)

2-(4-(N-(3,5-dimethoxy-4-methylphenylcarbonyl)-N-(3-phenylpropyl)aminomethyl)phenyloxy)benzoic acid TLC: Rf 0.38 (Dichloromethane:Methanol=9:1);
NMR (CDCl$_3$): δ 8.22 (dd, J=7.8, 1.8 Hz, 1H), 7.48 (ddd, J=7.8, 7.2, 1.8 Hz, 1H), 7.43-6.91 (m, 10H), 6.89-6.77 (m, 1H), 6.54 (s, 2H), 4.79-4.42 (m, 2H), 3.86-3.13 (m, 8H), 2.77-2.31 (m, 2H), 2.16-1.78 (m, 5H).

Example 3(39)

2-(4-(N-(3,4,5-trifluorophenylcarbonyl)-N-(3-phenylpropyl)aminomethyl)phenyloxy)benzoic acid TLC: Rf 0.41 (Dichloromethane:Methanol=9:1);
NMR (CDCl$_3$): δ 8.22 (dd, J=8.1, 1.8 Hz, 1H), 7.50 (ddd, J=8.1, 7.2, 1.8 Hz, 1H), 7.38-6.84 (m, 13H), 4.79-4.31 (m, 2H), 3.58-3.03 (m, 2H), 2.79-2.37 (m, 2H), 2.05-1.76 (m, 2H).

Example 3(40)

2-(4-(N-(3,5-dimethyl-4-methoxyphenylcarbonyl)-N-(3-phenylpropyl)aminomethyl)phenyloxy)benzoic acid TLC: Rf 0.36 (Dichloromethane:Methanol=9:1);
NMR (CDCl$_3$): δ 8.22 (dd, J=8.1, 1.8 Hz, 1H), 7.48 (ddd, J=8.1, 7.5, 1.8 Hz, 1H), 7.40-6.90 (m, 12H), 6.87-6.80 (m, 1H), 4.79-4.38 (m, 2H), 3.72 (s, 3H), 3.57-3.12 (m, 2H), 2.76-2.37 (m, 2H), 2.27 (s, 6H), 2.06-1.78 (m, 2H).

Example 3(41)

2-(4-(N-(2,3,4-trimethoxyphenylcarbonyl)-N-(3-phenylpropyl)aminomethyl)phenyloxy)benzoic acid TLC: Rf 0.59 (Dichloromethane:Methanol=9:1);
NMR (CDCl$_3$): δ 8.26-8.18 (m, 1H), 7.53-6.64 (m, 14H), 5.35-4.21 (m, 2H), 3.97-3.81 (m, 9H), 3.30-2.96 (m, 2H), 2.74-2.35 (m, 2H), 2.02-1.65 (m, 2H).

Example 3(42)

2-(4-(N-(2,3,6-trifluorophenylcarbonyl)-N-(3-phenylpropyl)aminomethyl)phenyloxy)benzoic acid TLC: Rf 0.44 (Dichloromethane:Methanol=9:1);
NMR (CDCl$_3$): δ 8.24-8.16 (m, 1H), 7.53-7.45 (m, 1H), 7.37-6.79 (m, 13H), 4.88-4.38 (m, 2H), 3.60-3.04 (m, 2H), 2.78-2.39 (m, 2H), 2.03-1.75 (m, 2H).

Example 3(43)

2-(4-(N-(3,5-dimethoxy-4-methylphenylcarbonyl)-N-(3-phenylpropyl)aminomethyl)phenyloxy)-4-chlorobenzoic acid TLC: Rf 0.70 (Dichloromethane:Methanol=9:1);
NMR (CDCl$_3$): δ 8.12 (d, J=8.7 Hz, 1H), 7.50-6.70 (m, 11H), 6.54 (s, 2H), 4.80-4.50 (m, 2H), 3.90-3.60 (m, 6H), 3.60-3.10 (m, 2H), 2.80-2.40 (m, 2H), 2.20-1.80 (m, 5H).

Example 3(44)

2-(4-(N-(2-(2,6-dichlorophenyl)ethylcarbonyl)-N-(2-trifluoromethylphenylmethyl)aminomethyl)phenyloxy)benzoic acid TLC: Rf 0.43 (Dichloromethane:Methanol=9:1);
NMR (DMSO-$d_6$): δ 7.82 (dd, J=7.8, 1.8 Hz, 1H), 7.77-7.14 (m, 11H), 6.96-6.83 (m, 3H), 4.75-4.67 (m, 2H), 4.60-4.53 (m, 2H), 3.20-3.05 (m, 2H), 2.80-2.45 (m, 2H).

Example 3(45)

2-(4-(N-(2-(3-chlorophenyl)ethylcarbonyl)-N-(2-trifluoromethylphenylmethyl)aminomethyl)phenyloxy)benzoic acid TLC: Rf 0.38 (Dichloromethane:Methanol=9:1);
NMR (DMSO-$d_6$): δ 7.85-7.10 (m, 13H), 6.98-6.80 (m, 3H), 4.70-4.45 (m, 4H), 2.98-2.60 (m, 4H).

Example 3(46)

2-(4-(N-(3,5-dimethoxy-4-methylphenylcarbonyl)-N-(3-(3-fluorophenyl)propyl)aminomethyl)phenyloxy)benzoic acid TLC: Rf 0.46 (Dichloromethane:Methanol=9:1);
NMR (DMSO-$d_6$): δ 12.82 (brs, 1H), 7.82 (dd, J=7.8, 1.8 Hz, 1H), 7.55 (m, 1H), 7.38-6.92 (m, 8H), 6.88 (d, J=8.7 Hz, 2H), 6.55 (s, 2H), 4.75-4.38 (m, 2H), 3.80-3.58 (m, 6H), 3.40-3.00 (m, 2H), 2.68-2.30 (m, 2H), 1.98 (s, 3H), 1.96-1.70 (m, 2H).

Example 3(47)

(2-(4-(N-(4-methoxyphenylcarbonyl)-N-(3-phenylpropyl)aminomethyl)phenyl)phenyl)acetic acid TLC: Rf 0.56 (Dichloromethane:Methanol=15:1);
NMR (CDCl$_3$): δ 7.45-6.90 (m, 15H), 6.86 (d, J=8.7 Hz, 2H), 4.80-4.50 (m, 2H), 3.81 (s, 3H), 3.60 (s, 2H), 3.60-3.20 (m, 2H), 2.70-2.40 (m, 2H), 2.00-1.80 (m, 2H).

Example 3(48)

(2-(4-(N-(3,5-dimethoxyphenylcarbonyl)-N-(3-phenylpropyl)aminomethyl)phenyl)phenyl)acetic acid TLC: Rf 0.53 (Dichloromethane:Methanol=15:1);
NMR (DMSO-$d_6$): δ 7.40-6.90 (m, 14H), 6.60-6.50 (m, 2H), 4.80-4.40 (m, 2H), 3.80-3.60 (m, 6H), 3.60-3.10 (m, 4H), 2.70-2.30 (m, 2H), 2.00-1.80 (m, 2H).

Example 3(49)

(2-(4-(N-(2,5-dichlorophenylcarbonyl)-N-(3-phenylpropyl)aminomethyl)phenyl)phenyl)acetic acid TLC: Rf 0.54 (Dichloromethane:Methanol=19:1);
NMR (DMSO-$d_6$): δ 7.60-6.80 (m, 16H), 5.00-4.30 (m, 2H), 3.80-3.40 (m, 2H), 3.30-2.80 (m, 2H), 2.70-2.30 (m, 2H), 2.00-1.70 (m, 2H).

Example 3(50)

(4-(N-(3,4,5-trimethoxyphenylcarbonyl)-N-(3-phenylpropyl)aminomethyl)phenyloxy)acetic acid TLC: Rf 0.24 Dichloromethane:Methanol=9:1);
NMR (CDCl$_3$): δ 7.40-6.90 (m, 7H), 6.88 (d, J=8.7 Hz, 2H), 6.59 (s, 2H), 4.70-4.40 (m, 4H), 3.95-3.60 (m, 9H), 3.60-3.10 (m, 2H), 2.75-2.35 (m, 2H), 2.10-1.80 (m, 2H).

Example 3(51)

(4-(N-(3,5-dimethyl-4-hydroxyphenylcarbonyl)-N-(3-phenylpropyl)aminomethyl)phenyloxy)acetic acid TLC: Rf 0.18 (Dichloromethane:Methanol=9:1);
NMR (CDCl$_3$): δ 7.30-6.90 (m, 7H), 6.98 (s, 2H), 6.81 (d, J=8.4 Hz, 2H), 4.70-4.40 (m, 4H), 3.50-3.10 (m, 2H), 2.70-2.30 (m, 2H), 2.17 (s, 6H), 2.00-1.75 (m, 2H).

Example 3(52)

(2-(N-(3,4,5-trimethoxyphenylcarbonyl)-N-(3-phenylpropyl)aminomethyl)phenyloxy)acetic acid TLC: Rf 0.54 (Dichloromethane:Methanol=9:1);
NMR (CDCl$_3$): δ 7.40-6.40 (m, 11H), 4.90-4.50 (m, 4H), 3.95-3.10 (m, 11H), 2.80-2.40 (m, 2H), 2.10-1.80 (m, 2H).

Example 3(53)

(2-(N-(3,5-dimethoxy-4-methylphenylcarbonyl)-N-(3-phenylpropyl)aminomethyl)phenyloxy)acetic acid TLC: Rf 0.62 (Dichloromethane:Methanol=9:1);
NMR (CDCl$_3$): δ 7.40-6.40 (m, 11H), 4.90-4.50 (m, 4H), 3.80-3.10 (m, 8H), 2.80-2.40 (m, 2H), 2.10-1.80 (m, 5H).

Example 3(54)

(3-(N-(3,4,5-trimethoxyphenylcarbonyl)-N-(3-phenylpropyl)aminomethyl)phenyl)acetic acid TLC: Rf 0.48 (Dichloromethane:Methanol=9:1);
NMR (CDCl$_3$): δ 7.34-6.90 (m, 9H), 6.59, 6.51 (s, 2H), 4.81-4.43 (m, 2H), 3.83-3.10 (m, 13H), 2.79-2.32 (m, 2H), 2.12-1.78 (m, 2H).

Example 3(55)

(3-(N-(3,5-dimethoxy-4-methylphenylcarbonyl)-N-(3-phenylpropyl)aminomethyl)phenyl)acetic acid TLC: Rf 0.41 (Dichloromethane:Methanol=9:1);
NMR (CDCl$_3$): δ 7.33-6.90 (m, 9H), 6.53, 6.46 (s, 2H), 4.78-4.43 (m, 2H), 3.88-3.11 (m, 10H), 2.74-2.33 (m, 2H), 2.14-1.73 (m, 5H).

Example 3(56)

(4-(N-(3,4,5-trimethoxyphenylcarbonyl)-N-(3-phenyl-2-propenyl)aminomethyl)phenyloxy)acetic acid TLC: Rf 0.29 (Dichloromethane:Methanol=9:1);
NMR (DMSO-$d_6$): δ 12.26 (s, 1), 7.48-7.18 (m, 9H), 6.82-6.65 (m, 2H), 6.51 (m, 1H), 6.31 (m, 1H), 4.72-4.40 (m, 2H), 4.25-3.80 (m, 2H), 3.82-3.50 (m, 9H), 3.55 (s, 2H).

Example 3(57)

(4-(N-(3,5-dimethoxy-4-methylphenylcarbonyl)-N-(3-phenyl-2-propenyl)aminomethyl)phenyl)acetic acid TLC: Rf 0.32 (Dichloromethane:Methanol=9:1);
NMR (DMSO-$d_6$): δ 12.26 (s, 1H), 7.50-7.18 (m, 9H), 6.80-6.44 (m, 3H), 6.31 (m, 1H), 4.75-4.40 (m, 2H), 4.25-3.84 (m, 2H), 3.82-3.50 (m, 6H), 3.55 (s, 2H), 1.98 (s, 3H).

Example 3(58)

(4-(N-(3,5-dimethoxyphenylcarbonyl)-N-(3-phenyl-2-propenyl)aminomethyl)phenyl)acetic acid TLC: Rf 0.34 (Dichloromethane:Methanol=9:1);
NMR (DMSO-$d_6$): δ 12.27 (s, 1H), 7.46-7.12 (m, 9H), 6.65-6.38 (m, 4H), 6.27 (m, 1H), 4.72-4.40 (m, 2H), 4.20-3.82 (m, 2H), 3.82-3.60 (m, 6H), 3.55 (s, 2H).

Reference Example 3

2-(4-(3-phenylpropyl)aminomethyl)phenyloxy)benzoic acid methyl ester

The title compound having the following physical data was obtained by the same procedure as described in Reference example 3 using 2-(4-formylphenyloxy)benzoic acid instead of the compound prepared in Reference example 1.

TLC: Rf 0.61 (Dichloromethane:Methanol=9:1);
NMR (CDCl$_3$): δ 7.95-7.90 (m, 1H), 7.50-7.40 (m, 1H), 7.30-7.15 (m, 8H), 7.00-6.90 (m, 3H), 3.81 (s, 3H), 3.76 (s, 2H), 2.70-2.60 (m, 4H), 1.90-1.80 (m, 2H).

Example 4

2-(4-(N-(3,5-dimethoxy-4-hydroxyphenylcarbonyl)-N-(3-phenylpropyl)aminomethyl)phenyloxy)benzoic acid methyl ester To a solution of 3,5-dimethoxy-4-hydroxybenzoic acid (77 mg) in N,N-dimethylformamide (1.5 ml), the compound prepared in Reference example 3 (50 mg), PS-carbodiimide (420 mg, Cat. No.: 800371, Argonaut Technologies, Inc.) and 1-hydroxybenztriazole hydrate (60 mg) were added and the mixture was stirred for 1 day at room temperature.

PS-trisamine (340 mg, Cat. No.: 800230, Argonaut Technologies, Inc.) was added to the reaction mixture and the mixture was stirred for 2 hours at room temperature. The reaction mixture was purified by column chromatography on alumina ($Al_2O_3$) (Ethyl acetate:Methanol=19:1). The residue was purified by column chromatography on silica gel (Hexane:Ethyl acetate=1:1) to give the compound of the present invention (44 mg) having the following physical data.

TLC: Rf 0.13 (Hexane:Ethyl acetate=1:1).

Example 5

2-(4-(N-(3,5-dimethoxy-4-hydroxyphenylcarbonyl)-N-(3-phenylpropyl)aminomethyl)phenyloxy)benzoic acid The compound of the present invention having the following physical data was obtained by the same procedure as described in Example 2 the compound prepared in Example 4 instead of the compound prepared in Example 1.

TLC: Rf 0.36 (Dichloromethane:Methanol=12:1);
NMR ($CDCl_3$): δ 8.22 (dd, J=1.5, 7.5 Hz, 1H), 7.50-7.45 (m, 1H), 7.40-7.00 (m, 10H), 6.83 (d, J=8.1 Hz, 1H), 6.64 (s, 2H), 5.55 (s, 1H), 4.65 (s, 2H), 3.95-3.70 (m, 6H), 3.60-3.20 (m, 2H), 2.70-2.40 (m, 2H), 2.10-1.80 (m, 2H).

Examples 5(1)-5(141)

The following compounds of the present invention were obtained by the same procedures as described in Reference example 3, Example 4 and Example 5 using the compounds prepared in Reference example 1 or corresponding aldehyde and 3-phenylpropylamine or corresponding amine.

Example 5(1)

2-(4-(N-(3,5-dimethyl-4-hydroxyphenylcarbonyl)-N-(3-phenylpropyl)aminomethyl)phenyloxy)benzoic acid TLC: Rf 0.35 (Dichloromethane:Methanol=12:1);
NMR ($CDCl_3$): δ 8.25-6.80 (m, 15H), 4.80-4.50 (m, 2H), 3.50-3.20 (m, 2H), 2.80-2.40 (m, 2H), 2.30-2.20 (m, 6H), 2.00-1.80 (m, 2H).

Example 5(2)

2-(4-(N-(2-chloro-4,5-dimethoxyphenylcarbonyl)-N-(3-phenylpropyl)aminomethyl)phenyloxy)benzoic acid TLC: Rf 0.47 (Dichloromethane:Methanol=12:1);
NMR ($CDCl_3$): δ 8.30-6.70 (m, 15H), 5.30-4.30 (m, 2H), 4.00-3.75 (m, 6H), 3.60-3.00 (m, 2H), 2.80-2.40 (m, 2H), 2.10-1.80 (m, 2H).

Example 5(3)

2-(4-(N-(3,4,5-trimethoxyphenylcarbonyl)-N-(3-phenylpropyl)aminomethyl)phenyloxy)-4-chlorobenzoic acid TLC: Rf 0.37 (Dichloromethane:Methanol=12:1);
NMR ($CDCl_3$): δ 8.13 (d, J=8.4 Hz, 1H), 7.40-6.70 (m, 11H), 6.61 (s, 2H), 4.80-4.40 (m, 2H), 3.90-3.70 (m, 9H), 3.60-3.20 (m, 2H), 2.80-2.40 (m, 2H), 2.10-1.80 (m, 2H).

Example 5(4)

2-(4-(N-(3,5-dimethoxy-4-hydroxyphenylcarbonyl)-N-(3-phenylpropyl)aminomethyl)phenyloxy)-4-chlorobenzoic acid TLC: Rf 0.25 (Dichloromethane:Methanol=12:1);
NMR ($CDCl_3$): δ 8.13 (d, J=8.7 Hz, 1H), 7.40-6.60 (m, 13H), 5.65 (s, 1H), 4.70-4.50 (m, 2H), 3.90-3.70 (m, 6H), 3.60-3.20 (m, 2H), 2.70-2.40 (m, 2H), 2.00-1.80 (m, 2H).

Example 5(5)

2-(4-(N-(4-difluoromethoxyphenylcarbonyl)-N-(3-phenylpropyl)aminomethyl)phenyloxy)-4-chlorobenzoic acid TLC: Rf 0.34 (Dichloromethane:Methanol=12:1);
NMR($CDCl_3$): δ 8.13 (d, J=8.4 Hz, 1H), 7.50-650 (m, 16H), 4.80-4.40 (m, 2H), 3.60-3.10 (m, 2H), 2.80-2.40 (m, 2H), 2.00-1.80 (m, 2H).

Example 5(6)

2-(4-(N-(2-chloro-4,5-dimethoxyphenylcarbonyl)-N-(3-phenylpropyl)aminomethyl)phenyloxy)-4-chlorobenzoic acid TLC: Rf 0.37 (Dichloromethane:Methanol=12:1);
NMR ($CDCl_3$): δ 8.15-8.10 (m, 1H), 7.50-6.70 (m, 13H), 5.30-4.30 (m, 2H), 4.00-3.75 (m, 6H), 3.20-2.60 (m, 2H), 2.50-1.90 (m, 2H), 1.90-1.60 (m, 2H).

Example 5(7)

2-(4-(N-(2,5-dichlorophenylcarbonyl)-N-(3-phenylpropyl)aminomethyl)phenyloxy)-4-chlorobenzoic acid TLC: Rf 0.37 (Dichloromethane:Methanol=12:1);
NMR ($CDCl_3$): δ 8.15-8.10 (m, 1H), 7.40-6.80 (m, 14H), 5.20-4.30 (m, 2H), 3.95-3.00 (m, 2H), 2.80-2.40 (m, 2H), 2.10-1.70 (m, 2H).

Example 5(8)

2-(4-(N-(3,4,5-trimethoxyphenylcarbonyl)-N-(3-phenylpropyl)aminomethyl)phenyloxy)-4-methoxybenzoic acid TLC: Rf 0.37 (Dichloromethane:Methanol=12:1);
NMR ($CDCl_3$): δ 8.18 (d, J=8.7 Hz, 1H), 7.40-6.60 (m, 13H), 4.80-4.50 (m, 2H), 4.00-3.70 (m, 12H), 3.60-3.20 (m, 2H), 2.80-2.40 (m, 2H), 2.10-1.80 (m, 2H).

Example 5(9)

2-(4-(N-(2,5-dichlorophenylcarbonyl)-N-(3-phenylpropyl)aminomethyl)phenyloxy)-4-methoxybenzoic acid TLC: Rf 0.38 (Dichloromethane:Methanol=12:1);
NMR ($CDCl_3$): δ 8.20-8.15 (m, 1H), 7.40-6.90 (m, 12H), 6.80-6.70 (m, 1H), 6.35-6.30 (m, 1H), 5.20-4.30 (m, 2H), 3.76 (s, 3H), 3.90-3.00 (m, 2H), 2.80-2.40 (m, 2H), 2.10-1.70 (m, 2H).

Example 5(10)

2-(4-(N-(3,4,5-trimethoxyphenylcarbonyl)-N-(3-phenylpropyl)aminomethyl)phenyloxy)-5-chlorobenzoic acid TLC: Rf 0.50 (Dichloromethane:Methanol=9:1);
NMR (CDCl$_3$): δ 8.13 (d, J=2.7 Hz, 1H), 7.43 (dd, J=8.7, 2.7 Hz, 1H), 7.39-6.93 (m, 9H), 6.84-6.77 (m, 1H), 6.60 (s, 2H), 4.80-4.38 (m, 2H), 3.95-3.63 (m, 9H), 3.62-3.11 (m, 2H), 2.78-2.30 (m, 2H), 2.09-1.79 (m, 2H).

Example 5(11)

2-(4-(N-(3,5-dimethoxyphenylcarbonyl)-N-(3-phenylpropyl)aminomethyl)phenyloxy)-5-chlorobenzoic acid TLC: Rf 0.49 (Dichloromethane:Methanol=9:1);
NMR (CDCl$_3$): δ 8.18-8.13 (m, 1H), 7.43 (dd, J=8.7, 2.7 Hz, 1H), 7.39-6.93 (m, 9H), 6.84-6.77 (m, 1H), 6.54-6.45 (m, 3H), 4.79-4.41 (m, 2H), 3.88-3.65 (m, 6H), 3.57-3.38 (m, 1H), 3.31-3.11 (m, 1H), 2.76-2.37 (m, 2H), 2.07-1.78 (m, 2H).

Example 5(12)

2-(4-(N-(3,5-dimethoxy-4-methylphenylcarbonyl)-N-(3-phenylpropyl)aminomethyl)phenyloxy)-5-chlorobenzoic acid TLC: Rf 0.49 (Dichloromethane:Methanol=9:1);
NMR (CDCl$_3$): δ 8.15 (d, J=2.7 Hz, 1H), 7.43 (dd, J=8.7, 2.7 Hz, 1H), 7.39-6.90 (m, 9H), 6.84-6.76 (m, 1H), 6.53 (s, 2H), 4.79-4.43 (m, 2H), 3.86-3.65 (m, 6H), 3.60-3.11 (m, 2H), 2.76-2.37 (m, 2H), 2.13-1.75 (m, 5H).

Example 5(13)

2-(4-(N-(3,5-dimethyl-4-hydroxyphenylcarbonyl)-N-(3-phenylpropyl)aminomethyl)phenyloxy)-5-chlorobenzoic acid TLC: Rf 0.35 (Dichloromethane:Methanol=9:1);
NMR (CDCl$_3$): δ 8.15 (d, J=2.7 Hz, 1H), 7.42 (dd, J=8.7, 2.7 Hz, 1H), 7.38-6.91 (m, 11H), 6.83-6.77 (m, 1H), 4.77-4.45 (m, 2H), 3.60-3.11 (m, 2H), 2.75-2.30 (m, 2H), 2.21 (s, 6H), 2.00-1.79 (m, 2H).

Example 5(14)

2-(4-(N-(3,4,5-trimethoxyphenylcarbonyl)-N-(3-phenylpropyl)aminomethyl)phenyloxy)-5-methoxybenzoic acid TLC: Rf 0.49 (Dichloromethane:Methanol=9:1);
NMR (CDCl$_3$): δ 7.68 (d, J=3.3 Hz, 1H), 7.35-6.93 (m, 10H), 6.86-6.80 (m, 1H), 6.59 (s, 2H), 4.77-4.42 (m, 2H), 3.94-3.65 (m, 12H), 3.60-3.11 (m, 2H), 2.79-2.33 (m, 2H), 2.09-1.77 (m, 2H).

Example 5(15)

2-(4-(N-(3,5-dimethoxyphenylcarbonyl)-N-(3-phenylpropyl)aminomethyl)phenyloxy)-5-methoxybenzoic acid TLC: Rf 0.49 (Dichloromethane:Methanol=9:1);
NMR (CDCl$_3$): δ 7.70-7.66 (m, 1H), 7.36-6.94 (m, 10H), 6.86-6.80 (m, 1H), 6.53-6.45 (m, 3H), 4.78-4.60 (m, 1H), 4.58-4.39 (m, 1H), 3.86 (s, 3H), 3.84-3.68 (m, 6H), 3.58-3.39 (m, 1H), 3.27-3.10 (m, 1H), 2.73-2.37 (m, 2H), 2.04-1.77 (m, 2H).

Example 5(16)

2-(4-(N-(3,5-dimethoxy-4-methylphenylcarbonyl)-N-(3-phenylpropyl)aminomethyl)phenyloxy)-5-methoxybenzoic acid TLC: Rf 0.49 (Dichloromethane:Methanol=9:1);
NMR (CDCl$_3$): δ 7.69 (d, J=3.3 Hz, 1H), 7.36-6.78 (m, 11H), 6.53 (s, 2H), 4.79-4.41 (m, 2H), 3.86 (s, 3H), 3.84-3.64 (m, 6H), 3.60-3.15 (m, 2H), 2.77-2.36 (m, 2H), 2.19-1.78 (m, 5H).

Example 5(17)

2-(4-(N-(3,5-dimethyl-4-hydroxyphenylcarbonyl)-N-(3-phenylpropyl)aminomethyl)phenyloxy)-5-methoxybenzoic acid TLC: Rf 0.39 (Dichloromethane:Methanol=9:1);
NMR (CDCl$_3$): δ 7.67 (d, J=3.3 Hz, 1H), 7.33-6.81 (m, 13H), 4.76-4.44 (m, 2H), 3.86 (s, 3H), 3.59-3.16 (m, 2H), 2.69-2.30 (m, 2H), 2.20 (s, 6H), 1.99-1.78 (m, 2H).

Example 5(18)

2-(4-(N-(3,4,5-trimethoxyphenylcarbonyl)-N-(3-phenylpropyl)aminomethyl)phenyloxy)-4-methylbenzoic acid TLC: Rf 0.52 (Dichloromethane:Methanol=9:1);
NMR (CDCl$_3$): δ 8.10 (d, J=7.8 Hz, 1H), 7.38-6.92 (m, 10H), 6.65-6.57 (m, 3H), 4.79-4.44 (m, 2H), 3.95-3.64 (m, 9H), 3.63-3.11 (m, 2H), 2.77-2.38 (s, 2H), 2.32 (s, 3H), 2.10-1.81 (m, 2H).

Example 5(19)

2-(4-(N-(3,5-dimethoxyphenylcarbonyl)-N-(3-phenylpropyl)aminomethyl)phenyloxy)-4-methylbenzoic acid TLC: Rf 0.54 (Dichloromethane:Methanol=9:1);
NMR (CDCl$_3$): δ 8.10 (d, J=8.1 Hz, 1H), 7.39-6.96 (m, 10H), 6.65-6.57 (m, 4H), 4.79-4.42 (m, 2H), 3.86-3.68 (m, 6H), 3.58-3.42 (m, 1H), 3.29-3.16 (m, 1H), 2.76-2.36 (m, 2H), 2.32 (s, 3), 2.07-1.78 (m, 2H).

Example 5(20)

2-(4-(N-(3,5-dimethyl-4-hydroxyphenylcarbonyl)-N-(3-phenylpropyl)aminomethyl)phenylox)-4-methylbenzoic acid TLC: Rf 0.52 (Dichloromethane:Methanol=9:1);
NMR (CDCl$_3$): δ 8.10 (d, J=8.4 Hz, 1H), 7.40-6.96 (m, 12H), 6.63 (s, 1H), 5.00-4.45 (m, 2H), 3.57-3.16 (m, 2H), 2.78-2.37 (m, 2H), 2.31 (s, 3H), 2.22 (s, 6H), 2.00-1.80 (m, 2H).

Example 5(21)

2-(4-(N-(3,4,5-trimethoxyphenylcarbonyl)-N-(2-phenylethyl)aminomethyl)phenyloxy)-4-chlorobenzoic acid TLC: Rf 0.70 (Dichloromethane:Methanol=9:1);
NMR (CDCl$_3$): δ 8.01 (d, J=8.4 Hz, 1H), 7.50-6.75 (m, 11H), 6.55 (s, 2H), 4.95-4.30 (m, 2H), 3.90-3.40 (m, 11H), 3.05-2.95 (M, 2H).

Example 5(22)

2-(4-(N-(3,5-dimethoxy-4-methylphenylcarbonyl)-N-(2-phenylethyl)aminomethyl)phenyloxy)-4-chlorobenzoic acid TLC: Rf 0.70 (Dichloromethane:Methanol=9:1);
NMR (CDCl$_3$): δ 8.01 (d, J=8.4 Hz, 1H), 7.50-6.75 (m, 11H), 6.50 (s, 2H), 4.95-4.30 (m, 2H), 3.90-3.40 (m, 8H), 3.10-2.80 (m, 2H), 2.10-2.00 (m, 3H).

Example 5(23)

2-(4-(N-(3,4,5-trimethoxyphenylcarbonyl)-N-(4-phenylbutyl)aminomethyl)phenyloxy)-4-chlorobenzoic acid TLC: Rf 0.70 (Dichloromethane:Methanol=9:1);
NMR (CDCl$_3$): δ 8.01 (d, J=8.7 Hz, 1H), 7.50-6.80 (m, 11H), 6.60 (s, 2H), 4.80-4.50 (m, 2H), 3.90-3.60 (m, 9H), 3.60-3.20 (m, 2H), 2.70-2.45 (m, 2H), 1.80-1.40 (m, 4H).

Example 5(24)

2-(4-(N-(3,5-dimethoxy-4-methylphenylcarbonyl)-N-(4-phenylbutyl)aminomethyl)phenyloxy)-4-chlorobenzoic acid TLC: Rf 0.70 (Dichloromethane:Methanol=9:1);
NMR (CDCl$_3$): δ 8.01 (d, J=8.1 Hz, 1H), 7.50-6.80 (m, 11H), 6.54 (s, 2H), 4.80-4.50 (m, 2H), 3.80-3.60 (m, 6H), 3.60-3.20 (m, 2H), 2.70-2.40 (m, 2H), 2.15-2.00 (m, 3H), 1.80-1.40 (m, 4H).

Example 5(25)

2-(4-(N-(2-trifluoromethylphenylcarbonyl)-N-(3-(3-chlorophenyl)propyl)aminomethyl)phenyloxy)benzoic acid TLC: Rf 0.39 (Dichloromethane:Methanol=9:1);
NMR (DMSO-d$_6$): δ 7.88-6.83 (m, 16H), 4.70-4.35 (m, 2H), 3.40-2.95 (m, 2H), 2.75-2.38 (m, 2H), 1.95-1.70 (m, 2H).

Example 5(26)

2-(4-(N-(3,5-dichlorophenylcarbonyl)-N-(3-(3-trifluoromethoxyphenyl)propyl)aminomethyl)phenyloxy)benzoic acid TLC: Rf 0.40 (Dichloromethane:Methanol=9:1);
NMR (DMSO-d$_6$): δ 7.86-6.80 (m, 15H), 4.90-4.15 (m, 2H), 3.75-2.78 (m, 2H), 2.62-2.25 (m, 2H), 1.95-1.62 (m, 2H).

Example 5(27)

2-(4-(N-(2-trifluoromethylphenylcarbonyl)-N-(3-(2,6-dichlorophenyl)propyl)aminomethyl)phenyloxy)benzoic acid TLC: Rf 0.41 (Dichloromethane:Methanol=9:1);
NMR (DMSO-d$_6$): δ 7.88-6.92 (m, 15H), 4.90-4.15 (m, 2H), 3.80-2.80 (m, 2H), 2.60-2.45 (m, 2H), 1.82-1.60 (m, 2H).

Example 5(28)

2-(4-(N-(3,5-dichlorophenylcarbonyl)-N-(3-(2,6-dichlorophenyl)propyl)aminomethyl)phenyloxy)benzoic acid TLC: Rf 0.39 (Dichloromethane:Methanol=9:1);
NMR (DMSO-d$_6$): δ 7.85-6.82 (m, 14H), 4.70-4.38 (m, 2H), 3.50-2.80 (m, 2H), 2.65-2.40 (m, 2H), 1.85-1.60 (m, 2H).

Example 5(29)

2-(4-(N-(3,5-dimethoxy-4-methylphenylcarbonyl)-N-(3-(3-chlorophenyl)propyl)aminomethyl)phenyloxy)benzoic acid TLC: Rf 0.35 (Dichloromethane:Methanol=9:1);
NMR (DMSO-d$_6$): δ 12.83 (brs, 1H), 7.82 (dd, J=7.5, 1.8 Hz, 1H), 7.55 (ddd, J=7.5, 7.5, 1.5 Hz, 1H), 7.40-6.90 (m, 8H), 6.88 (d, J=8.1 Hz, 2H), 6.55 (s, 2H), 4.70-4.38 (m, 2H), 3.85-3.55 (m, 6H), 3.30-3.05 (m, 2H), 2.70-2.30 (m, 2H), 1.98 (s, 3H), 1.82 (brs, 2H).

Example 5(30)

2-(4-(N-(3,4,5-trimethoxyphenylcarbonyl)-N-(3-(3-chlorophenyl)propyl)aminomethyl)phenyloxy)benzoic acid TLC: Rf 0.36 (Dichloromethane:Methanol=9:1);
NMR (DMSO-d$_6$): δ 12.85 (brs, 1H), 7.82 (dd, J=7.5, 1.5 Hz, 1H), 7.55 (ddd, J=7.5, 7.5, 1.5 Hz, 1H), 7.38-7.12 (m, 7H), 6.96 (m, 1H), 6.88 (d, J=8.7 Hz, 2H), 6.62 (s, 2H), 4.70-4.40 (m, 2H), 3.80-3.60 (m, 9H), 3.40-3.00 (m, 2H), 2.60-2.30 (m, 2H), 1.82 (brs, 2H).

Example 5(31)

2-(4-(N-(3,5-dimethoxy-4-methylphenylcarbonyl)-N-(3-(3-trifluoromethylphenyl)propyl)aminomethyl)phenyloxy)benzoic acid TLC: Rf 0.33 (Dichloromethane:Methanol=9:1);
NMR (DMSO-d$_6$): δ 12.83 (brs, 1H), 7.82 (dd, J=7.8, 1.8 Hz, 1H), 7.54 (ddd, J=8.1, 8.1, 1.8 Hz, 1H), 7.46-6.90 (m, 8H), 6.88 (d, J=8.4 Hz, 2H), 6.56 (s, 2H), 4.70-4.40 (m, 2H), 3.80-3.60 (m, 6H), 3.42-3.00 (m, 2H), 2.72-2.38 (m, 2H), 1.97 (s, 3H), 1.90 (m, 2H).

Example 5(32)

2-(4-(N-(3,4,5-trimethoxyphenylcarbonyl)-N-(3-(3-trifluoromethoxyphenyl)propyl)aminomethyl)phenyloxy)benzoic acid TLC: Rf 0.29 (Dichloromethane:Methanol=9:1);
NMR (DMSO-$d_6$): δ 12.85 (brs, 1H), 7.82 (dd, J=7.5, 1.8 Hz, 1H), 7.55 (ddd, J=7.5, 7.5, 1.8 Hz, 1H), 7.46-6.92 (m, 8H), 6.88 (d, J=8.7 Hz, 2H), 6.63 (s, 2H), 4.70-4.35 (m, 2H), 3.80-3.60 (m, 9H), 3.40-3.10 (m, 2H), 2.70-2.40 (m, 2H), 1.85 (m, 2H).

Example 5(33)

2-(4-(N-(3,5-dimethoxy-4-methylphenylcarbonyl)-N-(3-(2,6-dichlorophenyl)propyl)aminomethyl)phenyloxy)benzoic acid TLC: Rf 0.33 (Dichloromethane:Methanol=9:1);
NMR (DMSO-$d_6$): δ 12.85 (brs, 1H), 7.82 (dd, J=7.5, 1.8 Hz, 1H), 7.54 (ddd, J=7.5, 7.5, 1.8 Hz, 1H), 7.50-7.15 (m, 6H), 6.96 (m, 1H), 6.90 (d, J=7.8 Hz, 2H), 6.62-6.45 (m, 2H), 4.70-4.40 (m, 2H), 3.80-3.60 (m, 6H), 3.52-3.10 (m, 2H), 2.95-2.55 (m, 2H), 1.97 (s, 3H), 1.90-1.60 (m, 2H).

Example 5(34)

2-(4-(N-(3,4,5-trimethoxyphenylcarbonyl)-N-(3-(2,6-dichlorophenyl)propyl)aminomethyl)phenyloxy)benzoic acid TLC: Rf 0.31 (Dichloromethane:Methanol=9:1);
NMR (DMSO-$d_6$): δ 12.85 (brs, 1H), 7.82 (dd, J=7.5, 1.8 Hz, 1H), 7.55 (ddd, J=7.5, 7.5, 1.8 Hz, 1H), 7.48-7.10 (m, 6H), 6.96 (m, 1H), 6.89 (d, J=8.1 Hz, 2H), 6.62 (s, 2H), 4.70-4.40 (m, 2H), 3.80-3.60 (m, 9H), 3.50-3.20 (m, 2H), 2.95-2.55 (m, 2H), 1.85-1.60 (m, 2H).

Example 5(35)

(2-(4-(N-(3,4,5-trimethoxyphenylcarbonyl)-N-(3-phenylpropyl)aminomethyl)phenyloxy)phenyl)acetic acid TLC: Rf 0.08 (Hexane:Ethyl acetate=1:1);
NMR (CDCl$_3$): δ 7.33-6.82 (m, 13H), 6.60 (s, 2H), 4.65-4.49 (m, 2H), 3.84 (s, 3H), 3.72 (s, 6H), 3.90-3.68 (m, 2H), 3.52, 3.22 (br s, 2H), 2.65, 2.46 (br s, 2H), 2.05-1.80 (m, 2H).

Example 5(36)

(2-(4-(N-(3,5-dimethoxyphenylcarbonyl)-N-(3-phenylpropyl)aminomethyl)phenyloxy)phenyl)acetic acid TLC: Rf 0.20 (Hexane:Ethyl acetate=1:1);
NMR (CDCl$_3$): δ 7.33-6.84 (m, 13H), 6.50 (s, 2H), 6.46 (s, 1H), 4.67, 4.43 (s, 2H), 3.78-3.71 (m, 8H), 3.49, 3.18 (s, 2H), 2.65, 2.42 (s, 2H), 1.97, 1.83 (s, 2H).

Example 5(37)

(2-(4-(N-(3,5-dimethoxy-4-hydroxyphenylcarbonyl)-N-(3-phenylpropyl)aminomethyl)phenyloxy)phenyl)acetic acid TLC: Rf 0.61 (Dichloromethane:Methanol=9:1);
NMR (CDCl$_3$): δ 7.33-7.08 (m, 10H), 6.96-6.82 (m, 3H), 6.63 (s, 2H), 4.57 (s, 2H), 3.79 (s, 2H), 3.71 (s, 6H), 3.60-3.10 (m, 2H), 2.69-2.49 (m, 2H), 2.05-1.81 (m, 2H).

Example 5(38)

(2-(4-(N-(4-difluoromethoxyphenylcarbonyl)-N-(3-phenylpropyl)aminomethyl)phenyloxy)phenyl)acetic acid TLC: Rf 0.12 (Hexane:Ethyl acetate=1:1);
NMR (CDCl$_3$): δ 7.43-6.84 (m, 17H), 6.52 (t, J=75 Hz, 1H), 4.68, 4.43 (br s, 2H), 3.71 (s, 2H), 3.49, 3.16 (br s, 2H), 2.64, 2.42 (br s, 2H), 2.07-1.85 (m, 2H).

Example 5(39)

(2-(4-(N-(3,5-dimethoxy-4-methylphenylcarbonyl)-N-(3-phenylpropyl)aminomethyl)phenyloxy)phenyl)acetic acid TLC: Rf 0.13 (Hexane:Ethyl acetate 1:1);
NMR (CDCl$_3$): δ 7.33-6.84 (m, 13H), 6.53 (s, 2H), 4.67, 4.47 (br s, 2H), 3.77 (s, 2H), 3.71 (s, 6H), 3.52, 3.21 (br s, 2H), 2.65, 2.43 (br s, 2H), 2.07 (s, 3H), 2.13-1.84 (m, 2H).

Example 5(40)

(2-(4-(N-(3,5-dimethoxyphenylcarbonyl)-N-(3-phenylpropyl)aminomethyl)phenyl)-4,5-dimethoxyphenyl)acetic acid TLC: Rf 0.35 (Dichloromethane:Methanol=9:1);
NMR (CDCl$_3$): δ 7.39-7.10 (m, 8H), 7.05-6.94 (m, 1H), 6.86 (s, 1H), 6.82-6.71 (m, 1H), 6.57-6.51 (m, 2H), 6.50-6.44 (m, 1H), 4.83-4.68 (m, 1H), 4.59-4.48 (m, 1H), 3.92 (s, 3H), 3.87 (s, 3H), 3.84-3.68 (m, 6H), 3.63-3.51 (m, 3H), 3.31-3.18 (m, 1H), 2.76-2.64 (m, 1H), 2.50-2.38 (m, 1H), 2.08-1.73 (m, 2H).

Example 5(41)

(2-(4-(N-(3,4,5-trimethoxyphenylcarbonyl)-N-(3-phenylpropyl)aminomethyl)phenyl)-4,5-dimethoxyphenyl)acetic acid TLC: Rf 0.35 (Dichloromethane:Methanol=9:1);
NMR (CDCl$_3$): δ 7.35-6.90 (m, 9H), 6.87 (s, 1H), 6.74 (brs, 1H), 6.63 (s, 2H), 4.85-4.49 (m, 2H), 3.95-3.50 (m, 18H), 3.43-3.18 (m, 1H), 2.78-2.36 (m, 2H), 2.13-1.81 (m, 2H).

Example 5(42)

(2-(4-(N-(3,5-dimethoxy-4-methylphenylcarbonyl)-N-(3-phenylpropyl)aminomethyl)phenyl)-4,5-dimethoxyphenyl)acetic acid TLC: Rf 0.35 (Dichloromethane:Methanol=9:1);
NMR (CDCl$_3$): δ 7.40-6.90 (m, 9H), 6.87 (s, 1H), 6.74 (brs, 1H), 6.57 (s, 2H), 4.84-4.49 (m, 2H), 3.94-3.46 (m, 15H), 3.40-3.18 (m, 1H), 2.77-2.35 (m, 2H), 2.13-1.78 (m, 5H).

Example 5(43)

(2-(4-(N-(4-difluoromethoxyphenylcarbonyl)-N-(3-phenylpropyl)aminomethyl)phenyl)-4,5-dimethoxyphenyl)acetic acid TLC: Rf 0.33 (Dichloromethane:Methanol=9:1);
NMR (CDCl$_3$): δ 7.47-6.26 (m, 16H), 4.84-4.46 (m, 2H), 3.92-3.46 (s, 3H), 3.87 (m, 3H), 3.63-3.46 (m, 3H), 3.30-3.15 (m, 1H), 2.78-2.36 (m, 2H), 2.09-1.79 (m, 2H).

Example 5(44)

3-(2-(4-(N-(3,4 5-trimethoxyphenylcarbonyl)-N-(3-phenylpropyl)aminomethyl)phenyl)phenyl)propanoic acid TLC: Rf 0.41 (Dichloromethane:Methanol=9:1);
NMR (CDCl$_3$): δ 7.34-7.15 (m, 13H), 6.64 (s, 2H), 4.76-4.58 (m, 2H), 3.90-3.28 (m, 11H), 2.91 (t, J=9.0 Hz, 2H), 2.76-2.37 (m, 2H), 2.45 (t, J=9.0 Hz, 2H), 2.08-1.83 (m, 2H).

Example 5(45)

3-(2-(4-(N-(3,5-dimethoxyphenylcarbonyl)-N-(3-phenylpropyl)aminomethyl)phenyl)phenyl)propanoic acid TLC: Rf 0.41 (Dichloromethane:Methanol=9:1);
NMR (CDCl$_3$): δ 7.34-6.97 (m, 13H), 6.54 (s, 2H), 6.47 (s, 1H), 4.77, 4.53 (s, 2H), 3.79, 3.71 (s, 6H), 3.59-3.52, 3.29-3.18 (m, 2H), 2.97-2.85 (m, 2H), 2.72-2.60, 2.49-2.37 (m, 2H), 2.43 (t, J=9.0 Hz, 2H), 2.07-1.79 (m, 2H).

Example 5(46)

3-(2-(4-(N-(3,5-dimethoxy-4-hydroxyphenylcarbonyl)-N-(3-phenylpropyl)aminomethyl)phenyl)phenyl)propanoic acid TLC: Rf 0.30 (Dichloromethane:Methanol=9:1);
NMR (CDCl$_3$): δ 7.34-7.11 (m, 13H), 6.68 (s, 2H), 4.65 (s, 2H), 3.89-3.21 (m, 8H), 2.91 (t, J=9.0 Hz, 2H), 2.73-2.23 (m, 2H), 2.45 (t, J=9.0 Hz, 2H), 2.08-1.79 (m, 2H).

Example 5(47)

3-(2-(4-(N-(4-difluoromethoxyphenylcarbonyl)-N-(3-phenylpropyl)aminomethyl)phenyl)phenyl)propanoic acid TLC: Rf 0.42 (Dichloromethane:Methanol=9:1);
NMR (CDCl$_3$): δ 7.46-6.94 (m, 17H), 6.52 (t, J=75 Hz, 1H), 4.78, 4.52 (s, 2H), 3.55, 3.21 (s, 2H), 2.92 (t, J=9.0 Hz, 2H), 2.73-2.59, 2.48-2.38 (m, 2H), 2.43 (t, J=9.0 Hz, 2H), 2.07-1.81 (m, 2H).

Example 5(48)

3-(2-(4-(N-(2,5-dichlorophenylcarbonyl)-N-(3-phenylpropyl)aminomethyl)phenyl)phenyl)propanoic acid TLC: Rf 0.47 (Dichloromethane:Methanol=9:1);
NMR (CDCl$_3$): δ 7.37-6.94 (m, 16H), 5.08-5.06, 4.58-4.53, 4.43-4.31 (m, 2H), 3.99-3.87, 3.27-3.18, 3.10-3.02 (m, 2H), 2.96-2.86 (m, 2H), 2.75-2.66, 2.46-2.40 (m, 2H), 2.46-2.40 (m, 2H), 2.08-1.71 (m, 2H).

Example 5(49)

(3-(N-(3,4,5-trimethoxyphenylcarbonyl)-N-(3-phenylpropyl)aminomethyl)phenyloxy)acetic acid TLC: Rf 0.31 (Dichloromethane:Methanol=9:1);
NMR (CDCl$_3$): δ 7.40-6.60 (m, 9H), 6.59 (s, 2H), 4.70-4.40 (m, 4H), 3.90-3.10 (m, 11H), 2.80-2.30 (m, 2H), 2.10-1.80 (m, 2H).

Example 5(50)

(3-(N-(4-difluoromethoxyphenylcarbonyl)-N-(3-phenylpropyl)aminomethyl)phenyloxy)acetic acid TLC: Rf 0.35 (Dichloromethane:Methanol=9:1);
NMR (CDCl$_3$): δ 7.45-6.20 (m, 14H), 4.80-4.40 (m, 2H), 4.62 (s, 2H), 3.60-3.10 (m, 2H), 2.80-2.30 (m, 2H), 2.10-1.80 (m, 2H).

Example 5(51)

(3-(N-(3,5-dimethoxyphenylcarbonyl)-N-(3-phenylpropyl)aminomethyl)phenyloxy)acetic acid TLC: Rf 0.38 (Dichloromethane:Methanol=9:1);
NMR (CDCl$_3$): δ 7.40-6.40 (m, 12H), 4.80-4.40 (m, 4H), 3.80-3.60 (m, 6H), 3.60-3.10 (m, 2H), 2.80-2.30 (m, 2H), 2.10-1.70 (m, 2H).

Example 5(52)

(3-(N-(3,5-dimethoxy-4-methylphenylcarbonyl)-N-(3-phenylpropyl)aminomethyl)phenyloxy)acetic acid TLC: Rf 0.39 (Dichloromethane:Methanol=9:1);
NMR (CDCl$_3$): δ 7.30-6.70 (m, 9H), 6.53 (s, 2H), 4.80-4.40 (m, 2H), 4.62 (s, 2H), 3.80-3.10 (m, 8H), 2.80-2.30 (m, 2H), 2.20-1.80 (m, 5H).

Example 5(53)

(3-(N-(3,4,5-trimethoxyphenylcarbonyl)-N-(3-phenylpropyl)aminomethyl)-6-methoxyphenyloxy)acetic acid TLC: Rf 0.31 (Dichloromethane:Methanol=9:1);
NMR (CDCl$_3$): δ 7.30-6.70 (m, 8H), 6.59 (s, 2H), 4.70-4.40 (m, 2H), 4.64 (s, 2H), 3.95-3.00 (m, 14H), 2.80-2.40 (m, 2H), 2.10-1.80 (m, 2H).

Example 5(54)

(3-(N-(4-difluoromethoxyphenylcarbonyl)-N-(3-phenylpropyl)aminomethyl)-6-methoxyphenyloxy)acetic acid TLC: Rf 0.30 (Dichloromethane:Methanol=9:1);
NMR (CDCl$_3$): δ 7.40-6.20 (m, 13H), 4.70-3.80 (m, 7H), 3.50-3.00 (m, 2H), 2.80-2.30 (m, 2H), 2.00-1.80 (m, 2H).

Example 5(55)

(3-(N-(3,5-dimethoxyphenylcarbonyl)-N-(3-phenylpropyl)aminomethyl)-6-methoxyphenyloxy)acetic acid TLC: Rf 0.33 (Dichloromethane:Methanol=9:1);
NMR (CDCl$_3$): δ 7.40-6.40 (m, 11H), 4.70-4.30 (m, 4H), 4.00-3.00 (m, 11H), 2.70-2.30 (m, 2H), 2.00-1.70 (m, 2H).

Example 5(56)

(3-(N-(3,5-dimethoxy-4-methylphenylcarbonyl)-N-(3-phenylpropyl)aminomethyl)-6-methoxyphenyloxy)acetic acid TLC: Rf 0.33 (Dichloromethane:Methanol=9:1);
NMR (CDCl$_3$): δ 7.40-6.40 (m, 10H), 4.70-4.30 (m, 4H), 4.00-3.00 (m, 11H), 2.70-2.30 (m, 2H), 2.10-1.70 (m, 5H).

Example 5(57)

(4-(N-(3,5-dimethoxyphenylcarbonyl)-N-(3-phenylpropyl)aminomethyl)phenyloxy)acetic acid TLC: Rf 0.43 (Dichloromethane:Methanol=4:1);
NMR (CDCl$_3$): δ 7.32-7.12 (m, 5H), 7.08-6.94 (m, 2H), 6.86 (d, J=9.0 Hz, 2H), 6.55-6.43 (m, 3H), 4.66, 4.41 (s, 2H), 4.63 (s, 2H), 3.77, 3.70 (s, 6H), 3.47, 3.15 (s, 2H), 2.64, 2.40 (s, 2H), 1.96, 1.82 (s, 2H).

Example 5(58)

(4-(N-(4-difluoromethoxyphenylcarbonyl)-N-(3-phenylpropyl)aminomethyl)phenyloxy)acetic acid TLC: Rf 0.41 (Dichloromethane:Methanol=4:1);
NMR (CDCl$_3$): δ 7.43-7.32 (m, 2H), 7.28-6.93 (m, 9H), 6.87 (d, J=9.0 Hz, 2H), 6.52 (t, J=75 Hz, 1H), 4.67, 4.41 (s, 2H), 4.64 (s, 2H), 3.47, 3.13 (s, 2H), 2.63, 2.40 (s, 2H), 2.04-1.75 (m, 2H).

Example 5(59)

(4-(N-(3,5-dimethoxy-4-methylphenylcarbonyl)-N-(3-phenylpropyl)aminomethyl)phenyloxy)acetic acid TLC: Rf 0.43 (Dichloromethane:Methanol=4:1);
NMR (CDCl$_3$): δ 7.32-6.92 (m, 7H), 6.87 (d, J=9.0 Hz, 2H), 6.52 (s, 2H), 4.67, 4.65 (s, 2H), 4.63 (s, 2H), 3.77, 3.66 (s, 6H), 3.49, 3.17 (s, 2H), 2.64, 2.41 (s, 2H), 2.06 (s, 3H), 2.00-1.84 (s, 2H).

Example 5(60)

(4-(N-(3,4,5-trimethoxyphenylcarbonyl)-N-(3-phenylpropyl)aminomethyl)-2-methoxyphenyloxy)acetic acid TLC: Rf 0.35 (Dichloromethane:Methanol=9:1);
NMR (CDCl$_3$): δ 7.40-6.50 (m, 10H), 4.66 (S, 2H), 4.70-4.40 (m, 2H), 3.95-3.60 (m, 12H), 3.60-3.10 (m, 2H), 2.80-2.40 (m, 2H), 2.20-1.80 (m, 2H).

Example 5(61)

(4-(N-(3,5-dimethoxyphenylcarbonyl)-N-(3-phenylpropyl)aminomethyl)-2-methoxyphenyloxy)acetic acid TLC: Rf 0.35 (Dichloromethane:Methanol=9:1);
NMR (CDCl$_3$): δ 7.40-6.40 (m, 11H), 4.66 (S, 2H), 4.70-4.40 (m, 2H), 3.95-3.65 (m, 9H), 3.60-3.10 (m, 2H), 2.70-2.40 (m, 2H), 2.05-1.80 (m, 2H).

Example 5(62)

(4-(N-(3,5-dimethoxy-4-methylphenylcarbonyl)-N-(3-phenylpropyl)aminomethyl)-2-methoxyphenyloxy)acetic acid TLC: Rf 0.35 (Dichloromethane:Methanol=9:1);
NMR (CDCl$_3$): δ 7.40-6.40 (m, 10H), 4.66 (S, 2H), 4.70-4.40 (m, 2H), 3.95-3.60 (m, 9H), 3.60-3.10 (m, 2H), 2.70-2.30 (m, 2H), 2.20-1.80 (m, 5H).

Example 5(63)

(4-(N-(3,4,5-trimethoxyphenylcarbonyl)-N-(3-phenylpropyl)aminomethyl)-2-ethoxyphenyloxy)acetic acid TLC: Rf 0.35 (Dichloromethane:Methanol=9:1);
NMR (CDCl$_3$): δ 7.40-6.50 (m, 10H), 4.65 (S, 2H), 4.70-4.40 (m, 2H), 4.20-4.00 (m, 2H), 3.95-3.60 (m, 9H), 3.60-3.10 (m, 2H), 2.70-2.40 (m, 2H), 2.20-1.80 (m, 2H), 1.47 (t, J=6.9 Hz, 3H).

Example 5(64)

(4-(N-(3,5-dimethoxyphenylcarbonyl)-N-(3-phenylpropyl)aminomethyl)-2-ethoxyphenyloxy)acetic acid TLC: Rf 0.35 (Dichloromethane:Methanol=9:1);
NMR (CDCl$_3$): δ 7.40-6.40 (m, 11H), 4.64 (S, 2H), 4.70-4.40 (m, 2H), 4.20-4.00 (m, 2H), 3.95-3.60 (m, 6H), 3.60-3.10 (m, 2H), 2.70-2.40 (m, 2H), 2.10-1.80 (m, 2H), 1.46 (t, J=6.9 Hz, 3H).

Example 5(65)

(4-(N-(3,5-dimethoxy-4-methylphenylcarbonyl)-N-(3-phenylpropyl)aminomethyl)-2-ethoxyphenyloxy)acetic acid TLC: Rf 0.35 (Dichloromethane:Methanol=9:1);
NMR (CDCl$_3$): δ 7.40-6.40 (m, 10H), 4.64 (S, 2H), 4.70-4.40 (m, 2H), 4.20-4.00 (m, 2H), 3.95-3.60 (m, 6H), 3.60-3.10 (m, 2H), 2.70-2.40 (m, 2H), 2.10-1.80 (m, 5H), 1.47 (t, J=6.9 Hz, 3H).

Example 5(66)

(4-(N-(3,4,5-trimethoxyphenylcarbonyl)-N-(4-phenylbutyl)aminomethyl)phenyloxy)acetic acid TLC: Rf 0.38 (Dichloromethane:Methanol=9:1);
NMR (CDCl$_3$): δ 7.34-6.99 (m, 7H), 6.93-6.86 (m, 2H), 6.59 (s, 2H), 4.72-4.36 (m, 4H), 3.85-3.58 (m, 9H), 3.57-3.37 (m, 1H), 3.29-3.03 (m, 1H), 2.71-2.38 (m, 2H), 1.78-1.36 (m, 4H).

Example 5(67)

(4-(N-(3,5-dimethoxy-4-methylphenylcarbonyl)-N-(4-phenylbutyl)aminomethyl)phenyloxy)acetic acid TLC: Rf 0.38 (Dichloromethane:Methanol=9:1);
NMR (CDCl$_3$): δ 7.34-6.97 (m, 7H), 6.93-6.86 (m, 2H), 6.52 (s, 2H), 4.75-4.38 (m, 4H), 3.82-3.09 (m, 8H), 2.71-2.40 (m, 2H), 2.12-1.98 (m, 3H), 1.78-1.37 (m, 4H).

Example 5(68)

(4-(N-(3,5-dimethoxyphenylcarbonyl)-N-(4-phenylbutyl)aminomethyl)phenyloxy)acetic acid TLC: Rf 0.36 (Dichloromethane:Methanol=9:1);
NMR (CDCl$_3$): δ 7.32-6.99 (m, 7H), 6.93-6.84 (m, 2H), 6.55-6.42 (m, 3H), 4.73-4.35 (m, 4H), 3.79-3.60 (m, 6H), 3.50-3.36 (m, 1H), 3.22-3.09 (m, 1H), 2.69-2.38 (m, 2H), 1.74-1.36 (m, 4H).

Example 5(69)

(4-(N-(3,4,5-trimethoxyphenylcarbonyl)-N-(2-phenylethyl)aminomethyl)phenyloxy)acetic acid TLC: Rf 0.36 (Dichloromethane:Methanol=9:1);
NMR (CDCl$_3$): δ 7.45-6.85 (m, 9H), 6.53 (s, 2H), 4.84-4.61 (m, 3H), 4.39-4.20 (m, 1H), 3.95-3.37 (m, 12H), 3.09-2.68 (m, 2H).

Example 5(70)

(4-(N-(3,5-dimethoxy-4-methylphenylcarbonyl)-N-(2-phenylethyl)aminomethyl)phenyloxy)acetic acid TLC: Rf 0.36 (Dichloromethane:Methanol=9:1);
NMR (CDCl$_3$): δ 7.42-6.81 (m, 9H), 6.49 (s, 2H), 4.83-4.58 (m, 3H), 4.36-4.18 (m, 1H), 3.85-3.36 (m, 8H), 3.09-2.68 (m, 2H), 2.16-1.95 (m, 3H).

Example 5(71)

(4-(N-(3,5-dimethoxyphenylcarbonyl)-N-(2-phenylethyl)aminomethyl)phenyloxy)acetic acid TLC: Rf 0.36 (Dichloromethane:Methanol=9:1);
NMR (CDCl$_3$): δ 7.39-6.78 (m, 9H), 6.50-6.31 (m, 3H), 4.79-4.56 (m, 3H), 4.30-4.12 (m, 1H), 3.82-3.52 (m, 7H), 3.44-3.30 (m, 1H), 3.03-2.84 (m, 2H).

Example 5(72)

(4-(N-(3,4,5-trimethoxyphenylcarbonyl)-N-(3-phenyl-1-methylpropyl)aminomethyl)phenyloxy)acetic acid TLC: Rf 0.33 (Dichloromethane:Methanol=9:1);
NMR (CDCl$_3$): δ 7.50-6.80 (m, 9H), 6.59 (s, 2H), 4.80-4.00 (m, 3H), 4.63 (s, 2H), 4.00-3.60 (m, 9H), 2.50-1.60 (m, 4H), 1.40-1.10 (m, 3H).

Example 5(73)

(4-(N-(3,5-dimethoxy-4-methylphenylcarbonyl)-N-(3-phenyl-1-methylpropyl)aminomethyl)phenyloxy)acetic acid TLC: Rf 0.33 (Dichloromethane:Methanol=9:1);
NMR (CDCl$_3$): δ 7.40-6.80 (m, 9H), 6.53 (s, 2H), 4.80-4.00 (m, 3H), 4.59 (s, 2H), 4.00-3.60 (m, 6H), 2.80-1.60 (m, 7H), 1.40-1.20 (m, 3H).

Example 5(74)

(4-(N-(3,4,5-trimethoxyphenylcarbonyl)-N-(3-phenyl-2-methylpropyl)aminomethyl)phenyloxy)acetic acid TLC: Rf 0.33 (Dichloromethane:Methanol=9:1);
NMR (CDCl$_3$): δ 7.40-6.80 (m, 9H), 6.57 (s, 2H), 5.00-4.40 (m, 2H), 4.65 (s, 2H), 4.00-3.60 (m, 9H), 3.60-1.80 (m, 5H), 1.00-0.70 (m, 3H).

Example 5(75)

(4-(N-(3,5-dimethoxy-4-methylphenylcarbonyl)-N-(3-phenyl-2-methylpropyl)aminomethyl)phenyloxy)acetic acid TLC: Rf 0.33 (Dichloromethane:Methanol=9:1);
NMR (CDCl$_3$): δ 7.40-6.80 (m, 9H), 6.51 (s, 2H), 5.00-4.40 (m, 2H), 4.65 (s, 2H), 3.90-3.60 (m, 6H), 3.60-1.80 (m, 8H), 1.00-0.60 (m, 3H).

Example 5(76)

(4-(N-(3,4,5-trimethoxyphenylcarbonyl)-N-(3-phenylbutyl)aminomethyl)phenyloxy)acetic acid TLC: Rf 0.33 (Dichloromethane:Methanol=9:1);
NMR (CDCl$_3$): δ 7.40-6.80 (m, 9H), 6.55 (s, 2H), 4.64 (s, 2H), 4.70-4.30 (m, 2H), 3.90-3.60 (m, 9H), 3.60-1.70 (m, 5H), 1.40-1.00 (m, 3H).

Example 5(77)

(4-(N-(3,5-dimethoxy-4-methylphenylcarbonyl)-N-(3-phenylbutyl)aminomethyl)phenyloxy)acetic acid TLC: Rf 0.33 (Dichloromethane:Methanol=9:1);
NMR (CDCl$_3$): δ 7.40-6.80 (m, 9H), 6.49 (s, 2H), 4.63 (s, 2H), 4.70-4.30 (m, 2H), 3.90-2.30 (m, 9H), 2.20-1.70 (m, 5H), 1.40-1.00 (m, 3H).

Example 5(78)

4-(N-(3,4,5-trimethoxyphenylcarbonyl)-N-(3-phenylpropyl)aminomethyl)benzoic acid TLC: Rf 0.51 (Dichloromethane:Methanol=9:1);
NMR (CDCl$_3$): δ 8.14-8.06 (m, 2H), 7.45-6.88 (m, 7H), 6.59 (s, 2H), 4.87-4.50 (m, 2H), 3.96-3.09 (m, 11H), 2.78-2.33 (m, 2H), 2.18-1.78 (m, 2H).

Example 5(79)

4-(N-(3,5-dimethoxy-4-methylphenylcarbonyl)-N-(3-phenylpropyl)aminomethyl)benzoic acid TLC: Rf 0.49 (Dichloromethane:Methanol=9:1);
NMR (CDCl$_3$): δ 8.14-8.05 (m, 2H), 7.47-6.85 (m, 7H), 6.53 (s, 2H), 4.87-4.50 (m, 2H), 3.89-3.09 (m, 8H), 2.78-2.38 (m, 2H), 2.18-1.70 (m, 5H).

Example 5(80)

4-(N-(3,5-dimethoxyphenylcarbonyl)-N-(3-phenylpropyl)aminomethyl)benzoic acid

TLC: Rf 0.46 (Dichloromethane:Methanol=9:1)
NMR (CDCl$_3$): δ 8.09-8.05 (m, 2H), 7.44-6.92 (m, 7H), 6.55-6.43 (m, 3H), 4.85-4.45 (m, 2H), 3.89-3.61 (m, 6H), 3.58-3.10 (m, 2H), 2.78-2.35 (m, 2H), 2.08-1.75 (m, 2H).

Example 5(81)

4-(N-(3,4,5-triethoxyphenylcarbonyl)-N-(3-phenylpropyl)aminomethyl)benzoic acid

TLC: Rf 0.44 (Dichloromethane:Methanol=9:1);
NMR (CDCl$_3$): δ 8.10-8.05 (m, 2H), 7.46-6.90 (m, 7H), 6.58 (s, 2H), 4.89-4.47 (m, 2H), 4.18-3.76 (m, 6H), 3.61-3.10 (m, 2H), 2.78-2.30 (m, 2H), 2.08-1.72 (m, 2H), 1.58-1.25 (m, 9H).

Example 5(82)

3-(N-(3,4,5-trimethoxyphenylcarbonyl)-N-(3-phenylpropyl)aminomethyl)benzoic acid TLC: Rf 0.44 (Dichloromethane:Methanol=9:1);
NMR (CDCl$_3$): δ 8.06-7.94 (m, 2H), 7.62-6.90 (m, 7H), 6.63 (s, 2H), 4.90-4.43 (m, 2H), 3.96-3.64 (m, 9H), 3.62-3.11 (m, 2H), 2.78-2.32 (m, 2H), 2.11-1.79 (m, 2H).

Example 5(83)

3-(N-(3,5-dimethoxy-4-methylphenylcarbonyl)-N-(3-phenylpropyl)aminomethyl)benzoic acid TLC: Rf 0.44 (Dichloromethane:Methanol=9:1);
NMR (CDCl$_3$): δ 8.06-7.94 (m, 2H), 7.66-6.90 (m, 7H), 6.56 (s, 2H), 4.90-4.43 (m, 2H), 3.90-3.10 (m, 8H), 2.78-2.32 (m, 2H), 2.17-1.79 (m, 5H).

Example 5(84)

3-(N-(3,5-dimethoxyphenylcarbonyl)-N-(3-phenylpropyl)aminomethyl)benzoic acid

TLC: Rf 0.45 (Dichloromethane:Methanol=9:1);
NMR (CDCl$_3$): δ 8.08-7.86 (m, 2H), 7.63-6.92 (m, 7H), 6.56-6.43 (m, 3H), 4.86-4.48 (m, 2H), 3.88-3.63 (m, 6H), 3.57-3.15 (m, 2H), 2.72-2.37 (m, 2H), 2.09-1.76 (m, 2H).

Example 5(85)

3-(N-(3,4,5-triethoxyphenylcarbonyl)-N-(3-phenylpropyl)aminomethyl)benzoic acid

TLC: Rf 0.50 (Dichloromethane:Methanol=9:1);
NMR (CDCl$_3$): δ 8.06-7.92 (m, 2H), 7.63-6.92 (m, 7H), 6.61 (s, 2H), 4.90-4.46 (m, 2H), 4.15-3.84 (m, 6H), 3.63-3.09 (m, 2H), 2.78-2.26 (m, 2H), 2.09-1.78 (m, 2H), 1.51-1.29 (m, 9H).

Example 5(86)

(4-(N-(3,4,5-trimethoxyphenylcarbonyl)-N-(3-phenylpropyl)aminomethyl)phenyl)acetic acid TLC: Rf 0.59 (Dichloromethane:Methanol=9:1);
NMR (CDCl$_3$): δ 7.35-6.89 (m, 9H), 6.58 (s, 2H), 4.69, 4.51 (s, 2H), 3.89-3.19 (m, 13H), 2.65, 2.43 (s, 2H), 2.05-1.77 (m, 2H).

Example 5(87)

(4-(N-(3,5-dimethoxyphenylcarbonyl)-N-(3-phenylpropyl)aminomethyl)phenyl)acetic acid TLC: Rf 0.59 (Dichloromethane:Methanol=9:1);
NMR (CDCl$_3$): δ 7.32-6.95 (m, 9H), 6.50-6.44 (m, 3H), 4.70, 4.46 (s, 2H), 3.78, 3.68 (s, 6H), 3.64 (s, 2H), 3.50, 3.16 (s, 2H), 2.64, 2.40 (s, 2H), 1.97, 1.83 (s, 2H).

Example 5(88)

(4-(N-(4-difluoromethoxyphenylcarbonyl)-N-(3-phenylpropyl)aminomethyl)phenyl)acetic acid TLC: Rf 0.57 (Dichloromethane:Methanol=9:1);
NMR (CDCl$_3$): δ 7.43-6.90 (m, 13H), 6.51 (t, J=75 Hz, 1H), 4.72, 4.47 (s, 2H), 3.65 (s, 2H), 3.49, 3.14 (s, 2H), 2.64, 2.41 (s, 2H), 2.04-1.75 (m, 2H).

Example 5(89)

(4-(N-(3,4,5-trimethoxyphenylcarbonyl)-N-(3-(2-methylphenyl)propyl)aminomethyl)phenyl)acetic acid TLC: Rf 0.51 (Dichloromethane:Methanol=9:1);
NMR (CDCl$_3$): δ 7.37-6.78 (m, 8H), 6.59 (s, 2H), 4.82-4.42 (m, 2H), 3.99-3.42 (m, 12H), 3.39-3.08 (m, 1H), 2.71-2.05 (m, 5H), 2.03-1.68 (m, 2H).

Example 5(90)

(4-(N-(3,5-dimethoxy-4-methylphenylcarbonyl)-N-(3-(2-methylphenyl)propyl)aminomethyl)phenyl) acetic acid TLC: Rf 0.47 (Dichloromethane:Methanol=9:1);
NMR (CDCl$_3$): δ 7.37-6.78 (m, 8H), 6.53 (s, 2H), 4.81-4.42 (m, 2H), 3.90-3.14 (m, 10H), 2.77-1.67 (m, 10H).

Example 5(91)

(4-(N-(3,5-dimethoxyphenylcarbonyl)-N-(3-(2-methylphenyl)propyl)aminomethyl)phenyl)acetic acid TLC: Rf 0.44 (Dichloromethane:Methanol=9:1);
NMR (CDCl$_3$): δ 7.36-6.82 (m, 8H), 6.53-6.42 (m, 3H), 4.80-4.41 (m, 2H), 3.95-3.47 (m, 9H), 3.31-3.14 (m, 1H), 2.69-2.52 (m, 1H), 2.43-2.09 (m, 4H), 2.01-1.69 (m, 2H).

Example 5(92)

(4-(N-(3,4,5-trimethoxyphenylcarbonyl)-N-(3-(3-methylphenyl)propyl)aminomethyl)phenyl)acetic acid TLC: Rf 0.40 (Dichloromethane:Methanol=9:1);
NMR (CDCl$_3$): δ 7.39-6.69 (m, 8H), 6.59 (s, 2H), 4.80-4.41 (m, 2H), 3.97-3.06 (m, 13H), 2.71-2.09 (m, 5H), 2.08-1.75 (m, 2H).

Example 5(93)

(4-(N-(3,5-dimethoxy-4-methylphenylcarbonyl)-N-(3-(3-methylphenyl)propyl)aminomethyl)phenyl) acetic acid TLC: Rf 0.40 (Dichloromethane:Methanol=9:1);
NMR (CDCl$_3$): δ 7.36-6.64 (m, 8H), 6.52 (m, 2H), 4.80-4.39 (m, 2H), 3.89-3.40 (m, 9H), 3.30-3.09 (m, 1H), 2.71-1.74 (m, 10H).

Example 5(94)

(4-(N-(3,5-dimethoxyphenylcarbonyl)-N-(3-(3-methylphenyl)propyl)aminomethyl)phenyl)acetic acid TLC: Rf 0.40 (Dichloromethane:Methanol=9:1);
NMR (CDCl$_3$): δ 7.27-6.72 (m, 8H), 6.52-6.39 (m, 3H), 4.76-4.39 (m, 2H), 3.87-3.59 (m, 8H), 3.56-3.40 (m, 1H), 3.24-3.06 (m, 1H), 2.66-2.52 (m, 1H), 2.42-2.19 (m, 4H), 2.05-1.72 (m, 2H).

Example 5(95)

(4-(N-(3,4,5-trimethoxyphenylcarbonyl)-N-(3-(4-methylphenyl)propyl)aminomethyl)phenyl)acetic acid TLC: Rf 0.40 (Dichloromethane:Methanol=9:1);
NMR (CDCl$_3$): δ 7.35-6.77 (m, 8H), 6.58 (s, 2H), 4.76-4.41 (m, 2H), 3.92-3.39 (m, 12H), 3.34-3.10 (m, 1H), 2.69-2.18 (m, 5H), 2.09-1.78 (m, 2H).

Example 5(96)

(4-(N-(3,5-dimethoxy-4-methylphenylcarbonyl)-N-(3-(4-methylphenyl)propyl)aminomethyl)phenyl) acetic acid TLC: Rf 0.42 (Dichloromethane:Methanol=9:1);
NMR (CDCl$_3$): δ 7.35-6.75 (m, 8H), 6.52 (s, 2H), 4.78-4.39 (m, 2H), 3.88-3.08 (m, 10H), 2.70-1.72 (m, 10H).

Example 5(97)

(4-(N-(3,5-dimethoxyphenylcarbonyl)-N-(3-(4-methylphenyl)propyl)aminomethyl)phenyl)acetic acid TLC: Rf 0.42 (Dichloromethane:Methanol=9:1);
NMR (CDCl$_3$): δ 7.29-6.79 (m, 8H), 6.51-6.41 (m, 3H), 4.78-4.39 (m, 2H), 3.86-3.59 (m, 8H), 3.56-3.38 (m, 1H), 3.26-3.06 (m, 1H), 2.68-2.51 (m, 1H), 2.44-2.27 (m, 4H), 2.06-1.72 (m, 2H).

Example 5(98)

(4-(N-(3,4,5-trimethoxyphenylcarbonyl)-N-(3-(2-methoxyphenyl)propyl)aminomethyl)phenyl)acetic acid TLC: Rf 0.41 (Dichloromethane:Methanol=9:1);
NMR (CDCl$_3$): δ 7.27-7.05 (m, 6H), 6.98-6.76 (m, 2H), 6.59 (s, 2H), 4.79-4.46 (m, 2H), 3.93-3.45 (m, 15H), 3.33-3.10 (m, 1H), 2.72-2.36 (m, 2H), 2.07-1.77 (m, 2H).

Example 5(99)

(4-(N-(3,5-dimethoxy-4-methylphenylcarbonyl)-N-(3-(2-methoxyphenyl)propyl)aminomethyl)phenyl) acetic acid TLC: Rf 0.37 (Dichloromethane:Methanol=9:1);
NMR (CDCl$_3$): δ 7.26-7.03 (m, 6H), 6.96-6.71 (m, 2H), 6.53 (s, 2H), 4.79-4.42 (m, 2H), 3.89-3.44 (m, 12H), 3.29-3.09 (m, 1H), 2.72-2.34 (m, 2H), 2.16-1.72 (m, 5H).

Example 5(100)

(4-(N-(3,5-dimethoxyphenylcarbonyl)-N-(3-(2-methoxyphenyl)propyl)aminomethyl)phenyl)acetic acid TLC: Rf 0.34 (Dichloromethane:Methanol=9:1);
NMR (CDCl$_3$): δ 7.32-7.03 (m, 6H), 6.96-6.74 (m, 2H), 6.56-6.40 (m, 3H), 4.79-4.41 (m, 2H), 3.87-3.39 (m, 12H), 3.23-3.04 (m, 1H), 2.70-2.32 (m, 2H), 2.01-1.72 (m, 2H).

Example 5(101)

(4-(N-(3,4,5-trimethoxyphenylcarbonyl)-N-(3-(3-methoxyphenyl)propyl)aminomethyl)phenyl)acetic acid TLC: Rf 0.32 (Dichloromethane:Methanol=9:1);
NMR (CDCl$_3$): δ 7.30-7.03 (m, 5H), 6.83-6.45 (m, 5H), 4.77-4.41 (m, 2H), 3.95-3.42 (m, 15H), 3.35-3.09 (m, 1H), 2.70-2.29 (m, 2H), 2.08-1.76 (m, 2H).

Example 5(102)

(4-(N-(3,5-dimethoxy-4-methylphenylcarbonyl)-N-(3-(3-methoxyphenyl)propyl)aminomethyl)phenyl)acetic acid TLC: Rf 0.32 (Dichloromethane:Methanol=9:1);
NMR (CDCl$_3$): δ 7.37-7.03 (m, 5H), 6.85-6.42 (m, 5H), 4.78-4.39 (m, 2H), 3.88-3.39 (m, 12H), 3.33-3.07 (m, 1H), 2.72-2.23 (m, 2H), 2.14-1.70 (m, 5H).

Example 5(103)

(4-(N-(3,5-dimethoxyphenylcarbonyl)-N-(3-(3-methoxyphenyl)propyl)aminomethyl)phenyl)acetic acid TLC: Rf 0.32 (Dichloromethane:Methanol=9:1);
NMR (CDCl$_3$): δ 7.35-7.03 (m, 6H), 6.85-6.40 (m, 5H), 4.78-4.39 (m, 2H), 3.86-3.60 (m, 11H), 3.58-3.40 (m, 1H), 3.29-3.04 (m, 1H), 2.68-2.30 (m, 2H), 2.04-1.70 (m, 2H).

Example 5(104)

(4-(N-(3,4,5-trimethoxyphenylcarbonyl)-N-(3-(4-methoxyphenyl)propyl)aminomethyl)phenyl)acetic acid TLC: Rf 0.32 (Dichloromethane:Methanol=9:1);
NMR (CDCl$_3$): δ 7.35-6.65 (m, 8H), 6.58 (s, 2H), 4.78-4.39 (m, 2H), 3.90-3.39 (m, 15H), 3.30-2.99 (m, 1H), 2.68-2.19 (m, 2H), 2.09-1.71 (m, 2H).

Example 5(105)

(4-(N-(3,5-dimethoxy-4-methylphenylcarbonyl)-N-(3-(4-methoxyphenyl)propyl)aminomethyl)phenyl)acetic acid TLC: Rf 0.34 (Dichloromethane:Methanol=9:1);
NMR (CDCl$_3$): δ 7.38-6.67 (m, 8H), 6.52 (s, 2H), 4.78-4.40 (m, 2H), 3.89-3.39 (m, 12H), 3.29-3.01 (m, 1H), 2.68-2.23 (m, 2H), 2.17-1.72 (m, 5H).

Example 5(106)

(4-(N-(3,5-dimethoxyphenylcarbonyl)-N-(3-(4-methoxyphenyl)propyl)aminomethyl)phenyl)acetic acid TLC: Rf 0.39 (Dichloromethane:Methanol=9:1);
NMR (CDCl$_3$): δ 7.38-6.69 (m, 8H), 6.58-6.40 (m, 3H), 4.78-4.38 (m, 2H), 3.84-3.38 (m, 11H), 3.57-3.36 (m, 1H), 3.23-3.07 (m, 1H), 2.63-2.25 (m, 2H), 2.02-1.69 (m, 2H).

Example 5(107)

(4-(N-(3,4,5-trimethoxyphenylcarbonyl)-N-(3-(2-chlorophenyl)propyl)aminomethyl)phenyl)acetic acid TLC: Rf 0.41 (Dichloromethane:Methanol=9:1);
NMR (CDCl$_3$): δ 7.37-6.89 (m, 8H), 6.59 (s, 2H), 4.81-4.45 (m, 2H), 3.96-3.15 (m, 13H), 2.87-2.44 (m, 2H), 2.09-1.78 (m, 2H).

Example 5(108)

(4-(N-(3,5-dimethoxy-4-methylphenylcarbonyl)-N-(3-(2-chlorophenyl)propyl)aminomethyl)phenyl)acetic acid TLC: Rf 0.41 (Dichloromethane:Methanol=9:1);
NMR (CDCl$_3$): δ 7.35-6.84 (m, 8H), 6.56-6.49 (m, 2H), 4.80-4.44 (m, 2H), 3.87-3.10 (m, 10H), 2.90-2.34 (m, 2H), 2.11-1.75 (m, 5H).

Example 5(109)

(4-(N-(3,5-dimethoxyphenylcarbonyl)-N-(3-(2-chlorophenyl)propyl)aminomethyl)phenyl)acetic acid TLC: Rf 0.54 (Dichloromethane:Methanol=9:1);
NMR (CDCl$_3$): δ 7.37-6.90 (m, 8H), 6.55-6.42 (m, 3H), 4.79-4.43 (m, 2H), 3.86-3.14 (m, 10H), 2.83-2.45 (m, 2H), 2.04-1.76 (m, 2H).

Example 5(110)

(4-(N-(3,4,5-trimethoxyphenylcarbonyl)-N-(3-(3-chlorophenyl)propyl)aminomethyl)phenyl)acetic acid TLC: Rf 0.54 (Dichloromethane:Methanol=9:1);
NMR (CDCl$_3$): δ 7.32-6.80 (m, 8H), 6.59 (s, 2H), 4.80-4.45 (m, 2H), 3.96-3.11 (m, 13H), 2.73-2.27 (m, 2H), 2.08-1.74 (m, 2H).

Example 5(111)

(4-(N-(3,5-dimethoxy-4-methylphenylcarbonyl)-N-(3-(3-chlorophenyl)propyl)aminomethyl)phenyl)acetic acid TLC: Rf 0.53 (Dichloromethane:Methanol=9:1);
NMR (CDCl$_3$): δ 7.30-6.74 (m, 8H), 6.52 (s, 2H), 4.79-4.42 (m, 2H), 3.82-3.12 (m, 10H), 2.74-1.68 (m, 7H).

Example 5(112)

(4-(N-(3,5-dimethoxyphenylcarbonyl)-N-(3-(3-chlorophenyl)propyl)aminomethyl)phenyl)acetic acid TLC: Rf 0.43 (Dichloromethane:Methanol=9:1);
NMR (CDCl$_3$): δ 7.33-6.79 (m, 8H), 6.49 (s, 2H), 6.45 (s, 1H), 4.75-4.42 (m, 2H), 3.86-3.61 (m, 8H), 3.63-3.08 (m, 2H), 2.69-2.29 (m, 2H), 2.02-1.70 (m, 2H).

Example 5(113)

(4-(N-(3,4,5-trimethoxyphenylcarbonyl)-N-(3-(4-chlorophenyl)propyl)aminomethyl)phenyl)acetic acid TLC: Rf 0.48 (Dichloromethane:Methanol=9:1);
NMR (CDCl$_3$): δ 7.30-6.77 (m, 8H), 6.59 (s, 2H), 4.76-4.39 (m, 2H), 3.97-3.06 (m, 13H), 2.73-1.71 (m, 4H).

Example 5(114)

(4-(N-(3,5-dimethoxy-4-methylphenylcarbonyl)-N-(3-(4-chlorophenyl)propyl)aminomethyl)phenyl) acetic acid TLC: Rf 0.49 (Dichloromethane:Methanol=9:1);
NMR (CDCl$_3$): δ 7.30-6.76 (m, 8H), 6.52 (s, 2H), 4.77-4.43 (m, 2H), 3.87-2.97 (m, 10H), 2.69-2.24 (m, 2H), 2.14-1.70 (m, 5H).

Example 5(115)

(4-(N-(3,5-dimethoxyphenylcarbonyl)-N-(3-(4-chlorophenyl)propyl)aminomethyl)phenyl)acetic acid TLC: Rf 0.59 (Dichloromethane:Methanol=9:1);
NMR (CDCl$_3$): δ 7.29-6.80 (m, 8H), 6.54-6.42 (m, 3H), 4.77-4.42 (m, 2H), 3.85-3.61 (m, 8H), 3.54-3.07 (m, 2H), 2.67-2.29 (m, 2H), 2.01-1.71 (m, 2H).

Example 5(116)

(4-(N-(3,4,5-trimethoxyphenylcarbonyl)-N-(3-(2-fluorophenyl)propyl)aminomethyl)phenyl)acetic acid TLC: Rf 0.33 (Dichloromethane:Methanol=9:1);
NMR (CDCl$_3$): δ 7.32-6.85 (m, 8H), 6.59 (s, 2H), 4.78-4.42 (m, 2H), 3.94-3.41 (m, 12H), 3.22 (m, 1H), 2.79-2.36 (m, 2H), 2.08-1.77 (m, 2H).

Example 5(117)

(4-(N-(3,5-dimethoxy-4-methylphenylcarbonyl)-N-(3-(2-fluorophenyl)propyl)aminomethyl)phenyl) acetic acid TLC: Rf 0.33 (Dichloromethane:Methanol=9:1);
NMR (CDCl$_3$): δ 7.38-6.82 (m, 8H), 6.52 (s, 2H), 4.78-4.42 (m, 2H), 3.89-3.41 (m, 9H), 3.20 (m, 1H), 2.77-2.34 (m, 2H), 2.11-1.75 (m, 5H).

Example 5(118)

(4-(N-(3,5-dimethoxyphenylcarbonyl)-N-(3-(2-fluorophenyl)propyl)aminomethyl)phenyl)acetic acid TLC: Rf 0.33 (Dichloromethane:Methanol=9:1);
NMR (CDCl$_3$): δ 7.35-6.87 (m, 8H), 6.57-6.40 (m, 3H), 4.71 (m, 1H), 4.48 (m, 1H), 3.83-3.59 (m, 8H), 3.51 (m, 1H), 3.17 (m, 1H), 2.67 (m, 1H), 2.43 (m, 1H), 2.05-1.76 (m, 2H).

Example 5(119)

(4-(N-(3,4,5-trimethoxyphenylcarbonyl)-N-(3-(3-fluorophenyl)propyl)aminomethyl)phenyl)acetic acid TLC: Rf 0.33 (Dichloromethane:Methanol=9:1);
NMR (CDCl$_3$): δ 7.35-6.64 (m, 8H), 6.59 (s, 2H), 4.81-4.42 (m, 2H), 3.92-3.06 (m, 13H), 2.78-2.23 (m, 2H), 2.10-1.71 (m, 2H).

Example 5(120)

(4-(N-(3,5-dimethoxy-4-methylphenylcarbonyl)-N-(3-(3-fluorophenyl)propyl)aminomethyl)phenyl) acetic acid TLC: Rf 0.33 (Dichloromethane:Methanol=9:1);
NMR (CDCl$_3$): δ 7.37-6.57 (m, 8H), 6.52 (s, 2H), 4.81-4.42 (m, 2H), 3.89-3.32 (m, 9H), 3.20 (m, 1H), 2.74-2.25 (m, 2H), 2.12-1.64 (m, 5H).

Example 5(121)

(4-(N-(3,5-dimethoxyphenylcarbonyl)-N-(3-(3-fluorophenyl)propyl)aminomethyl)phenyl)acetic acid TLC: Rf 0.33 (Dichloromethane:Methanol=9:1);
NMR (CDCl$_3$): δ 7.39-6.55 (m, 8H), 6.53-6.40 (m, 3H), 4.71 (m, 1H), 4.47 (m, 1H), 3.84-3.59 (m, 8H), 3.49 (m, 1H), 3.16 (m, 1H), 2.62 (m, 1H), 2.39 (m, 1H), 2.02-1.70 (m, 2H).

Example 5(122)

(4-(N-(3,4,5-trimethoxyphenylcarbonyl)-N-(3-(4-fluorophenyl)propyl)aminomethyl)phenyl)acetic acid TLC: Rf 0.33 (Dichloromethane:Methanol=9:1);
NMR (CDCl$_3$): δ 7.31-6.80 (m, 8H), 6.59 (s, 2H), 4.79-4.38 (m, 2H), 3.91-3.37 (m, 12H), 3.20 (m, 1H), 2.72-2.20 (m, 2H), 2.04-1.69 (m, 2H).

Example 5(123)

(4-(N-(3,5-dimethoxy-4-methylphenylcarbonyl)-N-(3-(4-fluorophenyl)propyl)aminomethyl)phenyl) acetic acid TLC: Rf 0.33 (Dichloromethane:Methanol=9:1);
NMR (CDCl$_3$): δ 7.37-6.79 (m, 8H), 6.51 (s, 2H), 4.78-4.41 (m, 2H), 3.89-3.37 (m, 9H), 3.19 (m, 1H), 2.70-2.22 (m, 2H), 2.16-1.67 (m, 5H).

Example 5(124)

(4-(N-(3,5-dimethoxyphenylcarbonyl)-N-(3-(4-fluorophenyl)propyl)aminomethyl)phenyl)acetic acid TLC: Rf 0.33 (Dichloromethane:Methanol=9:1);
NMR (CDCl$_3$): δ 7.37-6.79 (m, 8H), 6.55-6.40 (m, 3H), 4.70 (m, 1H), 4.46 (m, 1H), 3.83-3.54 (m, 8H), 3.47 (m, 1H), 3.14 (m, 1H), 2.60 (m, 1H), 2.37 (m, 1H), 2.01-1.68 (m, 2H).

Example 5(125)

(4-(N-(3,4,5-trimethoxyphenylcarbonyl)-N-(3-(indol-3-yl)propyl)aminomethyl)phenyl)acetic acid TLC: Rf 0.50 (Dichloromethane:Methanol=9:1);
NMR (CDCl$_3$): δ 8.02 (s, 1H), 7.63-6.87 (m, 9H), 6.59 (s, 2H), 4.76-4.41 (m, 2H), 3.83-3.16 (m, 13H), 2.85-1.74 (m, 4H).

Example 5(126)

(4-(N-(3,5-dimethoxy-4-methylphenylcarbonyl)-N-(3-(indol-3-yl)propyl)aminomethyl)phenyl)acetic acid TLC: Rf 0.50 (Dichloromethane:Methanol=9:1);
NMR (CDCl$_3$): δ 8.08-7.93 (m, 1H), 7.62-6.86 (m, 9H), 6.54 (s, 2H), 4.77-4.42 (m, 2H), 3.79-3.16 (m, 10H), 2.85-2.47 (m, 2H), 2.14-1.81 (m, 5H).

Example 5(127)

(4-(N-(3,5-dimethoxyphenylcarbonyl)-N-(3-(indol-3-yl)propyl)aminomethyl)phenyl)acetic acid TLC: Rf 0.46 (Dichloromethane:Methanol=9:1);
NMR (CDCl$_3$): δ 8.06-7.93 (m, 1H), 7.62-6.99, 6.95-6.87, 6.66-6.57 (m, 9H), 6.52-6.45 (m, 3H), 4.74-4.39 (m, 2H)) 3.79-3.17 (m, 10H), 2.84-2.47 (m, 2H), 2.12-1.80 (m, 2H).

Example 5(128)

(4-(N-(3,4,5-trimethoxyphenylcarbonyl)-N-(3-(3-trifluoromethylphenyl)propyl)aminomethyl)phenyl)acetic acid TLC: Rf 0.35 (Dichloromethane:Methanol=9:1);
NMR (CDCl$_3$): δ 7.48-7.07 (m, 8H), 6.60 (s, 2H), 4.79-4.43 (m, 2H), 3.90-3.39 (m, 12H), 3.22 (m, 1H), 2.79-2.35 (m, 2H), 2.09-1.74 (m, 2H).

Example 5(129)

(4-(N-(3,5-dimethoxy-4-methylphenylcarbonyl)-N-(3-(3-trifluoromethylphenyl)propyl)aminomethyl)phenyl)acetic acid TLC: Rf 0.35 (Dichloromethane:Methanol=9:1);
NMR (CDCl$_3$): δ 7.51-7.07 (m, 8H), 6.53 (s, 2H), 4.80-4.43 (m, 2H), 3.90-3.39 (m, 9H), 3.22 (m, 1H), 2.79-2.36 (m, 2H), 2.19-1.77 (m, 5H).

Example 5(130)

(4-(N-(3,5-dimethoxyphenylcarbonyl)-N-(3-(3-trifluoromethylphenyl)propyl)aminomethyl)phenyl)acetic acid TLC: Rf 0.35 (Dichloromethane:Methanol=9:1);
NMR (CDCl$_3$): δ 7.52-7.03 (m, 8H), 6.54-6.41 (m, 3H), 4.66 (m, 1H), 4.48 (m, 1H), 3.83-3.61 (m, 8H), 3.50 (m, 1H), 3.19 (m, 1H), 2.70 (m, 1H), 2.44 (m, 1H), 2.02-1.56 (m, 2H).

Example 5(131)

(4-(N-(3,4,5-trimethoxyphenylcarbonyl)-N-(3-(4-trifluoromethylphenyl)propyl)aminomethyl)phenyl)acetic acid TLC: Rf 0.35 (Dichloromethane:Methanol=9:1);
NMR (CDCl$_3$): δ 7.58-7.00 (m, 8H), 6.60 (s, 2H), 4.80-4.43 (m, 2H), 3.96-3.60 (m, 11H), 3.59-3.09 (m, 2H), 2.81-2.40 (m, 2H), 2.19-1.79 (m, 2H).

Example 5(132)

(4-(N-(3,5-dimethoxy-4-methylphenylcarbonyl)-N-(3-(4-trifluoromethylphenyl)propyl)aminomethyl)phenyl)acetic acid TLC: Rf 0.35 (Dichloromethane:Methanol=9:1);
NMR (CDCl$_3$): δ 7.59-6.95 (m, 8H), 6.53 (s, 2H), 4.80-4.37 (m, 2H), 3.90-3.32 (m, 9H), 3.21 (m, 1H), 2.79-2.34 (m, 2H), 2.16-1.70 (m, 5H).

Example 5(133)

(4-(N-(3,5-dimethoxyphenylcarbonyl)-N-(3-(4-trifluoromethylphenyl)propyl)aminomethyl)phenyl)acetic acid TLC: Rf 0.35 (Dichloromethane:Methanol=9:1);
NMR (CDCl$_3$): δ 7.59-6.96 (m, 8H), 6.54-6.40 (m, 3H), 4.71 (m, 1H), 4.48 (m, 1H), 3.85-3.62 (m, 8H), 3.49 (m, 1H), 3.17 (m, 1H), 2.70 (m, 1H), 2.45 (m, 1H), 2.06-1.75 (m, 2H).

Example 5(134)

3-(4-(N-(3,4,5-trimethoxyphenylcarbonyl)-N-(3-phenylpropyl)aminomethyl)phenyl)propanoic acid TLC: Rf 0.53 (Dichloromethane:Methanol=9:1);
NMR (CDCl$_3$): δ 7.36-6.85 (m, 9H), 6.60 (s, 2H), 4.78-4.41 (m, 2H), 3.97-3.03 (m, 11H), 3.00-2.89 (m, 2H), 2.73-2.31 (m, 4H), 2.09-1.74 (m, 2H).

Example 5(135)

3-(4-(N-(3,5-dimethoxy-4-methylphenylcarbonyl)-N-(3-phenylpropyl)aminomethyl)phenyl)propanoic acid TLC: Rf 0.49 (Dichloromethane:Methanol=9:1);
NMR (CDCl$_3$): δ 7.38-6.84 (m, 9H), 6.53 (s, 2H), 4.77-4.41 (m, 2H), 3.90-3.38 (m, 7H), 3.34-3.09 (m, 1H), 3.00-2.92 (m, 2H), 2.76-2.52 (m, 3H), 2.52-2.32 (m, 1H), 2.17-1.66 (m, 5H).

Example 5(136)

3-(4-(N-(3,5-dimethoxyphenylcarbonyl)-N-(3-phenylpropyl)aminomethyl)phenyl)propanoic acid TLC: Rf 0.47 (Dichloromethane:Methanol=9:1);
NMR (CDCl$_3$): δ 7.38-6.89 (m, 9H), 6.57-6.41 (m, 3H), 4.75-4.38 (m, 2H), 3.86-3.59 (m, 6H), 3.56-3.38 (m, 1H), 3.29-3.05 (m, 1H), 3.00-2.89 (m, 2H), 2.75-2.51 (m, 3H), 2.49-2.34 (m, 1H), 2.08-1.73 (m, 2H).

Example 5(137)

3-(4-(N-(3,5-dimethyl-4-hydroxyphenylcarbonyl)-N-(3-phenylpropyl)aminomethyl)phenyl)propanoic acid TLC: Rf 0.42 (Dichloromethane:Methanol=9:1);
NMR (CDCl$_3$): δ 7.36-6.88 (m, 11H), 4.78-4.40 (m, 2H), 3.57-3.09 (m, 2H), 2.99-2.89 (m, 2H), 2.71-2.29 (m, 4H), 2.18 (s, 6H), 2.00-1.72 (m, 2H).

Example 5(138)

4-(4-(N-(3,4,5-trimethoxyphenylcarbonyl)-N-(3-phenylpropyl)aminomethyl)phenyl)butanoic acid TLC: Rf 0.64 (Dichloromethane:Methanol=9:1);
NMR (CDCl$_3$): δ 7.40-6.90 (m, 9H), 6.50 (s, 2H), 4.79-4.42 (m, 2H), 3.98-3.11 (m, 11H), 2.79-2.27 (m, 6H), 2.10-1.78 (m, 4H).

Example 5(139)

4-(4-(N-(3,5-dimethoxyphenylcarbonyl)-N-(3-phenylpropyl)aminomethyl)phenyl)butanoic acid TLC: Rf 0.59 (Dichloromethane:Methanol=9:1);
NMR (CDCl$_3$): δ 7.33-6.92 (m, 9H), 6.51 (s, 2H), 6.45 (s, 1H), 4.70-4.45 (m, 2H), 3.78, 3.70 (s, 6H), 3.56-3.43, 3.24-3.09 (m, 2H), 2.69-2.34 (m, 6H), 2.04-1.75 (m, 4H).

Example 5(140)

4-(4-(N-(3,5-dimethyl-4-hydroxyphenylcarbonyl)-N-(3-phenylpropyl)aminomethyl)phenyl)butanoic acid TLC: Rf 0.56 (Dichloromethane:Methanol=9:1);
NMR (CDCl$_3$): δ 7.35-6.88 (m, 11H), 4.76-4.40 (m, 2H), 3.56-3.09 (m, 2H), 2.68-2.34 (m, 6H), 2.18 (s, 6H), 2.00-1.74 (m, 4H).

Example 5(141)

4-(4-(N-(3,5-dimethoxy-4-methylphenylcarbonyl)-N-(3-phenylpropyl)aminomethyl)phenyl)butanoic acid TLC: Rf 0.59 (Dichloromethane:Methanol=9:1);
NMR (CDCl$_3$): δ 7.37-6.83 (m, 9H), 6.54 (s, 2H), 4.78-4.39 (m, 2H), 3.87-3.03 (m, 8H), 2.75-2.52 (m, 3H), 2.50-2.29 (m, 3H), 2.14-1.72 (m, 7H).

Examples 6(1)-6(127)

The following compounds of the present invention were obtained by the same procedures as described in Reference example 3, Example 4 and Example 5 using the compounds prepared in Reference example 1 or corresponding aldehyde and 3-phenylpropylamine or corresponding amine.

Example 6(1)

2-(4-(N-(2-methoxyphenylcarbonyl)-N-(3-phenylpropyl)aminomethyl)phenyl)benzoic acid HPLC retention time (min): 4.06;
Mass Data: 959 (2M+H)$^+$, 480 (M+H)$^+$.

Example 6(2)

2-(4-(N-(3-methoxyphenylcarbonyl)-N-(3-phenylpropyl)aminomethyl)phenyl)benzoic acid HPLC retention time (min): 4.09;
Mass Data: 959 (2M+H)$^+$, 480 (M+H)$^+$.

Example 6(3)

2-(4-(N-(4-methoxyphenylcarbonyl)-N-(3-phenylpropyl)aminomethyl)phenyl)benzoic acid HPLC retention time (min): 4.07;
Mass Data: 959 (2M+H)$^+$, 480 (M+H)$^+$.

Example 6(4)

2-(4-(N-(4-ethoxyphenylcarbonyl)-N-(3-phenylpropyl)aminomethyl)phenyl)benzoic acid HPLC retention time (min): 4.18;
Mass Data: 987 (2M+H)$^+$, 494 (M+H)$^+$.

Example 6(5)

2-(4-(N-(4-benzyloxyphenylcarbonyl)-N-(3-phenylpropyl)aminomethyl)phenyl)benzoic acid HPLC retention time (min): 4.33;
Mass Data: 556 (M+H)$^+$.

Example 6(6)

2-(4-(N-(4-isopropyloxyphenylcarbonyl)-N-(3-phenylpropyl)aminomethyl)phenyl)benzoic acid HPLC retention time (min): 4.24;
Mass Data: 508 (M+H)$^+$.

Example 6(7)

2-(4-(N-(4-difluoromethoxyphenylcarbonyl)-N-(3-phenylpropyl)aminomethyl)phenyl)benzoic acid HPLC retention time (min): 4.12;
Mass Data: 516 (M+H)$^+$.

Example 6(8)

2-(4-(N-(4-trifluoromethoxyphenylcarbonyl)-N-(3-phenylpropyl)aminomethyl)phenyl)benzoic acid HPLC retention time (min): 4.27;
Mass Data: 534 (M+H)$^+$.

Example 6(9)

2-(4-(N-(4-trifluoromethylphenylcarbonyl)-N-(3-phenylpropyl)aminomethyl)phenyl)benzoic acid HPLC retention time (min): 4.25;
Mass Data: 518 (M+H)$^+$.

Example 6(10)

2-(4-(N-(4-methylthiophenylcarbonyl)-N-(3-phenylpropyl)aminomethyl)phenyl)benzoic acid HPLC retention time (min): 4.18;
Mass Data: 991 (2M+H)$^+$, 496 (M+H)$^+$.

Example 6(11)

2-(4-(N-(2-methylphenylcarbonyl)-N-(3-phenylpropyl)aminomethyl)phenyl)benzoic acid HPLC retention time (min): 4.14;
Mass Data: 927 (2M+H)$^+$, 464 (M+H)$^+$.

Example 6(12)

2-(4-(N-(3-methylphenylcarbonyl)-N-(3-phenylpropyl)aminomethyl)phenyl)benzoic acid HPLC retention time (min): 4.18;
Mass Data: 927 (2M+H)$^+$, 464 (M+H)$^+$.

Example 6(13)

2-(4-(N-(4-methylphenylcarbonyl)-N-(3-phenylpropyl)aminomethyl)phenyl)benzoic acid HPLC retention time (min): 4.18;
Mass Data: 927 (2M+H)$^+$, 464 (M+H)$^+$.

Example 6(14)

2-(4-(N-(4-ethylphenylcarbonyl)-N-(3-phenylpropyl)aminomethyl)phenyl)benzoic acid HPLC retention time (min): 4.26;
Mass Data: 955 (2M+H)$^+$, 478 (M+H)$^+$.

Example 6(15)

2-(4-(N-(4-isopropylphenylcarbonyl)-N-(3-phenylpropyl)aminomethyl)phenyl)benzoic acid HPLC retention time (min): 4.35;
Mass Data: 983 (2M+H)$^+$, 492 (M+H)$^+$.

Example 6(16)

2-(4-(N-(2-fluorophenylcarbonyl)-N-(3-phenylpropyl)aminomethyl)phenyl)benzoic acid HPLC retention time (min): 4.10;
Mass Data: 935 (2M+H)$^+$, 468 (M+H)$^+$.

Example 6(17)

2-(4-(N-(3-fluorophenylcarbonyl)-N-(3-phenylpropyl)aminomethyl)phenyl)benzoic acid HPLC retention time (min): 4.11;
Mass Data: 935 (2M+H)$^+$, 468 (M+H)$^+$.

Example 6(18)

2-(4-(N-(4-fluorophenylcarbonyl)-N-(3-phenylpropyl)aminomethyl)phenyl)benzoic acid HPLC retention time (min): 4.11;
Mass Data: 935 (2M+H)$^+$, 468 (M+H)$^+$.

Example 6(19)

2-(4-(N-(4-(N,N-dipropylaminosulfonyl)phenylcarbonyl)-N-(3-phenylpropyl)aminomethyl)phenyl)benzoic acid HPLC retention time (min): 4.28;
Mass Data: 613 (M+H)$^+$.

Example 6(20)

2-(4-(N-(4-methoxy-3-chlorophenylcarbonyl)-N-(3-phenylpropyl)aminomethyl)phenyl)benzoic acid HPLC retention time (min): 4.16;
Mass Data: 514 (M+H)$^+$.

Example 6(21)

2-(4-(N-(4-methoxy-3-nitrophenylcarbonyl)-N-(3-phenylpropyl)aminomethyl)phenyl)benzoic acid HPLC retention time (min): 4.03;
Mass Data: 525 (M+H)$^+$.

Example 6(22)

2-(4-(N-(3-methoxy-4-methylphenylcarbonyl)-N-(3-phenylpropyl)aminomethyl)phenyl)benzoic acid HPLC retention time (min): 4.22;
Mass Data: 987 (2M+H)$^+$, 494 (M+H)$^+$.

Example 6(23)

2-(4-(N-(2-methoxy-4-methylthiophenylcarbonyl)-N-(3-phenylpropyl)aminomethyl)phenyl)benzoic acid HPLC retention time (min): 4.18;
Mass Data: 526 (M+H)$^+$.

Example 6(24)

2-(4-(N-(2-methoxy-4-chlorophenylcarbonyl)-N-(3-phenylpropyl)aminomethyl)phenyl)benzoic acid HPLC retention time (min): 4.20;
Mass Data: 514 (M+H)$^+$.

Example 6(25)

2-(4-(N-(3,4-dimethoxyphenylcarbonyl)-N-(3-phenylpropyl)aminomethyl)phenyl)benzoic acid HPLC retention time (min): 3.99;
Mass Data: 510 (M+H)$^+$.

Example 6(26)

2-(4-(N-(2,4-dimethoxyphenylcarbonyl)-N-(3-phenylpropyl)aminomethyl)phenyl)benzoic acid HPLC retention time (min): 4.09;
Mass Data: 510 (M+H)$^+$.

Example 6(27)

2-(4-(N-(3,5-dimethoxyphenylcarbonyl)-N-(3-phenylpropyl)aminomethyl)phenyl)benzoic acid HPLC retention time (min): 4.10;
Mass Data: 510 (M+H)$^+$.

Example 6(28)

2-(4-(N-(2,3-dimethoxyphenylcarbonyl)-N-(3-phenylpropyl)aminomethyl)phenyl)benzoic acid HPLC retention time (min): 4.07;
Mass Data: 510 (M+H)$^+$.

Example 6(29)

2-(4-(N-(2-chloro-4,5-dimethoxyphenylcarbonyl)-N-(3-phenylpropyl)aminomethyl)phenyl)benzoic acid HPLC retention time (min): 4.08;
Mass Data: 544 (M+H)$^+$.

Example 6(30)

2-(4-(N-(2-chloro-5-methylphenylcarbonyl)-N-(3-phenylpropyl)aminomethyl)phenyl)benzoic acid HPLC retention time (min): 4.25;
Mass Data: 995 (2M+H)$^+$, 498 (M+H)$^+$.

Example 6(31)

2-(4-(N-(2-methyl-4-chlorophenylcarbonyl)-N-(3-phenylpropyl)aminomethyl)phenyl)benzoic acid HPLC retention time (min): 4.27;
Mass Data: 995 (2M+H)$^+$, 498 (M+H)$^+$.

Example 6(32)

2-(4-(N-(2-fluoro-5-methylphenylcarbonyl)-N-(3-phenylpropyl)aminomethyl)phenyl)benzoic acid HPLC retention time (min): 4.17;
Mass Data: 963 (2M+H)$^+$, 482 (M+H)$^+$.

Example 6(33)

2-(4-(N-(5-fluoro-2-methylphenylcarbonyl)-N-(3-phenylpropyl)aminomethyl)phenyl)benzoic acid HPLC retention time (min): 4.15;
Mass Data: 963 (2M+H)$^+$, 482 (M+H)$^+$.

Example 6(34)

2-(4-(N-(2-fluoro-4-trifluoromethylphenylcarbonyl)-N-(3-phenylpropyl)aminomethyl)phenyl)benzoic acid HPLC retention time (min): 4.27;
Mass Data: 536 (M+H)$^+$.

Example 6(35)

2-(4-(N-(3,4-difluorophenylcarbonyl)-N-(3-phenylpropyl)aminomethyl)phenyl)benzoic acid HPLC retention time (min): 4.15;
Mass Data: 971 (2M+H)$^+$, 486 (M+H)$^+$.

Example 6(36)

2-(4-(N-(4-(pyrrol-1-yl)phenylcarbonyl)-N-(3-phenylpropyl)aminomethyl)phenyl)benzoic acid HPLC retention time (min): 4.23;
Mass Data: 515 (M+H)$^+$.

Example 6(37)

2-(4-(N-(5-butylpyridin-2-ylcarbonyl)-N-(3-phenylpropyl)aminomethyl)phenyl)benzoic acid HPLC retention time (min): 4.21;
Mass Data: 507 (M+H)$^+$.

Example 6(38)

2-(4-(N-(2-chloro-3-methylphenylcarbonyl)-N-(3-phenylpropyl)aminomethyl)phenyl)benzoic acid HPLC retention time (min): 4.21;
Mass Data: 995 (2M+H)$^+$, 498 (M+H)$^+$.

Example 6(39)

2-(4-(N-(2-chloro-4-fluorophenylcarbonyl)-N-(3-phenylpropyl)aminomethyl)phenyl)benzoic acid HPLC retention time (min): 4.17;
Mass Data: 502 (M+H)$^+$.

Example 6(40)

2-(4-(N-(5-(2-chloro-5-trifluoromethylphenyl)furan-2-ylcarbonyl)-N-(3-phenylpropyl)aminomethyl)phenyl)benzoic acid HPLC retention time (min): 4.53;
Mass Data: 618 (M+H)$^+$.

Example 6(41)

2-(4-(N-(5-(4-chlorophenyl)furan-2-ylcarbonyl)-N-(3-phenylpropyl)aminomethyl)phenyl)benzoic acid HPLC retention time (min): 4.46;
Mass Data: 550 (M+H)$^+$.

Example 6(42)

2-(4-(N-(5-(3-trifluoromethylphenyl)furan-2-ylcarbonyl)-N-(3-phenylpropyl)aminomethyl)phenyl)benzoic acid HPLC retention time (min): 4.43;
Mass Data: 584 (M+H)$^+$.

Example 6(43)

2-(4-(N-(benzothiophen-2-ylcarbonyl)-N-(3-phenyl-propyl)aminomethyl)phenyl)benzoic acid HPLC retention time (min): 4.28;
Mass Data: 506 (M+H)$^+$.

Example 6(44)

2-(4-(N-(indol-5-ylcarbonyl)-N-(3-phenylpropyl)aminomethyl)phenyl)benzoic acid

HPLC retention time (min): 4.06;
Mass Data: 977 (2M+H)$^+$, 489 (M+H)$^+$.

Example 6(45)

2-(4-(N-(4-difluoromethoxyphenylcarbonyl)-N-(3-phenylpropyl)aminomethyl)phenyl)benzoic acid HPLC retention time (min): 4.07;
Mass Data: 516 (M+H)$^+$.

Example 6(46)

2-(4-(N-(4-dimethylaminophenylcarbonyl)-N-(3-phenylpropyl)aminomethyl)phenyl)benzoic acid HPLC retention time (min): 3.67;
Mass Data: 985 (2M+H)$^+$, 493 (M+H)$^+$.

Example 6(47)

2-(4-(N-(4-methylsulfonylphenylcarbonyl)-N-(3-phenylpropyl)aminomethyl)phenyl)benzoic acid HPLC retention time (min): 3.82;
Mass Data: 528 (M+H)$^+$.

Example 6(48)

2-(4-(N-(4-nitrophenylcarbonyl)-N-(3-phenylpropyl)aminomethyl)phenyl)benzoic acid HPLC retention time (min): 4.02;
Mass Data: 989 (2M+H)$^+$, 495 (M+H)$^+$.

Example 6(49)

2-(4-(N-(4-methylcarbonylphenylcarbonyl)-N-(3-phenylpropyl)aminomethyl)phenyl)benzoic acid HPLC retention time (min): 3.93;
Mass Data: 983 (2M+H)$^+$, 492 (M+H)$^+$.

Example 6(50)

2-(4-(N-(3-dimethylaminophenylcarbonyl)-N-(3-phenylpropyl)aminomethyl)phenyl)benzoic acid HPLC retention time (min): 3.55;
Mass Data: 479 (M−Me+H)$^+$.

Example 6(51)

2-(4-(N-(3-carboxyphenylcarbonyl)-N-(3-phenylpropyl)aminomethyl)phenyl)benzoic acid HPLC retention time (min): 3.76;
Mass Data: 987 (2M+H)$^+$, 494 (M+H)$^+$.

Example 6(52)

2-(4-(N-(3-chlorophenylcarbonyl)-N-(3-phenylpropyl)aminomethyl)phenyl)benzoic acid HPLC retention time (min): 4.13;
Mass Data: 967 (2M+H)$^+$, 484 (M+H)$^+$.

Example 6(53)

2-(4-(N-(2-chlorophenylcarbonyl)-N-(3-phenylpropyl)aminomethyl)phenyl)benzoic acid HPLC retention time (min): 4.07;
Mass Data: 967 (2M+H)$^+$, 484 (M+H)$^+$.

Example 6(54)

2-(4-(N-(4-methoxy-3-cyclopentyloxyphenylcarbonyl)-N-(3-phenylpropyl)aminomethyl)phenyl)benzoic acid HPLC retention time (min): 4.20;
Mass Data: 564 (M+H)$^+$.

Example 6(55)

2-(4-(N-(2-methoxy-5-chlorophenylcarbonyl)-N-(3-phenylpropyl)aminomethyl)phenyl)benzoic acid HPLC retention time (min): 4.12;
Mass Data: 514 (M+H)$^+$.

Example 6(56)

2-(4-(N-(2-methoxy-5-fluorophenylcarbonyl)-N-(3-phenylpropyl)aminomethyl)phenyl)benzoic acid HPLC retention time (min): 4.02;
Mass Data: 995 (2M+H)$^+$, 498 (M+H)$^+$.

Example 6(57)

2-(4-(N-(2,5-dimethoxyphenylcarbonyl)-N-(3-phenylpropyl)aminomethyl)phenyl)benzoic acid HPLC retention time (min): 3.99;
Mass Data: 510 (M+H)$^+$.

Example 6(58)

2-(4-(N-(4-methoxy-3-fluorophenylcarbonyl)-N-(3-phenylpropyl)aminomethyl)phenyl)benzoic acid HPLC retention time (min): 4.01;
Mass Data: 995 (2M+H)$^+$, 498 (M+H)$^+$.

Example 6(59)

2-(4-(N-(2,5-dichlorophenylcarbonyl)-N-(3-phenyl-propyl)aminomethyl)phenyl)benzoic acid HPLC retention time (min): 4.16;
Mass Data: 518 (M+H)$^+$.

Example 6(60)

2-(4-(N-(3,5-dichlorophenylcarbonyl)-N-(3-phenyl-propyl)aminomethyl)phenyl)benzoic acid HPLC retention time (min): 4.26;
Mass Data: 518 (M+H)$^+$.

Example 6(61)

2-(4-(N-(2-fluoro-6-chlorophenylcarbonyl)-N-(3-phenylpropyl)aminomethyl)phenyl)benzoic acid HPLC retention time (min): 4.09;
Mass Data: 502 (M+H)$^+$.

Example 6(62)

2-(4-(N-(3,4-difluorophenylcarbonyl)-N-(3-phenyl-propyl)aminomethyl)phenyl)benzoic acid HPLC retention time (min): 4.07;
Mass Data: 971 (2M+H)$^+$, 486 (M+H)$^+$.

Example 6(63)

2-(4-(N-(2,3,4,5,6-pentafluorophenylcarbonyl)-N-(3-phenylpropyl)aminomethyl)phenyl)benzoic acid HPLC retention time (min): 3.91;
Mass Data: 539 (M+H)$^+$.

Example 6(64)

2-(4-(N-(1,3-dioxaindan-5-ylcarbonyl)-N-(3-phenyl-propyl)aminomethyl)phenyl)benzoic acid HPLC retention time (min): 3.98;
Mass Data: 987 (2M+H)$^+$, 494 (M+H)$^+$.

Example 6(65)

2-(4-(N-(3,4-dimethylphenylcarbonyl)-N-(3-phenyl-propyl)aminomethyl)phenyl)benzoic acid HPLC retention time (min): 4.18;
Mass Data: 955 (2M+H)$^+$, 478 (M+H)$^+$.

Example 6(66)

2-(4-(N-3,5-dimethylphenylcarbonyl)-N-(3-phenyl-propyl)aminomethyl)phenyl)benzoic acid HPLC retention time (min): 4.20;
Mass Data: 955 (2M+H)$^+$, 478 (M+H)$^+$.

Example 6(67)

2-(4-(N-(3,5-bis(trifluoromethyl)phenylcarbonyl)-N-(3-phenylpropyl)aminomethyl)phenyl)benzoic acid HPLC retention time (min): 4.27;
Mass Data: 586 (M+H)$^+$.

Example 6(68)

2-(4-(N-(3,5-dimethyl-4-hydroxyphenylcarbonyl)-N-(3-phenylpropyl)aminomethyl)phenyl)benzoic acid HPLC retention time (min): 3.91;
Mass Data: 987 (2M+H)$^+$, 494 (M+H)$^+$.

Example 6(69)

2-(4-(N-(2-chloro-4,5-difluorophenylcarbonyl)-N-(3-phenylpropyl)aminomethyl)phenyl)benzoic acid HPLC retention time (min): 4.12;
Mass Data: 520 (M+H)$^+$.

Example 6(70)

2-(4-(N-(3-trifluoromethyl-4-methylphenylcarbonyl)-N-(3-phenylpropyl)aminomethyl)phenyl)benzoic acid HPLC retention time (min) 4.22;
Mass Data: 532 (M+H)$^+$.

Example 6(71)

2-(4-(N-(4-chlorophenylmethylcarbonyl)-N-(3-phenylpropyl)aminomethyl)phenyl)benzoic acid HPLC retention time (min): 4.16;
Mass Data: 995 (2M+H)$^+$, 498 (M+H)$^+$.

Example 6(72)

2-(4-(N-(3-chlorophenylmethylcarbonyl)-N-(3-phenylpropyl)aminomethyl)phenyl)benzoic acid HPLC retention time (min): 4.17;
Mass Data: 995 (2M+H)$^+$, 498 (M+H)$^+$.

Example 6(73)

2-(4-(N-(2-chlorophenylmethylcarbonyl)-N-(3-phenylpropyl)aminomethyl)phenyl)benzoic acid HPLC retention time (min): 4.15;
Mass Data: 995 (2M+H)$^+$, 498 (M+H)$^+$.

Example 6(74)

2-(4-(N-(4-fluorophenylmethylcarbonyl)-N-(4-phenylpropyl)aminomethyl)phenyl)benzoic acid HPLC retention time (min): 4.09;
Mass Data: 963 (2M+H)$^+$, 482 (M+H)$^+$.

Example 6(75)

2-(4-(N-(4-methylphenylmethylcarbonyl)-N-(3-phenylpropyl)aminomethyl)phenyl)benzoic acid HPLC retention time (min): 4.14;
Mass Data: 955 (2M+H)$^+$, 478 (M+H)$^+$.

Example 6(76)

2-(4-(N-(4-dimethylaminophenylmethylcarbonyl)-N-(3-phenylpropyl)aminomethyl)phenyl)benzoic acid HPLC retention time (min): 3.48;
Mass Data: 507 (M+H)$^+$.

Example 6(77)

2-(4-(N-(4-trifluoromethoxyphenylmethylcarbonyl)-N-(3-phenylpropyl)aminomethyl)phenyl)benzoic acid HPLC retention time (min): 4.23;
Mass Data: 548 (M+H)$^+$.

Example 6(78)

2-(4-(N-(4-methoxyphenylmethylcarbonyl)-N-(3-phenylpropyl)aminomethyl)phenyl)benzoic acid HPLC retention time (min): 4.03;
Mass Data: 987 (2M+H)$^+$, 494 (M+H)$^+$.

Example 6(79)

2-(4-(N-(3-methoxyphenylmethylcarbonyl)-N-(3-phenylpropyl)aminomethyl)phenyl)benzoic acid HPLC retention time (min): 4.06;
Mass Data: 987 (2M+H)$^+$, 494 (M+H)$^+$.

Example 6(80)

2-(4-(N-(2-methoxyphenylmethylcarbonyl)-N-(3-phenylpropyl)aminomethyl)phenyl)benzoic acid HPLC retention time (min): 4.09;
Mass Data: 987 (2M+H)$^+$, 494 (M+H)$^+$.

Example 6(81)

2-(4-(N-(2,3-dimethoxyphenylmethylcarbonyl)-N-(3-phenylpropyl)aminomethyl)phenyl)benzoic acid HPLC retention time (min): 4.06;
Mass Data: 524 (M+H)$^+$.

Example 6(82)

2-(4-(N-(3,4-dimethoxyphenylmethylcarbonyl)-N-(3-phenylpropyl)aminomethyl)phenyl)benzoic acid HPLC retention time (min): 3.93;
Mass Data: 524 (M+H)$^+$.

Example 6(83)

2-(4-(N-(2,5-dimethoxyphenylmethylcarbonyl)-N-(3-phenylpropyl)aminomethyl)phenyl)benzoic acid HPLC retention time (min): 4.07;
Mass Data: 524 (M+H)$^+$.

Example 6(84)

2-(4-(N-(3,5-dimethoxyphenylmethylcarbonyl)-N-(3-phenylpropyl)aminomethyl)phenyl)benzoic acid HPLC retention time (min): 4.04;
Mass Data: 524 (M+H)$^+$.

Example 6(85)

2-(4-(N-(1-phenylpropylcarbonyl)-N-(3-phenylpropyl)aminomethyl)phenyl)benzoic acid HPLC retention time (min): 4.26;
Mass Data: 985 (2M+H)$^+$, 492 (M+H)$^+$.

Example 6(86)

(2-(4-(N-(4-difluoromethoxyphenylcarbonyl)-N-(3-phenylpropyl)aminomethyl)phenyl)phenyl)acetic acid HPLC retention time (min): 4.09;
Mass Data: 530 (M+H)$^+$.

Example 6(87)

(2-(4-(N-(2-difluoromethoxyphenylcarbonyl)-N-(3-phenylpropyl)aminomethyl)phenyl)phenyl)acetic acid HPLC retention time (min): 4.06;
Mass Data: 530 (M+H)$^+$.

Example 6(88)

(2-(4-(N-(2-methoxy-5-chlorophenylcarbonyl)-N-(3-phenylpropyl)aminomethyl)phenyl)phenyl)acetic acid HPLC retention time (min): 4.15;
Mass Data: 528 (M+H)$^+$.

Example 6(89)

(2-(4-(N-(2-methyl-5-fluorophenylcarbonyl)-N-(3-phenylpropyl)aminomethyl)phenyl)phenyl)acetic acid HPLC retention time (min): 4.11;
Mass Data: 991 (2M+H)$^+$, 496 (M+H)$^+$.

Example 6(90)

(2-(4-(N-(2,5-dichlorophenylcarbonyl)-N-(3-phenylpropyl)aminomethyl)phenyl)phenyl)acetic acid HPLC retention time (min): 4.21;
Mass Data: 532 (M+H)$^+$.

Example 6(91)

(2-(4-(N-(2,5-dimethoxyphenylcarbonyl)-N-(3-phenylpropyl)aminomethyl)phenyl)phenyl)acetic acid HPLC retention time (min): 4.03;
Mass Data: 524 (M+H)$^+$.

Example 6(92)

(2-(4-(N-(2-chloro-5-methylphenylcarbonyl)-N-(3-phenylpropyl)aminomethyl)phenyl)phenyl)acetic acid HPLC retention time (min): 4.19;
Mass Data: 512 (M+H)$^+$.

Example 6(93)

(2-(4-(N-(2-methoxy-5-fluorophenylcarbonyl)-N-(3-phenylpropyl)aminomethyl)phenyl)phenyl)acetic acid HPLC retention time (min): 4.06;
Mass Data: 512 (+H)$^+$.

Example 6(94)

(2-(4-(N-(3-chloro-4-methoxyphenylcarbonyl)-N-(3-phenylpropyl)aminomethyl)phenyl)phenyl)acetic acid HPLC retention time (min): 4.11;
Mass Data: 528 (M+H)$^+$.

Example 6(95)

(2-(4-(N-(3-methoxy-4-methylphenylcarbonyl)-N-(3-phenylpropyl)aminomethyl)phenyl)phenyl)acetic acid HPLC retention time (min): 4.18;
Mass Data: 508 (M+H)$^+$.

Example 6(96)

(2-(4-(N-(2-chloro-3-methylphenylcarbonyl)-N-(3-phenylpropyl)aminomethyl)phenyl)phenyl)acetic acid HPLC retention time (min): 4.18;
Mass Data: 512 (M+H)$^+$.

Example 6(97)

(2-(4-(N-(2-fluoro-6-chlorophenylcarbonyl)-N-(3-phenylpropyl)aminomethyl)phenyl)phenyl)acetic acid HPLC retention time (min): 4.10;
Mass Data: 516 (M+H)$^+$.

Example 6(98)

(2-(4-(N-(3,5-dichlorophenylcarbonyl)-N-(3-phenylpropyl)aminomethyl)phenyl)phenyl)acetic acid HPLC retention time (min): 4.30;
Mass Data: 532 (M+H)$^+$.

Example 6(99)

(2-(4-(N-(3,5-dimethoxyphenylcarbonyl)-N-(3-phenylpropyl)aminomethyl)phenyl)phenyl)acetic acid HPLC retention time (min): 4.06;
Mass Data: 524 (M+H)$^+$.

Example 6(100)

(2-(4-(N-(3,4,5-trimethoxyphenylcarbonyl)-N-(3-phenylpropyl)aminomethyl)phenyl)phenyl)acetic acid HPLC retention time (min): 3.97;
Mass Data: 554 (M+H)$^+$.

Example 6(101)

(2-(4-(N-(3,5-dimethyl-4-hydroxyphenylcarbonyl)-N-(3-phenylpropyl)aminomethyl)phenyl)phenyl)acetic acid HPLC retention time (min): 3.95;
Mass Data: 508 (M+H)$^+$.

Example 6(102)

(2-(4-(N-(2,5-difluoro-4-chlorophenylcarbonyl)-N-(3-phenylpropyl)aminomethyl)phenyl)phenyl)acetic acid HPLC retention time (min): 4.18;
Mass Data: 534 (M+H)$^+$.

Example 6(103)

(2-(4-(N-(2-chloro-4,5-difluorophenylcarbonyl)-N-(3-phenylpropyl)aminomethyl)phenyl)phenyl)acetic acid HPLC retention time (min): 4.16;
Mass Data: 534 (M+H)$^+$.

Example 6(104)

(2-(4-(N-(2-chloro-4,5-dimethoxyphenylcarbonyl)-N-(3-phenylpropyl)aminomethyl)phenyl)phenyl)acetic acid HPLC retention time (min): 4.02;
Mass Data: 558 (M+H)$^+$.

Example 6(105)

(2-(4-(N-(3,4-dimethoxyphenylcarbonyl)-N-(3-phenylpropyl)aminomethyl)phenyl)phenyl)acetic acid HPLC retention time (min): 3.93;
Mass Data: 524 (M+H)$^+$.

Example 6(106)

(2-(4-(N-(4-chlorophenylmethylcarbonyl)-N-(3-phenylpropyl)aminomethyl)phenyl)phenyl)acetic acid HPLC retention time (min): 4.21;
Mass Data: 512 (M+H)$^+$.

Example 6(107)

(2-(4-(N-(3-chlorophenylmethylcarbonyl)-N-(3-phenylpropyl)aminomethyl)phenyl)phenyl)acetic acid HPLC retention time (min): 4.18;
Mass Data: 512 (M+H)$^+$.

Example 6(108)

(2-(4-(N-(4-methoxyphenylmethylcarbonyl)-N-(3-phenylpropyl)aminomethyl)phenyl)phenyl)acetic acid HPLC retention time (min): 4.05;
Mass Data: 508 (M+H)$^+$.

Example 6(109)

(2-(4-(N-(4-methylphenylmethylcarbonyl)-N-(3-phenylpropyl)aminomethyl)phenyl)phenyl)acetic acid HPLC retention time (min): 4.16;
Mass Data: 983 (2M+H)$^+$, 492 (M+H)$^+$.

Example 6(110)

(2-(4-(N-(2,5-difluorophenylcarbonyl)-N-(3-phenylpropyl)aminomethyl)phenyl)phenyl)acetic acid HPLC retention time (min): 4.07;
Mass Data: 508 (M+H)$^+$.

Example 6(111)

(2-(4-(N-(2,3,6-trifluorophenylcarbonyl)-N-(3-phenylpropyl)aminomethyl)phenyl)phenyl)acetic acid HPLC retention time (min): 4.09;
Mass Data: 518 (M+H)$^+$.

Example 6(112)

(2-(4-(N-(2,4,5-trifluorophenylcarbonyl)-N-(3-phenylpropyl)aminomethyl)phenyl)phenyl)acetic acid HPLC retention time (min): 4.11;
Mass Data: 518 (M+H)$^+$.

Example 6(113)

(2-(4-(N-(4-methoxyphenylcarbonyl)-N-(3-phenylpropyl)aminomethyl)phenyl)phenyl)acetic acid HPLC retention time (min): 4.03;
Mass Data: 987 (2M+H)$^+$, 494 (M+H)$^+$.

Example 6(114)

2-(4-(N-(4-difluoromethoxyphenylcarbonyl)-N-(3-(4-methoxyphenyl)propyl)aminomethyl)phenyl)benzoic acid HPLC retention time (min): 4.03;
Mass Data: 546 (M+H)$^+$.

Example 6(115)

2-(4-(N-(2-difluoromethoxyphenylcarbonyl)-N-(3-(4-methoxyphenyl)propyl)aminomethyl)phenyl)benzoic acid HPLC retention time (min): 4.01;
Mass Data: 546 (M+H)$^+$.

Example 6(116)

2-(4-(N-(2-methoxy-5-chlorophenylcarbonyl)-N-(3-(4-methoxyphenyl)propyl)aminomethyl)phenyl)benzoic acid HPLC retention time (min): 4.07;
Mass Data: 544 (M+H)$^+$.

Example 6(117)

2-(4-(N-(2,5-dichlorophenylcarbonyl)-N-(3-(4-methoxyphenyl)propyl)aminomethyl)phenyl)benzoic acid HPLC retention time (min): 4.15;
Mass Data: 548 (M+H)$^+$.

Example 6(118)

2-(4-(N-(3-methoxy-4-methylphenylcarbonyl)-N-(3-(4-methoxyphenyl)propyl)aminomethyl)phenyl)benzoic acid HPLC retention time (min): 4.13;
Mass Data: 524 (M+H)$^+$.

Example 6(119)

2-(4-(N-(3,5-dichlorophenylcarbonyl)-N-(3-(4-methoxyphenyl)propyl)aminomethyl)phenyl)benzoic acid HPLC retention time (min): 4.24;
Mass Data: 548 (M+H)$^+$.

Example 6(120)

2-(4-(N-(3,5-dimethoxyphenylcarbonyl)-N-(3-(4-methoxyphenyl)propyl)aminomethyl)phenyl)benzoic acid HPLC retention time (min): 4.01;
Mass Data: 540 (M+H)$^+$.

Example 6(121)

2-(4-(N-(3,4,5-trimethoxyphenylcarbonyl)-N-(3-(4-methoxyphenyl)propyl)aminomethyl)phenyl)benzoic acid HPLC retention time (min): 3.92;
Mass Data: 570 (M+H)$^+$.

Example 6(122)

2-(4-(N-(3,5-dimethyl-4-hydroxyphenylcarbonyl)-N-(3-(4-methoxyphenyl)propyl)aminomethyl)phenyl)benzoic acid HPLC retention time (min): 3.90;
Mass Data: 524 (M+H)$^+$.

Example 6(123)

2-(4-(N-(2-chloro-4,5-difluorophenylcarbonyl)-N-(3-(4-methoxyphenyl)propyl)aminomethyl)phenyl)benzoic acid HPLC retention time (min): 4.11;
Mass Data: 550 (M+H)$^+$.

Example 6(124)

2-(4-(N-(2-chloro-4,5-dimethoxyphenylcarbonyl)-N-(3-(4-methoxyphenyl)propyl)aminomethyl)phenyl)benzoic acid HPLC retention time (min): 3.96;
Mass Data: 574 (M+H)$^+$.

Example 6(125)

2-(4-(N-(4-chlorophenylmethylcarbonyl)-N-(3-(4-methoxyphenyl)propyl)aminomethyl)phenyl)benzoic acid HPLC retention time (min): 4.15;
Mass Data: 528 (M+H)$^+$.

Example 6(126)

2-(4-(N-(4-methoxyphenylmethylcarbonyl)-N-(3-(4-methoxyphenyl)propyl)aminomethyl)phenyl)benzoic acid HPLC retention time (min): 4.01;
Mass Data: 524 (M+H)$^+$.

Example 6(127)

2-(4-(N-(2,3,6-trifluorophenylcarbonyl)-N-(3-(4-methoxyphenyl)propyl)aminomethyl)phenyl)benzoic acid HPLC retention time (min): 4.05;
Mass Data: 534 (M+H)$^+$.

Reference Example 4

N-methoxy-N-methyl-(3,4,5-trimethoxyphenyl)carboxamide

Under atmosphere of argon, to a solution of 3,4,5-trimethoxybenzoic acid (3 g) in dichloromethane (15 ml), oxalyl chloride (3.58 g) and catalytic amount of N,N-dimethylformamide were added at 0° C. and the mixture was stirred for 1 hour at room temperature. The reaction mixture was concentrated to give acyl chloride.

Under atmosphere of argon, to a solution of N,O-dimethylhydroxyamine hydrochloride (2.15 g) in dichloromethane (15 ml), a solution of the prepared acyl chloride in dichloromethane (15 ml) was added at 0° C. and the mixture was stirred for 30 minutes at room temperature.

Water was added to the reaction mixture and the mixture was extracted with ethyl acetate. The extract was washed with brine, dried over anhydrous sodium sulfate, concentrated under reduced pressure. The residue was purified by column chromatography on silica gel (Hexane:Ethyl acetate=from 4:1 to 1:1) to give the title compound (3.41 g) having the following physical data.

TLC: Rf 0.31 (Hexane:Ethyl acetate=1:2);
NMR (CDCl$_3$): δ 6.98 (s, 2H), 3.89 (s, 3H), 3.88 (s, 6H), 3.60 (s, 3H), 3.36 (s, 3H).

Reference Example 5

4-phenyl-1-(3,4,5-trimethoxyphenyl)butan-1-one

Under atmosphere of argon, to a solution of the compound prepared in Reference example 4 (300 mg) in tetrahydrofuran (5 ml), 1 M 3-phenylpropylmagnesium chloride in tetrahydrofuran (6 ml) was added at 0° C. and the mixture was stirred for 2.5 hours at room temperature.

Saturated aqueous solution of ammonium chloride was added to the reaction mixture and the mixture was extracted with ethyl acetate. The extract was washed with brine, dried over anhydrous sodium sulfate, concentrated under reduced pressure. The residue was purified by column chromatography on silica gel (Hexane:Ethyl acetate=5:1) to give the title compound (1.05 g) having the following physical data.

TLC: Rf 0.63 (Hexane:Ethyl acetate=1:1);
NMR (CDCl$_3$): δ 7.35-7.15 (m, 7H), 3.91 (s, 3H), 3.90 (s, 6H), 2.94 (t, J=7.2 Hz, 2H), 2.68 (t, J=7.2 Hz, 2H), 1.85-1.68 (m, 4H).

Example 7

2-(4-(2-(3,4,5-trimethoxyphenylcarbonyl)-4-phenylbutyl)phenyloxy)benzoic acid methyl ester Under atmosphere of argon, to a solution of the compound prepared in Reference example 5 (200 mg) in tetrahydrofuran (1 ml), N,N,N',N'',N''-pentamethyldiethylenetriamine (147 μl) was added at 0° C., then 2 M lithium diisopropylamide (610 μl) and a solution of 2-[4-(bromomethyl)phenoxy]benzoic acid (293 mg) in tetrahydrofuran (1 ml) was added to the mixture at −78° C. and the mixture was stirred for 2 hours at room temperature.

Saturated aqueous solution of ammonium chloride was added to the reaction mixture and the mixture was extracted with ethyl acetate. The extract was washed with brine, dried over anhydrous sodium sulfate, concentrated under reduced pressure. The residue was purified by column chromatography on silica gel (Hexane:Ethyl acetate=from 5:1 to 1:1) to give the compound of the present invention (153 mg) having the following physical data.

TLC: Rf 0.17 (Hexane:Ethyl acetate=3:1);
NMR (CDCl$_3$): δ 7.87 (dd, J=7.8, 1.8 Hz, 1H), 7.42 (m, 1H), 7.30-7.05 (m, 9H), 6.97 (s, 2H), 6.91 (m, 2H), 3.90 (s, 3H), 3.80 (s, 3H), 3.79 (s, 3H), 3.76 (s, 3H), 3.63 (m, 1H), 3.06 (dd, J=13.5, 8.1 Hz, 1H), 2.82 (dd, J=13.5, 5.7 Hz, 1H), 2.67 (m, 1H), 2.55 (m, 1H), 2.08 (m, 1H), 1.90 (m, 1H).

Example 8

2-(4-(2-(3,4,5-trimethoxyphenylcarbonyl)-4-phenyl-butyl)phenyloxy)benzoic acid

The compound of the present invention having the following physical data was obtained by the same procedure as described in Example 2 using the compound prepared in Example 7 instead of the compound prepared in Example 1.

TLC: Rf 0.35 (Dichloromethane:Methanol=9:1);

NMR (CDCl$_3$): δ 8.19 (dd, J=8.1, 1.8 Hz, 1H), 7.44 (m, 1H), 7.32-7.10 (m, 8H), 6.96 (s, 2H), 6.93 (m, 2H), 6.63 (d, J=8.4 Hz, 1H), 3.90 (s, 3H), 3.80 (s, 6H), 3.65 (m, 1H), 3.10 (dd, J=13.5, 8.7 Hz, 1H), 2.90 (dd, J=13.5, 5.4 Hz, 1H), 2.80-2.55 (m, 2H), 2.20 (m, 1H), 1.92 (m, 1H).

Examples 8(1)-8(8)

The following compounds of the present invention were obtained by the same procedures as described in Reference example 4, Reference example 5, Example 7 and Example 8 using 3,4,5-trimethoxybenzoic acid or corresponding carboxylic acid, 3-phenylpropylmagnesium chloride or corresponding compound (Grignard reagent) and 2-[4-(bromomethyl)phenoxy]benzoic acid or corresponding benzyl halide.

Example 8(1)

2-(4-(2-(3,4,5-trimethoxyphenylcarbonyl)-5-phenyl-pentyl)phenyloxy)benzoic acid

TLC: Rf 0.43 (Dichloromethane:Methanol=9:1);

NMR (CDCl$_3$): δ 8.19 (dd, J=7.8, 1.8 Hz, 1H), 7.45 (m, 1H), 7.30-7.08 (m, 8H), 7.04 (s, 2H), 6.95 (d, J=8.4 Hz, 2H), 6.63 (d, J=8.7 Hz, 1H), 3.90 (s, 3H), 3.85 (s, 6H), 3.65 (m, 1H), 3.07 (dd, J=13.5, 8.4 Hz, 1H), 2.83 (dd, J=13.5, 6.0 Hz, 1H), 2.60 (t, J=7.2 Hz, 2H), 1.98-1.45 (m, 4H).

Example 8(2)

2-(4-(2-(3,5-dimethoxy-4-methylphenylcarbonyl)-5-phenylpentyl)phenyloxy)benzoic acid TLC: Rf 0.43 (Dichloromethane:Methanol=9:1);

NMR (DMSO-d$_6$): δ 12.8 (s, 1H), 7.78 (dd, J=7.8, 1.8 Hz, 1H), 7.45 (m, 1H), 7.25-7.05 (m, 8H), 7.03 (s, 2H), 6.77 (d, J=8.4 Hz, 2H), 6.72 (d, J=8.4 Hz, 1H), 3.92 (m, 1H), 3.78 (s, 6H), 2.87 (dd, J=13.5, 8.4 Hz, 1H), 2.73 (dd, J=13.5, 6.0 Hz, 1H), 2.55-2.45 (m, 2H), 2.01 (s, 3H), 1.78-1.42 (m, 4H).

Example 8(3)

2-(4-(2-(3,5-dimethoxy-4-methylphenylcarbonyl)-5-phenylpentyl)phenyloxy)-4-methylbenzoic acid TLC: Rf 0.61 (Dichloromethane:Methanol=9:1);

NMR (DMSO-d$_6$): δ 12.6 (s, 1H), 7.70 (d, J=8.1 Hz, 1H), 7.25-7.00 (m, 10H), 6.75 (d, J=8.4 Hz, 2H), 6.61 (s, 1H), 3.90 (m, 1H), 3.78 (s, 6H), 2.88 (dd, J=13.5, 7.8 Hz, 1H), 2.72 (dd, J=13.5, 6.0 Hz, 1H), 2.55-2.45 (m, 2H), 2.22 (s, 3H), 2.00 (s, 3H), 1.78-1.45 (m, 4H).

Example 8(4)

3-(2-(3,4,5-trimethoxyphenylcarbonyl)-4-phenylbu-tyl)benzoic acid

TLC: Rf 0.48 (Dichloromethane:Methanol=9:1);

NMR (CDCl$_3$): δ 7.95-7.85 (m, 2H), 7.40-7.18 (m, 5H), 7.12-7.08 (m, 2H), 6.97 (s, 2H), 3.88 (s, 3H), 3.80 (s, 6H), 3.68 (m, 1H), 3.15 (dd, J=13.5, 8.4 Hz, 1H), 2.92 (dd, J=13.5, 6.0 Hz, 1H), 2.77-2.52 (m, 2H), 2.18 (m, 1H), 1.88 (m, 1H).

Example 8(5)

3-(2-(3,4,5-trimethoxyphenylcarbonyl)-5-phenylpen-tyl)benzoic acid

TLC: Rf 0.28 (Dichloromethane:Methanol=9:1);

NMR (CDCl$_3$): δ 7.92 (m, 1H), 7.88 (m, 1H), 7.40-7.06 (m, 7H), 7.04 (s, 2H), 3.88 (s, 3H), 3.84 (s, 6H), 3.68 (m, 1H), 3.12 (dd, J=13.5, 8.4 Hz, 1H), 2.90 (dd, J=13.5, 5.7 Hz, 1H), 2.58 (t, J=7.2 Hz, 2H), 1.98-1.50 (m, 4H).

Example 8(6)

(4-(2-(3,4,5-trimethoxyphenylcarbonyl)-4-phenylbu-tyl)phenyl)acetic acid

TLC: Rf 0.40 (Dichloromethane:Methanol=9:1);

NMR (CDCl$_3$): δ 7.28-7.06 (m, 9H), 6.95 (s, 2H), 3.88 (s, 3H), 3.78 (s, 6H), 3.62 (m, 1H), 3.57 (s, 2H), 3.07 (dd, J=13.5, 8.4 Hz, 1H), 2.83 (dd, J=13.5, 6.0 Hz, 1H), 2.67 (m, 1H), 2.55 (m, 1H), 2.16 (m, 1H), 1.87 (m, 1H).

Example 8(7)

(4-(2-(3,4,5-trimethoxyphenylcarbonyl)-5-phenyl-pentyl)phenyl)acetic acid

TLC: Rf 0.19 (Dichloromethane:Methanol=9:1);

NMR (CDCl$_3$): δ 7.30-7.05 (m, 9H), 7.00 (s, 2H), 3.87 (s, 3H), 3.82 (s, 6H), 3.60 (m, 1H), 3.57 (s, 2H), 3.03 (dd, J=13.5, 8.1 Hz, 1H), 2.76 (dd, J=13.5, 6.0 Hz, 1H), 2.56 (t, J=7.2 Hz, 2H), 1.90 (m, 1H), 1.70-1.50 (m, 3H).

Example 8(8)

(4-(2-(3,5-dimethoxy-4-methylphenylcarbonyl)-5-phenylpentyl)phenyl)acetic acid

TLC: Rf 0.52 (Dichloromethane:Methanol=9:1);

NMR (DMSO-d$_6$): δ 12.3 (s, 1H), 7.25-7.00 (m, 11H), 3.92 (m, 1H), 3.78 (s, 6H), 3.46 (s, 2H), 2.90 (dd, J=13.5, 7.8 Hz, 1H), 2.70 (dd, J=13.5, 6.0 Hz, 1H), 2.55-2.45 (m, 2H), 2.00 (s, 3H), 1.75-1.45 (m, 4H).

Examples 9(1)-9(7)

The following compounds of the present invention were obtained by the same procedures as described in Reference example 2, Example 1 and Example 2 using the compounds prepared in Reference example 1 or corresponding aldehyde, 3-phenylpropylamine or corresponding amine and 3,4,5-trimethoxybenzoic acid or corresponding carboxylic acid.

Example 9(1)

4-methyl-2-[4-({[3-(3-methylphenyl)propyl][oxo (phenyl)acetyl]amino}methyl)phenoxy]benzoic acid TLC: Rf 0.81 (Methanol:Dichloromethane=1:9);

NMR (CDCl$_3$): δ 8.11-6.60 (m, 16H), 4.72 and 4.38 (s, 2H), 3.51-3.12 (m, 2H), 2.67-2.40 (m, 2H), 2.34-2.27 (m, 6H), 2.03-1.80 (m, 2H).

Example 9(2)

2-[4-({(3,5-dimethoxy-4-methylbenzoyl)[2-(3-methylphenoxy)ethyl]amino}methyl)phenoxy]-4-methylbenzoic acid TLC: Rf 0.57 (Methanol:Dichloromethane=1:9);

NMR (CDCl$_3$): δ 8.11-8.07 (m, 1H), 7.53-6.47 (m, 12H), 4.99-4.66 (m, 2H), 4.43-3.56 (m, 10H), 2.35-2.27 (m, 6H), 2.13-2.02 (m, 3H).

Example 9(3)

2-(4-{[(3,5-dimethoxybenzoyl)(3-hydroxy-3-phenylpropyl)amino]methyl}phenoxy)-4-methylbenzoic acid TLC: Rf 0.43 (Dichloromethane:Methanol=9:1);

NMR (CDCl$_3$): δ 1.84-2.24 (m, 2H), 2.29-2.37 (m, 3H), 3.25-3.40 (m, 1H), 3.70-3.85 (m, 6H), 3.94-4.16 (m, 1H), 4.42-4.80 (m, 3H), 6.46-6.83 (m, 4H), 6.88-7.52 (m, 10H), 7.94-8.10 (m, 1H).

Example 9(4)

2-(4-{[(3,3-difluoro-3-phenylpropyl)(3 5-dimethoxy-4-methylbenzoyl)amino]methyl}phenoxy)-4-methylbenzoic acid TLC: Rf 0.26 (Methanol:Dichloromethane=1:19);

NMR (CDCl$_3$): δ 8.11-8.08 (m, 1H), 7.61-7.03 (m, 10H), 6.65-6.45 (m, 3H), 4.76-4.47 (m, 2H), 3.89-3.20 (m, 8H), 2.71-2.45 (m, 2H), 2.32 (s, 3H), 2.12-2.03 (m, 3H).

Example 9(5)

2-{2-[(3-phenylpropyl)(3,4,5-trimethoxybenzoyl) amino]ethoxy}benzoic acid

TLC: Rf 0.58 (Dichloromethane:Methanol=9:1);

NMR (CDCl$_3$): δ 8.18 (dd, J=3.0 Hz, 9.0 Hz, 1H), 7.59-7.54 (m, 1H), 7.28-7.13 (m, 5H), 7.06-7.00 (m, 2H), 6.59 (s, 2H), 4.52 (brs, 2H), 3.96-3.90 (m, 2H), 3.87 (s, 3H), 3.84 (s, 6H), 3.43 (brs, 2H), 2.51 (brs, 2H), 1.95-1.84 (m, 2H).

Example 9(6)

2-[(4-{[(3,5-dimethoxy-4-methylbenzoyl)(3-phenylpropyl)amino]methyl}phenyl)amino]benzoic acid TLC: Rf 0.52 (Dichloromethane:Methanol=9:1);

NMR (CDCl$_3$): δ 9.42 (br s, 1H), 8.04 (dd, J=1.5, 8.0 Hz, 1H), 7.41-6.91 (m, 11H), 6.80-6.75 (m, 1H), 6.57 (brs, 2H), 4.80-4.42 (m, 2H), 3.91-3.14 (m, 8H), 2.77-2.36 (m, 2H), 2.15-1.77 (m, 5H).

Example 9(7)

2-(4-{[(3,5-dimethoxy-4-methylbenzoyl)(3-hydroxy-3-phenylpropyl)amino]methyl}phenoxy)-4-methylbenzoic acid TLC: Rf 0.29 (Dichloromethane:Methanol=9:1);

NMR (CDCl$_3$): δ 1.82-2.14 (m, 5H), 2.32 (s, 3H), 3.32-3.84 (m, 8H), 4.46-4.80 (m, 3H), 6.53-6.68 (m, 3H), 7.03-7.13 (m, 3H), 7.24-7.44 (m, 7H), 8.09 (d, J=8.0 Hz, 1H).

Examples 10(1)-10(12)

The following compounds of the present invention were obtained by the same procedures as described in Reference example 3, Example 4 and Example 5 using the compounds prepared in Reference example 1 or corresponding aldehyde, 3-phenylpropylamine or corresponding amine and 3,5-dimethoxy-4-methylbenzoic acid or corresponding carboxylic acid.

Example 10(1)

(4-{[(3,5-dimethoxy-4-methylbenzoyl)(3-phenylpropyl)amino]methyl}phenyl)(difluoro)acetic acid TLC: Rf 0.10 (Dichloromethane:Methanol:Acetic acid=90:9:1);

NMR (CDCl$_3$): δ 7.53 (d, J=7.5 Hz, 2H), 7.35-6.87 (m, 7H), 6.57-6.36 (m, 2H), 4.77-4.47 (m, 2H), 3.83-3.15 (m, 8H), 2.71-2.36 (m, 2H), 2.16-1.76 (m, 5H).

Example 10(2)

[(4-{[(3,5-dimethoxy-4-methylbenzoyl)(3-phenylpropyl)amino]methyl}phenyl)amino](oxo)acetic acid TLC: Rf 0.17 (Dichloromethane:Methanol:Acetic acid=90:9:1);

NMR (CDCl$_3$): δ 9.04 (s, 1H), 7.64 (d, J=8.0 Hz, 2H), 7.41-6.91 (m, 7H), 6.54 (s, 2H), 4.79-4.45 (m, 2H), 3.82-3.00 (m, 8H), 2.75-2.34 (m, 2H), 2.14-1.76 (m, 5H).

Example 10(3)

2-{[(3-{[(3,5-dimethoxy-4-methylbenzoyl)(3-phenylpropyl)amino]methyl}phenyl)amino] sulfonyl}benzoic acid TLC: Rf 0.16 (Dichloromethane:Methanol=9:1);

NMR (CDCl$_3$): δ 8.39-8.12 (m, 1H), 7.91-7.76 (m, 2H), 7.57-7.34 (m, 2H), 7.30-6.79 (m, 9H), 6.63-6.48 (m, 2H), 4.71-4.33 (m, 2H), 3.88-3.50 (m, 6H), 3.41-2.81 (m, 2H), 2.67-2.29 (m, 2H), 2.12-1.68 (m, 5H).

Example 10(4)

2-{[(4-{[(3,5-dimethoxy-4-methylbenzoyl)(3-phenylpropyl)amino]methyl}phenyl)sulfonyl] amino}benzoic acid TLC: Rf 0.25 (Dichloromethane:Methanol=9:1);

NMR (CDCl$_3$): δ 10.74-10.44 (m, 1H), 7.97-7.90 (m, 1H), 7.85-7.76 (m, 2H), 7.71-7.68 (m, 1H), 7.51-7.46 (m, 1H), 7.38-7.12 (m, 6H), 7.10-7.05 (m, 1H), 6.98-6.89 (m, 1H), 6.49 (s, 2H), 4.74-4.46 (m, 2H), 3.86-3.15 (m, 8H), 2.69-2.36 (m, 2H), 2.14-1.74 (m, 5H).

Example 10(5)

2-({2-[(3,5-dimethoxy-4-methylbenzoyl)(3-phenyl-propyl)amino]ethyl}thio)-1,3-thiazole-4-carboxylic acid TLC: Rf 0.30 (Dichloromethane:Methanol=9:1);
NMR (CDCl$_3$): δ 8.09 (s, 1H), 7.32-6.93 (m, 5H), 6.47 (s, 2H), 3.96-3.28 (m, 12H), 2.79-2.42 (m, 2H), 2.17-1.82 (m, 5H).

Example 10(6)

4'-{2-[(3,5-dimethoxy-4-methylbenzoyl)(3-phenyl-propyl)amino]ethyl}-2-biphenylcarboxylic acid TLC: Rf 0.59 (Dichloromethane:Methanol=9:1);
NMR (CDCl$_3$): δ 7.90-7.85 (m, 1H), 7.56-6.87 (m, 12H), 6.45 (s, 2H), 3.83-3.46 (m, 9H), 3.22-2.36 (m, 5H), 2.13-1.71 (m, 5H).

Example 10(7)

2-[4-({(3,5-dimethoxy-4-methylbenzoyl)[2-(1,3-thiazol-2-ylthio)ethyl]amino}methyl)phenoxy]-4-methylbenzoic acid TLC: Rf 0.51 (Dichloromethane:Methanol=9:1);
NMR (CDCl$_3$): δ 8.06 (d, J=8.0 Hz, 1H), 7.68-6.95 (m, 7H), 6.66 (s, 1H), 6.57 (s, 2H), 4.89-4.58 (m, 2H), 3.88-3.11 (m, 10H), 2.32 (s, 3H), 2.08 (s, 3H).

Example 10(8)

(4-{[(3,3-difluoro-3-phenylpropyl)(3-methylbutyryl)amino]methyl}phenoxy)acetic acid TLC: Rf 0.26 (Dichloromethane:Methanol=9:1);
NMR (CDCl$_3$): δ 7.50-7.37 (m, 5H), 7.14-7.13 (m, 2H), 6.93-6.81 (m, 2H), 4.68-4.63 (m, 2H), 4.51-4.44 (m, 2H), 3.52-3.34 (m, 4H), 2.53-2.09 (m, 5H), 0.99-0.89 (m, 6H).

Example 10(9)

4-methyl-2-[4-({[(2Z)-2-methyl-2-butenoyl][3-(3-methylphenyl)propyl]amino}methyl)phenoxy]benzoic acid TLC: Rf 0.60 (Methanol:Dichloromethane=1:9);
NMR (CDCl$_3$): δ 8.11-8.08 (m, 1H), 7.32-6.89 (m, 9H), 6.64-6.62 (m, 1H), 5.52-5.34 (m, 1H), 4.66 and 4.54 (s, 2H), 3.44-3.22 (m, 2H), 2.61-2.48 (m, 2H), 2.32-2.30 (m, 6H), 1.94-1.55 (m, 8H).

Example 10(10)

4'-{[(3-phenylpropyl)(2-propylpentanoyl)amino]methyl}-2-biphenylcarboxylic acid

TLC: Rf 0.49 (Chloroform:Methanol=9:1);
NMR (DMSO-d$_6$): δ 12.85-12.55 (br, 1H), 7.71-7.67 (m, 1H), 7.57-7.51 (m, 1H), 7.45-7.39 (m, 1H), 7.36-7.15 (m, 10H), 4.64 and 4.54 (m, 2H), 3.37-3.20 (m, 2H), 2.61-2.52 (m, 3H), 1.85-1.71 (m, 2H), 1.52-1.07 (m, 8H), 0.82-0.72 (m, 6H).

Example 10(11)

(4'-{[[methoxy(phenyl)acetyl](3-phenylpropyl)amino]methyl}-2-biphenylyl)acetic acid TLC: Rf 0.50 (Dichloromethane:Methanol=9:1).

Example 10(12)

(4'-{[[difluoro(phenyl)acetyl](3-phenylpropyl)amino]methyl}-2-biphenylyl)acetic acid TLC: Rf 0.11 (Dichloromethane:Methanol=9:1).

Reference Example 6

1-[(4-{[(3-phenylpropyl)amino]methyl}phenyl)sulfonyl]-2-piperidinecarboxylic acid methyl ester The title compound was obtained by the same procedure as described in Reference example 2 using 1-{(4-formylphenyl)sulfonyl}-2-piperidinecarboxylic acid methyl ester instead of the compound prepared in Reference example 1. This crude compound was used as a starting material of Example 11 without further purification.

Example 11

1-[(4-{[(3,5-dimethoxy-4-methylbenzoyl)(3-phenyl-propyl)amino]methyl}phenyl)sulfonyl]-2-piperidin-ecarboxylic acid methyl ester To a solution of the compound prepared in Reference example 6 (584 mg, 1.36 mmol) in dichloromethane (15ml), triethylamine (1.9 ml, 13.6 mmol) was added, then 3,5-dimethoxy-4-methylbenzoyl chloride (870 mg, 4.06 mmol) was added to the mixture on ice bath.

After the mixture was stirred for 10 minutes, the reaction mixture was washed with aqueous solution of sodium hydrogen carbonate, 1 N hydrochloric acid, water and brine sequentially, dried over anhydrous magnesium sulfate, concentrated under reduced pressure. The residue was purified by column chromatography on silica gel (Ethyl acetate:Hexane=1:2) to give the compound of the present invention having the following physical data.

TLC: Rf 0.39 (Ethyl acetate:Hexane=1:1).

Example 12

1-[(4-{[(3,5-dimethoxy-4-methylbenzoyl)(3-phenyl-propyl)amino]methyl}phenyl)sulfonyl]-2-piperidin-ecarboxylic acid The compound of the present invention having the following physical data was obtained by the same procedure as described in Example 2 using the compound prepared in Example 11 instead of the compound prepared in Example 1.

TLC: Rf 0.52 (Methanol:Dichloromethane=1:9);
NMR (CDCl$_3$): δ 7.79-7.73 (m, 2H), 7.42-6.87 (m, 7H), 6.54-6.48 (m, 2H), 4.85-4.48 (m, 3H), 4.02-3.08 (m, 10H), 2.75-2.35 (m, 2H), 2.20-1.19 (m, 11H).

Examples 13(1)-13(16)

The following compounds of the present invention were obtained by the same procedures as described in Reference example 6, Example 11 and Example 12 using the compounds prepared in Reference example 1 or corresponding aldehyde, 3-phenylpropylamine or corresponding amine and 3,5-dimethoxy-4-methylbenzoyl chloride or corresponding acyl chloride.

Example 13(1)

N-[(4-{[(3,5-dimethoxy-4-methylbenzoyl)(3-phenyl-propyl)amino]methyl}phenyl)sulfonyl]glycine TLC: Rf 0.21 (Methanol:Dichloromethane=1:9);

NMR (CDCl$_3$): δ 7.83-7.77 (m, 2H), 7.42-6.89 (m, 7H), 6.52-6.46 (m, 2H), 5.42 (t, J=5.0 Hz, 1H), 4.79-4.47 (m, 2H), 4.06-3.19 (m, 10H), 2.73-2.37 (m, 2H), 2.17-1.77 (m, 5H).

Example 13(2)

2-(4-{[(3,5-dimethoxy-4-methylbenzoyl)(3-phenyl-propyl)amino]methyl}benzoyl)benzoic acid TLC: Rf 0.54 (Dichloromethane:Methanol=9:1);

NMR (CDCl$_3$): δ 8.12-8.06 (m, 1H), 7.78-7.53 (m, 4H), 7.45-6.86 (m, 8H), 6.49 (s, 2H), 4.79-4.48 (m, 2H), 3.86-3.12 (m, 8H), 2.72-2.31 (m, 2H), 2.14-1.76 (m, 5H).

Example 13(3)

[(6-{[(3,5-dimethoxy-4-methylbenzoyl)(3-phenyl-propyl)amino]methyl}-3-pyridinyl)oxy]acetic acid TLC: Rf 0.66 (Dichloromethane:Methanol:Water=8:2:0.1);

NMR (DMSO-d$_6$): δ 13.5 (brs, 1H), 8.28 (brs, 1H), 7.36-6.98 (m, 7H), 6.70-6.57 (m, 2H), 4.77 (s, 2H), 4.67-4.46 (m, 2H), 3.80-3.20 (m, 8H), 2.60-2.30 (m, 2H), 2.10-1.70 (m, 5H).

Example 13(4)

(4-{2-[(3,5-dimethoxy-4-methylbenzoyl)(3-phenyl-propyl)amino]ethyl}phenyl)acetic acid TLC: Rf 0.51 (Dichloromethane:Methanol=9:1);

NMR (CDCl$_3$): δ 7.38-6.81 (m, 9H), 6.43 (s, 2H), 3.78 (s, 6H), 3.76-3.32 (m, 5H), 3.23-2.34 (m, 5H), 2.15-1.68 (m, 5H).

Example 13(5)

3-{3-[(3,5-dimethoxy-4-methylbenzoyl)(3-phenyl-propyl)amino]propoxy}benzoic acid TLC: Rf 0.50 (Ethyl acetate);

NMR (CDCl$_3$): δ 7.80-6.90 (m, 9H), 6.48 (s, 2H), 4.20-3.20 (m, 6H), 3.76 (s, 6H), 2.80-1.80 (m, 6H), 2.09 (s, 3H).

Example 13(6)

(4-{[(3,3-difluoro-3-phenylpropyl)(3,5-dimethoxy-4-methylbenzoyl)amino]methyl}phenyl)acetic acid TLC: Rf 0.58 (Methanol:Dichloromethane=1:9);

NMR (CD$_3$OD): δ 7.57-7.10 (m, 9H), 6.59-6.48 (m, 2H), 4.72 and 4.50 (brs, 2H), 3.84-3.55 (m, 10H), 2.69-2.32 (m, 2H), 2.10-1.95 (m, 3H).

Example 13(7)

4'-{[acetyl(2-phenylethyl)amino]methyl}-2-biphe-nylcarboxylic acid

TLC: Rf 0.43 (Chloroform:Methanol=9:1);

NMR (DMSO-d$_6$, 130° C.): δ 7.72-7.70 (m, 1H), 7.55-7.51 (m, 1H), 7.44-7.40 (m, 1H), 7.36-7.18 (m, 10H), 4.56 (s, 2H), 3.54 (t, J=7.5 Hz, 2H), 2.84 (t, J=7.5 Hz, 2H), 2.02 (s, 3H).

Example 13(8)

4'-{[pentanoyl(3-phenylpropyl)amino]-methyl}-2-biphenylcarboxylic acid

TLC: Rf 0.59 (Chloroform:Methanol=9:1);

NMR (CDCl$_3$): δ 7.97-7.89 (m, 1H), 7.59-7.51 (m, 1H), 7.46-7.10 (m, 11H), 4.60 and 4.53 (s, 2H), 3.43 (t, J=7.5 Hz, 2/2H), 3.22 (t, J=8.0 Hz, 2/2H), 2.58 (t, J=7.5 Hz, 2H), 2.33 (t, J=7.5 Hz, 2/2H), 2.25 (t, J=8.0 Hz, 2/2H), 1.93-1.80 (m, 2H), 1.67-1.55 (m, 2H), 1.39-1.22 (m, 2H), 0.92-0.85 (m, 3H).

Example 13(9)

(2E)-3-(4-{[pentanoyl(2-phenylethyl)amino]methyl}phenyl)acrylic acid

TLC: Rf 0.54 (Chloroform:Methanol=9:1);

NMR (CDCl$_3$): δ 7.75 (d, J=16 Hz, 1H), 7.54-7.48 (m, 2H), 7.34-7.10 (m, 7H), 6.44 and 6.42 (d, J=16 Hz, 1H), 4.61 and 4.36 (s, 2H), 3.61-3.55 and 3.49-3.43 (m, 2H), 2.90-2.79 (m, 2H), 2.33-2.23 (m, 2H), 1.69-1.56 (m, 2H), 1.39-1.26 (m, 2H), 0.94-0.86 (m, 3H).

Example 13(10)

3-(4-{[pentanoyl(2-phenylethyl)amino]methyl}phenyl)propionic acid

TLC: Rf 0.67 (Chloroform:Methanol=9:1);

NMR (CDCl$_3$): δ 7.33-7.01 (m, 9H), 4.57 and 4.31 (s, 2H), 3.55 and 3.42 (t, J=7.5 Hz, 2H), 2.97-2.76 (m, 4H), 2.65 (t, J=7.5 Hz, 2H), 2.32 and 2.23 (t, J=7.5 Hz, 2H), 1.68-1.55 (m, 2H), 1.38-1.25 (m, 2H), 0.90 and 0.88 (t, J=7.0 Hz, 3H).

Example 13(11)

4'-{[octanoyl(2-phenylethyl)amino]methyl}-2-biphe-nylcarboxylic acid

TLC: Rf 0.51 (Chloroform:Methanol=14:1);

NMR (DMSO-d$_6$, 130° C.): δ 7.71 (dd, J=7.5, 1.5 Hz, 1H), 7.55-7.51 (m, 1H), 7.44-7.40 (m, 1H), 7.35-7.17 (m, 10H), 4.57 (s, 2H), 3.54 (t, J=7.5 Hz, 2H), 2.83 (t, J=7.5 Hz, 2H), 2.29 (t, J=7.5 Hz, 2H), 1.60-1.52 (m, 2H), 1.35-1.24 (m, 8H), 0.88 (t, J=7.0 Hz, 3H).

Example 13(12)

4-methyl-2-[4-({(3-methylbutyryl)[3-(3-methylphe-nyl)propyl]amino}methyl)phenoxy]benzoic acid TLC: Rf 0.64 (Methanol:Dichloromethane=1:9);

NMR (CDCl$_3$): δ 8.10-8.07 (m, 1H), 7.24-6.93 (m, 9H), 6.64-6.60 (m, 1H), 4.58 and 4.52 (s, 2H), 3.42 and 3.22 (t, J=7.5 Hz, 2H), 2.57 (t, J=7.5 Hz, 2H), 2.33-2.29 (m, 6H), 2.24-2.09 (m, 3H), 1.95-1.79 (m, 2H), 0.96-0.91 (m, 6H).

Example 13(13)

4-methyl-2-[4-({(2-methylbutyryl)[3-(3-methylphenyl)propyl]amino}methyl)phenoxy]benzoic acid TLC: Rf 0.65 (Methanol:Dichloromethane=1:9);
NMR (CDCl$_3$): δ 8.10-8.07 (m, 1H), 7.23-6.93 (m, 9H), 6.62 (br s, 1H), 4.66-4.51 (m, 2H), 3.53-3.19 (m, 2H), 2.60-2.43 (m, 3H), 2.33-2.30 (m, 6H), 1.94-1.64 (m, 3H), 1.48-1.34 (m, 1H), 1.12-1.08 (m, 3H), 0.85 (t, J=7.5 Hz, 3H).

Example 13(14)

(4-{[3-biphenylyl(3,5-dimethoxy-4-methylbenzoyl)amino]methyl}phenyl)acetic acid

TLC: Rf 0.62 (Ethyl acetate:Methanol:Water=9:1:0.1);
NMR (CDCl$_3$): δ 7.40-7.21 (m, 11H), 7.16 (m, 1H), 6.93 (m, 1H), 6.57 (s, 2H), 5.16 (s, 2H), 3.63 (s, 2H), 3.57 (s, 6H), 1.98 (s, 3H).

Example 13(15)

2-(3,5-dimethyl-4-{[(3-phenylpropyl)(2-propylpentanoyl)amino]methyl}-1H-pyrazol-1-yl)benzoic acid hydrochloride TLC: Rf 0.35 (Chloroform:Methanol=10:1);
NMR (DMSO-d$_6$): δ 11.39 (brs, 1H), 7.89 (d, J=7.5 Hz, 1H), 7.70 (t, J=7.5 Hz, 1H), 7.60 (t, J=7.5 Hz, 1H), 7.40 (d, J=7.5 Hz, 1H), 7.37-7.10 (m, 5H), 4.46 (s, 2H), 3.11 (m, 2H), 2.56 (t, J=6.5 Hz, 2H), 2.46 (m, 1H), 2.05 (s, 3H), 1.96 (s, 3H), 1.85-1.60 (m, 2H), 1.60-1.35 (m, 2H), 1.35-1.00 (m, 6H), 0.80 (t, J=7.0 Hz, 6H).

Example 13(16)

2-(4-{[(2,5-dimethoxybenzoyl)(3-phenylpropyl)amino]methyl}-3,5-dimethyl-1H-pyrazol-1-yl)benzoic acid TLC: Rf 0.35 (Chloroform:Methanol=10:1);
NMR (DMSO-d$_6$): δ 12.85 (brs, 1H), 7.85 (m, 1H), 7.69 (m, 1H), 7.57 (m, 1H), 7.45-7.02 (m, 5H), 7.02-6.86 (m, 3H), 6.84-6.64 (m, 1H), 4.82 (d, J=14.5 Hz, 0.6H), 4.38 (d, J=14.5 Hz, 0.6H), 4.16 (s, 0.8H), 3.82-3.60 (m, 6H), 3.55 (m, 0.25H), 3.10 (m, 0.25H), 2.88 (t, J=7.5 Hz, 1.5H), 2.60 (m, 0.5H), 2.31 (t, J=7.5 Hz, 1.5H), 2.13 (s, 2H), 2.04 (s, 2H), 1.96 (s, 1H), 1.88 (s, 1H), 1.85-1.55 (m, 2H).

Reference Example 7

4'-{[(2-phenylethyl)amino]methyl}-2-biphenylcarboxylic acid methyl ester hydrochloride The title compound having the following physical data was obtained by the same procedure as described in Reference example 2 using 2-phenylethylamine instead of 3-phenylpropylamine.
TLC: Rf 0.50 (Dichloromethane:Methanol=10:1).

Example 14

4'-{[(2-phenylethyl)(phenylsulfonyl)amino]methyl}-2-biphenylcarboxylic acid methyl ester The compound of the present invention having the following physical data was obtained by the same procedure as described in Example 11 using the compound prepared in Reference example 7 and benzenesulfonyl chloride instead of 3,5-dimethoxy-4-methylbenzoyl chloride.
TLC: Rf 0.53 (Hexane:Ethyl acetate=2:1).

Example 15

4'-{[(2-phenylethyl)(phenylsulfonyl)amino]methyl}-2-biphenylcarboxylic acid

The compound of the present invention having the following physical data was obtained by the same procedure as described in Example 2 using the compound prepared in Example 14 instead of the compound prepared in Example 1.
TLC: Rf 0.59 (Chloroform:Methanol=9:1);
NMR (CDCl$_3$): δ 7.95-7.83 (m, 3H), 7.60-7.10 (m, 13H), 7.00-6.95 (m, 2H), 4.38 (s, 2H), 3.38-2.29 (m, 2H), 2.70-2.62 (m, 2H).

Example 16

4-{[(octylsulfonyl)(2-phenylethyl)amino]methyl}-2-biphenylcarboxylic acid

The compound of the present invention having the following physical data was obtained by the same procedures as described in Example 14 and Example 15 using the compound prepared in Reference example 7 and octylsulfonyl chloride instead of benzenesulfonyl chloride.
TLC: Rf 0.45 (Chloroform:Methanol=95:5);
NMR (CDCl$_3$): δ 7.91 (dd, J=1.0, 8.0 Hz, 1H), 7.56 (dt, J=1.0, 8.0 Hz, 1H), 7.50-7.10 (m, 11H), 4.46 (s, 2H), 3.45 (t, J=7.0 Hz, 2H), 2.82-2.72 (m, 4H), 1.80-1.60 (m, 2H), 1.40-1.20 (m, 10H), 0.87 (t, J=7.0 Hz, 3H).

Reference Example 8

(4-{1-[(3-phenylpropyl)amino]ethyl}phenoxy)acetic acid ethyl ester

Under atmosphere of argon, to a solution of (4-acetylphenoxy)acetic acid ethyl ester (525 mg, 2.36 mmol) in benzene (15 mL), 3-phenylpropylamine (319 mg, 2.36 mmol) and Molecular Sieve 4A (3.2 g) were added and the mixture was stirred for 1.5 hours. Then platinum oxide (120 mg) was added to the mixture, after argon was replaced with hydrogen, the mixture was stirred for 8 hours at room temperature.

After the reaction was terminated, the catalyst was removed by filtration with Cerite, and the filtrate was concentrated under reduced pressure. The residue was purified by column chromatography on silica gel (Hexane:Ethyl acetate=from 2:1 to Dichloromethane:Methanol=30:1) to give the title compound (427 mg) having the following physical data.
TLC: Rf 0.44 (Dichloromethane:Methanol=9:1);
NMR (CDCl$_3$): δ 7.30-7.10 (m, 7H), 6.86 (d, J=8.5 Hz, 2H), 4.61 (s, 2H), 4.28 (q, J=7.0 Hz, 2H), 3.70 (q, J=6.5 Hz, 1H), 4.68-2.40 (m, 4H), 2.82-1.70 (m, 2H), 1.31 (t, J=6.5 Hz, 3H), 1.30 (t, J=7.0 Hz, 3H).

Example 17

(4-{1-[(3,5-dimethoxy-4-methylbenzoyl)(3-phenylpropyl)amino]ethyl}phenoxy)acetic acid ethyl ester The compound of the present invention having the following physical data was obtained by the same procedure as described in Example 1 using the compound prepared in Reference example 8 and 3,5-dimethoxy-4-methylbenzoic acid instead of 3,4,5-trimethoxybenzoic acid.
TLC: Rf 0.52 (Hexane:Ethyl acetate=1:1).

Example 18

(4-{1-[(3,5-dimethoxy-4-methylbenzoyl)(3-phenyl-propyl)amino]ethyl}phenoxy)acetic acid The compound of the present invention having the following physical data was obtained by the same procedure as described in Example 2 using the compound prepared in Example 17 instead of the compound prepared in Example 1.
TLC: Rf 0.26 (Dichloromethane:Methanol=9:1);
NMR (CDCl$_3$): δ 7.40-7.00 (m, 7H), 6.87 (d, J=8.5 Hz, 2H), 6.56 (brs, 2H), 5.05 (m, 1H), 4.65 (s, 2H), 3.77 (s, 6H), 3.50-2.90 (m, 2H), 2.70-1.62 (m, 4H), 2.08 (s, 3H), 1.53 (d, J=7.0 Hz, 3H).

Example 19

4-methyl-2-(4-{[(3-phenylpropyl)(3,4,5-trimethoxy-benzyl)amino]methyl}phenoxy)benzoic acid methyl ester The compound of the present invention having the following physical data was obtained by the same procedure as described in Reference example 2 using 3,4,5-trimethoxybenzaldehyde instead of the compound prepared in Reference example 1 and 4-methyl-2-(4-{[(3-phenylpropyl)amino] methyl}phenoxy)benzoic acid methyl ester instead of 3-phenylpropylamine.
TLC: Rf 0.40 (Hexane:Ethyl acetate=2:1);
NMR (CDCl$_3$): δ 7.83 (d, J=8.0 Hz, 1H), 7.30-7.10 (m, 7H), 6.98 (d, J=8.0 Hz, 1H), 6.90 (d, J=8.5 Hz, 2H), 6.78 (s, 1H), 6.61 (s, 2H), 3.85 (s, 9H), 3.78 (s, 3H), 3.53 (s, 2H), 3.51 (s, 2H), 2.61 (t, J=7.5 Hz, 2H), 2.50 (t, J=7.5 Hz, 2H), 2.31 (s, 3H), 1.90-1.75 (m, 2H).

Example 20

4-methyl-2-(4-{[(3-phenylpropyl)(3,4,5-trimethoxy-benzyl)amino]methyl}phenoxy)benzoic acid The compound of the present invention having the following physical data was obtained by the same procedure as described in Example 2 using the compound prepared in Example 19 instead of the compound prepared in Example 1.
TLC: Rf 0.60 (Ethyl acetate);
NMR (CDCl$_3$): δ 8.11 (d, J=8.0 Hz, 1H), 7.40 (d, J=8.5 Hz, 2H), 7.27-7.02 (m, 9H), 6.62 (s, 2H), 3.86 (s, 6H), 3.84 (s, 3H), 3.58 (s, 2H), 3.55 (s, 2H), 2.62 (t, J=8.0 Hz, 2H), 2.53 (t, J=8.0 Hz, 2H), 2.29 (s, 3H), 1.86 (m, 2H).

Reference Example 9

N-(3,5-dimethoxybenzyl)-3-phenyl-1-propaneamine

The title compound having the following physical data was obtained by the same procedure as described in Reference example 2 using 3,5-dimethoxybenzaldehyde instead of the compound prepared in Reference example 1.
TLC: Rf 0.17 (Dichloromethane:Methanol=9:1).

Example 21

4'-{[(3,5-dimethoxybenzyl)(3-phenylpropyl)amino] carbonyl}-2-biphenylcarboxylic acid methyl ester The compound of the present invention having the following physical data was obtained by the same procedure as described in Example 1 using the compound prepared in Reference example 9 and 4-(2'-methoxycarbonylphenyl)benzoic acid instead of 3,4,5-trimethoxybenzoic acid.
TLC: Rf 0.47 (Hexane:Ethyl acetate=2:1).

Example 22

4'-{[(3,5-dimethoxybenzyl)(3-phenylpropyl)amino] carbonyl}-2-biphenylcarboxylic acid The compound of the present invention having the following physical data was obtained by the same procedure as described in Example 2 using the compound prepared in Example 21 instead of the compound prepared in Example 1.
TLC: Rf 0.57 (Dichloromethane:Methanol=9:1);
NMR (DMSO-d$_6$): δ 12.8 (s, 1H), 7.80-6.95 (m, 13H), 6.58-6.25 (m, 3H), 4.75-4.40 (m, 2H), 3.72 (s, 6H), 3.45-3.10 (m, 2H), 2.65-2.35 (m, 2H), 1.98-1.72 (m, 2H).

Example 23

4'-{[(2,5-dichlorobenzyl)(3-phenylpropyl)amino] carbonyl}-2-biphenylcarboxylic acid methyl ester The compound of the present invention having the following physical data was obtained by the same procedures as described in Reference example 9 and Example 21 using 2,5-dichlorobenzaldehyde instead of 3,5-dimethoxybenzaldehyde.
TLC: Rf 0.62 (Hexane:Ethyl acetate=1:1).

Example 24

4'-{[(2,5-dichlorobenzyl)(3-phenylpropyl)amino] carbonyl}-2-biphenylcarboxylic acid The compound of the present invention having the following physical data was obtained by the same procedure as described in Example 2 using the compound prepared in Example 23 instead of the compound prepared in Example 1.
TLC: Rf 0.53 (Dichloromethane:Methanol=9:1);
NMR (DMSO-d$_6$): δ 12.8 (s, 1H), 7.80-7.00 (m, 16H), 4.80-4.50 (m, 2H), 3.45-3.20 (m, 2H), 2.65-2.35 (m, 2H), 1.83 (m, 2H).

Example 25

{4-[((3-phenylpropyl){[(3,4,5-trimethoxyphenyl) amino]carbonyl}amino)methyl]phenyl}acetic acid methyl ester A solution of 3,4,5-trimethoxyphenyl isocyanate (160 mg) and {4-{(3-phenylpropyl)aminomethyl}phenyl}acetic acid methyl ester in toluene (5 mL) was stirred for 1 day.
1 N Hydrochloric acid was added to the reaction mixture and the mixture was extracted with ethyl acetate. The extract was washed with saturated aqueous solution of sodium hydrogen carbonate and brine, dried over sodium sulfate, concentrated under reduced pressure. The residue was purified by column chromatography on silica gel (Hexane:Ethyl acetate=from 9:1 to 1:1) to give the compound of the present invention (310 mg) having the following physical data.
TLC: Rf 0.27 (Hexane:Ethyl acetate=4:1).

Example 26

{4-[((3-phenylpropyl){[(3,4,5-trimethoxyphenyl)amino]carbonyl}amino)methyl]phenyl}acetic acid The compound of the present invention having the following physical data was obtained by the same procedure as described in Example 2 using the compound prepared in Example 25 instead of the compound prepared in Example 1.

TLC: Rf 0.63 (Dichloromethane:Methanol=9:1);
NMR (CDCl$_3$): δ 7.40-7.15 (m, 9H), 6.50 (s, 2H), 6.04 (s, 1H), 4.54 (s, 2H), 3.80 (s, 6H), 3.78 (s, 3H), 3.64 (s, 2H), 3.40-3.30 (m, 2H), 2.66 (t, J=7.0 Hz, 2H), 2.05-1.90 (m, 2H).

Example 27

2-[4-({[(benzylamino)carbonyl][3-(3-methylphenyl)propyl]amino}methyl)phenoxy]-4-methylbenzoic acid methyl ester The compound of the present invention having the following physical data was obtained by the same procedure as described in Example 25 using benzylisocyanate and 2-[4-[{3-(3-methylphenyl)propylamino}methyl]phenoxy]-4-methylbenzoic acid methyl ester.

TLC: Rf 0.31 (Hexane:Ethyl acetate=2:1).

Example 28

2-[4-({[(benzylamino)carbonyl][3-(3-methylphenyl)propyl]amino}methyl)phenoxy]-4-methylbenzoic acid The compound of the present invention having the following physical data was obtained by the same procedure as described in Example 2 using the compound prepared in Example 27 instead of the compound prepared in Example 1.

TLC: Rf 0.64 (Methanol:Dichloromethane=1:9);
NMR (CDCl$_3$): δ 8.10-8.07 (m, 1H), 7.34-6.90 (m, 14H), 6.61 (br s, 1H), 4.56-4.48 (m, 3H), 4.40 (d, J=5.5 Hz, 2H), 3.23 (t, J=7.5 Hz, 2H), 2.57 (t, J=7.5 Hz, 2H), 2.29 (s, 3H), 2.28 (s, 3H), 1.95-1.85 (m, 2H).

Reference Example 10

N-(4-bromophenyl)-3,4,5-trimethoxy-N-(3-phenylpropyl)benzamide

The title compound having the following physical data was obtained by the same procedure as described in Example 11 using (4-bromophenyl)(3-phenylpropyl)amine instead of the compound prepared in Reference example 6 and 3,4,5-trimethoxybenzoyl chloride instead of 3,5-dimethoxy-4-methylbenzoyl chloride.

TLC: Rf 0.63 (Hexane:Ethyl acetate=1:1).

Reference Example 11

N-(2'-formyl-4-biphenylyl)-3,4,5-trimethoxy-N-(3-phenylpropyl)benzamide

The title compound having the following physical data was obtained by the same procedure as described in Reference example 1 using 2-formylphenylboric acid instead of 4-formylphenylboric acid and the compound prepared in Reference example 10 instead of 2-bromobenzoic acid methyl ester.

TLC: Rf 0.58 (Hexane:Ethyl acetate=1:1).

Example 29

4'-[(3-phenylpropyl)(3,4,5-trimethoxybenzoyl)amino]-2-biphenylcarboxylic acid

Under atmosphere of argon, to a solution of the compound prepared in Reference example 11 (225 mg, 0.44 mmol) in a mixed solvent of acetonitrile (2 mL), water (2 mL) and tert-butanol (4 mL), sodium dihydrogen phosphate (82 mg), 2-methyl-2-butene (0.21 mL) and sodium chlorite (174 mg) were added sequentially and the mixture was stirred for 3 hours at room temperature.

Water was added to the reaction mixture and the mixture was extracted with ethyl acetate. The extract was washed with brine, dried over anhydrous sodium sulfate, concentrated under reduced pressure. The residue was purified by column chromatography on silica gel (Hexane:Ethyl acetate=20:1) to give the compound of the present invention (215 mg) having the following physical data.

TLC: Rf 0.61 (Dichloromethane:Methanol=9:1);
NMR (CDCl$_3$): δ 7.90 (dd, J=8.0, 1.0 Hz, 1H), 7.54 (dt, J=8.0, 1.0 Hz, 1H), 7.43 (dt, J=8.0, 1.0 Hz, 1H), 7.31-7.00 (m, 10H), 6.58 (s, 2H), 4.19-3.98 (m, 2H), 3.79 (s, 3H), 3.68 (s, 6H), 2.78-2.66 (m, 2H), 2.10-1.97 (m, 2H).

Example 30

4'-[pentanoyl(2-phenylethyl)amino]-2-biphenylcarboxylic acid

The compound of the present invention having the following physical data was obtained by the same procedures as described in Reference example 10, Reference example 11 and Example 29 using (4-bromophenyl)(2-phenylethyl)amine instead of (4-bromophenyl)(3-phenylpropyl)amine and valeryl chloride instead of 3,4,5-trimethoxybenzoyl chloride.

TLC: Rf 0.62 (Chloroform:Methanol=8:1);
NMR (DMSO-d$_6$): δ 7.77-7.16 (m, 13H), 3.86 (t, J=7.5 Hz, 2H), 2.79 (t, J=7.5 Hz, 2H), 2.03 (t, J=7.5 Hz, 2H), 1.50-1.35 (m, 2H), 1.30-1.10 (m, 2H), 0.77 (t, J=7.5 Hz, 3H).

Example 31

(4-{2-[(3,5-dimethoxy-4-methylphenyl)(hydroxy)methyl]-5-phenylpentyl}phenyl)acetic acid To a solution of the compound prepared in Example 8(8) (100 mg) in a mixed solvent of tetrahydrofuran (3 mL) and methanol (3 mL), sodium borohydride (100 mg) was added sequentially and the mixture was stirred for 1 hour at room temperature.

After the reaction was terminated, saturated aqueous solution of ammonium chloride was added to the reaction mixture and the mixture was extracted with ethyl acetate. The extract was washed with brine, dried over anhydrous sodium sulfate, concentrated under reduced pressure. The residue was purified by column chromatography on silica gel (Dichloromethane:Methanol=20:1) to give the compound of the present invention (69 mg) having the following physical data.

TLC: Rf 0.30 (Dichloromethane:Methanol=9:1);

NMR (CDCl$_3$): δ 7.30-7.02 (m, 9H), 6.52-6.42 (m, 2H), 4.60 (m, 1H), 3.82-3.77 (m, 6H), 3.62 (s, 2H), 2.88-2.40 (m, 4H), 2.10-1.98 (m, 4H), 1.78-1.30 (m, 4H).

Example 32

2-(4-{[(3,5-dimethoxy-4-methylbenzoyl)(3-oxo-3-phenylpropyl)amino]methyl}phenoxy)-4-methylbenzoic acid To a solution of the compound prepared in Example 9(7) (74 mg) in dimethoxyethane (2 mL), manganese dioxide (64 mg) was added and the mixture was stirred for 2 days at room temperature, then manganese dioxide (150 mg, 138 mg) was additionally added in twice and the mixture was stirred for 1 day.

The reaction mixture was diluted with ethyl acetate, and the mixture was filtrated with cerite. The filtrate was concentrated under reduced pressure. The residue was purified by column chromatography on silica gel (Dichloromethane:Methanol=49:1) to give the compound of the present invention (48 mg) having the following physical data.

TLC: Rf 0.38 (Dichloromethane:Methanol=9:1);

NMR (CDCl$_3$): δ 2.07 (s, 3H), 2.32 (s, 3H), 3.40-3.92 (m, 10H), 4.62-4.76 (m, 2H), 6.54-6.64 (m, 3H), 7.02-7.12 (m, 3H), 7.26-7.62 (m, 5H), 7.95-8.13 (m, 3H).

Example 33

[(6-{[(3,5-dimethoxy-4-methylbenzoyl)(3-phenylpropyl)amino]methyl}-1-oxide-3-pyridinyl)oxy]acetic acid Under atmosphere of argon, to a solution of the compound prepared in Example 13(3) (100 mg) in dichloromethane (10 mL), 2-chloroperbenzoic acid (47 mg) was added and the mixture was stirred for 30 minutes.

The reaction mixture was concentrated under reduced pressure. The residue was purified by column chromatography on silica gel (dichloromethane:methanol:acetic acid=from 80:2:1 to 60:2:1, then 40:2:1) to give the compound of the present invention (60 mg) having the following physical data.

TLC: Rf 0.35 (Dichloromethane:Methanol:Acetic acid=20:2:1);

NMR (DMSO-d$_6$): δ 8.13 (br s, 1H), 7.45-6.95 (m, 7H), 6.70-6.40 (m, 2H), 4.76 (s, 2H), 4.64-4.42 (m, 2H), 3.90-3.10 (m, 8H), 2.65-2.30 (m, 2H), 2.10-1.70 (m, 5H).

Example 34

2-{4-[3-oxo-5-phenyl-2-(3,4,5-trimethoxybenzoyl)pentyl]phenoxy}benzoic acid benzyl ester To a solution of 5-phenyl-1-(3,4,5-trimethoxyphenyl)-1,3-pentanedione (137 mg) in a mixed solvent of acetonitrile (2.9 mL) and dimethylsulfoxide (0.48 mL), 2-(4-bromomethylphenoxy)benzoic acid benzyl ester (159 mg), potassium carbonate (61 mg) and cesium carbonate (3 mg) were added and the mixture was stirred for 1 day at room temperature.

Ice was added to the reaction mixture and the mixture was extracted with diethyl ether. The extract was washed with brine, dried over magnesium sulfate, concentrated under reduced pressure. The residue was purified by column chromatography on silica gel (Hexane:Ethyl acetate=from 5:1 to 3:1) followed by the purification by p-TLC to give the compound of the present invention (110 mg) having the following physical data.

TLC: Rf 0.29 (Hexane:Ethyl acetate=3:1).

Example 35

2-{4-[3-oxo-5-phenyl-2-(3,4,5-trimethoxybenzoyl)pentyl]phenoxy}benzoic acid

To a solution of the compound prepared in Example 34 (100 mg) in Methanol (2 mL), 10% palladium on carbon (10 mg) was added and the mixture was stirred vigorously for 1 hour under atmosphere of hydrogen.

Catalyst was removed by filtration with cerite, and filtrate was concentrated under reduced pressure. The residue was purified by p-TLC to give the compound of the present invention (75 mg) having the following physical data.

TLC: Rf 0.40 (Dichloromethane:Methanol=10:1);

NMR (CDCl$_3$): δ 8.19 (dd, J=8.0, 1.5 Hz, 1H), 7.45 (m, 1H), 7.30-7.06 (m, 10H), 6.96 (d, J=8.5 Hz, 2H), 6.73 (d, J=8.5 Hz, 1H), 4.61 (m, 1H), 3.92 (s, 3H), 3.85 (s, 6H), 3.34 (dd, J=14.0, 8.0 Hz, 1H), 3.23 (dd, J=14.0, 6.5 Hz, 1H), 2.90-2.60 (m, 4H).

Example 36

2-(4-{[6,7,8-trimethoxy-4-oxo-2-(2-phenylethyl)-3(4H)-quinazolinyl]methyl}phenoxy)benzoic acid methyl ester A solution of 2-{4-(aminomethyl)phenoxy}benzoic acid methyl ester (152 mg) and 6,7,8-trimethoxy-2-(2-phenylethyl)-4H-3,1benzoxazin-4-one (200 mg) in pyridine (4 mL) was stirred for 1 day at 90° C.

Water was added to the reaction mixture and the mixture was extracted with ethyl acetate. The extract was washed with brine, dried over sodium sulfate, concentrated under reduced pressure. The residue was purified by column chromatography on silica gel to give the compound of the present invention (161 mg) having the following physical data.

TLC: Rf 0.29 (Hexane:Ethyl acetate=1:1);

NMR (CDCl$_3$): δ 7.93-7.88 (m, 1H), 7.50-7.41 (m, 2H), 7.31-7.08 (m, 8H), 6.97-6.86 (m, 3H), 5.32 (s, 2H), 4.09 (s, 3H), 4.04 (s, 3H), 3.67 (s, 3H), 3.78 (s, 3H), 3.23-3.04 (m, 4H).

Example 37

2-(4-{[6,7,8-trimethoxy-4-oxo-2-(2-phenylethyl)-3(4H)-quinazolinyl]methyl }phenoxy)benzoic acid The compound of the present invention having the following physical data was obtained by the same procedure as described in Example 2 using the compound prepared in Example 36 instead of the compound prepared in Example 1.

TLC: Rf 0.55 (Dichloromethane:Methanol=9:1);

NMR (CDCl$_3$): δ 8.19 (dd, J=8.0, 2.0 Hz, 1H), 7.49-7.42 (m, 2H), 7.31-7.16 (m, 8H), 7.08-7.02 (m, 2H), 6.81 (dd, J=8.5, 1.0 Hz, 1H), 5.36 (s, 2H), 4.10 (s, 3H), 4.05 (s, 3H), 3.97 (s, 3H), 3.24-3.06 (m, 4H).

Reference Example 12

4-(methoxymethoxy)benzaldehyde

To a solution of 4-hydroxybenzaldehyde (5.0 g) in dichloromethane (80 mL), diisopropylethylamine (7.84 mL) and methoxymethylchloride (3.42 mL) were added on ice bath and the mixture was stirred for 1 hour at room temperature.

1 N Hydrochloric acid was added to the reaction mixture and the mixture was extracted with dichloromethane. The extract was washed with saturated aqueous solution of sodium hydrogen carbonate and brine, dried over sodium sulfate, concentrated under reduced pressure to give the title compound (8.43 g) having the following physical data.

TLC: Rf 0.54 (Hexane:Ethyl acetate=2:1);

NMR (CDCl$_3$): δ 9.91 (s, 1H), 7.87-7.82 (m, 2H), 7.17-7.13 (m, 2H), 5.26 (s, 2H), 3.50 (s, 3H).

Reference Example 13

N-{(1Z)-[4-(methoxymethoxy)phenyl]methylene}-3-phenyl-1-propaneamine

To a solution of the compound prepared in Reference example 12 (520 mg) in dichloromethane (15 mL), 3-phenylpropylamine (445 mg) was added and the mixture was stirred for 1 hour at room temperature.

The reaction mixture was dried over anhydrous sodium sulfate, concentrated under reduced pressure to give the title compound. This crude compound was used as a starting material of Reference example 14 without further purification.

Reference Example 14

4,5,6-trimethoxy-3-[4-(methoxymethoxy)phenyl]-2-(3-phenylpropyl)-1-isoindolinone To a solution of 3,4,5-trimethoxy-N-phenylbenzamide (1.05 g) in tetrahydrofuran (18 mL), n-butyl lithium (1.55M Hexane solution, 1.4 mL) was dropped at −78° C. and the mixture was stirred for 2 hours at temperature from −20° C. to −10° C. Then the solution, which was prepared in the way hereinafter described [Boron trifluoride diethyl ether complex (472 μL) was added to the solution of the compound prepared in Reference example 13 in tetrahydrofuran (6 mL) at −40° C., and stirred for 5 minutes at about −25° C.], was dropped to the mixture at −78° C. and the temperature of the reaction mixture was raised to 80° C., and the mixture was stirred for 3 hours.

Saturated aqueous solution of sodium hydrogen carbonate was added to the reaction mixture and the mixture was extracted with ethyl acetate. The extract was washed with brine, dried over sodium sulfate, concentrated under reduced pressure. The residue was purified by column chromatography on silica gel (Hexane:Ethyl acetate=from 6:1 to 1:1) to give the title compound (218 mg) having the following physical data.

TLC: Rf 0.25 (Hexane:Ethyl acetate=2:1);

NMR (CDCl$_3$): δ 7.26-6.96 (m, 10H), 5.35 (s, 1H), 5.18-5.13 (m, 2H), 3.93 (s, 3H), 3.93-3.86 (m, 1H), 3.86 (s, 3H), 3.47 (s, 3H), 3.34 (s, 3H), 2.92-2.83 (m, 1H), 2.59 (t, J=8.0 Hz, 2H), 1.90-1.78 (m, 2H).

Example 38

{4-[5,6,7-trimethoxy-3-oxo-2-(3-phenylpropyl)-2,3-dihydro-1H-isoindol-1-yl]phenoxy}acetic acid methyl ester To a solution of the compound prepared in Reference example 14 (218 mg) in 1,4-dioxane (5 mL), 4 N HCl/dioxane (2.2 mL) was added and the mixture was stirred for 1 hour.

1 N Hydrochloric acid was added to the reaction mixture and the mixture was extracted with ethyl acetate. The extract was washed with brine, dried over sodium sulfate, concentrated under reduced pressure to give a crude product (214 mg).

107 mg of the crude product was dissolved by acetone (2.5 mL), and the mixture was added by potassium carbonate (41 mg) and bromoacetic acidmethyl (27 μL) and the mixture was stirred for 1 day.

1 N Hydrochloric acid was added to the reaction mixture and the mixture was extracted with ethyl acetate. The extract was washed with brine, dried over sodium sulfate, concentrated under reduced pressure. The residue was purified by column chromatography on silica gel (Hexane:Ethyl acetate=from 1:1 to 1:2) to give the compound of the present invention (97 mg) having the following physical data.

TLC: Rf 0.48 (Hexane:Ethyl acetate=1:1);

NMR (CDCl$_3$): δ 7.27-7.11 (m, 6H), 7.07-7.02 (m, 2H), 6.87-6.83 (m, 2H), 5.35 (s, 1H), 4.62 (s, 2H), 3.93 (s, 3H), 3.93-3.84 (m, 1H), 3.85 (s, 3H), 3.80 (s, 3H), 3.31 (s, 3H), 2.91-2.82 (m, 1H), 2.59 (t, J=7.5 Hz, 2H), 1.89-1.78 (m, 2H).

Example 39

{4-[5,6,7-trimethoxy-3-oxo-2-(3-phenylpropyl)-2,3-dihydro-1H-isoindol-1-yl]phenoxy}acetic acid The compound of the present invention having the following physical data was obtained by the same procedure as described in Example 2 using the compound prepared in Example 38 instead of the compound prepared in Example 1.

TLC: Rf 0.55 (Dichloromethane:Methanol:Acetic acid=90:9:1);

NMR (CDCl$_3$): δ 7.26-7.10 (m, 6H), 7.05-7.02 (m, 2H), 6.88-6.85 (m, 2H), 5.34 (s, 1H), 4.64 (s, 2H), 3.92 (s, 3H), 3.92-3.84 (m, 1H), 3.84 (s, 3H), 3.32 (s, 3H), 2.89-2.80 (m, 1H), 2.60-2.55 (m, 2H), 1.87-1.75 (m, 2H).

Example 40

2-[4-(3-benzyl-6,7,8-trimethoxy-4-oxo-1,2,3,4-tetrahydro-2-quinazolinyl)phenoxy]-4-methylbenzoic acid methyl ester To a solution of 2-amino-N-benzyl-3,4,5-trimethoxybenzamide (276 mg) in dimethylacetamide (10 mL), 2-(4-formylphenoxy)-4-methylbenzoic acid methyl ester (400 mg) and acetic acid (0.5 mL) were added and the mixture was stirred for 5 hours at 105° C.

The reaction mixture was poured into saturated aqueous solution of sodium hydrogen carbonate and the mixture was extracted with ethyl acetate. The extract was washed with water and brine, dried over magnesium sulfate, concentrated under reduced pressure to give the compound of the present invention. This crude compound was used as a starting material of Example 41 without further purification.

Example 41

2-[4-(3-benzyl-6,7,8-trimethoxy-4-oxo-1,2,3,4-tetrahydro-2-quinazolinyl)phenoxy]-4-methylbenzoic acid The compound of the present invention having the following physical data was obtained by the same procedure as described in Example 2 using the compound prepared in Example 40 instead of the compound prepared in Example 1.

TLC: Rf 0.62 (Methanol:Dichloromethane=1:9);

NMR (CD$_3$OD): δ 7.81 (d, J=8.0 Hz, 1H), 7.34-7.20 (m, 8H), 7.08-7.04 (m, 1H), 6.83-6.77 (m, 3H), 5.69 (s, 1H), 5.41 (d, J=15.5 Hz, 1H), 3.92 (d, J=15.5 Hz, 1H), 3.86 (s, 3H), 3.81 (s, 3H), 3.69 (s, 3H), 2.32 (s, 3H).

Example 42

4-methyl-2-{4-[6,7,8-trimethoxy-4-oxo-3-(2-phenyl-ethyl)-1,2,3,4-tetrahydro-2-quinazolinyl]phenoxy}benzoic acid methyl ester The compound of the present invention having the following physical data was obtained by the same procedure as described in Example 40 using 2-amino-3,4,5-trimethoxy-N-(2-phenylethyl)-benzamide instead of 2-amino-N-benzyl-3,4,5-trimethoxybenzaldehyde.

TLC: Rf 0.48 (Hexane:Ethyl acetate=1:1).

Example 43

4-methyl-2-{4-[6,7,8-trimethoxy-4-oxo-3-(2-phenyl-ethyl)-3,4-dihydro-2-quinazolinyl]phenoxy}benzoic acid methyl ester To a solution of the compound prepared in Example 42 (211 mg) in acetone (5 mL), potassium permanganate (344 mg) was added and the mixture was stirred for 1.5 hours at room temperature.

The reaction mixture was diluted with water and the mixture was extracted with ethyl acetate. The extract was washed with water and brine, dried over magnesium sulfate, concentrated under reduced pressure. The residue was purified by column chromatography on silica gel (Hexane:Ethyl acetate=2:1) to give the compound of the present invention (176 mg) having the following physical data.

TLC: Rf 0.49 (Hexane:Ethyl acetate=1:1).

Example 44

4-methyl-2-{4-[6,7,8-trimethoxy-4-oxo-3-(2-phenyl-ethyl)-3,4-dihydro-2-quinazolinyl]phenoxy}benzoic acid The compound of the present invention having the following physical data was obtained by the same procedure as described in Example 2 using the compound prepared in Example 43 instead of the compound prepared in Example 1.

TLC: Rf 0.48 (Methanol:Dichloromethane=1:9);

NMR (CDCl$_3$): δ 8.10 (d, J=8.0 Hz, 1H), 7.55 (s, 1H), 7.39-7.32 (m, 2H), 7.23-7.18 (m, 3H), 7.14-7.07 (m, 3H), 6.94-6.88 (m, 2H), 6.77 (s, 1H), 4.27 (t, J=7.5 Hz, 2H), 4.05 (s, 3H), 4.04 (s, 3H), 4.02 (s, 3H), 2.94 (t, J=7.5 Hz, 2H), 2.38 (s, 3H).

Reference Example 15

2-(4-{(Z)-[(3-phenylpropyl)imino]methyl}phenoxy)benzoic acid methyl ester

The title compound was obtained by the same procedure as described in Reference example 13 using 2-(4-formylpheoxy)benzoic acid methyl ester instead of the compound prepared in Reference example 12. This crude compound was used as a starting material of Example 45 without further purification.

Example 45

2-{4-[4-oxo-3-(3-phenylpropyl)-3,4-dihydro-2H-1,3-benzothiazin-2-yl]phenoxy}benzoic acid methyl ester A solution of the compound prepared in Reference example 15 (430 mg) and thiosalicylic acid (178 mg) in xylene (10 mL) was refluxed for 3 hours.

The reaction mixture was diluted with ethyl acetate, and washed with saturated aqueous solution of sodium hydrogen carbonate, water and brine, dried over magnesium sulfate, concentrated under reduced pressure. The residue was purified by column chromatography on silica gel (Hexane:Ethyl acetate=4:1) to give the compound of the present invention having the following physical data.

TLC: Rf 0.38 (Hexane:Ethyl acetate=2:1).

Example 46

2-{4-[4-oxo-3-(3-phenylpropyl)-3,4-dihydro-2H-1,3-benzothiazin-2-yl]phenoxy}benzoic acid The compound of the present invention having the following physical data was obtained by the same procedure as described in Example 2 using the compound prepared in Example 45 instead of the compound prepared in Example 1.

TLC: Rf 0.48 (Methanol:Dichloromethane=1:9);

NMR (CDCl$_3$): δ 8.19-8.10 (m, 2H), 7.49-7.40 (m, 1H), 7.35-7.08 (m, 11H), 6.97-6.89 (m, 2H), 6.83-6.76 (m, 1H), 5.61 (s, 1H), 4.38-4.28 (m, 1H), 3.13-3.03 (m, 1H), 2.82-2.65 (m, 2H), 2.13-2.00 (m, 2H).

Reference Example 16

(4R)-1-(3,5-dimethoxy-4-methylbenzoyl)-4-hydroxy-L-proline methyl ester

The title compound having the following physical data was obtained by the same procedure as described in Example 11 using (4R)-4-hydroxy-L-proline methyl ester hydrochloride instead of the compound prepared in Reference example 6.

TLC: Rf 0.29 (Ethyl acetate).

Reference Example 17

(4R)-1-(3,5-dimethoxy-4-methylbenzoyl)-4-(methoxymethoxy)-2-(2-phenylvinyl)pyrrolidine To a solution of the compound prepared in Reference example 16 (1.75 g) in dichloromethane (25 mL), methoxymethylchloride (0.48 mL) and diisopropylethylamine (1.2 mL) were added and the mixture was stirred for 1 day.

0.5 N Hydrochloric acid was added to the reaction mixture and the mixture was extracted with ethyl acetate. The extract was washed with brine, dried over sodium sulfate, concentrated under reduced pressure. The residue was purified by column chromatography on silica gel (Hexane:Ethyl acetate=from 9:1 to 1:1) to give crude product (1.52 g).

Then a solution of the crude product in tetrahydrofuran (40 mL), lithium borohydride (180 mg) was added and the mixture was stirred for 1 hour.

0.5 N Hydrochloric acid was added to the reaction mixture and the mixture was extracted with ethyl acetate. The extract was washed with saturated aqueous solution of sodium hydrogen carbonate and brine, dried over sodium sulfate, concentrated under reduced pressure to give crude product (1.39 g).

Next a solution of the crude product in dimethylsulfoxide (20 mL), triethylamine (2.0 mL) and sulfur trioxide pyridine complex (1.3 g) were added and the mixture was stirred for 1.5 hours.

0.5 N Hydrochloric acid was added to the reaction mixture and the mixture was extracted with ethyl acetate. The extract was washed with water and brine, dried over sodium sulfate, concentrated under reduced pressure to give crude product (1.13 g).

To a solution of benzyl(triphenyl)phosphonium chloride (1.95 g) in tetrahydrofuran (35 mL), potassium tert-butoxide (560 mg) was added on ice bath, and the mixture was stirred for 30 minutes, then the mixture was added by the above crude product, and stirred for 30 minutes.

Saturated aqueous solution of ammonium chloride was added to the reaction mixture and the mixture was extracted with ethyl acetate. The extract was washed with brine, dried over sodium sulfate, concentrated under reduced pressure. The residue was purified by column chromatography on silica gel (Hexane:Ethyl acetate=from 9:1 to 1:1) to give the title compound (1.59 g, E/Z mixture) having the following physical data.

TLC: Rf 0.50 and 0.67 (Ethyl acetate).

Reference Example 18

(3R)-1-(3,5-dimethoxy-4-methylbenzoyl)-5-(2-phenylethyl)-3-pyrrolidinol

To a solution of the compound prepared in Reference example 17 (1.59 g) in a mixed solvent of methanol (5 mL) and tetrahydrofuran (20 mL), 10% palladium on carbon (100 mg) was added and the mixture was stirred for 1 day atmosphere of hydrogen.

After catalyst was removed, the filtrate was concentrated under reduced pressure to give the crude product (780 mg). Then the crude product was added by 4 N HCl/dioxane (20 mL) and stirred for 1 hour.

Solvent was concentrated under reduced pressure. The residue was added by saturated aqueous solution of sodium hydrogen carbonate, and the mixture was extracted with ethyl acetate. The extract was washed with brine, dried over sodium sulfate, concentrated under reduced pressure. to give the title compound (722 mg) having the following physical data.

TLC: Rf 0.33 (Ethyl acetate).

Example 47

3-{[(3S)-1-(3,5-dimethoxy-4-methylbenzoyl)-5-(2-phenylethyl)-3-pyrrolidinyl]oxy}benzoic acid methyl ester To a solution of the compound prepared in Reference example 18 (80 mg) in tetrahydrofuran (3 mL), 3-hydroxybenzoic acid methyl ester (40 mg), azodicarboxylic acid dipiperidide (83 mg) and triphenylphosphine (86 mg) were added and the mixture was stirred for 1 day.

The solvent was concentrated under reduced pressure. The residue was purified by column chromatography on silica gel (Hexane:Ethyl acetate=10:1) to give the compound of the present invention (62.8 mg) having the following physical data.

TLC: Rf 0.32 (Hexane:Ethyl acetate=1:1).

Example 48

3-{[(3S)-1-(3,5-dimethoxy-4-methylbenzoyl)-5-(2-phenylethyl)-3-pyrrolidinyl]oxy}benzoic acid The compound of the present invention having the following physical data was obtained by the same procedure as described in Example 2 using the compound prepared in Example 47 instead of the compound prepared in Example 1.

TLC: Rf 0.51 (Dichloromethane:Methanol=9:1);

NMR (CDCl$_3$): δ 7.74 (d, J=7.5 Hz, 1H), 7.56 (s, 1H), 7.40 (t, J=8.0 Hz, 1H), 7.35-7.00 (m, 6H), 6.61 (s, 2H), 5.00-4.90 (m, 1H), 4.70-4.50 (m, 1H), 4.00-3.60 (m, 8H), 2.80-2.00 (m, 9H).

Example 49

4-{[(3S)-1-(3,5-dimethoxy-4-methylbenzoyl)-5-(2-phenylethyl)-3-pyrrolidinyl]oxy}benzoic acid methyl ester The compound of the present invention having the following physical data was obtained by the same procedure as described in Example 47 using 4-hydroxybenzoic acid methyl ester instead of 3-hydroxybenzoic acid methyl ester.

TLC: Rf 0.62 (Ethyl acetate).

Example 50

4-{[(3S)-1-(3,5-dimethoxy-4-methylbenzoyl)-5-(2-phenylethyl)-3-pyrrolidinyl]oxy}benzoic acid The compound of the present invention having the following physical data was obtained by the same procedure as described in Example 2 using the compound prepared in Example 49 instead of the compound prepared in Example 1.

TLC: Rf 0.34 (Dichloromethane:Methanol=19:1);

NMR (CDCl$_3$): δ 2.30 (m, 9H), 3.94 (m, 8H), 4.79 (m, 2H), 6.59 (s, 2H), 6.89 (d, J=8.0 Hz, 2H), 7.20 (m, 2H), 7.51 (m, 2H), 7.68 (m, 1H), 8.06 (d, J=8.5 Hz, 2H).

Reference Example 19

(3S)-1-(3,5-dimethoxy-4-methylbenzoyl)-5-(2-phenylethyl)-3-pyrrolidinol

The title compound having the following physical data was obtained by the same procedures as described in Example 47 and Example 48 using benzoic acid instead of 3-hydroxybenzoic acid methyl ester.

TLC: Rf 0.27 (Ethyl acetate).

Example 51

3-{[(3R)-1-(3,5-dimethoxy-4-methylbenzoyl)-5-(2-phenylethyl)-3-pyrrolidinyl]oxy}benzoic acid methyl ester The compound of the present invention having the following physical data was obtained by the same procedure as described in Example 47 using the compound prepared in Reference example 19 instead of the compound prepared in Reference example 18.

TLC: Rf 0.22 (Hexane:Ethyl acetate=2:1).

Example 52

3-{[(3R)-1-(3,5-dimethoxy-4-methylbenzoyl)-5-(2-phenylethyl)-3-pyrrolidinyl]oxy}benzoic acid The compound of the present invention having the following physical data was obtained by the same procedure as described in Example 2 using the compound prepared in Example 51 instead of the compound prepared in Example 1.

TLC: Rf 0.33 (Dichloromethane:Methanol=19:1);

NMR (CDCl$_3$): δ 1.97 (m, 5H), 2.49 (m, 2H), 2.72 (m, 2H), 3.68 (m, 8H), 4.58 (m, 1H), 4.86 (m, 1H), 6.62 (s, 2H), 7.04 (m, 1H), 7.26 (m, 6H), 7.48 (m, 1H), 7.68 (m, 1H).

Reference Example 20

5-(benzyloxy)-1-(phenylsulfonyl)-1H-indole

To a suspension of sodium hydride (920 mg) in tetrahydrofuran (10 mL), a solution of 5-benzyloxyindole (4.5 g) in tetrahydrofuran (10 mL) was added on ice bath and the mixture was stirred for 30 minutes at room temperature. To this mixture, benzenesulfonyl chloride (2.8 mL) was added on ice bath, and the mixture was stirred for 1 hour at 40° C.

Saturated aqueous solution of ammonium chloride was added to the reaction mixture on ice bath and the mixture was extracted with ethyl acetate. The extract was washed with brine, dried over sodium sulfate, concentrated under reduced pressure. The residue was purified by column chromatography on silica gel to give the title compound (6.4 g) having the following physical data.

TLC: Rf 0.74 (Benzene:Ethyl acetate=20:1).

Reference Example 21

[5-(benzyloxy)-1-(phenylsulfonyl)-1H-indole-2-yl](3,5-dimethoxyphenyl)methanone

To a solution of the compound prepared in Reference example 20 (540 mg) in tetrahydrofuran (5 mL), lithium diisopropylamide (1.8 M solution, 1.24 mL) was added at −78° C. and the temperature of the mixture was raised up to −20° C. for 30 minutes.

The reaction mixture was cooled to −78° C. again, a solution of N,3,5-trimethoxy-N-methylbenzamide (670 mg) in tetrahydrofuran (5 mL) was added hereto, and the mixture was stirred for 30 minutes and the temperature of the mixture was raised up to 0° C. for 2 hours.

Saturated aqueous solution of ammonium chloride was added to the reaction mixture and the mixture was extracted with ethyl acetate. The extract was washed with brine, dried over sodium sulfate, concentrated under reduced pressure. The residue was purified by column chromatography on silica gel to give the title compound (640 mg) having the following physical data.

TLC: Rf 0.41 (Hexane:Ethyl acetate=2:1);

NMR (CDCl$_3$): δ 8.05-7.99 (m, 3H), 7.61-7.33 (m, 8H), 7.18-7.03 (m, 4H), 6.88-6.86 (m, 1H), 6.70 (t, J=2.0 Hz, 1H), 5.08 (s, 2H), 3.83 (s, 6H).

Reference Example 22

[5-(benzyloxy)-1H-indole-2-yl](3,5-dimethoxyphenyl)methanone

To a solution of the compound prepared in Reference example 21 (350 mg) in a mixed solvent of tetrahydrofuran (4 mL) and methanol (2 mL), 2 N aqueous solution of sodium hydroxide (2 mL) added and the mixture was stirred for 2 hours at 60° C.

Water was added to the reaction mixture at 0° C. and the mixture was extracted with ethyl acetate. The extract was washed with brine, dried over sodium sulfate, concentrated under reduced pressure. The residue was purified by column chromatography on silica gel to give the title compound (230 mg) having the following physical data.

TLC: Rf 0.43 (Hexane:Ethyl acetate=2:1);

NMR (CDCl$_3$): δ 9.17 (br, s, 1H), 7.49-7.30 (m, 6H), 7.16-7.09 (m, 5H), 6.70 (t, J=2.5 Hz, 1H), 5.11 (s, 2H), 3.87 (s, 6H).

Reference Example 23

[5-(benzyloxy)-1-(2-phenylethyl)-1H-indole-2-yl](3,5-dimethoxyphenyl)methanone

To a solution of the compound prepared in Reference example 22 (230 mg) in N,N-dimethylformamide (5 mL), potassium carbonate (163 mg) and 2-phenethyl bromide (160 µL) were added sequentially and the mixture was stirred for 2 hours at 80° C., then stirred for 2 days at 120° C.

Saturated aqueous solution of ammonium chloride was added to the reaction mixture and the mixture was extracted with ethyl acetate. The extract was washed with brine, dried over sodium sulfate, concentrated under reduced pressure. The residue was purified by column chromatography on silica gel to give the title compound (110 mg) having the following physical data.

TLC: Rf 0.58 (Hexane:Ethyl acetate=2:1).

Example 53

{[2-(3,5-dimethoxybenzoyl)-1-(2-phenylethyl)-1H-indole-5-yl]oxy}acetic acid ethyl ester To a solution of the compound prepared in Reference example 23 (110 mg) in a mixed solvent of ethyl acetate (2 mL) and ethanol (2 mL), 10% palladium on carbon (20 mg) was added and the mixture was stirred vigorously for 2 hours at 50° C. under atmosphere of hydrogen.

Catalyst was removed by filtration with cerite, and filtrate was concentrated under reduced pressure to give the crude product (98 mg).

To a solution of this crude product in acetone (2 mL), potassium carbonate (60 mg) and bromoacetic acid ethyl ester (64 µL) were added sequentially and the mixture was stirred for 1 day at room temperature.

Saturated aqueous solution of ammonium chloride was added to the reaction mixture and the mixture was extracted with ethyl acetate. The extract was washed with brine, dried over anhydrous sodium sulfate, concentrated under reduced pressure. The residue was purified by column chromatography on silica gel to give the compound of the present invention (120 mg) having the following physical data.

TLC: Rf 0.26 (Hexane:Ethyl acetate=3:1);

NMR (CDCl$_3$): δ 7.33-7.11 (m, 7H), 7.02-7.00 (m, 1H), 6.95-6.93 (m, 3H), 6.67 (t, J=2.0 Hz, 1H), 4.77 (t, J=8.0 Hz, 2H), 4.65 (s, 2H), 4.28 (q, J=7.0 Hz, 2H), 3.84 (s, 6H), 3.13 (t, J=8.0 Hz, 2H), 1.31 (t, J=7.0 Hz, 3H).

Example 54

{[2-(3,5-dimethoxybenzoyl)-1-(2-phenylethyl)-1H-indole-5-yl]oxy}acetic acid

The compound of the present invention having the following physical data was obtained by the same procedure as described in Example 2 using the compound prepared in Example 53 instead of the compound prepared in Example 1.

TLC: Rf 0.21 (Dichloromethane:Methanol=9:1);

NMR (CDCl$_3$): δ 7.34-7.05 (m, 8H), 6.96-6.93 (m, 3H), 6.68 (t, J=2.5 Hz, 1H), 4.83-4.74 (m, 2H), 4.72 (s, 2H), 3.85 (s, 6H), 3.17-3.10 (m, 2H).

Example 55

2-{[2-(3,5-dimethoxybenzoyl)-1-(2-phenylethyl)-1H-indole-6-yl]oxy}benzoic acid The compound of the present invention having the following physical data was obtained by the same procedures as described in Reference example 20, Reference example 21, Reference example 22, Reference example 23, Example 53 and Example 54 using 6-benzyloxyindole instead of 5-benzyloxyindole and 2-fluorobenzoic acid methyl ester instead of 2-phenethyl bromide.

TLC: Rf 0.54 (Dichloromethane:Methanol=9:1);

NMR (CDCl$_3$): δ 8.25 (dd, J=8.0, 2.5 Hz, 1H), 7.70-7.65 (m, 1H), 7.52-7.45 (m, 1H), 7.28-7.07 (m, 7H), 6.99-6.87 (m, 4H), 6.82-6.77 (m, 1H), 6.70 (t, J=2.5 Hz, 1H), 4.75 (t, J=7.0 Hz, 2H), 3.87 (s, 6H), 3.13 (t, J=7.0 Hz, 2).

Reference Example 24

6-bromo-1-(phenylsulfonyl)-1H-indole

The title compound having the following physical data was obtained by the same procedure as described in Reference example 20 using 6-bromoindole instead of 5-benzyloxyindole.

TLC: Rf 0.71 (Hexane:Ethyl acetate=2:1).

Reference Example 25

[6-bromo-1-(phenylsulfonyl)-1H-indole-2-yl](3,5-dimethoxyphenyl)methanone

The title compound having the following physical data was obtained by the same procedure as described in Reference example 21 using the compound prepared in Reference example 24 instead of the compound prepared in Reference example 20.

TLC: Rf 0.57 (Hexane:Ethyl acetate=2:1).

Reference Example 26

(6-bromo-1H-indole-2-yl)(3,5-dimethoxyphenyl)methanone

The title compound having the following physical data was obtained by the same procedure as described in Reference example 22 using the compound prepared in Reference example 25 instead of the compound prepared in Reference example 21.

TLC: Rf 0.70 (Hexane:Ethyl acetate=2:1).

Reference Example 27

[6-bromo-1-(2-phenylethyl)-1H-indole-2-yl](3,5-dimethoxyphenyl)methanone

The title compound having the following physical data was obtained by the same procedure as described in Reference example 23 using the compound prepared in Reference example 26 instead of the compound prepared in Reference example 22.

TLC: Rf 0.45 (Hexane:Ethyl acetate=4:1).

Example 56

2-[2-(3,5-dimethoxybenzoyl)-1-(2-phenylethyl)-1H-indole-6-yl]benzoic acid methyl ester The compound of the present invention having the following physical data was obtained by the same procedure as described in Reference example 1 using the compound prepared in Reference example 27 instead of 2-bromobenzoic acid methyl ester and 2-methoxycarbonylphenylboric acid instead of 4-formylphenylboric acid.

TLC: Rf 0.50 (Hexane:Ethyl acetate=2:1).

Example 57

2-[2-(3,5-dimethoxybenzoyl)-1-(2-phenylethyl)-1H-indole-6-yl]benzoic acid

The compound of the present invention having the following physical data was obtained by the same procedure as described in Example 2 using the compound prepared in Example 56 instead of the compound prepared in Example 1.

TLC: Rf 0.53 (Dichloromethane:Methanol=9:1);

NMR (CDCl$_3$): δ 8.00-6.70 (m, 16H), 4.80 (t, J=7.5 Hz, 2H), 3.86 (s, 6H), 3.16 (t, J=7.5 Hz, 2H).

Example 58

2-[2-(3,5-dimethoxybenzoyl)-1-(2-phenylethyl)-1H-indole-5-yl]benzoic acid

The compound of the present invention having the following physical data was obtained by the same procedures as described in Reference example 24, Reference example 25, Reference example 26, Reference example 27, Example 56 and Example 57 using 5-bromoindole instead of 6-bromoindole.

TLC: Rf 0.70 (Dichloromethane:Methanol=9:1);

NMR (CDCl$_3$): δ 7.98-7.95 (m, 1H), 7.63-7.10 (m, 11H), 7.05 (s, 1H), 6.97 (d, J=2.5 Hz, 2H), 6.68 (t, J=2.5 Hz, 1H), 4.80 (t, J=7.5 Hz, 2H), 3.84 (s, 6H), 3.18 (t, J=7.5 Hz, 2H).

Reference Example 28

(4-bromo-2-nitrophenyl)(2-phenylethyl)amine

To a solution of 4-bromo-1-fluoro-2-nitrobenzene (5.0 g) in N,N-dimethylformamide (25 mL), 2-phenylethylamine (6.3 mL) was added on ice bath, then immediately the temperature of the mixture was raised to room temperature and 30 minutes later, the mixture was heated to 60° C., and stirred for 2 hours.

Ice was added to the reaction mixture and the mixture was extracted with diethyl ether. The extract was washed with brine, dried over magnesium sulfate, concentrated under reduced pressure to give the title compound (7.3 g) having the following physical data.

TLC: Rf 0.53 (Hexane:Ethyl acetate=5:1);

NMR (CDCl$_3$): δ 8.30 (d, J=2.5 Hz, 1H), 8.07 (br, s, 1H), 7.48 (ddd, J=9.0, 2.5, 0.5 Hz, 1H), 7.40-7.20 (m, 5H), 6.76 (d, J=9.0 Hz, 1H), 3.58-3.52 (m, 2H), 3.02 (t, J=7.0 Hz, 2H).

Reference Example 29

4-bromo-N$^1$-(2-phenylethyl)-1,2-benzenediamine

A solution of the compound prepared in Reference example 28 (3.0 g) in acetic acid (12 mL) was heated to 120° C., iron powder (1.75 g) was added hereto, and the mixture was stirred for 2 hours.

After catalyst was removed, the filtrate was concentrated under reduced pressure. Water and 1 N aqueous solution of sodium hydroxide was added to the residue and the mixture was extracted with ethyl acetate. The extract was washed with brine, dried over sodium sulfate, concentrated under reduced pressure to give the title compound (690 mg) having the following physical data.

TLC: Rf 0.93 (Dichloromethane:Methanol=10:1);

NMR (CDCl$_3$): δ 7.40-7.20 (m, 5H), 6.91 (dd, J=8.5, 2.5 Hz, 1H), 6.82 (d, J=2.5 Hz, 1H), 6.54 (d, J=8.5 Hz, 1H), 3.36 (t, J=7.0 Hz, 2H), 3.30 (br, s, 3H), 2.96 (t, J=7.0 Hz, 2H).

Reference Example 30

5-bromo-1-(2-phenylethyl)-1H-benzimidazole

A solution of the compound prepared in Reference example 29 (650 mg) in formic acid (8 mL) was refluxed for 1 hour.

The reaction mixture was concentrated under reduced pressure. The residue was poured into water and the mixture was extracted with ethyl acetate. The extract was washed with brine, dried over magnesium sulfate, concentrated under reduced pressure. The residue was purified by column chromatography on silica gel (Hexane:Ethyl acetate=from 2:1 to 1:1) to give the title compound (645 mg) having the following physical data.

TLC: Rf 0.11 (Hexane:Ethyl acetate=1:1);

NMR (CDCl$_3$): δ 7.93 (d, J=2.0 Hz, 1H), 7.57 (s, 1H), 7.39 (dd, J=8.5, 2.0 Hz, 1H), 7.35-7.20 (m, 4H), 7.00-6.95 (m, 2H), 4.38 (t, J=7.0 Hz, 2H), 3.12 (t, J=7.0 Hz, 2H).

Reference Example 31

[5-bromo-1-(2-phenylethyl)-1H-benzimidazol-2-yl] (3,4,5-trimethoxyphenyl)methanone The title compound having the following physical data was obtained by the same procedure as described in Reference example 21 using the compound prepared in Reference example 30 instead of the compound prepared in Reference example 20 and N,3,4,5-tetramethoxy-N-methylbenzamide instead of N,3,5-trimethoxy-N-methylbenzamide.

TLC: Rf 0.87 (Hexane:Ethyl acetate=1:2);

NMR (CDCl$_3$): δ 8.04 (dd, J=2.0, 0.5 Hz, 1H), 7.56-7.51 (m, 2H), 7.49 (d, J=2.0 Hz, 1H), 7.28-7.08 (m, 6H), 4.80 (t, J=7.0 Hz, 2H), 3.96 (s, 3H), 3.93 (s, 6H), 3.19 (t, J=7.0 Hz, 2H).

Example 59

2-[1-(2-phenylethyl)-2-(3,4,5-trimethoxybenzoyl)-1H-benzimidazol-5-yl]benzoic acid methyl ester The compound of the present invention having the following physical data was obtained by the same procedure as described in Reference example 1 using the compound prepared in Reference example 31 instead of 2-bromobenzoic acid methyl ester and 2-methoxycarbonylphenylboric acid instead of 4-formylphenylboric acid.

TLC: Rf 0.35 (Hexane:Ethyl acetate=2:1);

NMR (CDCl$_3$): δ 7.90-7.86 (m, 2H), 7.61-7.53 (m, 3H), 7.48-7.37 (m, 4H), 7.28-7.20 (m, 5H), 4.83 (t, J=7.5 Hz, 2H), 3.96 (s, 3H), 3.94 (s, 6H), 3.66 (s, 3H), 3.16 (t, J=7.5 Hz, 2H).

Example 60

2-[1-(2-phenylethyl)-2-(3,4,5-trimethoxybenzoyl)-1H-benzimidazol-5-yl]benzoic acid The compound of the present invention having the following physical data was obtained by the same procedure as described in Example 2 using the compound prepared in Example 59 instead of the compound prepared in Example 1.

TLC: Rf 0.44 (Dichloromethane:Methanol=10:1);

NMR (CDCl$_3$): δ 7.92 (s, 1H), 7.88 (d, J=8.0 Hz, 1H), 7.60-7.40 (m, 6H), 7.30-7.10 (m, 6H), 4.78 (t, J=8.0 Hz, 2H), 3.93 (s, 3H), 3.90 (s, 6H), 3.22 (t, J=8.0 Hz, 2H).

Examples 61(1)-61(2)

The following compounds of the present invention were obtained by the same procedures as described in Reference example 28, Reference example 29, Reference example 30, Reference example 31, Example 59 and Example 60 using 4-bromo-1-fluoro-2-nitrobenzene or corresponding fluoride, N,3,4,5-tetramethoxy-N-methylbenzamide or corresponding amide and 2-methoxycarbonylphenylboric acid or corresponding boric acid.

Example 61(1)

2-[2-(3,5-dimethoxybenzoyl)-1-(2-phenylethyl)-1H-benzimidazol-6-yl]benzoic acid TLC: Rf 0.50 (Dichloromethane:Methanol=10:1);

NMR (CDCl$_3$): δ 7.86-7.74 (m, 2H), 7.56 (t, J=7.5 Hz, 1H), 7.44-7.08 (m, 11H), 6.71 (t, J=2.0 Hz, 1H), 4.74 (t, J=7.5 Hz, 2H), 3.84 (s, 6H), 3.16 (t, J=7.5 Hz, 2H).

Example 61(2)

3-[2-(3,5-dimethoxybenzoyl)-1-(2-phenylethyl)-1H-benzimidazol-6-yl]benzoic acid TLC: Rf 0.51 (Dichloromethane:Methanol=10:1);

NMR (CDCl$_3$): δ 8.35 (t, J=1.5 Hz, 1H), 8.14 (dt, J=8.5, 1.5 Hz, 1H), 7.98 (d, J=8.5 Hz, 1H), 7.86 (dt, J=8.5, 1.5 Hz, 1H), 7.66-7.58 (m, 2H), 7.47 (m, 1H), 7.39 (d, J=2.5 Hz, 2H), 7.26-7.08 (m, 5H), 6.73 (t, J=2.5 Hz, 1H), 4.89 (t, J=7.5 Hz, 2H), 3.87 (s, 6H), 3.25 (t, J=7.5 Hz, 2H).

Examples 62(1)-62(4)

The following compounds of the present invention were obtained by the same procedures as described in Reference example 28, Reference example 29, Reference example 30 and Reference example 31 using 4-bromo-1-fluoro-2-nitrobenzene or corresponding fluoride and N,3,5-trimethoxy-N-methylbenzamide.

Example 62(1)

2-(3,5-dimethoxybenzoyl)-1-(2-phenylethyl)-1H-benzimidazol-5-carboxylic acid TLC: Rf 0.35 (Dichloromethane:Methanol=10:1);

NMR (CDCl$_3$): δ 8.73 (d, J=1.0 Hz, 1H), 8.16 (dd, J=8.5, 1.5 Hz, 1H), 7.42 (d, J=8.5 Hz, 1H), 7.38 (d, J=2.5 Hz, 2H), 7.24-7.08 (m, 5H), 6.74 (t, J=2.5 Hz, 1H), 4.84 (t, J=7.5 Hz, 2H), 3.87 (s, 6H), 3.21 (t, J=7.5 Hz, 2H).

Example 62(2)

[2-(3,5-dimethoxybenzoyl)-1-(2-phenylethyl)-1H-benzimidazol-6-yl]acetic acid

TLC: Rf 0.40 (Dichloromethane:Methanol=10:1);
NMR (CD$_3$OD): δ 7.70 (d, J=8.5 Hz, 1H), 7.55 (s, 1H), 7.33 (dd, J=8.5, 1.5 Hz, 1H), 7.10-6.92 (m, 7H), 6.76 (t, J=2.5 Hz, 1H), 4.90-4.80 (m, 2H), 3.82 (s, 6H), 3.78 (s, 2H), 3.15 (t, J=7.0 Hz, 2H).

Example 62(3)

{[2-(3,5-dimethoxybenzoyl)-1-(2-phenylethyl)-1H-benzimidazol-6-yl]oxy}acetic acid TLC: Rf 0.48 (Dichloromethane:Methanol:Water=8:2: 0.1);
NMR (CD$_3$OD): δ 7.65 (d, J=9.0 Hz, 1H), 7.12-6.94 (m, 9H), 6.76 (t, J=2.5 Hz, 1H), 4.95-4.80 (m, 2H), 4.72 (s, 2H), 3.83 (s, 6H), 3.15 (t, J=7.0 Hz, 2H).

Example 62(4)

2-{[2-(3,5-dimethoxybenzoyl)-1-(2-phenylethyl)-1H-benzimidazol-6-yl]oxy}benzoic acid TLC: Rf 0.42 (Dichloromethane:Methanol=10:1);
NMR (CDCl$_3$): δ 8.27 (dd, J=8.0, 1.5 Hz, 1H), 7.92 (d, J=9.0 Hz, 1H), 7.50 (m, 1H), 7.40 (d, J=2.0 Hz, 2H), 7.30-7.02 (m, 7H), 6.95 (d, J=2.0 Hz, 1H), 6.78 (m, 1H), 6.74 (t, J=2.0 Hz, 1H), 4.76 (t, J=7.5 Hz, 2H), 3.87 (s, 6H), 3.18 (t, J=7.5Hz, 2H).

Reference Example 32

7-(benzyloxy)-3,4-dihydro-2,3(1H)-isoquinolinedicarboxylic acid, 3-benzyl ester,2-tert-butyl ester To a solution of 7-hydroxy-1,2,3,4-tetrahydro-3-isoquinolinecarboxylic acid (1.0 g) in a mixed solvent of 1,4-dioxane (16 mL) and water (8 mL), 1 N aqueous solution of sodium hydroxide (8 mL) and di-tert-butyl dicarbonate (1.97 mL) were added and the mixture was stirred for 4 hours.

1 N Hydrochloric acid was added to the reaction mixture and the mixture was extracted with ethyl acetate. The extract was washed with brine, dried over sodium sulfate, concentrated under reduced pressure to give crude product (2.59 g).

To a solution of the crude compound in N,N-dimethylformamide (20 mL), potassium carbonate (2.42 g) and benzyl bromide (2.1 mL) were added and the mixture was stirred for 2 hours.

1 N Hydrochloric acid was added to the reaction mixture and the mixture was extracted with ethyl acetate. The extract was washed with saturated aqueous solution of sodium hydrogen carbonate and brine sequentially, dried over sodium sulfate, concentrated under reduced pressure. The residue was purified by column chromatography on silica gel (Hexane:Ethyl acetate=from 49:1 to 9:1) to give the title compound (3.86 g) having the following physical data.

TLC: Rf 0.58 (Hexane:Ethyl acetate=4:1);
NMR (CDCl$_3$): δ 7.44-6.71 (m, 13H), 5.20-4.80 (m, 5H), 4.64 (d, J=16.5 Hz, 1H), 4.47 (t, J=16.5 Hz, 1H), 3.30-3.10 (m, 2H), 1.56-1.40 (m, 9H).

Reference Example 33

7-hydroxy-3-(2-phenylethyl)-3,4-dihydro-2(1H)-isoquinolinecarboxylic acid tert-butyl ester To a solution of the compound prepared in Reference example 32 (3.44 g) in tetrahydrofuran (15 mL), lithium borohydride (237 mg) was added sequentially and the mixture was stirred for 2 hours.

1 N Hydrochloric acid was added to the reaction mixture and the mixture was extracted with ethyl acetate. The extract was washed with brine, dried over sodium sulfate, concentrated under reduced pressure. The residue was purified by column chromatography on silica gel (Hexane:Ethyl acetate=from 4:1 to 2:1) to give a crude product (2.25 g).

To a solution of the crude product in dimethylsulfoxide (30 mL), triethylamine (4.2 mL) and sulfur trioxide pyridine complex (2.9 g) were added and the mixture was stirred for 2 hours.

1 N Hydrochloric acid was added to the reaction mixture and the mixture was extracted with ethyl acetate. The extract was washed with brine, dried over sodium sulfate, concentrated under reduced pressure to give a crude product.

To a solution of benzyl(triphenyl)phosphonium chloride (4.74 g) in tetrahydrofuran (30 mL), potassium tert-butoxide (1.5 g) was added on ice bath, and the mixture was stirred for 30 minutes, then the mixture was added by the solution of the above crude product in tetrahydrofuran (10 mL), and stirred for 5 minutes.

1 N Hydrochloric acid was added to the reaction mixture and the mixture was extracted with ethyl acetate. The extract was washed with brine, dried over sodium sulfate, concentrated under reduced pressure to give a crude product (2.68 g).

Then to a solution of the crude product in a mixed solvent of methanol (2 mL) and tetrahydrofuran (20 mL), 10% palladium on carbon (260 mg) was added and the mixture was stirred vigorously for 4 hours under atmosphere of hydrogen.

After catalyst was removed by filtration filtrate was concentrated under reduced pressure. The residue was purified by column chromatography on silica gel (Hexane:Ethyl acetate=from 9:1 to 3:1) to give the title compound (1.00 g) having the following physical data.

TLC: Rf 0.25 (Hexane:Ethyl acetate=9:1);
NMR (CDCl$_3$): δ 7.29-7.12 (m, 5H), 6.96 (d, J=8.5 Hz, 1H), 6.68-6.55 (m, 2H), 5.58 (s, 1H), 4.97-4.36 (m, 2H), 4.16 (d, J=17.0 Hz, 1H), 3.00 (dd, J=5.5, 16.0 Hz, 1H), 2.69-2.52 (m, 3H), 1.86-1.55 (m, 2H), 1.48 (s, 9H).

Reference Example 34

{[3-(2-phenylethyl)-1,2,3,4-tetrahydro-7-isoquinolinyl]oxy}acetic acid methyl ester To a solution of the compound prepared in Reference example 33 (330 mg) in acetone (5 mL), potassium carbonate (155 mg) and bromoacetic acid methyl ester (103 μL) were added and the mixture was stirred for 17 hours.

1 N Hydrochloric acid was added to the reaction mixture and the mixture was extracted with ethyl acetate. The extract was washed with brine, dried over sodium sulfate, concentrated under reduced pressure to give a crude product (395 mg). Then the crude product was added by 4 N HCl/dioxane (10 mL), and the mixture was stirred for 1 hour.

The reaction mixture was concentrated under reduced pressure to give the title compound (335 mg) having the following physical data.

TLC: Rf 0.39 (Dichloromethane:Methanol=9:1);

NMR (CDCl$_3$): δ 7.33-7.17 (m, 6H), 6.90 (dd, J=2.5, 8.5 Hz, 1H), 6.80 (d, J=2.5 Hz, 1H), 4.71 (s, 2H), 4.39 (d, J=17 Hz, 1H), 4.34 (d, J=17 Hz, 1H), 3.76 (s, 3H), 3.22 (dd, J=5.0, 17 Hz, 1H), 2.94-2.74 (m, 3H), 2.21-1.94 (m, 2H).

Example 63

{[2-(3,5-dimethoxy-4-methylbenzoyl)-3-(2-phenylethyl)-1,2,3,4-tetrahydro-7-isoquinolinyl]oxy}acetic acid methyl ester The compound of the present invention having the following physical data was obtained by the same procedure as described in Example 4 using the compound prepared in Reference example 34 instead of the compound prepared in Reference example 3 and 3,5-dimethoxy-4-methylbenzoic acid instead of 3,5-dimethoxy-4-hydroxybenzoic acid.

TLC: Rf 0.41 (Hexane:Ethyl acetate=1:1).

Example 64

{[2-(3,5-dimethoxy-4-methylbenzoyl)-3-(2-phenylethyl)-1,2,3,4-tetrahydro-7-isoquinolinyl]oxy}acetic acid The compound of the present invention having the following physical data was obtained by the same procedure as described in Example 2 using the compound prepared in Example 63 instead of the compound prepared in Example 1.

TLC: Rf 0.47 (Dichloromethane:Methanol:Acetic acid=90:10:1);

NMR (CDCl$_3$): δ 7.30-6.43 (m, 10H), 5.50-4.17 (m, 5H), 3.86-3.80 (m, 6H), 3.23-2.39 (m, 4H), 2.18-1.55 (m, 5H).

Examples 65(1)-65(2)

The following compounds of the present invention were obtained by the same procedures as described in Reference example 32, Reference example 33, Reference example 34, Example 63 and Example 64 using 7-hydroxy-1,2,3,4-tetrahydro-3-isoquinolinecarboxylic acid or corresponding carboxylic acid and 2-fluorobenzoic acid methyl ester.

Example 65(1)

2-{[2-(3,5-dimethoxy-4-methylbenzoyl)-3-(2-phenylethyl)-1,2,3,4-tetrahydro-7-isoquinolinyl]oxy}benzoic acid TLC: Rf 0.51 (Dichloromethane:Methanol=9:1);

NMR (CDCl$_3$): δ 8.20 (m, 1H), 7.49 (m, 1H), 7.06 (m, 10H), 6.60 (m, 2H), 5.34 (m, 1H), 4.48 (m, 2H), 3.80 (m, 6H), 3.20 (m, 1H), 2.66 (m, 3H), 1.88 (m, 5H).

Example 65(2)

2-{[2-(3,5-dimethoxy-4-methylbenzoyl)-3-(2-phenylethyl)-1,2,3,4-tetrahydro-6-isoquinolinyl]oxy}benzoic acid TLC: Rf 0.49 (Dichloromethane:Methanol=9:1);

NMR (CDCl$_3$): δ 1.89 (m, 5H), 2.65 (m, 3H), 3.21 (m, 1H), 3.82 (m, 6H), 4.49 (m, 2H), 5.32 (m, 1H), 6.56 (s, 2H), 7.11 (m, 10H), 7.49 (m, 1H), 8.21 (dd, J=8.0, 1.5 Hz, 1H).

Reference Example 35

3-(2-phenylethyl)-7-{[(trifluoromethyl)sulfonyl]oxy}-3,4-dihydro-2(1H)-isoquinolinecarboxylic acid tert-butyl ester To a solution of the compound prepared in Reference example 33 (500 mg) in pyridine (15 mL), trifluoromethanesulfonic anhydride (286 μL) was added on ice bath and the mixture was stirred for 2 hours at room temperature.

1 N Hydrochloric acid was added to the reaction mixture and the mixture was extracted with ethyl acetate. The extract was washed with saturated aqueous solution of sodium hydrogen carbonate and brine, dried over anhydrous sulfate, concentrated under reduced pressure. The residue was purified by column chromatography on silica gel (Hexane:Ethyl acetate=from 9:1 to 4:1) to give the title compound having the following physical data.

TLC: Rf 0.48 (Hexane:Ethyl acetate=4:1);

NMR (CDCl$_3$): δ 1.61 (m, 11H), 2.62 (m.3H), 3.07 (dd; J=17, 6.0 Hz, 1H), 4.20 (m, 1H), 4.73 (m, 2H), 7.16 (m, 8H).

Reference Example 36

7-(2-formylphenyl)-3-(2-phenylethyl)-3,4-dihydro-2 (1H)-isoquinolinecarboxylic acid tert-butyl ester The title compound having the following physical data was obtained by the same procedure as described in Reference example 1 using the compound prepared in Reference example 35 instead of 2-bromobenzoic acid methyl ester and 2-formylphenylboric acid instead of 4-formylphenylboric acid.

TLC: Rf 0.33 (Hexane:Ethyl acetate=9:1);

NMR (CDCl$_3$): δ 9.99 (s, 1H), 8.04-8.01 (m.1H), 7.66-7.61 (m, 1H), 7.52-7.42 (m, 2H), 7.29-7.13 (m, 8H), 5.10-4.42 (m, 2H), 4.27 (d, J=17.5 Hz, 1H), 3.16 (dd, J=16, 5.5 Hz, 1H), 2.76-2.56 (m, 3H), 1.92-1.57 (m, 2H), 1.50 (s, 9H).

Reference Example 37

3-{2-[3-(2-phenylethyl)-1,2,3,4-tetrahydro-7-isoquinolinyl]phenyl}propionic acid ethyl ester To a solution of the compound prepared in Reference example 36 (200 mg) in tetrahydrofuran (15 mL), (diethoxyphosphoryl)acetic acid ethyl ester (99 μL) and sodium hydride (19 mg) were added on ice bath and the mixture was stirred for 1 day.

1 N Hydrochloric acid was added to the reaction mixture and the mixture was extracted with ethyl acetate. The extract was washed with saturated aqueous solution of sodium hydrogen carbonate and brine sequentially, dried over sodium sulfate, concentrated under reduced pressure. The residue was purified by column chromatography on silica gel (Hexane:Ethyl acetate=4:1) to give the crude product (206 mg).

Then to a solution of the crude product in ethanol (8 mL), 10% palladium on carbon (40 mg) was added and the mixture was stirred vigorously for 2 hours under atmosphere of hydrogen.

After catalyst was removed by filtration, filtrate was concentrated under reduced pressure to give a crude product (197 mg). The crude product was added by 4 N HCl/dioxane (5 mL), and the mixture was stirred for 2 hours.

The reaction mixture was concentrated under reduced pressure to give the title compound (206 mg) having the following physical data.

NMR (CDCl$_3$): δ 1.16 (m, 3H), 2.12 (m, 2H), 2.40 (m, 2H), 2.85 (m, 4H), 3.37 (m, 3H), 4.01 (q, J=7.0 Hz, 2H), 4.47 (s, 2H), 7.24 (m, 12H).

Example 66

3-{2-[3-(2-phenylethyl)-2-(3,4,5-trimethoxybenzoyl)-1,2,3,4-tetrahydro-7-isoquinolinyl]phenyl}propionic acid ethyl ester The compound of the present invention having the following physical data was obtained by the same procedure as described in Example 4 using the compound prepared in Reference example 37 instead of the compound prepared in Reference example 3 and 3,4,5-trimethoxybenzoic acid instead of 3,5-dimethoxy-4-hydroxybenzoic acid.
TLC: Rf 0.61 (Hexane:Ethyl acetate=1:1).

Example 67

3-{2-[3-(2-phenylethyl)-2-(3,4,5-trimethoxybenzoyl)-1,2,3,4-tetrahydro-7-isoquinolinyl]phenyl}propionic acid The compound of the present invention having the following physical data was obtained by the same procedure as described in Example 2 using the compound prepared in Example 66 instead of the compound prepared in Example 1.
TLC: Rf 0.23 (Dichloromethane:Methanol=49:1);
NMR (CDCl$_3$): δ 7.33-7.01 (m, 12H), 6.64 (s, 2H), 5.54-5.13 (m, 1H), 4.75-4.20 (m, 2H), 3.92-3.82 (m, 9H), 3.67-2.40 (m, 8H), 2.13-1.69 (m, 2H).

Reference Example 38

3-(2-phenylethyl)-6-{[(trifluoromethyl)sulfonyl]oxy}-3,4-dihydro-2(1H)-isoquinolinecarboxylic acid tert-butyl ester The title compound having the following physical data was obtained by the same procedure as described in Reference example 35 using 6-hydroxy-3-(2-phenylethyl)-3,4-dihydro-2(1H)-isoquinolinecarboxylic acid tert-butyl ester instead of the compound prepared in Reference example 33.
TLC: Rf 0.56 (Hexane:Ethyl acetate=4:1).

Reference Example 39

2-[3-(2-phenylethyl)-1,2,3,4-tetrahydro-6-isoquinolinyl]benzoic acid methyl ester To the crude product which was obtained by the same procedure as described in Reference example 1 using the compound prepared in Reference example 38 instead of 2-bromobenzoic acid methyl ester and 2-methoxycarbonylphenylboric acid instead of 4-formylphenylboric acid, 4 N HCl/dioxane was added and stirred for 2 hours. The reaction mixture was concentrated to give the title compound having the following physical data.
TLC: Rf 0.40 (Ethyl acetate:Methanol=9:1).

Example 68

2-[2-(3,5-dimethoxy-4-methylbenzoyl)-3-(2-phenylethyl)-1,2,3,4-tetrahydro-6-isoquinolinyl]benzoic acid methyl ester The title compound having the following physical data was obtained by the same procedure as described in Example 4 using the compound prepared in Reference example 39 instead of the compound prepared in Reference example 3 and 3,5-dimethoxy-4-methylbenzoic acid instead of 3,5-dimethoxy-4-hydroxybenzoic acid.
TLC: Rf 0.59 (Hexane:Ethyl acetate=1:1).

Example 69

2-[2-(3,5-dimethoxy-4-methylbenzoyl)-3-(2-phenylethyl)-1,2,3,4-tetrahydro-6-isoquinolinyl]benzoic acid The compound of the present invention having the following physical data was obtained by the same procedure as described in Example 2 using the compound prepared in Example 68 instead of the compound prepared in Example 1.
TLC: Rf 0.44 (Dichloromethane:Methanol=9:1);
NMR (CDCl$_3$): δ 1.88 (m, 5H), 2.65 (m, 3H), 3.26 (dd, J=16.0 Hz, 5.5 Hz, 1H), 3.83 (m, 6H), 4.48 (m, 2H), 5.34 (m, 1H), 6.58 (m, 2H), 7.09 (m, 8H), 7.34 (m, 1H), 7.42 (m, 1H), 7.55 (m, 1H), 7.93 (dd, J=8.0 Hz, 1.0 Hz, 1H).

Reference Example 40

(4-(N-(3,5-dimethoxy-4-methylphenylcarbonyl)-N-(3-phenylpropyl)aminomethyl)phenyl)acetamide Under atmosphere of argon, a solution of the compound prepared in Example 2(4) (400 mg, 0.868 mmol) in dichloromethane (4 mL) was cooled to 0° C., and added by oxalyl chloride (221 mg, 1.74 mmol) and catalytic amount of N,N-dimethylformamide sequentially and the mixture was stirred for 1 hour with raising a temperature of the mixture to room temperature. The reaction mixture was concentrated under reduced pressure to prepare an acyl chloride.
The mixed solvent of 28% aqueous solution of ammonia (5 mL) and tetrahydrofuran (5 mL) was cooled to 0° C., and dropped by a solution of the prepared acyl chloride in tetrahydrofuran (5 mL), and stirred for 20 minutes.
The reaction mixture was extracted with ethyl acetate. The extract was washed with brine, dried over sodium sulfate, concentrated under reduced pressure to give the title compound (400 mg) having the following physical data.
TLC: Rf 0.40 (Dichloromethane:Methanol=9:1);
NMR (CDCl$_3$): δ 7.42-6.90 (m, 9H), 6.53 (s, 2H), 5.37 (br, s, 2H), 4.80-4.42 (m, 2H), 3.88-3.60 (m, 6H), 3.60-3.10 (m, 2H), 3.57 (s, 2H), 2.75-2.32 (m, 2H), 2.12-1.70 (m, 5H)

Reference Example 41

(4-(N-(3,5-dimethoxy-4-methylphenylcarbonyl)-N-(3-phenylpropyl)aminomethyl)phenyl)acetonitrile Under atmosphere of argon, to a solution of the compound prepared in Reference example 40 (395 mg, 0.859 mmol) in dichloromethane (5 mL), pyridine (208 μL, 2.58 mmol), and trifluoromethansulfonic anhydride (289 μL, 1.72 mmol) were added at 0° C. and the mixture was stirred for 2 hours.
Water was added to the reaction mixture and the mixture was extracted with ethyl acetate. The extract was washed with brine, dried over sodium sulfate, concentrated under reduced pressure. The residue was purified by column chromatography on silica gel (Hexane:Ethyl acetate=from 3:1 to 2:1) to give the title compound (290 mg) having the following physical data.
NMR (CDCl$_3$): δ 7.40-6.90 (m, 9H), 6.52 (s, 2H), 4.80-4.40 (m, 2H), 3.90-3.60 (m, 6H), 3.74 (s, 2H), 3.60-3.10 (m, 2H), 2.78-2.30 (m, 2H), 2.18-1.76 (m, 2H), 2.07 (s, 3H).

Example 70

3,5-dimethoxy-4-methyl-N-(3-phenylpropyl)-N-[4-(1H-tetrazol-5-ylmethyl)benzyl]benzamide To a solution of the compound prepared in Reference example 41 (283 mg, 0.640 mmol) in toluene (4 mL), trimethyltin azide (263 mg, 1.28 mmol) was added and the mixture was refluxed for 15 hours.

The reaction mixture was filtrated with cerite. The filtrate was concentrated under reduced pressure. The residue was purified by column chromatography on silica gel (Hexane: Ethyl acetate=12:1) to give the compound of the present invention (130 mg) having the following physical data.

TLC: Rf 0.69 (Dichloromethane:Methanol=4:1);
NMR (DMSO-$d_6$): δ 7.40-6.85 (m, 9H), 6.54 (s, 2H), 4.70-4.35 (m, 2H), 4.26 (s, 2H), 3.85-3.45 (m, 6H), 3.40-3.04 (m, 2H), 2.65-2.25 (m, 2H), 2.05-1.70 (m, 5H).

Examples 71(1)-71(2)

The following compounds of the present invention were obtained by the same procedures as described in Reference example 40, Reference example 41 and Example 70 using corresponding carboxylic acid instead of the compound prepared in Example 2(4).

Example 71(1)

3,5-dimethoxy-4-methyl-N-(3-phenylpropyl)-N-{4-[2-(1H-tetrazol-5-yl)phenoxy]benzyl}benzamide TLC: Rf 0.31 (Dichloromethane:Methanol=9:1);
NMR (DMSO-$d_6$): δ 8.08 (d, J=8.0 Hz, 1H), 7.54 (m, 1H), 7.44-6.82 (m, 11H), 6.57 (s, 2H), 4.75-4.40 (m, 2H), 3.80-3.60 (m, 6H), 3.42-3.08 (m, 2H), 2.65-2.28 (m, 2H), 1.98 (s, 3H), 1.97-1.75 (m, 2H).

Example 71(2)

3,4,5-trimethoxy-N-(3-phenylpropyl)-N-{4-[2-(1H-tetrazol-5-yl)phenoxy]benzyl}benzamide TLC: Rf 0.35 (Dichloromethane:Methanol=9:1);
NMR (DMSO-$d_6$): δ 8.08 (dd, J=8.0, 2.0 Hz, 1H), 7.54 (m, 1H), 7.42-6.85 (m, 11H), 6.64 (s, 2H), 4.72-4.40 (m, 2H), 3.82-3.60 (m, 9H), 3.30-3.02 (m, 2H), 2.50-2.30 (m, 2H), 1.95-1.75 (m, 2H).

Example 72

2-{[1-butyl-2-(3,5-dimethoxybenzoyl)-1H-benzimidazol-6-yl]oxy}benzoic acid

The following compounds of the present invention were obtained by the same procedures as described in Reference example 28, Reference example 29, Reference example 30 and Reference example 31 using 2-(3-fluoro-4-nitrophenoxy)benzoic acid instead of 4-bromo-1-fluoro-2-nitrobenzene and butylamine instead of 2-phenylethylamine.

TLC: Rf 0.46 (Dichloromethane:Methanol=9:1);
NMR (CDCl$_3$): δ 8.25 (dd, J=2.0, 8.0 Hz, 1H), 7.94 (d, J=8.5 Hz, 1H), 7.50-7.20 (m, 5H), 7.14 (dd, J=2.5, 9.0 Hz, 1H), 6.88 (d, J=8.5 Hz, 1H), 6.75 (t, J=2.5 Hz, 1H), 4.51 (t, J=7.5 Hz, 2H), 3.86 (s, 6H), 1.90-1.80 (m, 2H), 1.50-1.35 (m, 2H), 0.95 (t, J=7.5 Hz, 3H).

BIOLOGICAL Example

The antagonistic activity of the compound against LPA receptor in the present invention is proved by experiment shown in the following. For example, the antagonistic activity of the compounds against EDG-2 was proved by experiment shown in the following.

A series of the procedure is based on the basic gene manipuration technique, that is gene overexpressed cells are prepared and a conventional method was utilized. The usual method of measurement was improved for getting enhancement of measurement precision and/or measurement sensitivity of the evaluation of compounds in the present invention. A detailed method of the experiment was shown in the following clause.

Evaluation of EDG-2 antagonistic activity by monitoring the change of intracellular calcium ion concentration Evaluation of EDG-2 antagonistic activity was carried out by using Chinese hamster ovary (CHO) cells which overexpressed human EDG-2 gene. Those cells were cultured with Ham's F12 medium (GIBCO BRL company No. 11765-047) containing 10% FBS (fetal bovine serum), penicillin/streptomycin and blasticidin (5 μg/ml). At first in oreder to uptake Fura2-AM(Dojindo company No. 348-05831) into the cells cells, cells were incubated for 60 minutes at 37 degrees. in Fura2-AM(5 μM) solution [Ham's F12 medium containing 10% FBS, 20 mM HEPES buffer (pH 7.4) and 2.5 mM probenecid (Sigma company No. P-8761)]. Next, it was washed with Hanks solution containing HEPES buffer (20 mM, pH 7.4) and probenecid (2.5 mM) once, and immersed into the Hanks solution. Plates were set in fluorescent drug screening system (Hamamatsu photonics company, FDSS-2000) and intracellular calcium ion concentration was measured for 30 seconds with no stimulation and then solution of the compound of the present invention of formula (I) was added. Five minutes after adding thereto LPA (final concentration: 100 nM) was added, the increase of intracellular calcium ion concentrations before and after the addition of LPA (excitation wave length: 340 nM and 380 nM; fluorescent wave length: 500 nm) were measured every 3 seconds. The compound of the present invention represented by the formula (I) was dissolved in dimethyl sulfoxide (DMSO), and it was added so that the final concentration became 1 nM to 10 μM. 1-oleoyl (18:1)-LPA(Sigma) or 1-linolenoyl (18:3)-LPA was used as LPA. 1-linolenoyl (18:3)-LPA was synthesized and purified in the either way shown below. (i) the way of synthesizing 1-linolenoyl (18:3)-LPA from (18:3)-LPC (linolenoyl (18:3)-lysophosphatidylcholine) (Sedary company) by PLD (phospholipase D), or (ii) the way of synthesizing 18:3-LPC (linolenoyl (18:3)-lysophosphatidylcholine) from 18:3-PC(linolenoyl (18:3)-phosphatidylcholine) (Avanti Polar Lipids) by PLA$_2$, followed by synthesizing LPA from it by PLD (phospholipase D). EDG-2 antagonistic activity was calculated as an inhibition rate (%) by the following equation, wherein the peak value of LPA (final concentration: 100 nM) in a well into which DMSO containing no test compound represented by the formula (I) was added was regarded as a control value (A), and in the cells treated with the test compound the difference (B) between the value before addition of the test compound and that after the addition was obtained and compared with the control value.

Inhibition rate (%)=[(A−B)/A]×100

The IC$_{50}$ value was calculated as a concentration of the compound to be tested which showed 50% inhibition.

As a result, the compound of the present invention showed inhibitory activity at 10 μM. For example, the IC$_{50}$ value of the compound of Example 2(1), 2(4), 3(33) and 8(1) were respectively 0.19 μM, 0.15 μM, 0.095 μM and 0.11 μM:

FORMULATION Example 1

The following components were admixed in a conventional manner, punched out to give 100 tablets each containing 50 mg of active ingredient.

| | |
|---|---|
| 2-(4-(N-(3,4,5-trimethoxyphenylcarbonyl)-N-(3-phenylpropyl)aminomethyl)phenyl)benzoic acid | 5.0 g |
| carcium carboxymethyl cellulose (disintegrant) | 0.2 g |
| magnesium stearate (lubricant) | 0.1 g |
| microcrystalline cellulose | 4.7 g |

FORMULATION Example 2

The following components were admixed in a conventional technique. The solution was sterilized in a conventional technique, filled in ampoules 5 ml each and freeze-dried over in a conventional technique to give 100 ampoules each containing 20 mg of active ingredient.

| | |
|---|---|
| 2-(4-(N-(3,4,5-trimethoxyphenylcarbonyl)-N-(3-phenylpropyl)aminomethyl)phenyl)benzoic acid | 2.0 g |
| mannitol | 20 g |
| distilled water | 1000 mL |

The invention claimed is:

1. A compound represented by the following formula (I-B):

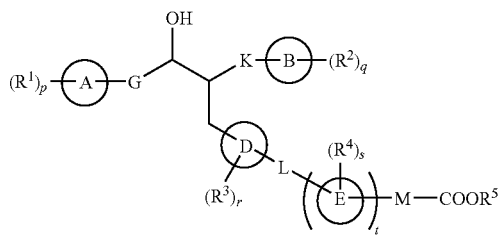

wherein $R^1$, $R^2$, $R^3$ and $R^4$ each independently represents (1) C1-8 alkyl, (2) C2-8 alkenyl, (3) a halogen atom, (4) trihalomethyl, (5) Cycl, (6) —$OR^6$, or (7) C1-8 alkyl substituted with —$OR^6$ or Cycl;

$R^6$ represents (1) a hydrogen atom, (2) C1-8 alkyl, (3) C2-8 alkenyl, (4) Cycl, (5) methyl substituted with 1 to 3 halogen, or (6) C1-8 alkyl substituted with Cycl;

Cycl represents a C3-10 monocyclic or bicyclic carbocyclic group;

G represents a bond,

K and M each independently represents (1) a bond, (2) C1-8 alkylene, or (3) C2-8 alkenylene;

L represents a bond or an oxygen atom;

Ring A represents a C3-7 monocyclic carbocyclic group;

Ring B represents a C3-10 monocyclic or bicyclic carbocyclic group

Ring D represents a pyrrole, pyrazole, 1,3,4-oxadiazole, thiazole or imidazole ring;

Ring E represents a C6 monocyclic aromatic carbocyclic group;

p, q, r and s each independently represents 0 or an integer of from 1 to 3, in which $R^1$s are the same or different when p represents 2 or more; $R^2$s are the same or different when q represents 2 or more; $R^3$s are the same or different when r represents 2 or more; and $R^4$s are the same or different when s represents 2 or more, respectively;

t represents 0 or 1; and $R^5$ represents (1) a hydrogen atom or (2) C1-8 alkyl, or a salt thereof.

2. A pharmaceutical composition comprising the compound according to claim 1 or a salt thereof and a pharmaceutically acceptable carrier.

* * * * *